US012655448B2

(12) United States Patent
Ruan et al.

(10) Patent No.: US 12,655,448 B2
(45) Date of Patent: Jun. 16, 2026

(54) HELPER-DEPENDENT ADENOVIRAL GENE THERAPY DELIVERY AND EXPRESSION SYSTEM

(71) Applicant: Baylor College of Medicine, Houston, TX (US)

(72) Inventors: Zhechao Ruan, Houston, TX (US); Kilian Guse, Hamburg (DE); Brendan Lee, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 897 days.

(21) Appl. No.: 17/358,904

(22) Filed: Jun. 25, 2021

(65) Prior Publication Data

US 2022/0017923 A1     Jan. 20, 2022

Related U.S. Application Data

(63) Continuation of application No. 14/763,326, filed as application No. PCT/IB2014/000071 on Jan. 27, 2014, now abandoned.

(60) Provisional application No. 61/756,516, filed on Jan. 25, 2013.

(51) Int. Cl.
| | |
|---|---|
| *C12N 15/861* | (2006.01) |
| *A61K 48/00* | (2006.01) |
| *A61P 19/02* | (2006.01) |
| *C12N 15/86* | (2006.01) |

(52) U.S. Cl.
CPC .......... *C12N 15/86* (2013.01); *A61K 48/0058* (2013.01); *C12N 2710/10043* (2013.01); *C12N 2710/10343* (2013.01); *C12N 2800/24* (2013.01)

(58) Field of Classification Search
None
See application file for complete search history.

(56) References Cited

U.S. PATENT DOCUMENTS

| | | | |
|---|---|---|---|
| 5,747,072 A | 5/1998 | Davidson et al. | |
| 5,919,676 A | 7/1999 | Graham et al. | |
| 6,083,750 A | 7/2000 | Chamberlain et al. | |
| 6,743,774 B1 | 6/2004 | Jay | |
| 6,890,528 B1 | 5/2005 | Colloca | |
| 7,419,808 B2 | 9/2008 | Zhang et al. | |
| 8,877,445 B2 * | 11/2014 | Shackney | A61P 35/00 |
| | | | 702/19 |
| 10,301,647 B2 | 5/2019 | Lee et al. | |
| 11,746,359 B2 * | 9/2023 | Ruan | C12N 15/86 |
| | | | 435/320.1 |
| 2001/0006948 A1 | 7/2001 | Kang et al. | |
| 2002/0081719 A1 | 6/2002 | Massaad | |
| 2002/0099024 A1 | 7/2002 | Wickham et al. | |
| 2002/0146392 A1 | 10/2002 | Graham et al. | |

| | | | |
|---|---|---|---|
| 2003/0091536 A1 | 5/2003 | Frisbee et al. | |
| 2003/0104626 A1 | 6/2003 | Fallaux et al. | |
| 2004/0072741 A1 | 4/2004 | Jay | |
| 2005/0260596 A1 | 11/2005 | Fallaux et al. | |
| 2008/0019975 A1 | 1/2008 | Gorman | |
| 2008/0038233 A1 | 2/2008 | Freemont et al. | |
| 2009/0023196 A1 | 1/2009 | Fallaux et al. | |
| 2009/0104148 A1 | 4/2009 | Jay et al. | |
| 2009/0274688 A1 | 11/2009 | Boyle et al. | |
| 2010/0215731 A1 | 8/2010 | Emans et al. | |
| 2010/0254937 A1 | 10/2010 | Han et al. | |
| 2010/0255572 A1 | 10/2010 | Schmidt et al. | |
| 2012/0045764 A1 | 2/2012 | Grompe | |
| 2013/0102028 A1 * | 4/2013 | Chun | A01K 67/0275 |
| | | | 800/9 |
| 2015/0031083 A1 | 1/2015 | Lee et al. | |
| 2015/0118187 A1 | 4/2015 | Shapir et al. | |
| 2015/0232836 A1 | 8/2015 | Krieg | |
| 2015/0361452 A1 | 12/2015 | Ruan et al. | |
| 2016/0304572 A1 | 10/2016 | Schmidt et al. | |

(Continued)

FOREIGN PATENT DOCUMENTS

| | | |
|---|---|---|
| EP | 0 832 267 B1 | 2/2002 |
| EP | 0 821 739 B1 | 6/2003 |

(Continued)

OTHER PUBLICATIONS

Ruan et al, Treatment of osteoarthritis using a helper-dependent adenoviral vector retargeted to chondrocytes, Molecular Therapy—Methods & Clinical Development (2016) pp. 1-8.*
Paz-Gonzalez et al, An Atlas of the Knee Joint Proteins and Their Role in Osteoarthritis Defined by Literature Mining, Mol Cell Proteomics (2023), pp. 1-14.*
Takahata et al, Regulatory Mechanisms of Prg4 and Gdf5 Expression in Articular Cartilage and Functions in Osteoarthritis. Int. J. Mol. Sci. 2022, pp. 1-15.*
Stone et al,Combinatorial Prg4 and II-1ra Gene Therapy Protects Against Hyperalgesia and Cartilage Degeneration in Post-Traumatic Osteoarthritis, Human Gene Therapy, 2019, p. 225-235.*
Evans et al, Gene Delivery to Joints by Intra-Articular Injection, Human Gene Therapy, 2019, pp. 1-13.*

(Continued)

*Primary Examiner* — Maria Marvich
(74) *Attorney, Agent, or Firm* — Knobbe, Martens, Olson & Bear, LLP

(57) ABSTRACT

The present invention relates to gene therapy delivery and expression systems comprising at least one helper-dependent adenoviral vector containing a nucleic acid sequence encoding for proteoglycan 4 (PRG4) or a biologically active fragment thereof. The invention further relates to a pharmaceutical composition comprising a therapeutically effective amount of at least one helper-dependent adenoviral vector containing said nucleic acid sequence encoding for proteoglycan 4 (PRG4), or a homolog thereof from any other species, or a biologically active fragment thereof. The invention also relates to the use of the novel gene therapy delivery and expression system according to the invention for use in the prevention and/or treatment of camptodactyly-arthropathy-coxa vara-pericarditis (CACP), or a musculoskeletal disorder such as a joint disorder or joint disease.

22 Claims, 8 Drawing Sheets

Specification includes a Sequence Listing.

(56) References Cited

U.S. PATENT DOCUMENTS

| | | | |
|---|---|---|---|
| 2019/0350968 A1 | 11/2019 | Erwin | |
| 2019/0376080 A1 | 12/2019 | Lee et al. | |
| 2020/0071371 A1 | 3/2020 | Ghivizzani | |
| 2022/0073948 A1 | 3/2022 | Lee et al. | |
| 2022/0282280 A1 | 9/2022 | Ruan et al. | |
| 2022/0348963 A1 | 11/2022 | Lee et al. | |
| 2022/0403415 A1 | 12/2022 | Kelley | |
| 2023/0158170 A1 | 5/2023 | Senter | |
| 2024/0102049 A1 | 3/2024 | Ruan et al. | |

FOREIGN PATENT DOCUMENTS

| | | | |
|---|---|---|---|
| WO | WO 02/082908 A1 | | 10/2002 |
| WO | WO 2005/016130 A2 | | 2/2005 |
| WO | WO 05/085421 | | 9/2005 |
| WO | WO 07/002261 | | 1/2007 |
| WO | WO 2008143816 | * | 11/2008 |
| WO | WO 10/052505 | | 5/2010 |
| WO | WO_2010135736 A2 | * | 11/2010 |
| WO | WO 10/138939 | | 12/2010 |
| WO | WO 2013/114199 A1 | | 8/2013 |
| WO | WO 14/115022 | | 7/2014 |
| WO | WO 17/191274 | | 11/2017 |
| WO | WO 20/132226 | | 6/2020 |
| WO | WO 00/46360 | | 8/2020 |
| WO | WO 22/241228 | | 11/2022 |

OTHER PUBLICATIONS

Jerebtsova et al, A Simple Technique to Establish a Long-Term Adenovirus Mediated Gene Transfer to the Heart of Newborn Mice, Cardiovasc Hematol Disord Drug Targets. Jun. 2009 ; 9(2): 136-140.*

Sandig et al, Optimization of the helper-dependent adenovirus system for production and potency in vivo, PNAS, 2000, pp. 1002-1007.*

Adiaansen et al. "Gene therapy as a therapeutic approach for thetreatment of rheumatoid arthritis: innovative vectors and therapeutic genes", Rheumatology 45:656-668 (2006).

Bakker, A. et al, "C3-Tat/HIV-regulated intraarticular human interleukin-1 receptor antagonist gene therapy results in efficient inhibition of collagen-induced arthritis superior to cytomegalovirus-regulated expression of the same transgene", Arthritis & Rheumatism, 46:6:1661-1670, (2006).

Borzi, R. et al., "Matrix metalloproteinase 13 loss associated with impaired extracellular matrix remodeling disrupts Chondrocyte differentiation by concerted effects on multiple regulatory factors", Arthritis & Rheumatism, 62:8:2370-2381, (2010).

Brunetti-Pierri et al, "Transgene expression up to 7 years in non-human primates following hepatic transduction with helper-dependent adenoviral vectors", Human Gene Therapy, vol. 24, pp. 1-5 (2013).

Caron, J. et al, "Chondroprotective effect of Intraarticular injections of interleukin-1 receptor antagonist in experimental osteoarthritis", Arthritis & Rheumatism, 39:9: 1535-1544, (1996).

Coles, J. et al, "Loss of cartilage structure, stiffness, and frictional properties in mice lacking PRG4", Arthritis & Rheumatism, 62:6:1666-1674, (2010).

Daheshia, M. et al, "The interleukin 1-beta pathway in the pathogenesis of osteoarthritis", The Journal of Rheumatology, 35:12:2306-2312, (2008).

Dinser et al. "Comparison of long-term transgene expression after non-viral and adenoviral gene transfer into primary articular chondrocytes", Histochemistry and Cell Biology 116:69-77 (2001).

Echtermeyer, F. et al, "Syndecan-4 regulates ADAMTS-5 activation and cartilage breakdown in osteoarthritis", Nature Medicine, 15:9:1072-1077, (2009).

Evans et al. "Gene Therapy for Rheumatic Diseases", Arthritis & Rheumatism, vol. 42, No. 1, p. 1-16 (1999).

Evans et al. "Osteoarthritis gene therapy", Gene Therapy, vol. 11, pp. 379-389, http://www.nature.com/gt, (2004).

Flannery, C. et al, "Prevention of cartilage degeneration in a rat model of osteoarthritis by inreaarticular treatment with recombinant lubricin", Arthritis & Rheumatism, 60:3:840-847, (2009).

Ghivizzani et al. "Direct adenovirus-mediated gene transfer of interleukin 1 and tumor necrosis factor a soluble receptors to rabbit knees with experimental arthritis has local and distal anti-arthritic effects", Proc. Natl. Acad. Sci. USA, vol. 95, pp. 4613-4618, (1998).

Horwood, N. et al, "High-efficiency gene transfer into nontransformed cells: utility for studying gene regulation and analysis of potential therapeutic targets", Arthritis Research, vol. 4, Suppl. 3, p. S215-S225, (2002).

Jay, G. et al, "The role of lubricin in the mechanical behavior of synovial fluid", PNAS, 104:15:6194-6199, (2007).

Johnson, K. et al, "A stem cell-based approach to cartilage repair", Scienceexpress, Internet article: http://www.sciencemag.org/content/early/recent, p. 1 /10 .1126/science.1215157 (2012).

Kay, J. et al, "Intra-articular gene delivery and expression of interleukin-1 Ra mediated by self-complementary adenoassociated virus", The Journal of Gene Medicine, vol. 11, pp. 605-614, (2009).

Matthews, G. et al, "Emerging drugs for osteoarthritis", Expert Opin Emerg Drugs, 16(3): 479-491 (2011).

Mitani, K. et al, "Rescue, propagation, and partial purification of a helper virus-dependent adenovirus vector", Proc. Natl. Acad. Sci., vol. 92, pp. 3854-3858, USA, (1995).

Nobuhiro, A. et al, "Enhancement of bone repair with a helper-dependent adenoviral transfer of bone morphogenetic protein-2", Biochemical and Biophysical Research Communications, 297:3:523-527, (2002).

Palmer, D. et al, "Improved system for helper-dependent adenoviral vector production", Molecular Therapy, 8:5:846-852, (2003).

Parks, R. et al, "A helper-dependent adenovirus vector system: Removal of helper virus by Cre-mediated excision of the viral packaging signal", Proc. Natl. Acad. Sci., vol. 93, p. 13565-13570, (1996).

Parks, R. et al, "Improvements in adenoviral vector technology: overcoming barriers for gene therapy", Clinical Genetics, vol. 58, pp. 1-11, (2000).

Rhee, D. et al, "The secreted glycoprotein lubricin protects cartilage surfaces and inhibits synovial cell overgrowth", The Journal of Clinical Investigation, 115:3:622-631, (2005).

Ruan, M. et al, "Protoglycan 4 expression protects against the development of osteoarthritis", Science Translational Medicine, 5:176:176ra34-176ra34, p. 3-4, (2013).

Saito, T. et al, "Transcriptional regulation of endochondral ossification by HIF-2alpha during skeletal growth and osteoarthritis development", Nature Medicine, 16:6:678-687, (2010).

Smith et al. "Secretory Interleukin-1 Receptor Antagonist Gene Expression Requires both a PU.1 and a Novel Composite NF-κB/PU.1/GA-binding Protein Binding Site", JBC, p. 24272-24279 (1998).

Vetrini et al. "Gene Therapy with Helper-Dependent Adenoviral Vectors: Current Advances and Future Perspectives", Viruses, p. 1886-1917 (2010).

Yeh and Perricaudet, "Advances in adenoviral vectors: from genetic engineering to their biology", FASEB Journal 11 (8):615-23 (1997).

Backstrom et al, "Recombinant MUC1 mucin with a breast cancer-like O-glycosylation produced in large amounts in Chinese-hamsterovary cells", Biochem. J., 376:677-686 (2003).

Bakker et al. "A tropism-modified adenoviral vector increased the effectiveness of gene therapy for arthritis", Gene Therapy, vol. 8, No. 23, p. 1785-1793 (2001).

Bergelson et al. "Isolation of a Common Receptor for Coxsackie B Viruses and Adenoviruses 2 and 5", Science, vol. 275, p. 1320-1323 (1997).

Brunetti-Pierri, R. et al. "Acute Toxicity After High-Dose Systemic Injection of Helper-Dependent Adenoviral Vectors into Nonhuman Primates", Human Gene Therapy, vol. 15, p. 35-46 (2004).

Castel et al, "Repeat instability as the basis for human diseases and as a potential target for therapy", Mol. Cell Biol., 11 :165-170 (Mar. 2010).

(56)          References Cited

OTHER PUBLICATIONS

Castello et al, "Helper-dependent adenoviral vectors for liver-directed gene therapy of primary hyperoxaluria type 1" Gene Therapy, p. 1-6 (2015).
Chen et al, "Persistence in muscle of an adenoviral vector that lacks all viral genes", Proc. Natl. Acad. Sci. USA, 94:1645-1650 (Mar. 1997).
Frisbie et al. "Treatment of experimental equine osteoarthritis by in vivo delivery of the equine interleukin-1 receptor antagonist gene", Gene Therapy (2002) 9, 12-20.
Goodrich et al. "scAAVIL-1ra dosing trial in a large animal model and validation of long-term expression with repeat administration for osteoarthritis therapy", Gene Therapy, vol. 22, No. 7, p. 536-545 (2015).
Goodrich et al. "Direct adenovirus-mediated IGF-I gene transduction of synovium induces persisting synovial fluid IGF-I ligand elevations", Gene Therapy, vol. 13, p. 1253-1262 (2006).
Goodrich et al. "Ex Vivo Serotype-Specific Transduction of Equine Joint Tissue by Self-Complementary Adeno-Associated Viral Vectors", Human Gene Therapy, vol. 20, p. 1697-1702 (2009).
Goossens et al. "Infection Efficiency of Type 5 Adenoviral Vectors in Synovial Tissue Can Be Enhanced With a Type 16 Fiber", Arthritis & Rheumatism, vol. 44, No. 3, p. 570-577, (2001).
Goossens et al. "The Influence of Synovial Fluid on Adenovirus-Mediated Gene Transfer to the Synovial Tissue", Arthritis & Rheumatism, vol. 44, No. 1, p. 48-52 (2001).
Harui et al. "Frequency and Stability of Chromosomal Integration of Adenovirus Vectors", Journal of Virology, Jul. 1999, vol. 73, No. 7, p. 6141-6146.
Ishihara et al. "Inflammation and Immune Response of Intra-Articular Serotype 2 Adeno-Associated Virus or Adenovirus Vectors in a Large Animal Model", Arthritis, vol. 2012, Article ID: 735472, 8 pages, (2012).
Kochanek, "High-capacity adenoviral vectors for gene transfer and somatic gene therapy", Human Gene Therapy, 10:2451-2459 (Oct. 10, 1999).
Manno et al, "MY-mediated factor IX gene transfer to skeletal muscle in patients with severe hemophilia B", Blood, 101(8):2963-2972 {Apr. 15, 2003).
Morral et al. "Lethal Toxicity, Severe Endothelial Injury, and a Threshold Effect with High Doses of an Adenoviral Vector in Baboons", Human Gene Therapy, vol. 13, p. 143-154 (2002).
Muruve et al. "Helper-Dependent Adenovirus Vectors Elicit Intact Innate but Attenuated Adaptive Host Immune Responses In Vivo", Journal of Virology, vol. 78, No. 11, p. 5966-5972 (2004).
Nathwani et al, "Adenovirus-associated virus vector-mediated gene transfer in Hemophilia B", N. Engl. J. Med., p. 1-9 (Dec. 10, 2011).
Ogawa et al. "Mechanical motion promotes expression of Prg4 in articular cartilage via multiple CREB-dependent, fluid flow shear stress-induced signaling pathways", Genes & Development, 2013, 28:127-139.
Roessler et al. "Inhibition of Interleukin-1-Induced Effects in Synoviocytes Trans duce d with the Human IL-1 Receptor Antagonist cDNA Using an Adenoviral Vector", Human Gene Therapy, 1995, pp. 307-316.
Schmidt et al, Disulfide-bonded multimers of proteoglycan 4 (PRG4) are present in normal synovial fluids, Biochimica et Biophysica Acta 1790 (2009) 375-384.
White II et al, "Gene therapy for hemophilia A", Textbook of Hemophilia, Chapter 39, pp. 226-228, Blackwell Publishing Lid (2007).
Willett, K., et al., "Immunology of AAV-Mediated Gene Transfer in the Eye," Frontiers in Immunology, Aug. 2013, vol. 4, 8 pages.
Accession No. NM_001082525.2 Equus caballus interleukin 1 receptor antagonist (IL1RN), mRNA, 2015, 3 pages.
Accession No. NM_001082770 Oryctolagus cuniculus interleukin 1 receptor antagonist (ILIRN, mRNA 2011, 2 pages.
Accession No. NM_174357.3, Bos taurus interleukin 1 receptor antagonist (IL1RN), mRNA, 2009, 2 pages.

Bae et al., 2014, Is There Clinical Improvement Associated with Saline Injection for Discogenic Low Back Pain: Comparison of RCTs, Proceedings of the NASS 29th Annual Meeting/ The Spine Journal 14:32S.
Benneker et al., 2005, 2004 Young investigator award winner: vertebral endplate marrow contact channel occlusions and intervertebral disc degeneration, Spine, 30(2):167-173.
Bibby et al., 2004, Effect of nutrient deprivation on the viability of intervertebral disc cells, Eur Spine J. 13:695-701.
Brooks, 2002, Impact of osteoarthritis on individuals and society: how much disability? Social consequences and health economic implications., Current Opinion Rheumatol, 14:573-577.
Brunetti-Pierri et al, May 2011, Multi-Year Transgene expression in nonhuman primates following Hepatic transduction with helper-dependent adenoviral vectors, American Society of Gene & Cell Therapy, Annual Meeting 2011 Molecular Therapy, 19(Supp. 1).
Butterman, 2004, The effect of spinal steroid injections for degenerative disc disease, Spine Journal, 4:495-505.
Cao et al., 2011, The promotion of cartilage defect repair using adenovirus mediated Sox9 gene transfer of rabbit bone marrow mesenchymal stem cells, Biomaterials, 32:3910-3920.
Caron et al., 2003, Principals and practices of joint disease treatment, In: Diagnosis and management of lameness in the horse, 1st Edition, Philadelphia: Saunders, pp. 746-764.
Chen et al., Jan. 19, 2018, Sirt6 overexpression suppresses senescence and apoptosis of nucleus pulposus cells by inducing autophagy in a model of intervertebral disc degeneration, Cell Death & Disease, 9(2), 13 pp.
Chen et al., Oct. 16, 2021, SIRT6 inhibits endothelial-to-mesenchymal transition through attenuating the vascular endothelial inflammatory response, International Immunopharmacology 101(108240), 9 pp.
Chen et al., Oct. 2010, Effects of adenovirus-mediated bFGF, IL-1Ra and IGF-1 gene transfer on human osteoarthritic chondrocytes and osteoarthritis in rabbits, Experimental and Molecular Medicine, 42(10):684-695.
Daya et al, 2008, Gene Therapy Using Adeno-Associated Virus Vectors, Clin. Microbiol. Rev, 21(4):583-593.
Dehne et al., 2009, Chondrogenic differentiation potential of osteoarthritic chondrocytes and their possible use in matrix-associated autologous chondrocyte transplantation, Arthritic Research and Therapy, 11(5):R133.
Dinarello, 2003, Chapter 27-Interlukin-1 family, in The Cytokine Handbook, 4th Edition, 2:643-668.
Dolan et al., 2001, An EMG technique for measuring spinal loading during asymmetric lifting, Clin. Biomech. 16(Supplement 1):S17-S24.
Dolan et al., 2001, Recent advanced in lumbar spinal mechanics and their significance for modelling, Clin.Biomech. 16(Supplement 1):S8-S16.
Dong et al., May 2023, Modulation of SIRT6 activity acts as an emerging therapeutic implication for pathological disorders in the skeletal system, Genes & Diseases, 10(3):864-876.
Eskola et al., 2012, Gender difference in genetic association between IL1A variant and early lumbar disc degeneration: a three-year follow-up, Int J Mol Epidemiol Genet. 3(3):195-204.
Evans et al., 1994,, Gene therapy for arthritis, Gene Therapeutics: Methods and Applications of direct Gene Transferm, Birkhauser: Boston, MA, pp. 320-343.
Flexion Press Release, Apr. 29, 2018, Flexion Therapeutics Announces Presentation of Positive FX201 Data at the Osteoarthritis Research Society International World Congress, 2 pp.
Fumoto et al., 2013, Targeted Gene Delivery: Importance of Administration Routes, Chapter 1 in Novel Gene Therapy Approaches, Intech, pp. 3-31.
Giannoukakis et al., Sep. 1999, Adenoviral gene transfer of the interleukin-1 receptor antagonist protein to human islets prevents IL-1β-induced β-cell impairment and activation of islet cell apoptosis in vitro, Diabetes, 48:1730-1736.
Glasson et al., 2020, The OARSI histopathology initiative—recommendations for histological assessments of osteoarthritis in the mouse, Osteoarthritic and Cartilage, 18:S17-S23.

(56)                    References Cited

OTHER PUBLICATIONS

Goodrich et al.., 2013, Optimization of scAAVIL-Ira In Vitro and In Vivo to Deliver High Levels of Therapeutic Protein for Treatment of Osteoarthritis, Molecular Therapy Nucleic Acids, 5(2):e70, 10 pp.

Goupille et al., 2007, Is interleukin-1 a good target for therapeutic intervention in intervertebral disc degeneration: lessons from the osteoarthritic experience, Arthritis Res Ther, 9(6):110.

Grol et al., Apr. 26-29, 2018, Interleukin-1 Receptor Antagonist Gene Therapy Prevents and Delays Surgically-Induced Osteoarthritis in Small and Large Animal Models, 2018 World Congress of Osteoarthritis, 26 pp.

Gruber et al., 1998, Analysis of aging and degeneration of the human intervertebral disc, Spine, 23(7):751-757.

Heathfield et al., 2008, Caveolin-1 expression and stress-induced premature senescence in human intervertebral disc degeneration, Arthritis Res. Ther., 10(4):1-9.

Hoyland et al., 2008, Investigation of the role of IK-1 and TNF in matrix degradation in the intervertebral disc, Rheumatology, 47:809-814.

Inkinen et al., Relative increase of biglycan and decorin and altered chondroitin sulfate epitopes in the degenerating human intervertebral disc, The Journal of Rheumatology, 25(3):506-514.

Kaditis et al., Mar. 14, 2007, Anti-inflammatory pharmacotherapy for wheezing in preschool children, Pediatric Pulmonology, 42(5):407-420.

Kang et al., Mar. 2017, Sirtuin 6 prevents matrix degradation through inhibition of the NF-[kappa]B pathway in intervertebral disc degeneration, Experimental Cell Research, 352(2):322-332.

Khan et al., 2017, Inflammatory biomarkers of low back pain and disc degeneration: a review, Ann. N.Y. Acad. Sci. 1410:68-84.

Khoury, Jul. 2007, Inflammation-inducible anti-TNF gene expression mediated by intra-articular injection of serotype 5 adeno-associated virus reduces arthritis, The Journal of Gene Medicine, 9(7):596-604.

Le Maitre et al., 2004, Localization of degradative enzymes and their inhibitors in the degenerate human intervertebral disc, J Pathol. 204:47-54.

Le Maitre et al., 2005, The role of interleukin-1 in the pathogenesis of human intervertebral disc degeneration, Arthritis Res Ther. 7:R732-R745.

Le Maitre et al., 2006, A preliminary in vitro study into the use of IL-1Ra gene therapy for the inhibition of intervertebral disc degeneration, Int J Exp Pathol. 87:17-28.

Le Maitre et al., 2007, Interleukin-1 receptor antagonist delivered directly and by gene therapy inhibits matrix degradation in the intact degenerate human intervertebral disc: an in situ zymographic and gene therapy study, Arthritis Res Ther, 9(4):R83.

Le Maitre et al., 2007, Matrix synthesis and degradation in human intervertebral disc degeneration, Arthritis Res Ther., 35(4):652-655.

Le Maitre et al., 2021, Development of a standardized histopathology scoring system for human intervertebral disc degeneration: an Orphopaedic Research Society Spine Section initiative, JOR Spine, 4:e1167.

Lee et al., 2017, Adenovirus-mediated gene delivery: potential applications for gene and cell-based therapies in the new era of personalized medicine, Genes & Diseases, 4:43-63.

Lin et al., Jun. 16, 2003, Enhancing adenovirus-mediated gene transfer in vitro and in vivo by addition of protamine and hydrocortisone, The Journal of Gene Medicine, 5(10):868-875.

Luoma et al., 2000, Low back pain in relation to lumbar disc degeneration, Spine, 25(4):487-492.

Makino et al., 2001, Inhibitory PAS domain protein is a negative regulator of hypoxia-inducible gene expression, Nature, 389(6863):550-554.

Marcelino et al., CACP, encoding a secreted proteoglycan, is mutated in camptodactyly-arthropathy-coxa vara pericarditis syndrome, Nature Genetics, 23:319-322.

Mern et al., 2014, Enhancing human nucleus pulposus cells for biological treatment approaches of degenerative intervertebral disc diseases: a systematic review, J Tissue Eng Regen Med, 8:925-936.

Mingozzi et al., 2007, CD8+ T-cell responses to adeno associated virus capsid in humans, Nature Medicine, 13(4):419-422.

Molladavoodi et al., 2019, Mechanobiology of annulus fibrosus and nucleus pulposus cells in intervertebral discs, Cell Tissue Res, 379:429-444.

Mwale et al., 2004, Distinction between the extracellular matrix of the nucleus pulposus and hyaline cartilage: a requisite for tissue engineering of intervertebral disc, European Cells and Materials, 8:58-64.

Nakao et al., 1997, Identification of SMAD7, a TGFbeta-inducible antagonist of TGF-beta signalling, Nature, 389(6651):631-635.

NCT00126724 Study of Intra-articular Delivery of tgAAC94 in Inflammatory Arthritis Subjects, 11 pages, 2005.

NCT00617032 Phase 1 Dose Escalation Study of Intra-Articular Administration of tgAAC94, 8 pages, 2008.

NCT02790723 Safety of Intra-Articular Sc-rAAV2.51L-1Ra in Subjects With Moderate Knee Oa (AAVIL-1Ra), 2016.

Oren et al, "Short tandem repeats, segmental duplications, gene deletion, and genomic instability in a rapidly diversified immune gene family", BMC Genomics, 17:900-919 (2016).

Palmer et al., 2005, Helper-Dependent Adenoviral Vectors for Gene Therapy, Human Gene Therapy, 16:1-16.

Paul et al., Apr. 15, 2003, Potential use of Sox9 gene therapy for intervertebral degenerative disc disease, Spine, 28(8):755-763.

Paz Aparicio et al., 2011, The IL-1? (+3953 T/C) gene polymorphism associates to symptomatic lumbar disc herniation, Eur Spine J., 29(Suppl 3):S383-S389.

Pearson et al, "Repeat instability: mechanisms of dynamic mutations", Genetics, 6:729-742 (Oct. 2005).

Phillips et al., 2013, Interleukin-1 receptor antagonist deficient mice provide insights into pathogenesis of human intervertebral disc degeneration, Ann Rheum Dis, 72:1860-1867.

Phillips et al., 2013, The cytokine and chemokine expression profile of nucleus pulposus cells: implications for degeneration and regeneration of the intervertebral disc, Arthritis Res Ther. 15:R213.

Phillips et al., 2015, Potential roles of cytokines and chemokines in human intervertebral disc degeneration: interleukin-1 is a master regulator of catabolic processes, Osteoarthritis Cartilage, 23:1165-1177.

Pockert et al., Feb. 2009, Modified expression of the ADAMTX enzymes and tissue inhibitor of metalloproteinases 3 during human intervertebral disc degeneration, Arthritis Rheum. 69(2):482-491.

Pohl et al., Aug. 2016, Catabolic effects of endothelial cell-derived microparticles on disc cells: implications in intervertebral disc neovascularization and degeneration, pp. 1466-1474.

Pritzker et al., 2006, Osteoarthritis cartilage histopathology: grading and staging, Osteoarthritis and Cartilage, 14(1):13-29.

Roberts et al., 2006, Senescence in human intervertebral discs, Eur Spine J. 15(Suppl. 3):S312-S316.

Roberts et al., 2006, Topographical guidance of intervertebral disc cell growth in vitro: towards the development of tissue repair strategies for the anulus fibrosus, Eur Spine J. 15(Suppl. 3)S389-S396.

Ross et al., Sep. 2009, Host Cell Detection of Noncoding Stuffer DNA Contained in Helper-Dependent Adenovirus Vectors Leads to Epigenetic Repression of Transgene Expression. Journal of Virology, 83(17):8409-8417.

Ruan et al., Feb. 2013, Quantitative imaging of murine osteoarthritic cartilage by phase contrast micro-computed tomography, Arthritis Rheumatism, 65:2:388-396.

Rustenburg et al., 2018, Osteoarthritis and intervertebral disc degeneration: quite different, quite similar, JOR Spine, 1(4):e1033.

Sampara et al., 2018, Understanding the molecular biology of intervertebral disc degeneration and potential gene therapy strategies for regeneration: a review, Gene Therapy, 25:67-82.

Santangelo et al., 2010, Detectable Reporter Gene Expression following Transduction of Adenovirus and Adeno-Associated Virus Serotype 2 Vectors within Full-Thickness Osteoarthritic and Unaffected Canine Cartilage In Vitro and Unaffected Guinea Pig Cartilage In Vivo, Journal of Orthopedic Research, 28(2):149-155.

(56) References Cited

OTHER PUBLICATIONS

Shamji et al., Jul. 2010, Proinflammatory cytokine expression profile in degenerated and herniated human intervertebral disc tissues, Arthritis Rheum. 62(7):1974-1982.

Shankar et al., 2009, Anatomy and pathophysiology of intervertebral disc disease, Techniques in Regional Anesthesia and Pain Management, 13:67-75.

Sheskey et al., Oct. 2020, Handbook of Pharmaceutical Excipients Ninth edition, TOC, 3 pp.

Solovieva et al., 2004, Possible association of interleukin 1 gene locus polymorphisms with low back pain, Pain, 109:8-19.

Solovieva et al., 2005, Intervertebral disc degeneration in relation to the COL9A3 and the IL-1? gene polymorphism, Eur Spine J. 15:613-618.

Solovieva et al., Sep. 2004, Interleukin 1 polymorphisms and intervertebral disc degeneration, Epidemiology. 15(5):626-633.

Stienen et al., 2017, Validation of the baseline severity stratification of objective functional impairment in lumbar degenerative disc disease, J Neurosurg Spine 26:598-604.

Suzuki et al., 2010, MyD88-Dependent Silencing of Transgene Expression During the Innate and Adaptive Immune Response to Helper-Dependent Adenovirus, Human Gene Therapy, 21:325-336.

Suzuki et al., Jan. 2010, Large-scale production of high-quality helper-dependent adenoviral vectors using adherent cells in cell factories, Human Gene Therapy, 21(1):120-126.

Tellez et al., 2005, Adenoviral overexpression of interleukin-1 receptor antagonist protein increases β-cell replication in rat pancreatic islets, Gene Therapy, 12:120-128.

The United States pharmacopeia, USP 30, The National formulary: NF 25, May 1, 2007 (TOC).

Toh et al., 2005, Enhancement of Adenovirus-Mediated Gene Delivery to Rheumatoid Arthritis Synoviocytes and Synovium by Fiber Modifications: Role of Arginine-Glycine-Aspartic Acid (RGD)- and Non-RGD-Binding Integrins, Journal of Immunology, 175(11):7687-7698.

Toietta et al., Feb. 2002, Generation of helper-dependent adenoviral vectors by homologous recombination, Molecular Therapy: The Journal of the American Society of Gene Therapy, 5(2):204-210.

Ulrich-Vintner et al., 2004, In vivo gene delivery to articular chondrocytes mediated by an adeno-associated virus vector, Journal of Orthopedic Research, 22:726-734.

Vo et al., Aug. 2016, Molecular mechanisms of biological aging in intervertebral discs, Orthop Res., pp. 1289-1306.

Wang et al., 2006, Adenovirus expressing niterleukin-1 receptor antagonist alleviates allergic airway inflammation in a murine model of asthma, Gene Therapy, 13:1414-1421.

Wang et al., 2015, MMPs and ADAMTSs in intervertebral disc degeneration, Clinica Chimica Acta, 448:238-246.

Xie et al., Sep. 29, 2020, Sirtuin 6: A potential therapeutic target for cardiovascular diseases, Pharmacological Research, 163(105214), 10 pp.

Yang et al., 1997, Overexpression of interleukin-1 receptor antagonist in the mouse brain reduces ischemic brain injury, Brain Research, 751:181-188.

Gallaher et al., Sep. 2013, A rapid Q-PCR titration protocol for adenovirus and helper-dependent adenovirus vectors that produces biologically relevant results, J. Viral. Methods, 192(0):28-38.

Johnson, Dec. 6, 2018, Comments submitted by PDA for Docket ID: FDA-2008-D-0205, PDA, 10 pp.

Nixon et al., Nov. 2018, Disease-modifying osteoarthritis treatment with interleukin-1 receptor antagonist gene therapy in small and large animal models, Arthritis Rheumatol, 70(11):1757-1768.

Puntel et al., May 2006, Quantification of high-capacity helper-dependent adenoviral vector genomes in vitro and in vivo, using quantitative TaqMan real-time polymerase chain reaction, Human Gene Therapy, 17:531-544.

Roamer et al., 2019, Qualitative and quantitative host cell protein analysis using mass spectrometry, BioProcess International, retrieved on Apr. 25, 2025 from the Internet: <https://www.bioprocessintl.com/sponsored-content/qualitative-and-quantitative-host-cell-protein-analysis-using-mass-spectrometry>.

Ruan, Jan. 2013, Prevention of osteoarthritis by combination of prteoglycan 4 and interleukin 1 receptor antagonist expression, ASBMR 2013 Annual meeting, S200, https://www/asbmr.org/meetings/2013-abstracts.

Takahashi et al., 2006, Quantitation of adenovirus type 5 empty capsids, Analytical Biochemistry, 349:208-217.

U.S. Department of Health and Human Services Food and Drug Administration, Sep. 2016, Recommendations for Microbial Vectors used for Gene Therapy: Guidance for Industry, 27 pp.

Vellekamp et al., Oct. 10, 2001, Empty capsids in column-purified recombinant adenovirus preparations, Human Gene Therapy, 12:1923-1936.

* cited by examiner

A

B

C

D

A

B

C

A

B

C

HELPER-DEPENDENT ADENOVIRAL GENE THERAPY DELIVERY AND EXPRESSION SYSTEM

CROSS-REFERENCE TO RELATED APPLICATIONS

This is a continuation application of U.S. patent application Ser. No. 14/763,326, filed Jul. 24, 2015, which is a national stage filing in accordance with 35 U.S.C. § 371 of International Patent Application No. PCT/IB2014/000071, filed Jan. 27, 2014, which claims the benefit of U.S. Provisional Patent Application No. 61/756,516, filed Jan. 25, 2013, the entire contents of each of which are incorporated herein by reference.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: GEQB_001_02US_SeqList_ST25.txt, date recorded: Jun. 18, 2024, file size 241,912 bytes).

FIELD OF THE INVENTION

The present invention relates to gene therapy delivery and expression systems comprising at least one helper-dependent adenoviral vector containing a nucleic acid sequence encoding for proteoglycan 4 (PRG4) or a biologically active fragment thereof. The invention further relates to a pharmaceutical composition comprising a therapeutically effective amount of at least one helper-dependent adenoviral vector containing said nucleic acid sequence encoding for proteoglycan 4 (PRG4), or a homolog thereof from any other species, or a biologically active fragment thereof. The invention also relates to the use of the novel gene therapy delivery and expression system according to the invention for use in the prevention and/or treatment of camptodactyly-arthropathy-coxa vara-pericarditis (CACP), or a musculoskeletal disorder such as a joint disorder or joint disease.

BACKGROUND

Musculoskeletal conditions are the most common chronic conditions, affecting nearly one third of the human population. Musculoskeletal conditions are defined as conditions of the bones, muscles and their attachments such as joints, tendons and ligaments. They consist of a variety of different diseases that cause pain or discomfort in the bones, joints, tendons, ligaments, muscles or surrounding structures. Musculoskeletal disorders range from back pain to rheumatoid arthritis, and gout, and include different types of arthritis, tendinitis and musculoskeletal pain. Furthermore, musculoskeletal diseases or disorders include, but are not limited to arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis. Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

In addition, there are heritable disorders such as CAPC (camptodactyly-arthropathy-coxa vara-pericarditis) syndrome that have their origin in a non-functional PRG4 gene. The disorder results in synoviocyte hyperplasia and early onset osteoarthritis, the principal pathological features of the CAPC syndrome.

Osteoarthritis (OA) is an age-related or post-traumatic degenerative disease of the joint that is characterized by loss of articular cartilage, chondrocyte proliferation and hypertrophic differentiation, subchondral bone remodelling, inflammation, and finally, osteophyte formation (K. Johnson et al., A Stem Cell-Based Approach to Cartilage Repair. Science (New York, NY) 336, 717 (Jun. 10, 2012)). It is among the leading causes of chronic disability (Matthews, G. L., and Hunter, D. J. (2011), Emerging drugs for osteoarthritis. Expert Opin. Emerging Drugs 1-13). Surprisingly, given the impact of OA, relatively few genetic mouse models have been developed to provide insights into potential protective mechanisms that can modify the development of osteoarthritis. To date, most have been loss-of-function genetic models of cartilage degrading enzymes such as ADAMTS5 and MMP13 (F. Echtermeyer et al., Syndecan-4 regulates ADAMTS-5 activation and cartilage breakdown in osteoarthritis. *Nature Medicine*, 1 (Mar. 30, 2102); T. Saito et al., Transcriptional regulation of endochondral ossification by HIF-2a during skeletal growth and osteoarthritis development. *Nature Medicine* 16, 678 (Jun. 23, 2010); R. M. Borzi et al., Matrix metalloproteinase 13 loss associated with impaired extracellular matrix remodeling disrupts chondrocyte differentiation by concerted effects on multiple regulatory factors. *Arthritis & Rheumatism* 62, 2370 (May 13, 2010); J. D. Kay et al., Intra-articular gene delivery and expression of interleukin-1Ra mediated by self-complementary adeno-associated virus. *The journal of gene medicine* 11, 605 (July 2009)). Mice with loss of function mutation in Hif2a are also protected from osteoarthritis development, highlighting the importance of the hypoxia pathway in cartilage homeostasis.

Unfortunately, despite significant investment, the development of inhibitors of such pathways has not proven effective in the clinical setting.

Interestingly, loss-of-function mutations in proteoglycan 4 (PRG4) in humans cause Camptodactyly-Arthropathy-Coxa Vara-Pericarditis Syndrome (J. Marcelino et al., CACP, encoding a secreted proteoglycan, is mutated in camptodactyly-arthropathy-coxa vara-pericarditis syndrome. *Nature genetics* 23, 319 (November 1999)), which is characterized by early onset osteoarthritis. In addition, genetic knockout of PRG4 in mice also results in early osteoarthritis development (D. K. Rhee et al., The secreted glycoprotein lubricin protects cartilage surfaces and inhibits synovial cell overgrowth, *J Clin Invest* 115, 622 (March 2005); J. M. Coles et al., Loss of cartilage structure, stiffness, and frictional properties in mice lacking PRG4. *Arthritis & Rheumatism* 62, 1666 (Jul. 1, 2010)).

PRG4 is also known as lubricin or superficial zone protein or megakaryocyte stimulating factor precursor. It is a component of the cartilage extracellular matrix and synovial fluid (D. K. Rhee et al., The secreted glycoprotein lubricin protects cartilage surfaces and inhibits synovial cell overgrowth, *J Clin Invest* 115, 622 (March 2005)). PRG4 is present in synovial fluid and on the surface (superficial layer) of articular cartilage and therefore plays an important role in joint lubrication and synovial homeostasis. Unlike previous osteoarthritis targets, it is a secreted protein produced by superficial zone chondrocytes of the articular cartilage and by synovial lining cells in mammals (D, K. Rhee et al., The secreted glycoprotein lubricin protects cartilage surfaces and inhibits synovial cell overgrowth. *J*

*Clin Invest* 115, 622 (March 2005)). The PRG4 gene encodes for glycoprotein of approximately 345 kDa. PRG4 provides synovial fluid with the ability to dissipate strain energy under load and its recombinant protein has been reported to exert chondroprotective effects during the progression of OA in rats (G. D. Jay, J. R. Torres, M. L. Warman, M. C. Lederer, K. S. Breuer, The role of lubricin in the mechanical behavior of synovial fluid. *Proc Natl Acad Sci USA* 104, 6194 (Apr. 10, 2007); C. R. Flannery et al., Prevention of cartilage degeneration in a rat model of osteoarthritis by intraarticular treatment with recombinant lubricin. *Arthritis & Rheumatism* 60, 840 (April 2009)).

However, the long-term biological effects of PRG4 overexpression and the molecular mechanism of its potential therapeutic benefits are still poorly understood.

U.S. Pat. No. 6,743,774 A describes a gene therapy approach by administering to a mammal a nucleic acid encoding a therapeutic lubricating polypeptide, such as a lubricating fragment of megakaryocyte stimulating factor precursor by standard vectors and/or gene delivery systems. The gene delivery systems described include liposomes, receptor-mediated delivery systems, naked DNA, viral vectors such as herpes viruses, retro viruses, adenoviruses and adeno-associated viruses. U.S. Pat. No. 7,393,029 A describes polynucleotides for use in gene therapy encoding for recombinant lubricin.

Although some approaches suggest gene therapy for treating or preventing joint disorders such as osteoarthritis, no curative treatments are currently available. Medical treatment is mostly aimed at alleviating the symptoms using analgesic drugs rather than establishing worn away cartilage. An analgesic treatment usually involves steroids and non-steroidal anti-inflammatory drugs (NSAIDS), which have shown efficacy in the treatment of osteoarthritis for some decades. However, while these drugs can suppress joint inflammation, many of them are known to have deteriorating effects on the cartilage, which further worsens the underlying process of osteoarthritis development. Hyaluronic acid, which restores viscoelasticity and lubrication of the joints, has also been widely used. Furthermore, polysulphated glycosaminoglycans injected into the joint or intramuscularly as well as orally administered glucosamine and chondroitin sulphate have been used in the treatment for osteoarthritis, however, the efficacy has not been proven in large randomized trials. Thus, currently used therapies have only limited efficacy in the treatment of joint disorders such as osteoarthritis and their success often depends on the severity of the case. Moreover, these drugs must be administered frequently; sometimes in combination with each other. However, frequent drug injections into the joint are laborious, bear the risk for infections, cause stress for the patient and are costly. It follows that there is a clear and yet unmet medical need for more efficacious and sustained treatments that are at the same time also cost effective in the long run.

The role of PRG4 in joint disorders has been discussed. In addition, during osteoarthritis, interleukin-1 (Il-1) functions as a central mediator of inflammation (Daheshia, M., and YAO, J. Q. (2008). The Interleukin 1B Pathway in the Pathogenesis of Osteoarthritis, J Rheumatol 35, 2306). Moreover, Il-1 strongly inhibits cartilage matrix synthesis and can trigger matrix breakdown (Evans, C. H., Gouze, J. N. Gouze, E., Robbins, P. D, and Ghivizzani, S. C. (2004)). Osteoarthritis gene therapy, Gene Ther 11, 379-389). To neutralize the effect of Il-1 on synovial inflammation, treatment with interleukin-1 receptor antagonist (Il-1Ra) constitutes a promising concept in the therapy of osteoarthritis (Evans, C. H., Gauze, J. N., Gauze, E., Robbins, P. D., and Ghivizzani. S. C. (2004). Osteoarthritis gene therapy. Gene Ther 11, 379-389; Caron J P et al. Chondroprotective effect of intraarticular injections of interleukin-1 receptor antagonist in experimental osteoarthritis. Suppression of collagenase-1 expression. Arthritis Rheum 1996; 39:1535-1544)). On nucleic acid level, Il-1Ra is considerably conserved among mammalian species. For example, the cDNA sequences of human Il-1Ra (Accession no: NM_173842) shares 82% homology with the murine variant (Accession no: NM_031167), 84% with the equine variant (Accession no: NM_001082525), 84% with the canine variant (Accession no: NM_001003096), 84% with the lapine variant (Accession no: NM_001082770) and 82% with the bovine variant (Accession no: NM_174357).

Although gene therapy approaches using various gene therapy vectors are known, there is a need for a gene therapy delivery and expression system, which allows for the specific delivery of a therapeutic amount of an active agent to its target. In addition, the active agent shall exhibit its therapeutic effects for a prolonged amount of time. Adeno-associated viruses (AAV) are among the most widely used gene therapy vectors and have shown efficient transduction and long-term transgene expression in many tissues. AAVs have also been used in gene therapy approaches for joints. However, AAV transduction efficiency in joints has never been directly compared to transduction efficiency of other viral gene therapy vectors such as adenoviruses including helper-dependent adenoviral vectors.

Helper-dependent adenoviruses (HDAd), also known as gutless or high-capacity adenoviruses, are the latest generation of adenoviral vectors (Mitani, K., Graham, F. L. Caskey, C. T. & Kochanek, S. Rescue, propagation, and partial purification of a helper virus-dependent adenovirus vector. Proc Natl Acad Sci USA 92, 3854-3858 (1995); Parks, R. J. et al. A Helper-dependent adenovirus vector system: removal of helper virus by Cre-mediated excision of the viral packaging signal. Proc Natl Acad Sci USA 93, 13565-13570 (1996); Parks, R. J. Improvements in adenoviral vector technology: overcoming barriers for gene therapy. Clin. Genet. 58, 1-11 (2000)). These vectors are devoid of all viral sequences and are able to mediate long-term gene expression in various tissues (e.g. 7 years in the liver) in contrast to the more immunogenic first generation adenoviruses (Brunetti-Pierri, N., Ng, T., Iannitti, D., Cioffi, W., Stapleton, G., Law, M., Breinholt, J., Palmer; D., Grove, N., Rice, K., et al. (2013). Transgene Expression up to 7 Years in Nonhuman Primates Following Hepatic Transduction with Helper-Dependent Adenoviral Vectors. Hum Gene Ther 24, 761-765).

SUMMARY OF THE INVENTION

In one aspect, provided herein is a gene therapy delivery and expression system, comprising at least one helper-dependent adenoviral vector containing a nucleic acid sequence encoding proteoglycan 4 (PRG4), or a biologically active fragment thereof, which has chondoprotective activity, left and right adenoviral inverted terminal repeats (L ITR and R ITR), adenoviral packaging signal sequences and non-viral, non-coding stuffer nucleic acid sequences, wherein PRG4 expression in the at least one helper-dependent adenoviral vector is controlled by a ubiquitous, constitutive promoter, wherein (i) the helper-dependent adenoviral vector additionally comprises a nucleic acid sequence encoding interleukin-1 receptor antagonist (Il-1Ra), or (ii)

the delivery and expression system comprises a second helper-dependent adenoviral vector comprising a nucleic acid sequence encoding interleukin-1 receptor antagonist (Il-1Ra).

In some embodiments, the ubiquitous constitutive promoter is selected from the group consisting of elongation factor 1 alpha (EF1 alpha) promoter, cytomegalovirus (CMV) promoter, beta-actin promoter, simian virus 40 (SV40) early promoter, ubiquitin c promoter, glyceraldehyde 3-phosphate dehydrogenase (GAPDH) promoter, phosphoglycerate kinase (PGK) promoter.

In some embodiments, the helper-dependent adenoviral vector containing a nucleic acid sequence encoding proteoglycan 4 (PRG4) comprises a nucleic acid sequence set forth in SEQ ID NO 1, or SEQ ID NO 2, or a biologically active fragment thereof, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, wherein the helper-dependent adenoviral vector containing a nucleic acid sequence encoding PRG4, which comprises a biologically active fragment of SEQ ID NO 1, or SEQ ID NO 2, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, mediates chondoprotective activity.

In some embodiments, the nucleic acid sequence encoding proteoglycan 4 (PRG4) comprises a nucleic acid sequence set forth in SEQ ID NO 3, or SEQ ID NO 4, or a biologically active fragment thereof, or a homolog thereof from any other species, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, wherein the PRG4 encoded by the biologically active fragment of SEQ ID NO 3, or SEQ ID NO 4, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, has chondoprotective activity.

In some embodiments, the amino acid sequence of proteoglycan 4 (PRG4) comprises an amino acid sequence set forth in SEQ ID NO 5, or SEQ ID NO 6, or a biologically active fragment thereof, or a homolog thereof from any other species, or an amino acid sequence which has at least 50%, 60%, 70%, 80% or 90% sequence homology with an amino acid sequence set forth in SEQ ID NO 5, or SEQ ID NO 6, or a biologically active fragment thereof, wherein the amino acid sequence of PRG4, which comprises a biologically active fragment of the amino acid SEQ ID NO 5, or SEQ ID NO 6, or has at least 50%, 60%, 70%, 80% or 90% sequence homology with an amino acid sequence set forth in SEQ ID NO 5, or SEQ ID NO 6, or a biologically active fragment thereof, has chondoprotective activity.

In some embodiments, expression of interleukin-1 receptor antagonist (Il-1Ra) is controlled by an inflammation-inducible promoter selected from the group consisting of NF-κB promoter, interleukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above.

In some embodiments, the helper-dependent adenoviral vector comprising the nucleic acid sequence encoding interleukin-1 receptor antagonist (Il-1Ra), comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, wherein the helper-dependent adenoviral vector comprising the nucleic acid sequence encoding Il-1Ra, which comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, has Il1-Ra activity of inhibiting inflammatory and cartilage destructive mediators.

In some embodiments, the nucleic acid sequence encoding interleukin-1 receptor antagonist (Il-1Ra) comprises a nucleic acid sequence set forth in SEQ ID NO 10, or SEQ ID NO 11, or SEQ ID NO 12, or a biologically active fragment thereof, or wherein the nucleic acid sequence encoding for interleukin-1 receptor antagonist (Il-1Ra) comprises a nucleic acid sequence which has at least 50%, 60%, 70%, 80% or 90% sequence homology with a nucleic acid sequence set forth in SEQ ID NO 10, or SEQ ID NO 11, or SEQ ID NO 12, or a biologically active fragment thereof, wherein the Il-1Ra encoded by the biologically active fragment of SEQ ID NO 10, or SEQ ID NO 11, or SEQ ID NO 12, or the nucleic acid sequence which has at least 50%, 60%, 70%, 80% or 90% sequence homology with a nucleic acid sequence set forth in SEQ ID NO 10, or SEQ ID NO 11, or SEQ ID NO 12, or the biologically active fragment thereof, mediates Il1-Ra activity of inhibiting inflammatory and cartilage destructive mediators.

In some embodiments, the amino acid sequence of interleukin-1 receptor antagonist (Il-1Ra) comprises an amino acid sequence set forth in SEQ ID NO 13, SEQ ID NO 14, SEQ ID NO 15, or a biologically active fragment thereof, which has Il1-Ra activity of inhibiting inflammatory and cartilage destructive mediators.

In another aspect, provided herein is a pharmaceutical composition, comprising a therapeutically effective amount of at least one helper-dependent adenoviral vector containing a nucleic acid sequence encoding proteoglycan 4 (PRG4), or a biologically active fragment thereof, which has chondoprotective activity, left and right adenoviral inverted terminal repeats (L ITR and R ITR), adenoviral packaging signal sequences and non-viral, non-coding stuffer nucleic acid sequences, wherein PRG4 expression in the at least one helper-dependent adenoviral vector is controlled by a ubiquitous, constitutive promoter, wherein (i) the helper-dependent adenoviral vector additionally comprises a nucleic acid sequence encoding interleukin-1 receptor antagonist (Il-1Ra), or (ii) the delivery and expression system comprises a second helper-dependent adenoviral vector comprising a nucleic acid sequence encoding interleukin-1 receptor antagonist (Il-1Ra).

In some embodiments, the ubiquitous constitutive promoter is selected from the group consisting of elongation factor 1 alpha (EF 1 alpha) promoter, cytomegalovirus (CMV) promoter, beta-actin promoter, simian virus 40 (SV40) early promoter, ubiquitin c promoter, glyceraldehyde 3-phosphate dehydrogenase (GAPDH) promoter, phosphoglycerate kinase (PGK) promoter.

In some embodiments, wherein the helper-dependent adenoviral vector containing a nucleic acid sequence encoding proteoglycan 4 (PRG4) comprises a nucleic acid sequence set forth in SEQ ID NO 1, or SEQ ID NO 2, or a biologically active fragment thereof, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, wherein the helper-dependent adenoviral vector containing a nucleic acid sequence encoding PRG4, which comprises a biologically active fragment of SEQ ID NO 1, or SEQ ID NO 2, or a nucleic acid sequence which has at least 50%, 60%, 70%, 80% or 90% sequence homology with a nucleic acid sequence set forth in SEQ ID NO 1, or SEQ ID NO 2, or a biologically active fragment thereof, mediates chondoprotective activity.

In some embodiments, the nucleic acid sequence encoding proteoglycan 4 (PRG4) comprises a nucleic acid sequence set forth in SEQ ID NO 3, or SEQ ID NO 4, or a biologically active fragment thereof, or a homolog thereof from any other species, or a nucleic acid sequence which has at least 50%, 60%, 70%, 80% or 90% sequence homology with a nucleic acid sequence set forth in SEQ ID NO 3, SEQ ID NO 4, or a biologically active fragment thereof, wherein the PRG4 encoded by the biologically active fragment of SEQ ID NO 3, or SEQ ID NO 4, or a nucleic acid sequence which has at least 50%, 60%, 70%, 80% or 90% sequence homology with a nucleic acid sequence set forth in SEQ ID NO 3, or SEQ ID NO 4, or a biologically active fragment thereof, has chondoprotective activity.

In some embodiments, the amino acid sequence of proteoglycan 4 (PRG4) comprises an amino acid sequence set forth in SEQ ID NO 5, or SEQ ID NO 6, or a biologically active fragment thereof, or a homolog thereof from any other species, or an amino acid sequence which has at least 50%, 60%, 70%, 80% or 90% sequence homology with an amino acid sequence set forth in SEQ ID NO 5, or SEQ ID NO 6, or a biologically active fragment thereof, wherein the amino acid sequence of PRG4, which comprises a biologically active fragment of the amino acid SEQ ID NO 5, or SEQ ID NO 6, or has at least 50%, 60%, 70%, 80% or 90% sequence homology with an amino acid sequence set forth in SEQ ID NO 5, or SEQ ID NO 6, or a biologically active fragment thereof, has chondoprotective activity.

In some embodiments, expression of interleukin-1 receptor antagonist (11-1Ra) is controlled by an inflammation-inducible promoter selected from the group consisting of NF-κB promoter, interleukin 6 (II-6) promoter, interleukin-1 (II-1) promoter, tumor necrosis factor (INF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above.

In some embodiments, the helper-dependent adenoviral vector comprising the nucleic acid sequence encoding interleukin-1 receptor antagonist (II-1Ra), comprises a nucleic acid sequence which has at least 50%, 60%, 70%, 80 or 90% sequence homology with a nucleic acid sequence set forth in SEQ ID NO 7, or SEQ ID NO 8, or SEQ ID NO 9, or a biologically active fragment thereof, wherein the helper-dependent adenoviral vector comprising the nucleic acid sequence encoding II-1Ra, which comprises a nucleic acid sequence which has at least 50%, 60%, 70%, 80% or 90% sequence homology with a nucleic acid sequence set forth in SEQ ID NO 7, or SEQ ID NO 8, or SEQ ID NO 9, or a biologically active fragment thereof, has II1-Ra activity of inhibiting inflammatory and cartilage destructive mediators.

In some embodiments, the nucleic acid sequence encoding interleukin-1 receptor antagonist (II-1Ra) comprises a nucleic acid sequence set forth in SEQ ID NO 10, or SEQ ID NO 11, or SEQ ID NO 12, or a biologically active fragment thereof, or wherein the nucleic acid sequence encoding for interleukin-1 receptor antagonist (II-1Ra) comprises a nucleic acid sequence which has at least 50%, 60%, 70%, 80% or 90% sequence homology with a nucleic acid sequence set forth in SEQ ID NO 10, or SEQ ID NO 11, or SEQ ID NO 12, or a biologically active fragment thereof, wherein the II-1Ra encoded by the biologically active fragment of SEQ ID NO 10, or SEQ ID NO 11, or SEQ ID NO 12, or the nucleic acid sequence which has at least 50%, 60%, 70%, 80% or 90% sequence homology with a nucleic acid sequence set forth in SEQ ID NO 10, or SEQ ID NO 11, or SEQ ID NO 12, or the biologically active fragment thereof, mediates II1-Ra activity of inhibiting inflammatory and cartilage destructive mediators.

In some embodiments, the amino acid sequence of interleukin-1 receptor antagonist (II-1Ra) comprises an amino acid sequence set forth in SEQ ID NO 13, SEQ ID NO 14, SEQ ID NO 15, or a biologically active fragment thereof, which has II1-Ra activity of inhibiting inflammatory and cartilage destructive mediators.

In another aspect, provided herein is the gene therapy delivery and expression system according to any of the preceding embodiments for use in the prevention and/or treatment of camptodactyly-arthropathy-coxa vara-pericarditis (CACP) syndrome, or a musculoskeletal disorder, or a joint disorder or disease. In some embodiments, the disease or disorder is selected from the group consisting of arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis, Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

DETAILED DESCRIPTION

Figure 1:
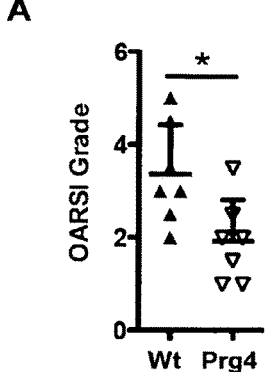
FIG. 1. Prg4 transgenic mice are protected from development of age-related osteoarthritis. A, Comparison of 10 month-old wild type mice and Prg4 transgenic mice knee joints by OARSI grade (*P<0.05, n=7. Wilcox rank test). B, Safranin O staining and immunohistochemistry (antibody used to the left) of 10 month-old wild type (Wt) and Prg4 transgenic mice. Black arrows indicate osteoarthritis changes in proximal tibial articular cartilage in sagittal section, Scale bar, 100 pm μm. C, Representative image of the reconstruction of articular cartilage in 10-month-old wild type and Prg4 transgenic mouse with femoral cartilage shown in blue and tibial cartilage shown in yellow. Red arrow indicates loss of cartilage. Scale bar, 500 μm. D, Quantification of articular cartilage volume and surface area of bone covered by cartilage in mouse knee joints by phase contrast μCT. (*P<0.01, n=5, t-test). Error bars indicate s.e.m.
Figure 1:
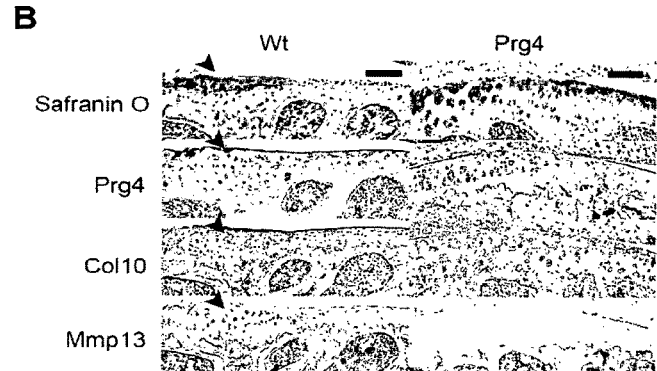
Figure 1:
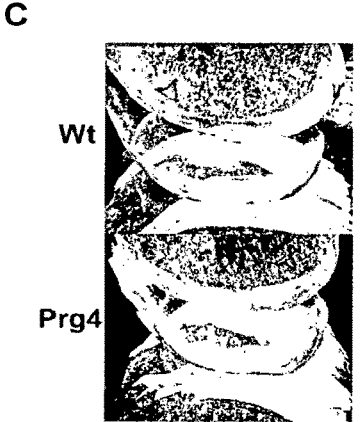
Figure 1:
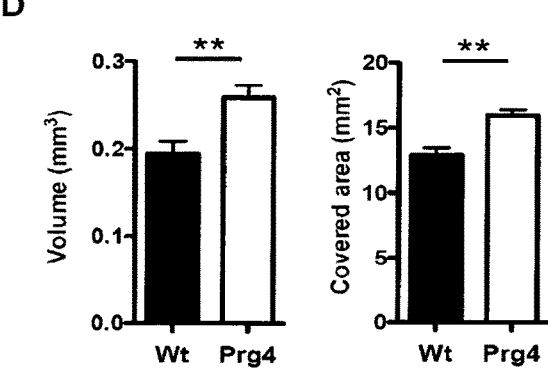

It is therefore an object of the present invention to provide an improved delivery and expression system that allows for long-term expression of biologically active proteoglycan 4 (PRG4) for use in the prevention and/or treatment of PRG4-dependent disorders such as camptodactyly-arthropathy-coxa vara-pericarditis (CACP) and disorders in which PRG4 overexpression is beneficial such as musculoskeletal disorders in particular joint disorders.

The solution for the problem is provided by a gene therapy delivery and expression system, comprising the technical features as claimed in claim 1. Preferred embodiments of the invention are subject-matter of the dependent claims.

The gene therapy delivery and expression system according to the present invention comprises at least one helper-dependent adenoviral vector containing a nucleic acid sequence encoding for proteoglycan 4 (PRG4), or a biologically active fragment thereof, left and right adenoviral inverted terminal repeats (L ITR and R ITR), adenoviral packaging signal sequences and non-viral, non-coding stuffer nucleic acid sequences.

Any known left or right adenoviral inverted terminal repeats (L ITR and R ITR), adenoviral packaging signal sequences and non-viral, non-coding stuffer nucleic acid sequences can be used for the production of the helper-dependent adenoviral vector (Parks, R. J., Chen, L., Anton, M., Sankar, U., Rudnicki, M. A., and Graham, F. L. (1996). A helper-dependent adenovirus vector system: removal of helper virus by Cre-mediated excision of the viral packaging signal. Proc Natl Acad Sci USA 93, 13565-13570; Palmer, D. and Ng, P. (2003). Improved system for helper-dependent adenoviral vector production. Mol Ther 8, 846-852).

The results and data shown herein are based on helper-dependent adenoviral constructs (HDAd) using in a first embodiment nucleic acid sequences or amino-acid sequences encoding for proteoglycan 4 (PRG4). Any homolog or variant showing a certain degree of sequence homology with either a nucleic acid sequence or an amino-acid sequence of proteoglycan 4 (PRG4) (or their variant such as lubricin, superficial zone protein or megakaryocyte stimulating factor precursor) is further comprised by the present invention. A homolog includes but is not limited to peptides, polypeptides, proteins or nucleic acid sequences from any species that shows homology with any proteoglycan (PRG4) described herein, For long-term expression of PRG4 in the affected tissue, for example in joints or osteoarthritic tissues, the at least one helper-dependent adenoviral vector of the invention is preferably controlled by a ubiquitous, constitutive promoter. Suitable promoters include, but are not limited to elongation factor 1 alpha (EF1 alpha) promoter, cytomegalovirus (CMV) promoter, beta-actin promoter, simian virus 40 (SV40) early promoter, ubiquitin c promoter, glyceraldehyde 3-phosphate dehydrogenase (GAPDH) promoter, phosphoglycerate kinase (PGK) promoter and other HDAd-suitable ubiquitous, constitutive promoters.

In a preferred embodiment, the helper-dependent adenoviral vector comprising proteoglycan 4 (PRG4) comprises a nucleic acid sequence set forth in SEQ ID NO 1 (human HDAd) or SEQ ID NO 2 (murine HDAd). Preferably, the nucleic acid sequence comprises a cDNA sequence of the PRG4 gene or a fragment thereof. Furthermore, any biologically active fragment such as nucleic acid sequences having sequence identity or a certain degree of homology with the human or murine PRG4 sequence disclosed herein is comprised by the present invention. The HDAd of the invention may vary in its non-coding elements as well as in the length of its coding insert. Therefore, also smaller or greater vector sizes of the helper-dependent adenoviral vector of the invention can be utilized for the purpose of the present invention in order to achieve the desired biological effects.

In a preferred embodiment, the helper-dependent adenoviral vector comprises a nucleic acid sequence which has at least 50%, 60%, 70%, 80% or 90% sequence homology with a vector sequence comprising a nucleic acid sequence set forth in SEQ ID NO 1 or SEQ ID NO 2, or a biologically effective fragment thereof.

A sequence homology of at least 50% with a nucleic acid sequence set forth in SEQ ID NO 1 or SEQ ID NO 2 can be sufficient in order to generate long-term expression of PRG4 at the target sites as along as the expressed PRG4 protein is biologically active.

In one embodiment the helper-dependent adenoviral vector comprises a nucleic sequence encoding for proteoglycan 4 (PRG4). The expression of human or mammalian PRG4 is preferred. The inserted nucleic acid sequence into the HDAd can be anyone, which shows sequence identity or sequence homology with a nucleic acid sequence set forth in SEQ ID NO 3 or SEQ ID NO 4. For the purpose of expression, it can be sufficient that only a part of the nucleic acid sequence set forth in SEC ID NO 3 or SEQ ID NO 4, or an extended version is sufficient for the generation of the vector and its biological activity. The biological activity can be measured by investigating chondoprotection.

Furthermore, also mutants, variants and homologs containing nucleic acid replacements within the amino acid or nucleic acid sequence of proteoglycan 4 (PRG4) are comprised by the present invention. In particular, the invention comprises a homolog of PRG4 from any other animal species having sequence homology with a sequence set forth in SEQ ID NO 3 or SEQ ID NO 4. For example, a homolog containing a nucleic acid sequence encoding for proteoglycan 4 (PRG4) preferably comprises a nucleic acid sequence, which has at least 50%, 60%, 70%, 80% or 90% sequence homology with a nucleic acid sequence set forth in SEQ ID NO 3, or SEQ ID NO 4, or a biologically effective fragment thereof.

The proteoglycan 4 (PRG4) used in the construction of the vector of the present invention can be also described by its amino acid sequence. Preferably, the proteoglycan 4 (PRG4) comprises an amino acid sequence set forth in SEQ ID NO 5 or SEQ ID NO 6, or a biologically active fragment thereof, or a homolog thereof from any other species. In a preferred embodiment, the amino acid sequence encoding for proteoglycan 4 (PRG4) comprises an amino acid sequence which has at least 50%, 60%, 70%, 80% or 90% sequence homology with an amino acid sequence set forth in SEQ ID NO 5, or SEQ ID NO 6, or a biologically active fragment thereof, or a homolog thereof from any other species.

The inventors show herein that a helper-dependent adenoviral vector containing the cDNA sequence of murine or human proteoglycan 4 (PRG4) under the control of a ubiquitous, constitutive promoter results in an overexpression of PRG4 in joints, which results in protection of mice from osteoarthritis. Since overexpression of PRG4 can be beneficial in many other diseases, the helper-dependent vector of the invention can be used for the manufacture of a medicament for the treatment and/or prevention of a variety musculoskeletal diseases and PRG4-dependent diseases. In particular, musculoskeletal disorders, which benefit from PRG4 over-expression would be characterised as those disorders where high concentrations of PRG4 confer a therapeutic or preventive effect. PRG4-dependent diseases or disorders would be characterised in that natural PRG4 expression is limited or inhibited, or in that intracellular or extracellular PRG4 RNA or protein levels are significantly reduced.

The inventors compared joint transduction efficiency of helper-dependent adenoviral vectors with different AAV serotype that had been reported by others to be useful in joint gene therapy approaches. Surprisingly, the inventors found that helper-dependent adenoviral vectors showed superior transduction compared with all tested AAV serotypes resulting in transduction of synoviocytes and chondrocytes. The inventors further showed that helper-dependent adenoviral vectors allow for transgene expression that persists for an extended period, whereby the need for repeated administrations of the medicament to an object suffering from a disease in which overexpression of PRG4 may be beneficial will be greatly reduced. In a model of osteoarthritis in mice, the inventors demonstrated that treatment of osteoarthritic joints with the HDAd-PRG4 results in lower osteoarthritis histology scores, indicating that PRG4 exhibits its biological effect by protecting the subject from post-traumatic osteoarthritis. Protection against osteoarthritis with HDAd-PRG4 was demonstrated using two different schemes. In the first scheme mice were injected with HDAd-PRG4 before osteoarthritis was induced. The results of this experiment show that HDAd-PRG4 can be used in the prevention of osteoarthritis. In the second scheme, osteoarthritis was induced before HDAd-PRG4 was injected. The results of this experiment demonstrate that HDAd-PRG4 can be used in the treatment of (pre-existing) osteoarthritis. In support of the biological effects of PRG4 in joints, experiments using Prg4-transgenic mice revealed a protection of the subjects against the development of osteoarthritis without other bone phenotypes.

Thus, overexpression of PRG4 under the control of a suitable ubiquitous, constitutive promoter in a HDAd allows for prevention and/or treatment of a variety of musculoskeletal diseases such as arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis. Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

Surprisingly, the inventors further found that a combined expression of PRG4 as induced by HDAd-PRG4 and inhibitors of inflammatory and cartilage destructive mediators results in beneficial therapeutic and protective effects. In particular, a combination of expressing of PRG4 and expressing interleukin-1 receptor antagonist (Il-1Ra) resulted in an increased efficiency in the treatment and/or prevention of musculoskeletal disorders.

In a preferred embodiment, the helper-dependent adenoviral vector therefore comprises a nucleic acid sequence encoding for inhibitors of inflammatory and cartilage destructive mediators such as cytokines including Il-1, TNFa, Il-6, Il-7 Il-8, Il-11, Il-15, Il-17, Il-18, Il-21, leukemia inhibitory factor (LIF), oncostatin M; matrix metalloproteases including MMP-1,3,9,13; aggrecanases including ADAMTS-1,4,5; toll-like receptors (TLR) such as TLR2, TLR4; and nuclear factor 'kappa-light-chain-enhancer' of activated B-cells (NF-κB).

In a preferred embodiment, the inhibitor of inflammatory and cartilage destructive mediator is interleukin-1 receptor antagonist (Il-1Ra). A combination of overexpression of PRG4 and Il-1Ra is beneficial for the treatment and/or prevention of the diseases mentioned therein. In a first embodiment, the cDNA sequence of interleukin-1 receptor antagonist can be contained in the same helper-dependent adenoviral vector, which contains the cDNA sequence encoding for proteoglycan 4 (PRG4). In a further embodiment, the cDNA sequence of interleukin-1 receptor antagonist can be contained in a second helper-dependent adenoviral vector, which only contains the cDNA sequence encoding for Il-1Ra.

The delivery and expression system of the invention can therefore comprise a second or further helper-dependent adenoviral vector comprising a nucleic acid sequence encoding for inhibitors of inflammatory and cartilage destructive mediators such as interleukin-1 receptor antagonist (Il-1Ra).

In a preferred embodiment, the cDNA of the inhibitor of inflammatory and cartilage destructive mediator (e.g. Il1-Ra cDNA) inserted into HDAd is controlled by an inflammation-inducible promoter. Preferred promoters include, but are not limited to promoters selected from the group consisting of NF-κB promoter, interleukin 6 (Il-6) promoter, interleukin-1 (Il-1) promoter, tumor necrosis factor (TNF) promoter, cyclooxygenase 2 (COX-2) promoter, complement factor 3 (C3) promoter, serum amyloid A3 (SAA3) promoter, macrophage inflammatory protein-1α (MIP-1α) promoter, or hybrid constructs of the above. The use of NF-κB promoter in HDAd for the purpose of an inflammation-dependent expression of Il-1Ra at the target sites is preferred.

In a preferred embodiment, the helper-dependent adenoviral vector containing the interleukin-1 receptor antagonist (Il-1Ra) comprises a nucleic acid sequence which has at least 50%, 60%, 70%, 80% or 90% sequence homology with a nucleic acid sequence set forth in SEQ ID NO 7 (human Il-1Ra), or SEQ ID NO 8 (murine Il-1Ra), SEQ ID NO 9 (equine Il-1Ra), or a biologically effective fragment thereof.

In a further embodiment, the nucleic acid sequence encoding for interleukin-1 receptor antagonist (Il-1Ra) comprises a nucleic acid sequence set forth in SEQ ID NO 10 (human Il-1Ra), or SEQ ID NO 11 (murine Il-1Ra), or SEQ ID NO 12 (equine Il-1Ra), or a biologically active fragment thereof, or a homolog thereof from any other species.

In a preferred embodiment, the amino acid sequence encoding for interleukin-1 receptor antagonist (Il-1Ra) comprises an amino acid sequence set forth in SEQ ID NO 13 (human Il-1Ra), or SEQ ID NO 14 (murine Il-1Ra), or SEQ ID NO 15 (equine Il-1Ra), or a biologically active fragment thereof, or a homolog thereof from any other species.

The present invention also relates to a pharmaceutical composition, comprising a therapeutically effective amount of at least one helper-dependent adenoviral vector containing a nucleic acid sequence encoding for proteoglycan 4 (PRG4), or a biologically active fragment thereof. Preferred embodiments of the pharmaceutical composition comprise helper-dependent adenoviral vectors or a combination of different helper-dependent adenoviral vectors comprising features as described above in more detail.

The gene therapy delivery and expression system according to the present invention is suitable for the preparation of a medicament for the use in the prevention and/or treatment of a variety of PRG4-dependent diseases. In a first embodiment the gene therapy delivery and expression system is used in the treatment and/or prevention of camptodactyly-arthropathy-coxa vara-pericarditis (CACP). The helper-dependent adenoviral vectors of the invention can further be used in the prevention and/or treatment of a musculoskeletal disorder, in particular the prevention and/or treatment of a joint disorder or disease. Examples of such diseases are arthropathies, all types of arthritis, including arthritis-related disorders, osteoarthritis, rheumatoid arthritis, gout and pseudo-gout, septic arthritis, psoriatic arthritis, ankylosing spondylitis, juvenile idiopathic arthritis, Still's disease, Reiter's syndrome, or tendinopathies including tendonitis, tendinosis, tenosynovitis; synovial disorders including synovitis; Bursa disorders including bursitis; equine musculoskeletal disorders including bone spavin, navicular syndrome, osselet.

The following examples show the beneficial therapeutic uses of the gene therapy delivery and expression system according to the present invention. In particular, it will be shown that intra-articular expression of proteoglycan 4 (PRG4) in mice protects against development of osteoarthritis (OA). The data are supported by long-term PRG4 expression under the type II collagen promoter (Col2a1) in transgenic mice. Accordingly long-term expression of PRG4 does not adversely affect skeletal development but protects from developing signs of age-related osteoarthritis.

The protective effect is also shown in a model of post-traumatic osteoarthritis created by cruciate ligament transection (CLT). Moreover, intra-articular injection of helper-dependent adenoviral virus (HDAd) expressing PRG4 protected against the development of post-traumatic osteoarthritis when administered either before or after injury. Gene expression profiling of mouse articular cartilage and in vitro cell studies show that PRG4 expression inhibits the transcriptional programs that promote cartilage catabolismand hypertrophy through the up-regulation of hypoxia inducible factor 3 alpha. Analyses of available human osteoarthritis datasets are consistent with the predictions of this model. Hence, the data provide insight into the mechanisms for osteoarthritis development and offer a potential chondroprotective approach to its treatment.

Moreover, injection of helper-dependent adenoviral vectors expressing PRG4 (HDAd-PRG4) and Il-1Ra (HDAd-Il1-Ra) in combination into joints of wild type mice after transection of cruciate ligaments exhibited protective effects against osteoarthritis. Co-injection of HDAd-PRG4 and HDAd-Il1-Ra at the same dose results in a greater extent of cartilage preservation compared to single vector injections.

As such PRG4 in single application or in combination with Il-1Ra is a novel target in chondoprotection using the helper-dependent adenoviral vectors of the invention.

Examples

Results
PRG4 Prevents Development of Age Related Osteoarthritis Changes

Figure 5:
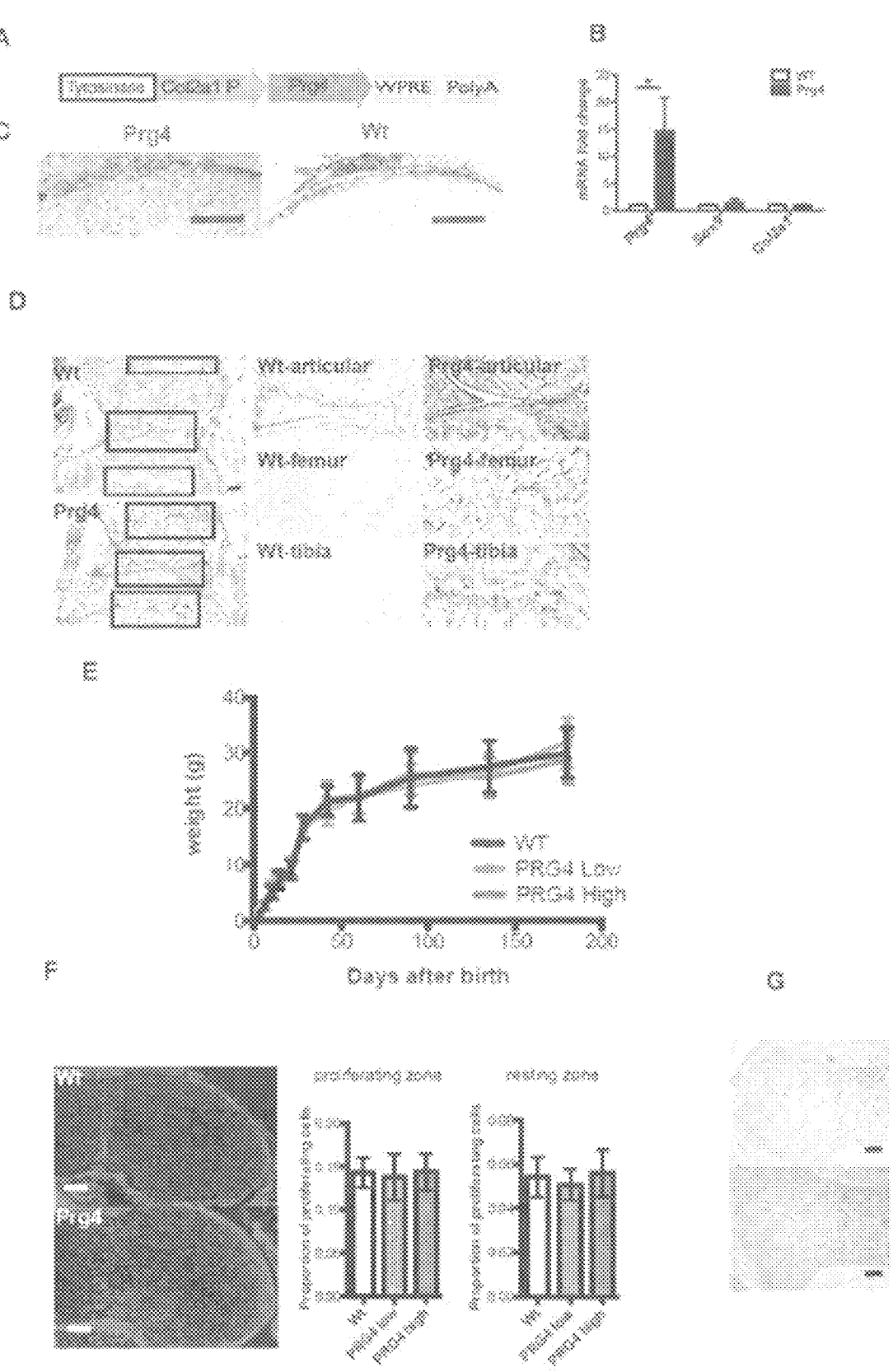
FIG. 5: PRG4 over-expression under the Col2a1 promoter does not adversely affect the development of mice. A, Schematic figure of the Prg4 transgenic mice construct. B, Rib cartilage expression levels of PRG4, Sox9 and Col2a1 in newborns (P1) PRG4 transgenic and wild type mice (*P<0.05, n=7-8, student t-test). C, Comparison of anti-PRG4 antibody stained femoral head section in wild type and Prg4 transgenic newborn mice. Scale bars, 100 μm. D, Comparison of anti-PRG4 antibody stained knee joints in Prg4 transgenic and wild type 3 month-old mice. The boxed areas to the left (articular area, distal femoral growth plate and proximal tibial growth plate) are enlarged at the right. Scale bars, 100 μm. E, Weight of Prg4 high expresser, low expresser and wild type mice (P<0.05, n=10-11). F, Representative image of BrdU (red) and DAPI (blue) staining in wild type and Prg4 transgenic P3 hind limbs. Staining signals were quantified by image J (P<0.05, n=7). Scale bars, 100 μm. G, Representative image of TUNEL (brown) and methyl green staining in wild type and Prg4 transgenic P3 hind limbs. No positive signals were visible in cartilage but they were present in overlying dermis and skin. Scale bar, 100 μm. Error bars indicate s.e.m.

To investigate the long-term effect of Prg4 over-expression, the inventors generated transgenic mice expressing Prg4 under the cartilage specific type II collagen promoter (Col2a1) (FIG. 5A). PRG4 transgenic mice expressed Prg4 ectopically in growth plate cartilage and over-express Prg4 in articular cartilage throughout development and adulthood (FIG. 5B-D). Macroscopically, the inventors detected no differences in growth or skeletal development in Prg4 transgenic mice when assessed by weight (FIG. 5E). Microscopically, markers of chondrocyte proliferation or apoptosis remained the same in Prg4 mice vs. wild type mice as assessed by BrdU staining (p=n.s. in both proliferating and resting zone of P1 chondrocytes) (FIG. 5F) and TUNEL staining (no positive signals in P1 chondrocytes) (FIG. 5G), respectively. These data suggested that ectopic over-expression of Prg4 in cartilage did not significantly affect chondrocyte or skeletal homeostasis.

The inventors sought to determine whether Prg4 over-expression in particular chondrocytes protected mice from age-related osteoarthritic changes. Relatively few studies have been performed to assess the development of age-related osteoarthritis in animal models (M. Silbermann, E. Livne, Age-related degenerative changes in the mouse mandibular joint. *Journal of Anatomy* 129, 507 (October 1979). Moreover, no gain of function model has been shown to be protective against age-related osteoarthritis. In an aging cohort, as assessed by the Osteoarthritis Research Society International (OARSI) histological grading scale (S. S. Glasson, M. G. Chambers, W. B. van den Berg, C. B. Little, The OARSI histopathology initiative-recommendations for histological assessments of osteoarthritis in the mouse. *Osteoarthritis and cxartilage OARSI, Osteoarthritis Research Society* 18, S17 (Oct. 1, 2010), the inventors observed that wild type FVB/N mice developed changes consistent with moderate osteoarthritis by 10 months of age, with a mean OARSI grade of 3.5. However, PRG4 transgenic mice at the same age exhibited a mean OARSI grade of 2 (p<0.05), suggesting less severe signs of osteoarthritis (FIG. 1A). The inventors next assessed the molecular differences in particular chondrocytes between the PRG4 and wild type mice. As Collagen type X (Col10a1) and matrix metalloproteinase 13 (Mmp13) are markers of cartilage hypertrophy and degradation, respectively, increased expression of Mmp13 and Col10a1 above the tide marks are hallmarks of osteoarthritis (T. Saito et al., Transcriptional regulation of endochondral ossification by HIF-2a during skeletal growth and osteoarthritis development. *Nature Medicine* 16, 678 (Jun. 23, 2010)). Encouragingly, the inventors detected increased expression of Col10a1 and Mmp13 in wild type mice with aging, while Prg4 transgenic mice did not show a qualitative increase in either marker in the noncalcified region of articular cartilage (FIG. 1b). These results suggest that Prg4 overexpression had a protective effect against osteoarthritis at the molecular and histological levels.

Figure 2:
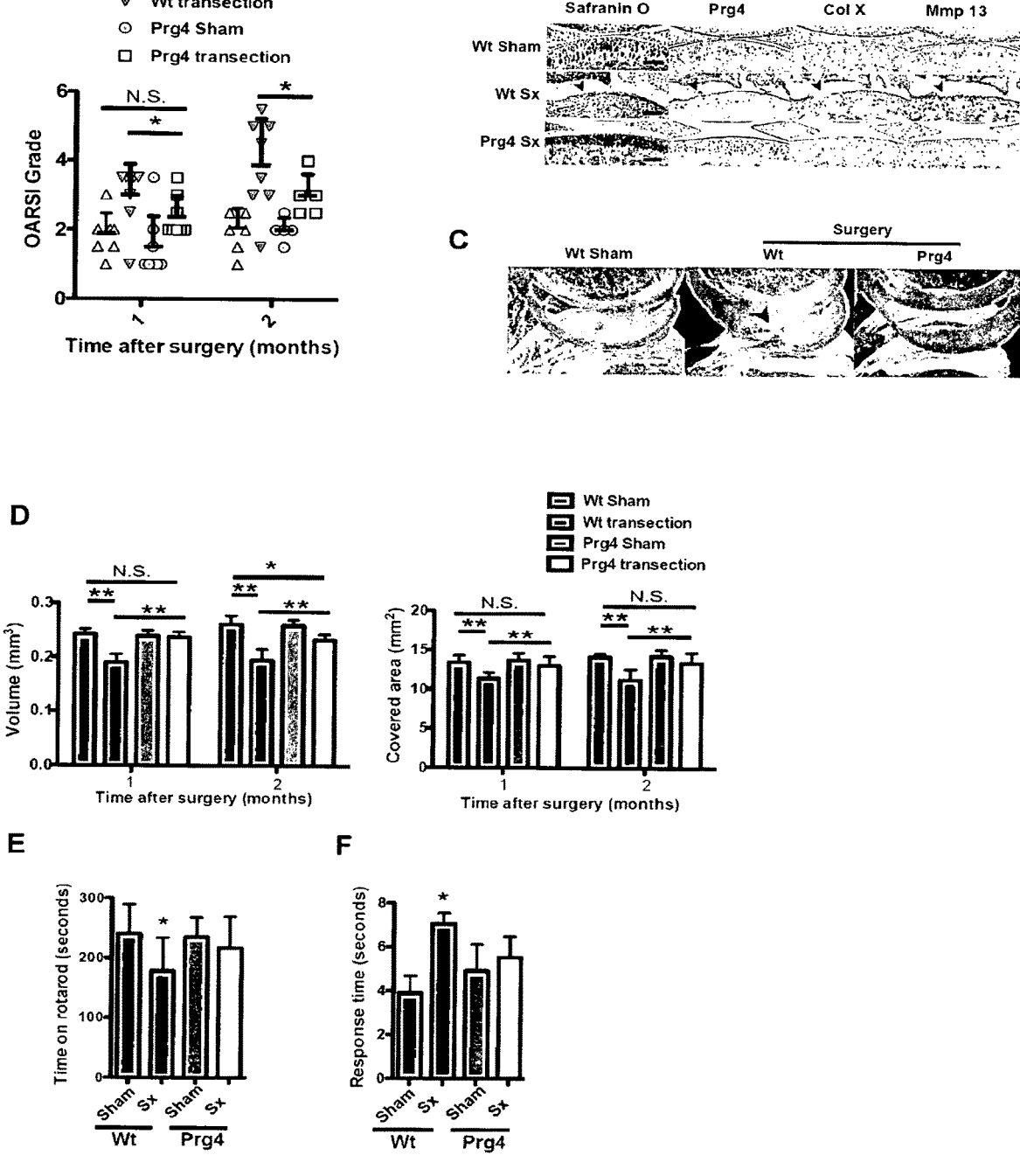
FIG. 2. Prg4 transgenic mice are protected from the development of post-traumatic osteoarthritis, A, Comparison of Prg4 transgenic mice and wild type mice knee joints by OARSI grade (*P<0.05, n=8, ANOVA). B, Safranin O staining and immunohistochemistry (antibody used listed above each column) of wild type sham (Wt Sham), wild type with transection (Wt Sx) and Prg4 transgenic mice with transection (Prg Sx). Black arrows indicate areas with osteoarthritis changes in saggital sections through the knee. Scale bar, 100 μm. C, Representative images of reconstruction of knee joints with phase contrast μCT with femoral cartilage shown in blue and tibial cartilage shown in yellow. Red arrow indicates loss of cartilage, Scale bar, 500 μm. D, Quantification of articular cartilage volume and surface area of bone covered by cartilage in mouse joints by phase contrast μCT (*P<0.01, **P<0.05, N.S.=not significant, n=5-6, ANOVA). E, Average time that mice stayed on rotating rod 2 months after cruciate ligament transection in rotarod analysis (*P<0.05, n=15, ANOVA). F, Response time of mice after placement onto a 55° C. platform in hotplate analysis (*P<0.05, n=10, ANOVA), Error bars indicate s.e.m.

A disadvantage of conventional histological endpoints is the lack of three-dimensional quantification as well as ascertainment bias based on choice of sections. Hence, the inventors applied an approach to quantify cartilage properties (e.g., volume, surface area, bone area covered by cartilage) based on three-dimensional reconstructions of phase contrast μCT imaging data (M. Ruan et al., Quantitative imaging of murine osteoarthritic cartilage by phase contrast micro-computed tomography. *Arthritis Rheum*, (2012)). Using this imaging technique, the inventors found that wild type mice showed a decrease in articular cartilage volume as well as in the bone area covered by cartilage (FIGS. 1C,D). In contrast, Prg4 transgenic mice showed preservation of articular cartilage volumes and surface area (p<0.01) (FIGS. 1C,D). Thus, as compared to wild type mice after transection, Prg4 transgenic mice had none of the histological, molecular and imaging findings characteristic of osteoarthritis. These data suggested that PRG4 over-expression may have protective effects in the context of age-related osteoarthritic-like changes.
PRG4 Prevents Development of Post-Traumatic Osteoarthritis To test whether PRG4 over-expression protects mice from the development of more aggressive, post-traumatic osteoarthritis, the inventors applied the knee cruciate ligament transection model recently developed in the inventors' lab, to both wild type and Prg4 transgenic mice (M. Ruan et al., Quantitative imaging of murine osteoarthritic cartilage by phase contrast micro-computed tomography. *Arthritis Rheum*, (2012). The inventors chose this approach because anterior cruciate ligament tears are a common cause of post-traumatic arthritis in humans. As assessed by the OARSI histological grading scale, wild type mice developed moderate and severe osteoarthritis one and two months after transection, respectively (FIG. 2A) (M. Ruan et al., Quantitative imaging of murine osteoarthritic cartilage by phase contrast micro-computed tomography. *Arthritis Rheum*, (2012). Prg4 transgenic mice showed a lower grade OARSI score compared to wild type mice one and two months after transection (FIG. 2A), Interestingly, one month after transection, the OARSI grade of cartilage from Prg4 transgenic mice was not significantly different from wild type mice after sham surgery (FIG. 2A), further supporting that PRG4 expression had a protective effect against osteoarthritis. In addition, the inventors detected increased expression of Col10a1 and Mmp13 in the noncalcified articular cartilage of wild type transected mice, but not in transected Prg4 transgenic mice or wild type mice after sham surgery (FIG. 2B).

The inventors next assessed the cartilage volume and bone area covered by cartilage after surgical transection using phase-contrast microCT (M. Ruan et al., Quantitative imaging of murine osteoarthritic cartilage by phase contrast micro-computed tomography. *Arthritis Rheum*, (2012)). After transection, wild type mice showed decrease in both cartilage volume and bone area covered by cartilage (p<0.01). In contrast, Prg4 transgenic mice showed articular cartilage volumes and areas similar to wild type mice after sham surgery (FIGS. 2C,D). Thus, as compared to wild type mice after transection, Prg4 transgenic mice had none of the histological, molecular or imaging findings characteristic of osteoarthritis.

Pain and motor dysfunction are also hallmarks of osteoarthritis and are typical causes of chronic disability (M. B. Goldling, S. R. Goldring, Osteoarthritis. *Journal of Cellular Physiology* 213, 626 (2007)), They also serve as important clinical end points for interventional trials. Therefore, the inventors applied rodent behavioral testing, i.e., rotarod and hotplate analyses, to evaluate for potential motor and/or sensory dysfunction in wild type vs. Prg4 transgenic mice after osteoarthritis induction. Surgically transected wild type mice showed a decreased time on the rotarod (p<0.05) and increased time on the hotplate (p<0.05), while Prg4 transgenic mice with and without transection were indistinguishable from wild type mice after sham surgery (p=n.s.) (FIGS. 2E,F). This suggested that Prg4 transgenic mice after transection had less motor or sensory impairments as compared to wild type mice, supporting that PRG4 prevented functional impairment in post-traumatic osteoarthritis.

Gene Transfer with Hdad-PRG4 Effectively Treats Osteoarthritis

To translate localized expression of PRG4 into a therapeutic approach, the inventors tested whether gene transfer into the joint could mediate long-term expression and chondroprotection in osteoarthritis. Since delivery of recombinant protein is often therapeutically limited by their short half-life, the inventors chose to use a viral gene transfer approach. The most studied viral vectors for gene transfer related to osteoarthritis treatment are adeno-associated virus (AAV) and adenovirus. Both have been shown to transduce chondrocytes in vitro in primary chondrocyte and cartilage organ cultures and in vivo in rabbit and rat knee joints (J. D. Kay et al., Intra-articular gene delivery and expression of interleukin-1 Ra mediated by self-complementary adeno-associated virus. *The journal of gene medicine* 11, 605 (July 2009); Y. Arai et al., Gene delivery to human chondrocytes by an adeno associated virus vector. *journal of Rheumatol* 27, 979 (April 2000); J. Gouze, Adenovirus-mediated gene transfer of glutamine: fructose-6-phosphate amidotransferase antagonizes the effects of interleukin-1β on rat chondrocytes. *Osteoarthritis and Cartilage* 12, 217 (April 2004)). However, no direct comparison has been made between the two viruses. After injection of GFP expressing helper-dependent adenovirus and AAVs of the serotypes 2; 2.5 and 6 into mouse knee joints ($10^9$ viral particles per joint in 5 ul), helper-dependent adenovirus was noted to exhibit higher transduction efficiency at 2 weeks post-injection (FIG. 3A).

While first generation adenovirus vectors (FGV) can mediate highly efficient tissue transduction, the immune response to viral proteins limits transgene expression. Previous studies performed by the inventors and others showed that helper-dependent adenoviral vectors (HDAd) devoid of viral coding genes could overcome this problem (D. J. Palmer, D. J. P. D. P. Ng, Helper-dependent adenoviral vectors for gene therapy. *Human gene therapy* 16, 1 (2005)). For example, a single injection of HDAd can mediate long-term transgene expression in small and large animal models for over 7 years in liver (N. Brunetti-Pierri, P. Ng, Helper-dependent adenoviral vectors for liver-directed gene therapy. *Hum Mol Genet* 20, R7 (Jun. 13, 2011)). Thus, the inventors tested whether HDAd could mediate long-term expression of luciferase in mouse joint compared to FGVs. Indeed, the inventors found that after a single infra-articular injection, HDAds mediated expression of luciferase in mouse knee joints for over one year, while FGV-mediated luciferase expression was lost by one month (FIG. 3B). To evaluate the dose response and cellular distribution of transduction, the inventors assessed mouse knee joints injected with $10^9$ vs. $10^8$ viral particles HDAd expressing beta-galactosidase. These doses were at least 10 and 100 times lower than the maximum tolerated systemic dose in humans (K. Relph, K. Harrington, H. Pandha, Recent developments and current status of gene therapy using viral vectors in the United Kingdom. *BMJ (Clinical research ed.)* 329, 839 (Oct. 9, 2004)).

Figure 3:
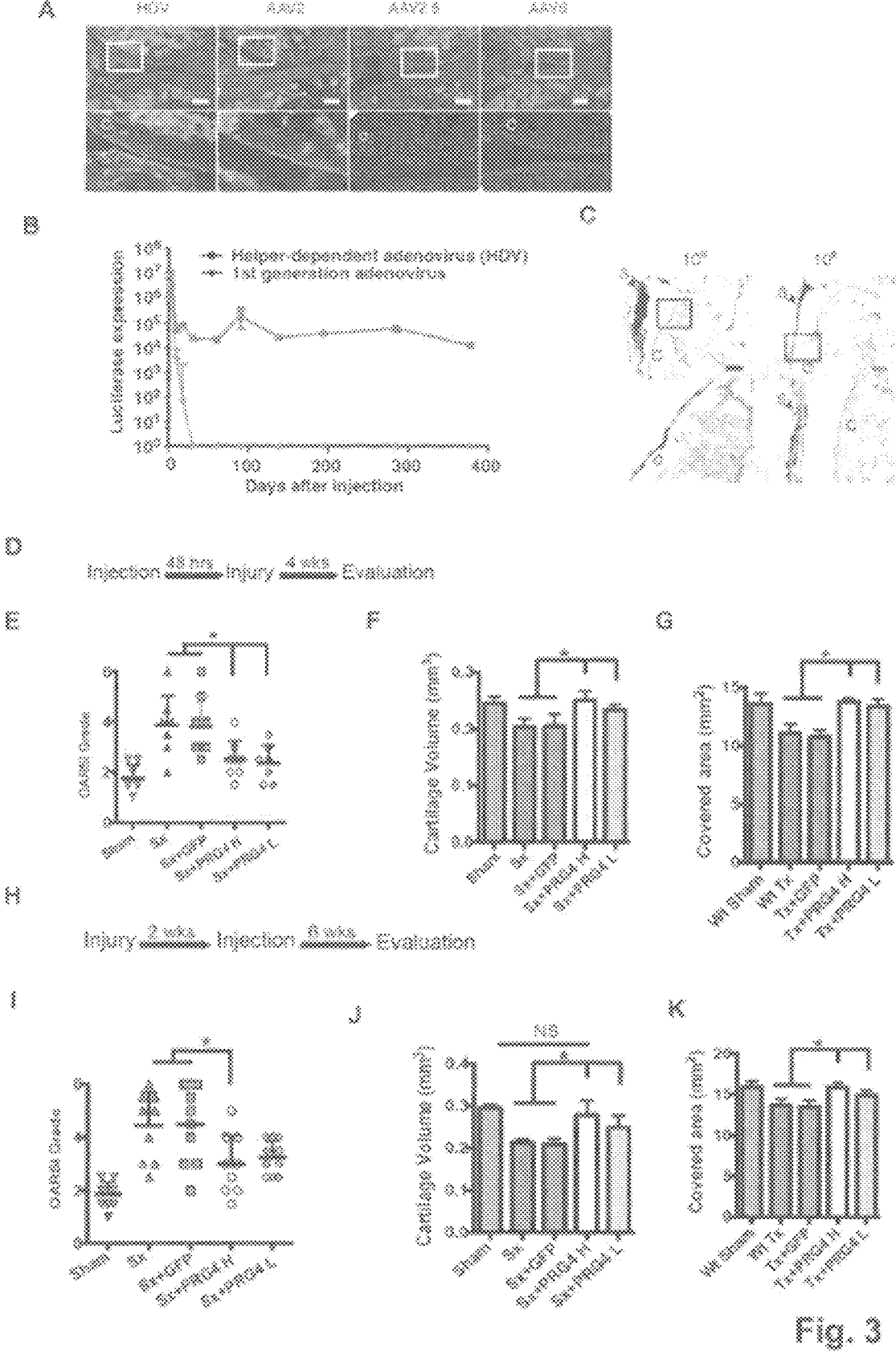
FIG. 3: PRG4 delivered by helper-dependent adenoviral vectors (HDAd) protects mice from development of osteoarthritis. A, Representative image comparing intra-articular injection of HDAd and different serotypes of AAV. Vectors ($10^9$ viral particles) each expressing GFP were injected intraarticularly into the knee joint. The lower panels are enlarged images of the boxed areas in the upper panels. Green: GFP, blue: DAPI. C: cartilage, S: synovium. Scale bar, 100 μm. B, Comparison of luciferase expression after intra-articular injection of first-generation adenoviral vector (FGV) and helper-dependent adenoviral vector (HDAd) (n=6) into the knee joint. C, Representative image of expression patterns of intra-articular injections of different doses of HDAD encoding □-galactosidase. The bottom images are enlarged areas of the black box in the upper images of saggital sections through the knee joint. C: Cartilage; S: Synovium. Scale bar, 100 μm. D-G, Scheme of experiment comparing the preventive effect HDAd-PRG4 injection and evaluation by OARSI grade and cartilage volume (D). Before transection, wild type mice were injected with HDAd-PRG4 intra-articularly at $10^9$ vp/joint (Sx+PRG4 H) or $10^8$ vp/joint (Sx+PRG4 L). Sham, transection without treatment (Sx) and injection of virus without transgene before transection (Sx+Vector) served as controls. Degree of osteoarthritis is presented by OARSI grade (E), cartilage volume (F) and cartilage surface area (G) (*P<0.05, n=8-10 in OARSI grading, n=5-6 in cartilage volume analysis, ANOVA). H-K, Scheme of experiment comparing the protective effect HDAd-PRG4 injection and evaluation by OARSI grade and cartilage volume (H). Two weeks after transection, wild type mice were injected with HDAd-PRG4 intra-articularly at $10^9$ vp/joint (Sx+PRG4 L) or $10^8$ vp/joint (Sx+PRG4 L), Sham, no treatment (Sx) and HDAd-GFP injection (Sx+GFP) served as controls.Degree of OA is presented by OARSI grade (I), cartilage volume (J) and cartilage surface area (K) (*P<0.05, n=8-10 in OARSI grading, n=5-6 in cartilage volume analysis, ANOVA). Error bars indicate s.e.m.

At the higher dose, HDAd transduced superficial layer chondrocytes and synoviocytes, while only synoviocytes were transduced at the lower dose (FIG. 3C). Thus, the inventors showed that HDAd was able to efficiently transduce synoviocytes and chondrocytes with maintaining transgene expression for at least one year.

Figure 6:
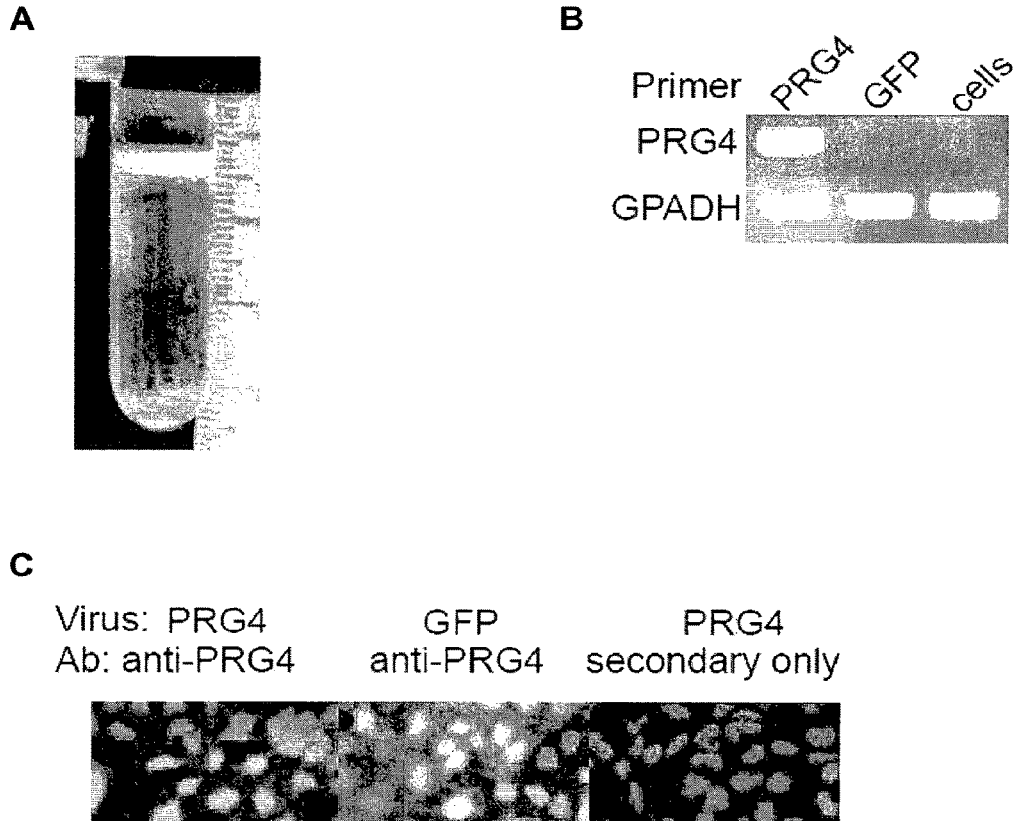
FIG. 6: Generation and characterization of HDAd-PRG4. A, HDAd-PRG4 band is visible in the last step of cesium chloride ultracentrifugation. The purified virus is the white band in the tube. B, PCR determination of PRG4 expression of HEK293 cells infected with HDAd-PRG4 (PRG4), HDAd-GFP (GFP), and sham treatment (cells). Gapdh is used as loading control. C, Immunofluorescence of HEK293 cells infected with HDAd-PRG4 (PRG4, red) and HDAd-GFP (GFP, green). DAPI (blue) was used as counter-stain.

To compare the effects of PRG4 expression from superficial layer chondrocytes vs. synoviocytes, the inventors treated mice at both doses with HDAd expressing PRG4 (FIG. 6A-C) 48 hours prior to surgical cruciate ligament transection. The inventors found that both low dose (mediating expression only in synoviocytes) and high dose (mediating expression in both synoviocytes and superficial zone chondrocytes) treatment with HDAd-PRG4 vector protected joints from osteoarthritis development (FIG. 3D-G). Since the clinical application of PRG4 for osteoarthritis would likely be administrated after an injury, the inventors next tested the efficacy of HDAd-PRG4 injection two weeks after osteoarthritis induction. In this context, injection of the lower dose of HDAd-PRG4 was sufficient to preserve cartilage volumes and prevent cartilage degradation as assessed by μCT, while higher dose injection showed protective effects both by histological OARSI grading and μCT assessment. Importantly, these data suggested that ectopic expression from synoviocytes was sufficient to achieve a certain degree of chondroprotection by acting in a non-cell-autonomous fashion (FIG. 3H-K).

Figure 4:
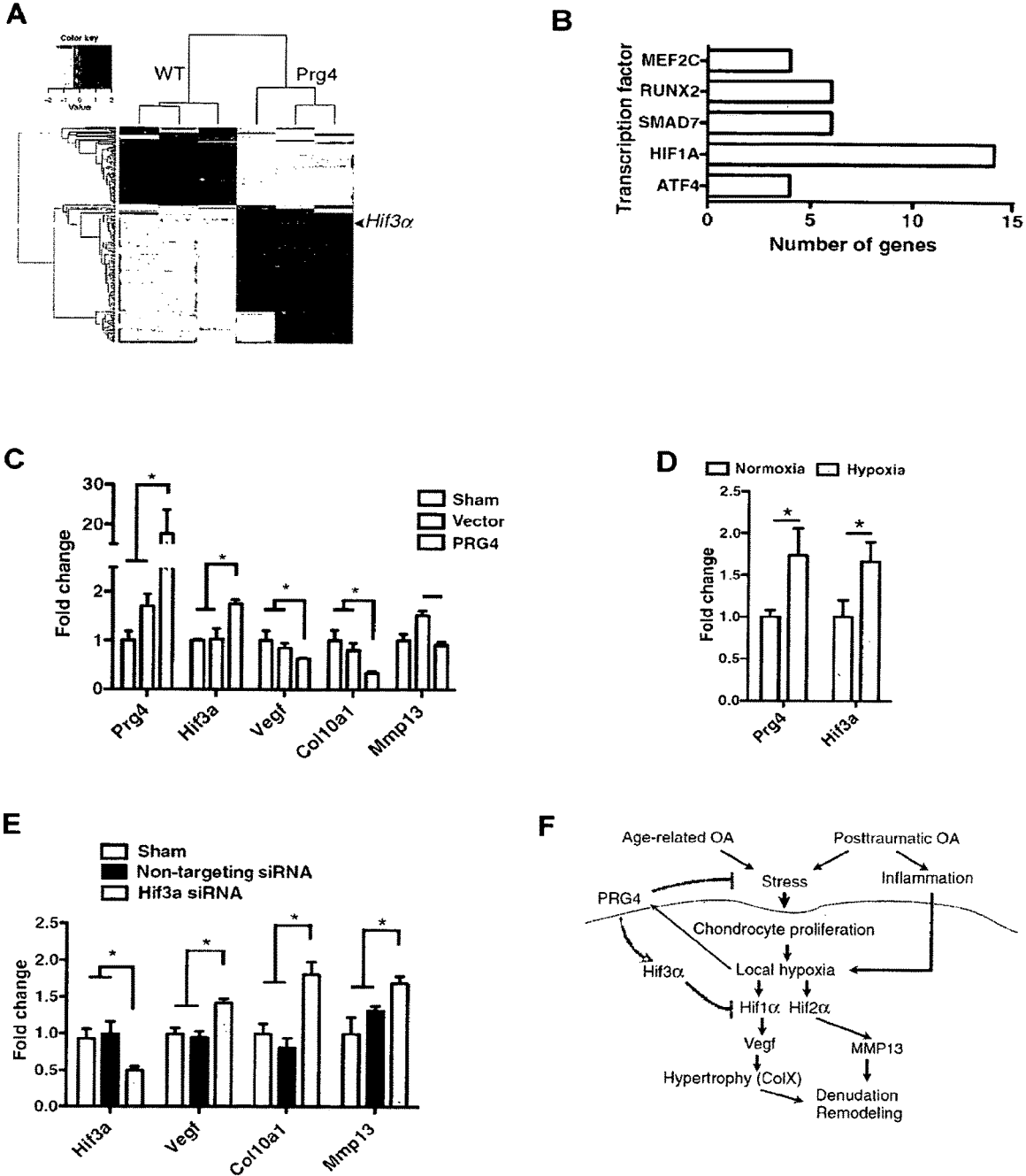
FIG. 4: PRG4 delays osteoarthritis by inhibiting cartilage catabolismand terminal hypertrophy. A, Microarray heat map analysis comparing superficial zone cartilage of wild type and Prg4 transgenic mice, Genes with expression changes larger than 1.5 fold and p-value less than 0.05 are plotted. B, Transcription factor activity changes predicted by Ingenuity Pathway Analysis. All transcription factors shown here were predicted to be suppressed by Ingenuity Pathway Analysis. X-axis indicates the number of genes/gene groups controlled by each transcription pathway in the gene list submitted. C, Changes in gene expression (Prg4, Hif3a, Vegf, Col10a1 and Mmp13) in C3H10T1/2 cells under hypoxia (1% oxygen for 8 hours). Cells are sham treated, infected with empty HDAd (vector) or with HDAd-PRG4 (PRG4) (*P<0.05, n=3, ANOVA). D, Changes of PRG4 and Hif3alpha expression under normoxia and hypoxia in TC71 Ewing sarcoma cells (*P<0.05, n=3, t-test). E, Changes of gene expression after Hif3alpha knockdown by siRNA (*P<0.05, n=3, ANOVA). F, Proposed model of PRG4 function in prevention of osteoarthritis development. Error bars indicate s.e.m.
Figure 7:
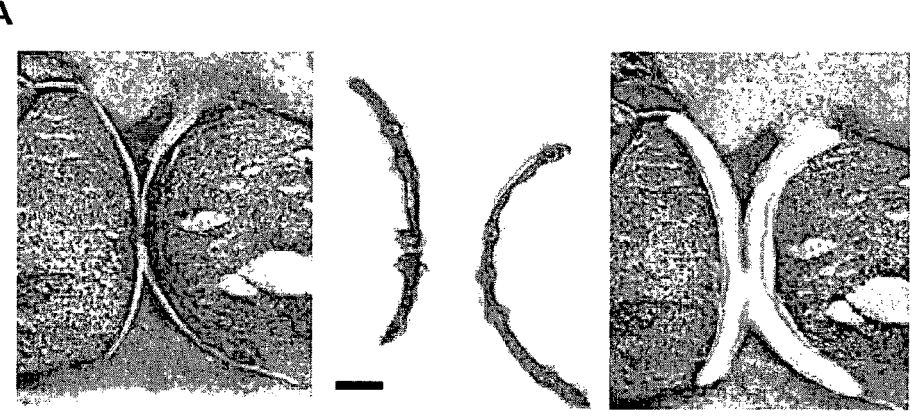
FIG. 7: Gene expression profiling of wild type vs. Prg4 transgenic superficial layer chondrocytes. A, Laser capture micro-dissection of superficial layer chondrocytes. Left to right: tissue before capturing, captured tissue on HS cap, and remaining tissue on the slide. Scale bar, 100 μm. B, Evaluation of Hif3a expression in superficial layer chondrocytes of wild type vs. Prg4 mice (*Py0.05, n=3, t-test). C, Evaluation of PRG4 expression in ATDC5 and C3H10T1/2 cells under normoxic and hypoxic conditions (*P<0.05, n=3, t-test), Error bars indicate s.e.m.
Figure 7:
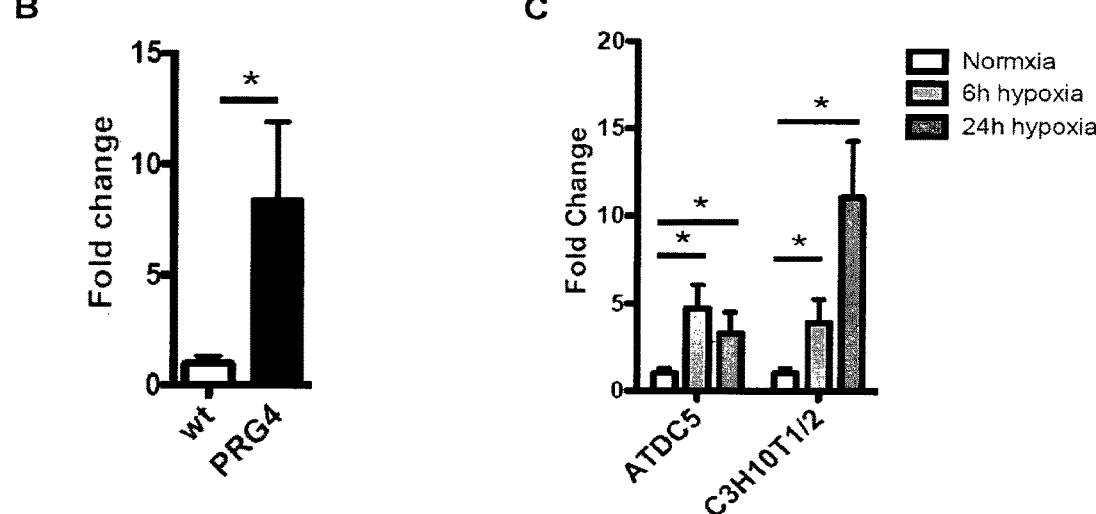

PRG4 Inhibits Transcriptional Programs of Chondrocyte Hypertrophy and Hypoxic Inducible Factors in Cartilage The potential mechanisms of the protective effects of PRG4 have only been partially deciphered. While previous studies have shown that PRG4 relieves mechanical stress in joints by changing synovial fluid dynamics and providing boundary lubrication (G. D. Jay, J. R, Torres, M. L. Warman, M. C. Laderer, K. S. Breuer, The role of lubricin in the mechanical behavior of synovial fluid. *Proc Natl Acad Sci USA* 104, 6194 (Apr. 10, 2007)), the inventors investigated whether PRG4 could directly affect cartilage metabolism and homeostasis. To assess the molecular effects of PRG4 on chondrocytes, the inventors performed transcriptional profiling on superficial layer chondrocytes obtained by laser capture in newborn wild type vs. Prg4 transgenic mice (FIG. 4A and FIG. 7A). Genes that were either up-regulated or repressed by greater than 1.5 fold (Dataset 1) were analyzed by Ingenuity Pathway Analysis to identify transcriptional programs that would be affected by Prg4 expression (Dataset 2). Interestingly, transcription factors that mediate chondrocyte hypertrophy and terminal differentiation (e.g. Mef2c, Runx2 and Atf4) showed decreased activity with PRG4 over-expression (K. S. Lee et al., Runx2 Is a Common Target of Transforming Growth Factor beta 1 and Bone Morphogenetic Protein 2, and Cooperation between Runx2 and Smad5 Induces Osteoblast-Specific Gene Expression in the Pluripotent Mesenchymal Precursor Cell Line C2C12. *Molecular and cellular biology* 20, 8783 (Dec. 1, 2000); X. Yang et al., ATF4 is a substrate of RSK2 and an essential regulator of osteoblast biology; implication for Coffin-Lowry Syndrome. *Cell* 117, 387 (May 30, 2004); M. A. Arnold et al., MEF2C Transcription Factor Controls Chondrocyte Hypertrophy and Bone Development. *Developmental Cell* 12, 377 (April 2007)). In addition, the inventors also noted down-regulation of Smad7, an inhibitor of the TGF-beta signaling pathway (A. Nakao et al., Identification of Smad7, a TGFbeta-inducible antagonist of TGF-beta signalling. *Nature* 389, 631 (Oct. 9, 1997)). TGFbeta signaling negatively regulates terminal differentiation of chondrocytes, and hence. PRG4 again would suppress hypertrophy by its actions on Smad7 (X. Yang et al., TGF-beta/Smad3 signals repress chondrocyte hypertrophic differentiation and are required for maintaining articular cartilage. *The Journal of cell biology* 153, 35 (May 2, 2001)). Finally, Hypoxia inducible factor 1 alpha unit (Hif1alpha), an essential transcription factor induced in response to hypoxia, was also predicted to have lower activity (FIG. 4B), while Hif3alpha a post-translational negative regulator of Hif1alpha and Hif2alpha was up-regulated (Y. Makino et al., Inhibitory PAS domain protein is a negative regulator of hypoxia-inducible gene expression. *Nature* 414, 550 (Nov. 29, 2001)). (FIG. 4A and FIG. 7B).

The inventors hypothesized that PRG4 could up-regulate Hif3alpha under hypoxic conditions to inhibit cartilage turnover. This effect would be mediated by down-regulating the Hif1alpha and Hif2alpha transcriptional activities. To test our hypothesis, the inventors measured Hif3alpha expression and downstream Hif target genes relevant to osteoarthritis progression under hypoxic conditions in C3H10T1/2 (mesenchymal stromal) cells. After injection of HDAd-PRG4, Hif3alpha was transcriptionally up-regulated while Vegf, Col101a1 and Mmp13, all markers of hypertrophy, were all down-regulated compared to empty vector (FIG. 4C) (T. Saito et al., Transcriptional regulation of endochondral ossification by HIF-2a during skeletal growth and osteoarthritis development. *Nature Medicine* 16, 678 (Jun. 23, 2010)). Next, the inventors assessed whether knockdown of Hif3alpha suppressed the effects caused by over-expression of PRG4. Since the expression of Hif3alpha is low in C3H10T1/2 cells, the inventors tested its expression in alternative chondrogenic lines. Interestingly, compared to under normoxic conditions, all cell lines tested showed increased PRG4 expression under hypoxic conditions (FIG. 4D and FIG. 7C). Consistent with this, Genomatix analysis identified a hypoxia response element in the promoter region of PRG4. The inventors found that Hif3alpha was highly expressed in TC71 Ewing sarcoma cells and further increased with up-regulation of PRG4 under hypoxic conditions (FIG. 4D). As predicted by our previous transcriptomic analysis, knockdown of Hif3alpha in TC71 cells led to down regulation of Hif1alpha and Hif2alpha target genes in the face of PRG4 up regulation (FIG. 4E). Our findings suggested that the secreted protein PRG4 could modify the balance of anabolic and catabolic programs in the context of osteoarthritis pathogenesis.

To investigate whether the signalling pathway discovered in mouse is conserved in humans, the inventors performed in silico analysis on gene expression profiling performed in human osteoarthritis patient samples available from the GEO database (S, Koelling et al., Migratory Chondrogenic Progenitor Cells from Repair Tissue during the Later Stages of Human Osteoarthritis, Stem Cell 4, 324 (May 3, 2009); T, Dehne, C. Karlsson, J. Ringe, M. Sittinger, A. Lindahl, Chondrogenic differentiation potential of osteoarthritic chondrocytes and their possible use in matrix-associated autologous chondrocyte transplantation. Arthritis research & therapy 11, R133 (2009)). The inventors discovered PRG4 and the proposed downstream effector, HIF3alpha, are upregulated in chondrocyte progenitor cells in OA patients by 2.6 fold (p<0.05) and 1.5 fold (p<0.01) respectively. In an independent array set comparing 3 dimensional cultured chondrocytes from osteoarthritis and healthy donors, the inventors observed a similar trend: PRG4 was upregulated by 1.4 fold (p<0.05) and HIF3alpha upregulated by 1.3 fold (p<0.05). In the context of osteoarthritis development, PRG4 and HIF3alpha may both be upregulated as a repair response. In contrast to the sustained over expression of PRG4 in our therapeutic models, this normal response in humans may be insufficient to prevent disease progression.

These data together showed that under the hypoxic conditions of cartilage, PRG4 over-expression may prevent osteoarthritis progression not only by exerting biomechanical effects on the synovial fluid and cartilage interface, but also by regulating the transcriptional networks that specify chondrocyte hypertrophy and catabolismartilage turnover mediated by Hif1alpha and Hif2alpha was inhibited by up-regulation of Hif3alpha. As cartilage degradation and hypertrophy are two hallmarks of osteoarthritis progression, it is not surprising that PRG4 has chondroprotective effects both in age-related and post-injury osteoarthritis (FIG. 4F). Osteoarthritis Gene Therapy can be Enhanced by Combined Gene Transfer of PRG 4 and Il-1Ra The inventors sought to evaluate whether the beneficial effect of over-expressing PRG4 in osteoarthritis joints can be further improved by combining it with gene therapy mediated expression of Il-1Ra. Il-1Ra blocks the effects of Il-1beta, which is one of the key drivers of inflammation and cartilage catabolismin osteoarthritis. Based on the different pathways that PRG4 and Il-1Ra exert their effects on, a combination of both might result in optimized inhibition of both cartilage breakdown and inflammation.

Figure 8:
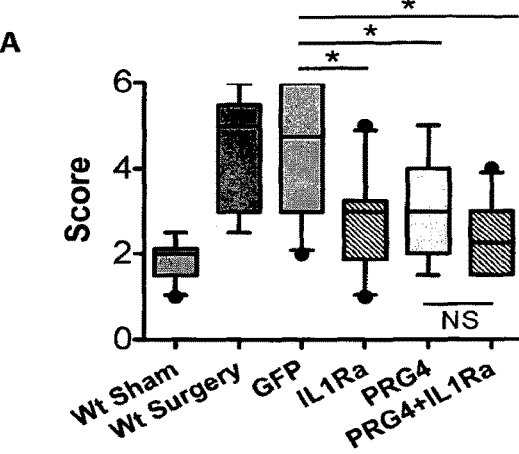
FIG. 8: A, Mice were treated with HDAd-PRG4 (PRG4), HDAd-II-1Ra (II1Ra) and combination therapy (PRG4+II1Ra) according to the scheme shown in FIG. 3 H. All three groups showed significantly lower histological score compared to no treatment and placebo treatment, suggesting therapeutic effects to HDAd-PRG4 and HDM-II-1Ra. The combination therapy showed a trend of being more effective, (ANOVA, N=8-10, *p<0.05); B, C, Mice were treated with HDAd-PRG4 (PRG4), HDAd-II1-Ra (II1Ra) and combination therapy according to the scheme shown in FIG. 3 H. Cartilage surface area (B) and cartilage volume (C) were quantified. All three groups showed significantly higher cartilage volume and surface area compared to no treatment and placebo treatment, suggesting therapeutic effects of HDAd-PRG4 and HDAd-II1Ra. The knees under combination therapy had more preserved cartilage volume and surface area (ANOVA, N=5, *p<0.05).
Figure 8:
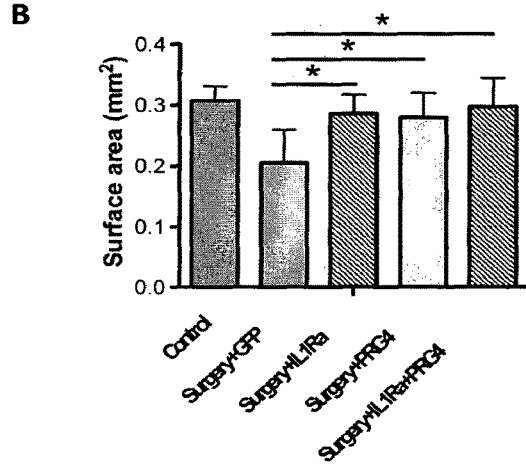
Figure 8:
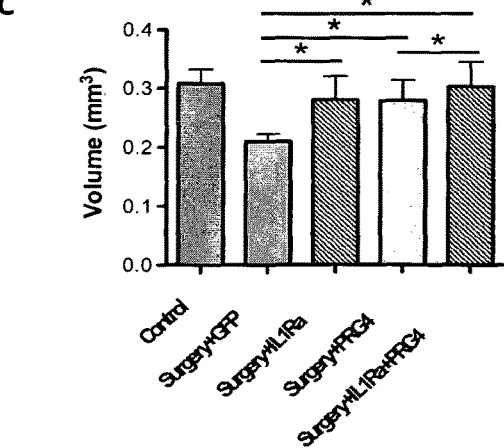

Mice had osteoarthritis induced and were injected with gene therapy vectors two weeks later. HDAd-PRG4. HDAd-Il-1Ra and the combination of both resulted in significantly lower osteoarthritis histology scores compared to the control vector HDAd-GFP and the no treatment group (FIG. 8A). Cartilage surface area was significantly higher in the HDAd-PRG4, HDAd-II-1Ra and combination group compared with HDAd-GFP (FIG. 8B). Furthermore, cartilage volume was significantly higher in the HDAd-PRG4, HDAd-II-1Ra and combination group compared with HDAd-GFP (FIG. 8C). The combination of HDAd-PRG and HDAd-II-1Ra resulted in significantly higher cartilage volume compared with single vector treatment. The combination therapy resulted also in lower average osteoarthritis score and higher average cartilage surface area; however, the difference in these parameters did not reach statistical significance although a trend to significance was present.

Discussion

The invention shows by using both transgenic mice expressing Proteoglycan 4 (PRG4), and intra-articular, helper-dependent adenoviral virus (HDAd) gene transfer that PRG4 is protective against the development of both post-traumatic and age-related osteoarthritis, without significant adverse effects on cartilage development. Gene therapy treatment with HDAd-PRG4 was effective when injected before and after onset of osteoarthritis suggesting that the treatment is both preventive and therapeutic. The beneficial effect can be further improved by combining PRG4 with anti-inflammatory II-1Ra gene therapy. The protective effects are demonstrated at molecular, histological and functional levels. The inventors further show that PRG4 over-expression inhibits transcriptional programs that promote cartilage catabolismand hypertrophy in part through the up-regulation of Hif3alpha. The concordant changes of PRG4 and HIF3alpha expression is also observed in gene expression profiling in human osteoarthritic patient samples.

Most genetics models reported to date show protection from osteoarthritis using histological endpoints at one month after surgical destabilization of the medical meniscus (DMM) to induce a mild, single condylar post-traumatic osteoarthritis, In addition, studies on osteoarthritis have been largely focused on loss of function mutations of genes in bone development such as Adamts5, Mmp13, Hif2alpha and Syndecan4 (F. Echtermeyer et al., Syndecan-4 regulates ADAMTS-5 activation and cartilage breakdown in osteoarthritis. *Nature Medicine,* 1 (Mar. 30, 2102); T. Saito et al., Transcriptional regulation of endochondral ossification by HIF-2a during skeletal growth and osteoarthritis development. *Nature Medicine* 16, 678 (Jun. 23, 2010); S, S. Glasson et al., Deletion of active ADAMTS5 prevents cartilage degradation in a murine model of osteoarthritis. *Nature* 434, 644 (Apr. 31, 2005); C. B. Little et al., Matrix metalloproteinase 13-deficient mice are resistant to osteoarthritic cartilage erosion but not chondrocyte hypertrophy or osteophyte development. *Arthritis & Rheumatism* 60, 3723 (December 2009)). In contrast to these studies, the inventors report the gain of function genetic model with a secreted protein PRG4 that protects against osteoarthritis development at least 2 months after transection of cruciate ligaments. This model mimics a common injury in humans and leads to osteoarthritis in both condylar structures of the knee. The establishment of a gain of function model using an endogenously produced secreted protein may make for easier clinical translation as compared to previous approaches targeting inhibition of specific matrix enzymes and/or intracellular transcription factors. Moreover, the demonstration of a beneficial effect on age-related cartilage changes supports the further study of this approach beyond injury model.

The established mechanisms that protect animals from osteoarthritis development mostly depend on inhibition of cartilage catabolic enzymes. ADAMTS5 was the first target to be discovered via in vivo genetic experiments (S. S. Glasson et al., Deletion of active ADAMTS5 prevents cartilage degradation in a murine model of osteoarthritis. *Nature* 434, 644 (Apr. 31, 2005)). Loss of Syndecan 4, similarly, works through ADAMTS5 inhibition (F. Echtermeyer et al., Syndecan-4 regulates ADAMTS-5 activation and cartilage breakdown in osteoarthritis. *Nature Medicine,* 1 (Mar. 30, 2102)). Recently, the discovery of the protective effects of Hif2alpha loss of function in OA extends this approach as Hif2alpha transcriptionally regulates the expression of catabolic enzymes including several MMPs and ADAMTS5 (T. Saito et al., Transcriptional regulation of endochondral ossification by HIF-2a during skeletal growth and osteoarthritis development. *Nature Medicine* 16, 678 (Jun. 23, 2010)). However, targeting anabolic pathways, including cell growth, differentiation and matrix synthesis, is equally important in osteoarthritis since chondrocyte proliferation, metaplasia and abnormal matrix synthesis have been long observed in osteoarthritis progression (K. P. Pritzker et al., Osteoarthritis cartilage histopathology: grading and staging. *Osteoarthritis Cartilage* 14, 13 (January 2006)). An interaction between cartilage anabolic and catabolic pathways is required to maintain homeostasis and their imbalance leads to osteoarthritis progression. A therapy that can affect both programs would potentially be most effective.

Low-grade inflammation is commonly observed in osteoarthritic joints (Felson D T. 2006. Clinical practice. Osteoarthritis of the knee. N Engl J Med 354:841-848). Besides maintaining and amplifying inflammation, the key inflammatory mediators in osteoarthritis such as II-1beta also trigger the expression of cartilage degrading enzymes such as collagenases and aggrecanases (Daheshia, M., and YAO, J. Q. (2008). The Interleukin 1β Pathway in the Pathogenesis of Osteoarthritis. J Rheumatol 35, 2306). Therefore, it seems important to inhibit both cartilage catabolismand joint inflammation in order to achieve efficient osteoarthritis treatment. Along these lines, the inventors show here that a gene therapy treatment combining helper-dependent adenoviral vectors expressing PRG4 and the anti-inflammatory II-1Ra seems to further improve osteoarthritis treatment over gene therapy with PRG4.alone.

Materials and Methods

Generation of transgenic mice. FVB/N mice were purchased from Jackson Laboratories (Bar Harbor, ME). This strain is the common background strain for transgenic mouse lines. All studies were performed with approval from the Baylor College of Medicine Institutional Animal Care and Use Committee (IACUC). All mice were housed under pathogen-free conditions in less than five per cage. Mice had free access to feed and water. Transgenic mice were generated by pronuclear microinjection. Founders were outcrossed for at least 3 generations to eliminate multiple insertions. Different lines were tested at the beginning to rule out position effect. Genotyping primers were designed to detect the WPRE element in the transgene cassette: F: TCTCTTTATGAGGAGTTGTGGCCC (SEQ ID NO: 40), R: CGACAACACCACGGAATTGTCAGT (SEQ ID NO: 41). To avoid the effects of potential post-menopausal bone loss, all the mice used in OA evaluation were males.

Cruciate ligament transection (CLT) surgery. CLT surgery and sham were performed as previously described in 8-week old male FVB/N mice and PRG4 transgenic mice (M. Ruan et al., Quantitative imaging of murine osteoarthritic cartilage by phase contrast micro-computed tomography. *Arthritis*

*Rheum*, (2012). Investigators were blinded to the genotype of the mice when surgery was performed.

Histology and immunohistochemistry. Mice were euthanized and samples were fixed with 4% paraformaldehyde (Sigma-Aldrich) overnight in 4° C. on a shaker. Samples from mice older than 4 days were decalcified in 14% EDTA for 5 days in 4° C. on a shaker. Samples from mice younger than 3 days were not decalcified. Paraffin embedding was performed as previously described. Samples were sectioned at 6 μm. Samples were stained with safranin O and fast green using standard protocols. Samples were scored by two independent pathologists masked to the procedure and genotypes. Immunohistochemistry were performed using primary antibody: anti-PRG4 (Abcam, ab 28484), anti-MMP13 (Millipore, MAB 13424), anti-CoIX (generous gift from Dr. Greg Lunstrum, Shriners Hospital for Children, Portland, OR), and secondary antibody: one-dropper-bottle HRP polymer conjugates (Invitrogen). BrdU staining was performed using anti-BrdU Alexa Fluor 594 (A21304, Invitrogen). Histomark trueblue (KPL) was used as developing reagent. TUNEL staining was performed using ApopTag Plus Peroxidase In situ Apoptosis Detection (Millipore Kit S7101) following manufacturer's protocol. All staining in the same experiment were done at the same time. Observer who quantified of BrdU and TUNEL staining was blinded to the genotype of the mice.

Beta-galactosidase staining. Staining was performed on samples embedded in optimal cutting temperature compound after fixation and decalcification. Samples were sectioned at 6 μm and stained with X-gal (X428IC Gold biotechnology) overnight and nuclear fast red (N3020 Sigma) as counter stain.

Rotarod analysis. Mice were placed onto an accelerating rotarod (UGO Basile, Varese, Italy). The duration to first failure to stay atop the rod was marked as first ride-around time. To rule out differences in learning skills between the two groups of mice, each group was assessed over three trials per day for 2 consecutive days (trials 1 to 6) before surgery. Mice were then randomly assigned into different groups. Another 6 trials were performed using the same conditions at the different time points after the surgery. Mice were given a 30 minutes inter-trial rest interval. Each trial had a maximum time of 5 minutes. Observer was blinded to the genotype and the procedure of the mice.

Hotplate analysis. Mice were placed on the hotplate at 55° C. (Columbus Instruments, Columbus, OH). The latency period for hind limb response (e.g. shaking, jumping, or licking) was recorded as response time before at different time points after surgery. Observer was blinded to the genotype and the procedure of the mice.

Phase contrast μCT scanning. Samples were prepared as previously described and scanned by Xradia uXCT at source voltage=40 kV, source power-8W, detector distance from sample=75 mm, source distance from sample=100 mm, image number taken=500, and exposure time for each image=30 (M. Ruan et al., Quantitative imaging of murine osteoarthritic cartilage by phase contrast micro-computed tomography. *Arthritis Rheum*, (2012)). The resolution of the scanning is 4 μm. After scanning, a random number was assigned to each sample to ensure blinded assessment during image processing.

Reconstruction and analysis of μCT data. Reconstruction of the data was performed using Xradia software and was transformed into dicom files. Reconstruction involves correction for beam hardening (constant-0.3), and correcting for center shift effects caused by difference between the center of sample rotation and the center of the detector. Samples were analyzed using TriBON software (RATOC, Tokyo, Japan). Observers were blinded to the procedure and sample number (M. Ruan et al., Quantitative imaging of murine osteoarthritic cartilage by phase contrast micro-computed tomography. *Arthritis Rheum*, (2012)).

Intra-articular Injection. Mice were anesthetized using 3% isoflurane. Joint area was shaved. HDAds were diluted in sterile PBS in 5 μl and injected by 25 μl CASTIGHT syringes (1702 Hamilton Company) and 33 gauge needles (7803-05 Hamilton Company).

Luciferase assay. Mice were injected with 2 mg D-luciferin (L9504 SIGMA) diluted in 100 μl PBS per mouse (25 grams) intraperitoneally. Mice were anesthetized using 3% isoflurane. Images were taken by Xenogen IVIS optical in vivo imaging system. Quantification was performed by living Imaging 4.2 using default settings. Image was collected for 10 minutes after the injection and normalized to control mice without luciferase injection.

Laser capture microdissection and RNA purification. Hind limbs of P1 littermates were collected and snap-frozen in liquid nitrogen. Then, samples were embedded in optimal cutting temperature compound. Frozen sections of 10 μm were generated on polyethylene napthalate (PEN)-membrane slides. Superficial layer chondrocytes were captured using HS Capsure LCM caps by Applied Biosciences Acturus Systems. RNA was then purified by Picopure RNA isolation kit.

Mouse Microarray and analysis. Microarrays were performed using Mouse WG-6 v2.0 Expression BeadChip (Illumina). Data was processed using the lumi package within the R statistical package. Variance-stabilizing transformation (VST) was performed, followed by quantile normalization of the resulting expression values. Differential expression was calculated using the limma package within R. Heat map was generated using normalized fold change. The resulting lists were then annotated and reviewed for candidates.

Human gene expression analysis. GEO archives GSE10575 titled "Migratory chondrogenic progenitor cells from repair tissue during the later stages of human osteoarthritis" (PMID: 19341622) and GSE16464, titled "Chondrogenic differentiation potential of osteoarthritis chondrocytes and their use in autologous chondrocyte transplantation" (PMID: 19723327) were both downloaded and analyzed using the web-based GEO2R, using the default settings, available through the GEO site. In archive GSE10575, three arrays of chondrogenic progenitor cells from osteoarthritis males were compared to two control arrays of the same cell type. Female samples were excluded because control samples are males (shown by the level of Xist expression). In archive GSE 16464, 3D-cultured chondrocytes from normal donors and 3D-cultured chondrocytes from OA donors were compared. Both archives used the Affymetrix Human Genome U133 Plus 2.0 Array platform.

Cell culture, transfection and infection. C3H10T1/2 cells were maintained in DMEM with 10% FBS; TC71 cells were maintained in RPMI 1640 with 10% FBS; ATDC5 cells were maintained in DMEM/F-12 1:1 mixture supplemented with 10% FBS. Cells were plated the day before transfection/infection so that it reached 70% confluency the next day. Lipofectamine 2000 was used as transfection reagent following protocols provided by manufacturer. Dharmacon on-target siRNA was used in the knockdown assay. HDAds were generated as previously described (M. Suzuki et al., Large-scale production of high-quality helper-dependent adenoviral vectors using adherent cells in all factories. *Human gene therapy* 21,120 (February 2010)). HDAd-PRG4 carries the murine PRG4 gene controlled by the constitutive EF1 promoter. HDAd-II-1Ra carries the murine II-1Ra gene controlled by an inflammation-inducible NF-κB promoter. To infect cells. HDAds were diluted at 5000 vp/cell and added in serum free media with minimal volume covering cells after aspiration. Two hours later, media containing virus was aspirated and culturing media was added back. For hypoxia experiments, cells were transferred to hypoxia chamber with 1% oxygen.

RNA purification and quantitative PCR. Cells were lysed with Trizol reagents (Invitrogen) and RNA was purified following manufacturer's protocol. To eliminate DNA contamination, samples were treated with RNase-free recombinant DNasel (Roche). Reverse-transcript PCR was conducted by superscript III first strand (18080-051 Invitrogen) following manufacturer's protocol. Taqman Universal PCR mastermix (Applied biosciences) and PerfeCTa SYBR Green SuperMix (Quanta BioSciences) were used in quantitative PCR. Primers used in quantitative PCR are listed as follows: mouse PRG4: F: ACTTCAGCTAAAGA-GACACGGAGT (SEQ ID NO: 16), R: GTTCAGGTGGTTCCTTGGTTGTAGTAA (SEQ ID NO: 17); Sox9: F: AAGCCACACGTCAAGCGACC (SEQ ID NO: 18), R: GTGCTGCTGATGCCGTAACT (SEQ ID NO: 19); Col2a1; F: GCTCATCCAGGGCTCCAATGATGTAG (SEQ ID NO: 20), R: CGGGAGGTCTTCTGTGATCGGTA (SEQ ID NO: 21); Gapdh: F: GCAAGAGAGGCCC-TATCCCAA (SEQ ID NO: 22); R: CTCCCTAGGCCCCTCCTGTTATT (SEQ ID NO: 23); Vegf. F: TGGACTTGTGTTGGGAGGAGGATG (SEQ ID

26

NO: 24), R: GCCTCTTCTTCCACCACCGTGTC (SEQ ID NO: 25); Mmp13: F: GCAATCTTTCTTTGGCT-TAGAGGT (SEQ ID NO: 26), R: GGTGTTTTGG-GATGCTTAGGGT (SEQ ID NO: 27); Col10a1: F: AAAGCTTACCCAGCAGTAGG (SEQ ID NO: 28), R: ACGTACTCAGAGGAGTAGAG (SEQ ID NO: 29); GAPDH: F: ATACCAGGAAATGAGCTTGACAAA (SEQ ID NO: 30), R: TGAAGGTCGGAGTCAACGGA (SEQ ID NO: 31); VEGF: F: GATCGGTGACAGTCACTAGCT-TATCT (SEQ ID NO: 32), R: TACACACAAATA-CAAGTTGCCA (SEQ ID NO: 33); MMP13F: TGCCCTTCTTCACACAGACACTAACGAAA (SEQ ID NO: 34), R: GGCCACATCTACTATTCTTACCACTGCTC (SEQ ID NO: 35); COL10AI: F: GCCCACTACCCAA-GACCAAGAC (SEQ ID NO: 36); R: GACCCCTCT-CACCTGGACGAC (SEQ ID NO: 37); HIF3A: F: GGCTGTTCCGCCTACGAGTA (SEQ ID NO: 38); R: AGCAAGGTGGGATGCTCTTG (SEQ ID NO: 39); PRG4: Hs00981633_ml (applied biosciences); mouse Hif3a: Mm00469375_ml (applied biosciences).

Statistics. Statistical significance comparing two groups with parametric data was assessed by Student's t test, Statistical analysis comparing multiple groups with parametric data was performed by one-way ANOVA followed by Tukey's post-hoc. Statistical analysis comparing different genotype with different procedure was performed by two-way ANOVA followed by Tukey's post-hoc, Normality was tested by Shapiro-Wilk Normality test. Histological grades were compared by Wilcox rank test. All analyses were performed by SPSS software or Sigma Plot. A P value of <0.05 was considered statistically significant.

Dataset 1: List of genes showing more than 1.5 fold change in the microarray analysis.

| | WTP1_1 | WTP1_2 | WIP1_3 | PG4P1_1 | PG4P1_2 | PG4P1_3 |
|---|---|---|---|---|---|---|
| 4930546H06Rik_ILMN_2717117 | 1,256363 | 1,360731 | 1,425929 | −1,48447 | −1,59768 | −1,52108 |
| Sesn_ILMN_2654074 | −1,25604 | −1,26072 | −1,28391 | 1,234927 | 1,170478 | 1,226371 |
| Ypel5_ILMN_1251071 | 1,224517 | 1,294585 | 1,311664 | −1,44517 | −1,32632 | −1,38253 |
| Bglap-rs1_ILMN 1233122 | 1,301868 | 2,023561 | 1,628096 | −3,0338 | −3,05449 | −2,56761 |
| AK038070_ILMN_2466021 | 1,257255 | 1,181603 | 1,204158 | −1,30391 | −1,20282 | −1,31808 |
| AK011460_ILMN_2452717 | −1,52912 | −1,85077 | −1,48354 | 1,474372 | 1,352955 | 1,304319 |
| Bglap1_ILMN 2610166 | 1,404137 | 2,037433 | 1,6235 | −4,09687 | −3,29889 | −2,57926 |
| Med18_ILMN_1214050 | −1,48231 | −1,26813 | −1,3871 | 1,212726 | 1,267995 | 1,335163 |
| Bglap1_ILMN_3101908 | 1,459117 | 2,042785 | 1,496434 | −3,82431 | −3,03438 | −2,43533 |
| Ppp1r3c_ILMN 2667091 | −1,65083 | −1,56199 | −1,48727 | 1,4376 | 1,167941 | 1,476123 |
| Bglap-rs1_ILMN_1220829 | 1,261849 | 2,094587 | 1,691356 | −3,64532 | −3,48459 | −2,55816 |
| Zfp46_ILMN_1215740 | −1,35114 | −1,26299 | −1,37143 | 1,277394 | 1,136789 | 1,32476 |
| Hist1h1c_ILMN_2855315 | 1,196666 | 1,423895 | 1,348674 | −1,49333 | −1,34167 | −1,62396 |
| Zfand2a_ILMN_1230489 | 1,273059 | 1,140929 | 1,34758 | −1,36636 | −1,26743 | −1,39361 |
| Ddx21_ILMN_2546724 | 1,305544 | 1,217222 | 1,179125 | −1,34811 | −1,20085 | −1,382 |
| Hist1h1c ILMN 2774537 | 1,170861 | 1,384453 | 1,428754 | −1,41392 | −1,42079 | −1,65332 |
| Ddx54_ILMN_2689678 | 1,130087 | 1,286618 | 1,299302 | −1,39565 | −1,2461 | −1,30723 |
| Rps15a_ILMN_2717621 | 1,315098 | 1,139016 | 1,449143 | −1,36561 | −1,52841 | −1,40807 |
| Bglap-rs1_ILMN_2944508 | 1,303982 | 2,185122 | 1,520279 | −3,70241 | −3,45533 | −2,31957 |
| Slc7a5_ILMN_2711948 | 1,201827 | 1,326767 | 1,430059 | −1,67471 | −1,48398 | −1,29808 |
| Csnkld_ILMN_2739965 | 1,11045 | 1,255629 | 1,292397 | −1,37356 | −1,22945 | −1,24982 |
| Dyrklb ILMN._3053158 | −1,46521 | −1,31006 | −1,19201 | 1,182241 | 1,294858 | 1,238163 |
| Hist2h3b ILMN._2934120 | 1,254913 | 1,119073 | 1,304197 | −1,38431 | −1,299 | −1,20538 |
| Nmd3_ILMN_1228859 | 1,262366 | 1,122484 | 1,224622 | −1,20301 | −1,36721 | −1,20793 |
| 1190005F20Rik_ILMN_2697918 | −1,21616 | −1,40512 | −1,44745 | 1,36511 | 1,269442 | 1,140632 |
| Lrrc59_ILMN_1252817 | 1,334493 | 1,222121 | 1,168151 | −1,47501 | −1,29518 | −1,21186 |
| Dusp8_ILMN_1228031 | 1,288724 | 1,069707 | 1,275318 | −1,27037 | −1,24915 | −1,28446 |
| AK053260_ILMN_1228804 | −1,53513 | −1,52115 | −1,78747 | 1,594074 | 1,424237 | 1,113431 |
| Eifla_ILMN_2698107 | 1,399002 | 1,348068 | 1,07882 | −1,44405 | −1,34553 | −1,35426 |
| AK021349_ILMN_1258961 | 1,382804 | 1,270095 | 1,173873 | −1,34656 | −1,59361 | −1,2452 |
| Csnkld_ILMN_1231035 | 1,104983 | 1,305878 | 1,354114 | −1,47277 | −1,23751 | −1,33697 |
| Cirbp_ILMN_2761594 | 1,08657 | 1,233789 | 1,298241 | −1,23605 | −1,35285 | −1,20021 |
| Plekhf2_ILMN_2798694 | 1,124677 | 1,171659 | 1,32521 | −1,2892 | −1,34384 | −1,16463 |
| Nfatc1_ILMN_1216522 | 1,286293 | 1,080945 | 1,308693 | −1,21468 | −1,39646 | −1,27436 |
| Clk1_ILMN_2428301 | −1,36643 | −1,38464 | −1,9415 | 1,450046 | 1,301662 | 1,279182 |
| Trove2_ILMN_1252725 | 1,195356 | 1,139589 | 1,272322 | −1,22692 | −1,41043 | −1,15117 |
| EG639396_ILMN_2877059 | −1,19236 | −1,20876 | −1,39289 | 1,317211 | 1,11903 | 1,179859 |
| Heatr1_ILMN_1214036 | 1,317403 | 1,264432 | 1,223294 | −1,64477 | −1,32574 | −1,20107 |

-continued

| Dataset 1: List of genes showing more than 1.5 fold change in the microarray analysis. | | | | | |
|---|---|---|---|---|---|
| | WTP1_1 | WTP1_2 | WIP1_3 | PG4P1_1 | PG4P1_2 | PG4P1_3 |

| | WTP1_1 | WTP1_2 | WIP1_3 | PG4P1_1 | PG4P1_2 | PG4P1_3 |
|---|---|---|---|---|---|---|
| BC027809_ILMN_1252263 | 1,357622 | 1,055984 | 1,444709 | −1,34453 | −1,47672 | −1,38744 |
| Ccdc130 ILMN._2756733 | −1,17101 | −1,26787 | −1,41093 | 1,342647 | 1,169009 | 1,136904 |
| Tmcc1_ILMN_1249710 | −1,26174 | −1,39677 | −1,70812 | 1,477478 | 1,22952 | 1,199067 |
| Arrdc4_ILMN_2648967 | 1,045261 | 1,574252 | 1,593893 | −1,83439 | −1,7299 | −1,50742 |
| AK044963_ILMN_1247942 | 1,321698 | 1,257721 | 1,270333 | −1,18779 | −1,38985 | −1,69824 |
| Arf2_ILMN_1214810 | 1,546019 | 1,353128 | 1,087012 | −1,4972 | −1,66445 | −1,34205 |
| 2610101N10Rik_ILMN_1252490 | −1,14039 | −1,40709 | −1,51568 | 1,290925 | 1,162057 | 1,299667 |
| Lrrc47_ILMN_2628551 | 1,117726 | 1,123233 | 1,383986 | −1,31904 | −1,23011 | −1,2438 |
| Srm_ILMN_2809611 | 1,485302 | 1,196046 | 1,150938 | −1,54798 | −1,39998 | −1,23852 |
| Gprc5a ILMN._2854943 | 1,320606 | 1,042922 | 1,353049 | −1,29647 | −1,25915 | −1,39294 |
| Ddx11_ILMN_2700550 | −1,20131 | −1,24547 | −1,33501 | 1,353463 | 1,204601 | 1,057541 |
| Deb1_ILMN_2652971 | 1,548657 | 1,086404 | 1,190474 | −1,36664 | −1,38753 | −1,38497 |
| Mif_ILMN_2867835 | 1,125532 | 1,187658 | 1,327057 | −1,3999 | −1,32759 | −1,12086 |
| Hoxd3_ILMN_1219807 | −1,19061 | −1,30954 | −1,55302 | 1,334377 | 1,316337 | 1,101846 |
| Cdc7_ILMN_1238374 | −1,31242 | −1,26666 | −1,86596 | 1,253473 | 1,281007 | 1,378172 |
| Zfp187_ILMN_.3067831 | −1,18727 | −1,40885 | −1,54414 | 1,457655 | 1,221198 | 1,121467 |
| 3300001P08Rik_ILMN_2727004 | −1,16879 | −1,39116 | −1,32235 | 1,224787 | 1,064016 | 1,330551 |
| Hoxc6_ILMN_1217328 | −1,33051 | −1,47422 | −1,40075 | 1,339994 | 1,496705 | 1,019485 |
| Rbm5_ILMN_2942492 | −1,29365 | −1,62199 | −1,68464 | 1,66198 | 1,236204 | 1,11868 |
| AK012053_ILMN_2469320 | −1,10834 | −1,3099 | −1,40348 | 1,32378 | 1,110387 | 1,187654 |
| Tmem128_ILMN_1248235 | 1,125965 | 1,138522 | 1,441919 | −1,45467 | −1,29997 | −1,19488 |
| Rbm5_ILMN_2942499 | −1,45228 | −1,59992 | −1,84238 | 1,607189 | 1,534819 | 1,001613 |
| E130016E03Rik_ILMN_3161959 | −1,2783 | −1,50572 | −1,71101 | 1,568022 | 1,337492 | 1,063614 |
| Tnfrsf12a_ILMN_2424299 | 1,680884 | 1,277593 | 1,075987 | −1,78329 | −1,46531 | −1,38442 |
| Prdm2_ILMN_1250454 | 1,173017 | 1,20632 | 1,256779 | −1,14469 | −1,19644 | −1,52795 |
| Srm_ILMN_1225880 | 1,332372 | 1,120064 | 1,166016 | −1,4506 | −1,22663 | −1,14034 |
| Cpt2_ILMN_2775123 | −1,20532 | −1,33083 | −1,38724 | 1,104396 | 1,131549 | 1,462135 |
| Twf1_ILMN_1244219 | 1,25757 | 1,126966 | 1,235596 | −1,49415 | −1,20089 | −1,13911 |
| AK076052_ILMN_2429108 | 1,076837 | 1,140505 | 1,40668 | −1,19618 | −1,25719 | −1,34308 |
| Farsa_ILMN_1257639 | 1,213878 | 1,216622 | 1,352934 | −1,12429 | −1,38604 | −1,65116 |
| Zfp84_ILMN_2506757 | −1,16964 | −1,18995 | −1,49011 | 1,301893 | 1,104954 | 1,226727 |
| Rnase4_ILMN_1235657 | −1,46403 | −1,24206 | −1,12261 | 1,323919 | 1,163284 | 1,133851 |
| Pim3_ILMN_2717667 | 1,123427 | 1,144501 | 1,541166 | −1,42121 | −1,21509 | −1,50536 |
| Rab5b_ILMN_1237467 | −1,54934 | −1,50901 | −1,79875 | 1,824154 | 1,27382 | 1,037959 |
| Tk1_ILMN_2605890 | −1,14797 | −1,19726 | −1,52316 | 1,200172 | 1,303368 | 1,13359 |
| Nrp1_ILMN_1247094 | −1,34674 | −1,14618 | −1,60363 | 1,244615 | 1,403199 | 1,113605 |
| 6030458C11Rik_ILMN_1234196 | −1,5397 | −1,45778 | −2,22228 | 1,702852 | 1,461039 | 1,050668 |
| Pold1_ILMN_2655577 | −1,24471 | −1,24541 | −1,4781 | 1,425738 | 1,253099 | 1,038272 |
| Prss35_ILMN_2609897 | 1,480951 | −1,03832 | 1,608742 | −1,44299 | −1,64698 | −1,54549 |
| Tppp3_ILMN_2655929 | −1,08048 | −1,39071 | −1,3892 | 1,218015 | 1,318692 | 1,098879 |
| Clec2d_ILMN_2603647 | −1,73457 | −1,2971 | −2,52661 | 1,280941 | 1,696474 | 1,279334 |
| Hif3a_ILMN_2649671 | −1,78312 | −1,6431 | −1,32223 | 1,73224 | 1,313779 | 1,028263 |
| Pnrc2_ILMN_2861331 | −1,12969 | −1,18773 | −1,58246 | 1,161941 | 1,19852 | 1,280471 |
| Myd116_ILMN 2722938 | 1,38863 | 1,149001 | 1,09759 | −1,13863 | −1,23126 | −1,4829 |
| Eln_ILMN_2697304 | 1,09603 | 1,310437 | 1,235098 | −1,20273 | −1,1346 | −1,54888 |
| Fbxo31_ILMN_2452855 | −1,16259 | −1,1719 | −1,62377 | 1,23252 | 1,296053 | 1,142115 |
| Zmym2_ILMN_2781493 | −1,1322 | −1,205 | −1,65697 | 1,259404 | 1,17403 | 1,249941 |
| Rad541_ILMN_2741985 | −1,14435 | −1,14233 | −1,57512 | 1,210268 | 1,2324 | 1,17319 |
| Nedd9_ILMN_2654186 | 1,300471 | 1,369214 | 1,006802 | −1,27054 | −1,16693 | −1,47168 |
| Gadd45g_ILMN_2744890 | 1,159873 | 1,093824 | 1,401321 | −1,50495 | −1,10425 | −1,29047 |
| Syncrip ILMN_1258420 | 1,212463 | 1,238146 | 1,1686 | −1,42916 | −1,42482 | −1,02121 |
| ler3_ILMN_1216764 | 1,881239 | 1,019378 | 1,168521 | −1,48139 | −1,66306 | −1,52784 |
| Galt_ILMN_2677567 | −1,21625 | −1,36275 | −1,40341 | 1,540977 | 1,172451 | 1,018011 |
| Map3k1_ILMN_2614380 | −1,22523 | −1,25855 | −1,72004 | 1,286516 | 1,479816 | 1,041544 |
| Rrp12_ILMN_2728118 | 1,330091 | 1,265982 | 1,182798 | −1,73253 | −1,45231 | −1,0467 |
| Dbp_ILMN_2616226 | −1,3989 | −1,2558 | −2,17137 | 1,654516 | 1,166472 | 1,207322 |
| Sfrs7_ILMN_2552490 | −1,09319 | −1,37266 | −1,50612 | 1,421972 | 1,225556 | 1,045249 |
| Tmem100_ILMN_1224014 | −1,53254 | −1,20266 | −1,67189 | 1,499528 | 1,458731 | −1,04208 |
| Rpap1 ILMN_1238065 | −1,22594 | −1,19809 | −1,41188 | 1,480394 | 1,120412 | 1,040978 |
| AK017419_ILMN_2416218 | 1,258403 | −1,04994 | 1,597254 | −1,40368 | −1,39738 | −1,30912 |
| Trpc2_ILMN_1220948 | −1,1478 | −1,20737 | −1,48702 | 1,435121 | 1,116418 | 1,076493 |
| Il11ra1_ILMN_1229957 | −1,17181 | −1,34116 | −1,36512 | 1,51528 | 1,033071 | 1,120113 |
| AK007736_ILMN_1258587 | −1,30198 | −1,1931 | −1,5084 | 1,02934 | 1,151676 | 1,549816 |
| Atpbd4_ILMN_1230688 | 1,212165 | 1,044319 | 1,518026 | −11629 | −1,29912 | −1,67838 |
| Tuba1c_ILMN_2476139 | 1,185176 | 1,22582 | 1,255489 | −1,65104 | −1,03071 | −1,31991 |
| Abhd14b_ILMN_3007862 | −1,17428 | −1,31793 | −1,82363 | 1,555108 | 1,207257 | 1,078925 |
| Ifi2712a_ILMN_2762944 | 1,023728 | 1,619691 | 1,164394 | −1,58706 | −1,19828 | −1,37445 |
| MIIS_ILMN_1217776 | −1,08848 | −1,35305 | −1,70073 | 1,363244 | 1,345082 | 1,045908 |
| AK029312_ILMN_1246692 | −1,1321 | −1,22047 | −1,47253 | 1,301738 | −1,00965 | 1,326047 |
| Cars2_ILMN_1218543 | −1,15407 | −1,26682 | −1,75735 | 1,471686 | 1,249823 | 1,053571 |
| Raver2_ILMN_1213278 | −1,20699 | −1,23934 | −1,94009 | 1,342784 | 1,066234 | 1,440154 |
| Mid1_ILMN_3159435 | 1,127098 | 1,038972 | 1,460931 | −1,13274 | −1,25072 | −1,44792 |
| AK078053_ILMN_1222351 | −1,10161 | −1,27506 | −1,55656 | 1,45516 | 1,108898 | 1,101466 |
| AK028672_ILMN_1246030 | 1,223792 | 1,161685 | 1,206628 | −1,02194 | −1,2642 | −1,56654 |
| AK043421_ILMN_2575994 | −1,26016 | −1,2699 | −2,19263 | 1,481949 | 1,406903 | 1,07406 |

Dataset 1: List of genes showing more than 1.5 fold change in the microarray analysis.

| | WTP1_1 | WTP1_2 | WIP1_3 | PG4P1_1 | PG4P1_2 | PG4P1_3 |
|---|---|---|---|---|---|---|
| AK085118_ILMN_2505392 | −1,11638 | −1,20699 | −1,48486 | 1,360363 | 1,232508 | 1,009408 |
| Lpp_ILMN_2463260 | 1,144334 | 1,172656 | 1,289494 | 1,004724 | −1,44657 | −1,43369 |
| NR 001461_ILMN_2445958 | −1,33534 | −1,58378 | −1,69795 | 1,861753 | 1,221821 | −1,05574 |
| Zfp52_ILMN_2838139 | −1,25077 | −1,21913 | −1,67899 | 1,544861 | 1,244823 | −1,00507 |
| AK004187_ILMN_2513451 | −1,30128 | −1,18771 | −1,30172 | 1,256082 | 1,421114 | −1,05914 |
| Gp1bb_ILMN_2653205 | 1,310991 | −1,01749 | 1,499583 | −1,20277 | −1,26174 | −1,71629 |
| BC037034_ILMN_1257019 | −1,07956 | −1,19392 | −1,58424 | 1,197539 | 1,32752 | 1,079839 |
| AK086317_ILMN_2580737 | 1,974206 | 1,266016 | 1,059287 | −1,17028 | −2,25587 | −2,48319 |
| NR 002848_ILMN_2966602 | −1,34056 | −1,63363 | −1,01451 | 1,281704 | 1,267341 | 1,107163 |
| Asns_ILMN_2643513 | 1,12627 | 1,082326 | 1,473384 | −1,63603 | −1,22191 | −1,12562 |
| AK005089_ILMN_2451115 | 1,054101 | 1,319016 | 1,421071 | −1,13881 | −1,24881 | −1,89777 |
| 6430706D22Rik ILMN_3011719 | −1,33993 | −1,32228 | −1,58013 | 1,622833 | 1,345146 | −1,11534 |
| 5330401P04Rik_ILMN_2520011 | −1,1508 | −1,17966 | −1,63107 | 1,427003 | 1,221601 | 1,021642 |
| Flcn_ILMN_1213483 | −1,17513 | −1,1274 | −1,55513 | 1,410583 | 1,179933 | 1,028483 |
| Per2_ILMN_2987862 | −1,21694 | −1,06498 | −1,65428 | 1,267989 | 1,067504 | 1,299293 |
| Ppm1m_ILMN_1224437 | −1,16175 | −1,17068 | −1,91121 | 1,437044 | 1,159707 | 1,165048 |
| AK084113_ILMN_2451389 | −1,16976 | −1,13767 | −1,70942 | 1,283512 | 1,371085 | 1,026543 |
| AK007605_ILMN_1239776 | 1,119895 | 1,118125 | 1,47604 | −1,14506 | −1,18395 | −1,76057 |
| Depdc6_ILMN_3163001 | −1,13115 | −1,20253 | −1,78263 | 1,08135 | 1,165515 | 1,47653 |
| Mterf_ILMN_2624809 | −1,0454 | −1,20426 | −1,5987 | 1,344071 | 1,147785 | 1,095675 |
| AK014695_ILMN_2748880 | −1,23553 | −1,24466 | −2,42903 | 1,564719 | 1,31189 | 1,098905 |
| Vat1I_ILMN_1226356 | −1,17602 | −1,20391 | −1,46333 | 1,144397 | −1,02032 | 1,511196 |
| Ankzf1_ILMN_2703321 | −1,20097 | −1,19701 | −1,82856 | 1,447617 | 1,36439 | −1,02771 |
| Tha1_ILMN_2594768 | −1,09096 | −1,25311 | −1,78214 | 1,402023 | 1,303303 | 1,018911 |
| Plekhf1_ILMN_2993334 | −1,08624 | −1,16026 | −1,78844 | 1,297336 | 1,242747 | 1,118284 |
| Gprasp1_ILMN_3142384 | −1,15055 | −1,14972 | −1,66918 | 1,014435 | 1,224737 | 1,422807 |
| Pdgfra_ILMN_1235932 | −1,28478 | −1,3484 | −1,50982 | 1,62719 | 1,311287 | −1,13736 |
| Mcm10_ILMN_2970532 | −1,0688 | −1,14651 | −1,70048 | 1,161108 | 1,296402 | 1,146574 |
| Fbp2_ILMN_2634905 | −1,67939 | −1,76924 | −2,20592 | −1,36206 | 1,508826 | 2,142995 |
| 111007M04Rik_ILMN_N2734060 | 1,125411 | 1,216839 | 1,439906 | −1,77901 | −1,60341 | 1,032062 |
| Suv420h2_ILMN_1260420 | −1,06155 | −1,32955 | −2,05337 | 1,396444 | 1,349127 | 1,073276 |
| Adat2_ILMN_2705097 | 1,042499 | 1,080097 | 1,530343 | −1,07116 | −1,36781 | −1,46542 |
| 1200016B10Rik_ILMN_1236716 | −1,08228 | −1,17359 | −1,66229 | 1,410154 | 1,112488 | 1,099721 |
| AK021262_ILMN_2546861 | −2,55735 | −2,96551 | −2,04609 | 2,589175 | 1,589228 | −1,65394 |
| NR 002848_ILMN_2438819 | −1,04157 | −1,19208 | −1,62472 | 1,102605 | 1,130335 | 1,352612 |
| Iqcb1_ILMN_2635348 | −1,25858 | −1,51247 | −1,07587 | 1,479027 | 1,112991 | 1,022781 |
| Sirpa_ILMN_2722996 | −1,55085 | 1,020695 | −1,42422 | 1,095271 | 1,397855 | 1,139231 |
| Kif1b_ILMN_2587761 | −1,10748 | −1,26856 | −1,71852 | −1,03298 | 1,275994 | 1,482789 |
| Glpbp2_ILMN_2600113 | −1,03362 | −1,24214 | −1,75238 | 1,314034 | 1,280253 | 1,062528 |
| Akap8I_ILMN_1242769 | −1,70634 | −1,79935 | −1,46855 | 1,863393 | 1,552434 | −1,31333 |
| AK029270_ILMN_1246021 | −1,36249 | −1,13168 | −2,29819 | 1,675332 | 1,15085 | 1,121103 |
| Timm8a1_ILMN_2896552 | 1,183976 | 1,065901 | 1,33591 | −1,5964 | −1,26281 | −1,0041 |
| Cpt2_ILMN_2775122 | −1,31568 | −1,57523 | −1,10064 | −1,0034 | 1,133167 | 1,566763 |
| Mif_ILMN_1260512 | 1,004975 | 1,323347 | 1,316609 | −1560996 | −1,34456 | −1,0099 |
| Cenpl_ILMN_2676726 | −1,07561 | −1,16457 | −1,74209 | 1,300334 | 1,282306 | 1,05495 |
| Ccdc86_ILMN_2730003 | 1,079631 | 1,174875 | 1,493109 | −1,81679 | −1,39094 | −1,01727 |
| Cited2_ILMN_2477221 | −1,25941 | −1,07229 | −1,54732 | −1,01603 | 1,188502 | 1,45439 |
| Tle6_ILMN_2900617 | −1,25696 | −1,29766 | −2,43442 | 1,763195 | 1,23855 | 1,021292 |
| Mrml_ILMN_2649654 | −1,12291 | −1,18885 | −1,88148 | 1,496945 | 1,102948 | 1,136915 |
| Tsc22d3_ILMN_3150811 | −1,46991 | −1,23229 | −1,52848 | 1,715752 | 1,257691 | −1,13571 |
| Wnk1_ILMN_1234955 | −1,1436 | −1,18321 | −1,62288 | 1,476736 | 1,220566 | −1,03422 |
| Gstt3_ILMN_2665715 | −1,15761 | −1,16266 | −1,67614 | 1,531124 | 1,053215 | 1,095113 |
| Ppm1k_ILMN_2923615 | −1,08558 | −1,15334 | −1,64931 | 1,404428 | 1,134997 | 1,066046 |
| Clk4_ILMN_2851710 | −1,15318 | −1,33127 | −1,79737 | 1,595963 | 1,307868 | −1,08522 |
| Il11ra2_ILMN_2619594 | −1,04918 | −1,28561 | −1,57792 | 1,475052 | 1,023734 | 1,136498 |
| Cars2_ILMN_2670601 | −1,09189 | −1,14083 | −1,62876 | 1,389033 | 1,161988 | 1,042614 |
| Pbx1_ILMN_2559669 | −1,2673 | −1,25299 | −2,278 | 1,703366 | 1,314599 | −1,04615 |
| Acot11_ILMN_1227579 | −1,16373 | −1,10948 | −1,73831 | 1,422989 | 1,008933 | 1,232184 |
| Neat1_ILMN_2493030 | −1,1433 | −1,74898 | −4,34058 | 1,651763 | 1,528512 | 1,142921 |
| AK020467_ILMN_2506727 | −1,09908 | −1,81523 | −1,30434 | 1,576618 | 1,226821 | −1,03184 |
| Calb2_ILMN_2827729 | −1,13166 | −1,24465 | −1,58857 | 1,188467 | 1,548766 | −1,05688 |
| Rassf4_ILMN_2956092 | −1,19773 | −1,02283 | −1,71608 | 1,100194 | 1,347195 | 1,157291 |
| Tia1_ILMN_1215055 | −1,07031 | −1,11087 | −1,74002 | 1,144017 | 1,141023 | 1,305753 |
| Csnk2a1_ILMN_1218670 | −1,22304 | −1,30599 | −2,00138 | 1,579869 | 1,464052 | −1,14536 |
| INV_ILMN_1257729 | −1,19494 | −1,45406 | −1,54665 | 1,780692 | 1,124428 | −1,08257 |
| Fam109a_ILMN_2668178 | −1,1457 | −1,10631 | −2,07282 | 1,126329 | 1,371624 | 1,242875 |
| Clspn_ILMN_2858359 | −1,09104 | −1,12459 | −2,01152 | 1,193798 | 1,211273 | 1,292024 |
| AK051059_ILMN_2419748 | −1,0608 | −1,16991 | −1,93243 | 1,379757 | 1,164043 | 1,141268 |
| Unc5c_ILMN_2461668 | −1,01081 | 1,174419 | 1,441474 | −1,35249 | −1,00552 | −1,51306 |
| AK078921_ILMN_2462678 | −1,11083 | −1,23212 | −1,74051 | 1,561371 | 1,188618 | −1,03775 |
| Sgk_ILMN_1213954 | 1,274151 | 1,55087 | −1,15069 | −1,29135 | −1,183 | −1,4572 |
| Disp1_ILMN_2772288 | −1,08894 | −1,41679 | −1,49469 | 1,632533 | 1,126658 | −1,05526 |
| Gadd45g_ILMN 2903945 | 1,451953 | 1,318414 | 1,04743 | −2,13919 | 1,014627 | −1,42835 |
| LOC100040259_ILMN_1244853 | −1,18313 | 1,187774 | 1,974228 | −1,83552 | −1,42003 | −1,34451 |
| _ILMN 1245646 | −1,02956 | 1,218253 | 1,413033 | −1,59167 | −1,26363 | −1,02272 |

-continued

Dataset 1: List of genes showing more than 1.5 fold change in the microarray analysis.

| | WTP1_1 | WTP1_2 | WIP1_3 | PG4P1_1 | PG4P1_2 | PG4P1_3 |
|---|---|---|---|---|---|---|
| Tmem 129_ILMN_2429215 | −1,09374 | −1,11964 | −2,07634 | 1,200101 | 1,167903 | 1,342939 |
| Tusc4_ILMN_2454195 | −1,08831 | −1,10728 | −1,85511 | 1,369108 | 1,179966 | 1,089908 |
| Map3k12_ILMN_2725370 | −1,12888 | −1,35818 | −2,18302 | 1,726495 | 1,263127 | −1,07506 |
| Ndrg2_ILMN_2771991 | −1,07046 | −1,1445 | −2,06977 | 1,291192 | 1,095454 | 1,322285 |
| Rrp15_ILMN_2629856 | 1,004134 | −1,02887 | 1,835502 | −1,43385 | −1,48925 | −1,22032 |
| Mum1_ILMN_1215647 | −1,06142 | −1,13778 | −1,74536 | 1,418322 | 1,083703 | 1,103988 |
| AK052106_ILMN_1255302 | −1,05526 | −1,20509 | −1,60772 | 1,39953 | 1,257665 | −1,06004 |
| Tlcd1_ILMN_2781458 | −1,02375 | −1,3448 | −2,10692 | 1,475982 | 1,34724 | −1,0186 |
| Trps1_ILMN_1226073 | −1,06444 | −1,5275 | −1,78979 | 1,757446 | 1,159398 | −1,07492 |
| Ly6a_ILMN_1255416 | −3,17206 | −1,0932 | −1,29711 | 1,461767 | 1,331041 | 1,206246 |
| Accs_ILMN_2776485 | −1,22008 | −1,009 | −1,65779 | 1,41732 | 1,13865 | 1,030122 |
| App12_ILMN_1219978 | −1,24559 | −1,27531 | −2,11094 | 1,865122 | 1,161517 | −1,09567 |
| Cox412_ILMN_2612178 | 1,089127 | 1,158668 | 1,326957 | 1,008061 | −1,18331 | −1,74794 |
| Clk1_ILMN_1254814 | −1,07911 | −1,22534 | −2,01559 | 1,568467 | 1,193925 | −1,00131 |
| Clspn_ILMN_2623056 | −1,05233 | −1,08879 | −1,82761 | 1,147235 | 1,150539 | 1,28634 |
| Ncrna00166_ILMN_1222196 | −1,03988 | −1,16428 | −1,98635 | 1,39944 | 1,094827 | 1,181747 |
| C4b_ILMN_3049559 | −1,10606 | −1,15706 | −2,05407 | 1,351722 | 1,414119 | −1,0215 |
| Nfatc4_ILMN_2647331 | −1,37338 | −1,25155 | −1,20467 | 1,5856 | 1,183728 | −1,14491 |
| AK036974_ILMN_1222598 | −1,0959 | −1,17652 | −1,59093 | 1,5362 | 1,079376 | −1,00664 |
| Slc5a3_ILMN_1233078 | −1,17885 | −1,23164 | −1,89385 | 1,499145 | 1,458686 | −1,17105 |
| Abcd4_ILMN_1245547 | −1,16716 | −1,03031 | −1,70307 | 1,428297 | 1,110164 | 1,047001 |
| Spnb2_ILMN_1214394 | −1,0152 | −1,12231 | −1,88513 | 1,152147 | 1,231002 | 1,210335 |
| Prelp_ILMN_2739760 | −1,11189 | −1,53571 | −1,7425 | 1,801632 | 1,224774 | −1,17762 |
| 5830411K21Rik_ILMN_1217032 | −1,39544 | −1,00477 | −1,90468 | 1,069172 | 1,653072 | 1,04086 |
| Bmp4_ILMN_1215252 | −1,23614 | −1,17177 | −1,52917 | 1,595397 | 1,230579 | −1,16592 |
| Hoxd8_ILMN_2693052 | −1,07822 | −1,07856 | −1,81581 | 1,155206 | 1,051639 | 1,387814 |
| 1810013L24Rik_ILMN_2616630 | −1,18506 | 1,006997 | −2,02702 | 1,342216 | 1,132491 | 1,18112 |
| 5430432N15Rik_ILMN_2622089 | −1,48775 | −1,75547 | 1,115626 | 1,119898 | 1,119461 | 1,403214 |
| Stxbp3a_ILMN_1245393 | −1,41728 | −1,33413 | −1,13258 | 1,577382 | 1,23735 | −1,18035 |
| Ehd1_ILMN_2628757 | −1,17445 | 1,186862 | 1,650685 | −1,45395 | −1,2074 | −1,25788 |
| Raf1_ILMN_1237730 | −1,07621 | −1,19935 | −1,61396 | 1,5239 | 1,171328 | −1,08435 |
| Tbc1d2b_ILMN_2819859 | −1,07046 | −1,08129 | −2,17266 | 1,290826 | 1,221243 | 1,168665 |
| Ppox_ILMN_2826816 | −1,06553 | −1,21576 | −1,96091 | 1,443881 | 1,371369 | −1,09439 |
| Eraf_ILMN_2619200 | −1.14473 | 1,597198 | 1,416693 | −2,1079 | 1,035463 | −1,65928 |
| Hbb-b1_ILMN_1244316 | 1,271854 | 1,441461 | 1,216162 | −2,80858 | 1,193409 | −1,91916 |
| Chst5_ILMN_2665754 | 1,01614 | −1,33756 | −1,72423 | 1,103901 | −1,00597 | 1,558293 |

Dataset 2: List of transcription factors predicted by Ingenuity Pathway Analysis to be
activated or inhibited. Positive z score suggests activation and negative z score.

| Transcription Regulation | Regulation z-score | p-value of overlap | Target molecules in dataset | Molecular Type |
|---|---|---|---|---|
| PPARA | 2.196 | 1.89E−01 | ASNS, CHKA, Clec2d (includes others), CPT2, FABP3, HIST1H1C, IGFBP5, KIF2C, LGALS4, RETSAT, SRM, TOP2A | ligand-dependent nuclear receptor |
| STAT5B | 2.038 | 1.42E−01 | MYL2, TNNC1, TNNT1, TPM3, TROVE2 | transcription regulator |
| PPARD | 2.036 | 1.29E−01 | ACTG2, CPT2, FABP3, FN1, LGALS4, TNFRSF12A | ligand-dependent nuclear receptor |
| ESR1 | 2.021 | 3.42E−01 | BMP4, Clec2d (includes others), DDX21, HOXC6, IER3, IGFBP5, SGK1, TGFB3 | ligand-dependent nuclear receptor |
| FOX03 | −2.188 | 2.97E−01 | IER3, PPPIR15A, SGK1, SLC1A4 | transcription regulator |
| MEF2C | 2.359 | 2.06E−02 | Bglap (includes others), IBSP, MYL2, TNNC1 | transcription regulator |
| FOS | −2.58 | 3.37E−01 | CASZ1, CDON, FN1, HBA1/HBA2, HBB, IBSP, IGFBP5, KIF1B, LGALS4, NFATC1, S100A8, S100A9, SIRPA | transcription regulator |
| GATA4 | −2.64 | 1.61E−02 | ACTC1, ACTG2, MYLA, MYLPF, TNNC1 | transcription regulator |
| MY0CD | −2.976 | 1.88E−04 | ACTG2, GJA5, LPP, MYL2, MYL4, MYLPF | transcription regulator |
| SRF | −3.454 | 1.05E−03 | ACTC1, ACTG2, GADD45G, HIF3A, LBH, MYL2, MYL3, MYL4, Myl9, MYLPF, RAF1, TNNC1, TNNT1, ZMYM2 | transcription regulator |

-continued

Dataset 2: List of transcription factors predicted by Ingenuity Pathway Analysis to be
activated or inhibited. Positive z score suggests activation and negative z score.

| Transcription Regulation | Regulation z-score | p-value of overlap | Target molecules in dataset | Molecular Type |
|---|---|---|---|---|
| GLI1 | 1.845 | 1.78E–01 | LMNA, NDRG2, PDGFRA, S100A9, TMEM100, WIF1 | transcription regulator |
| E2F1 | 1.844 | 3.83E–01 | BMP4, DDX11/DDX12P, MCM10 (includes EG: 307126), NRP1 (includes EG: 18186), POLD1, PRDM2, RAD54L, TK1, TOP2A | transcription regulator |
| SATB1 | 0.865 | 3.41E–02 | ABTB1, HBB, HSPA8, SGK1, TSC22D3, YPEL5 | transcription regulator |
| CEBPD | 0.795 | 3.70E–02 | ASNS, IGFBP5, MBP, MIA, PDGFRA | transcription regulator |
| TFAP2C | 0.427 | 3.11E–03 | HIST1H1C, MBP, NRP1 (includes EG: 18186), TK1, ZMYND11 | transcription regulator |
| SMARCB1 | 0.271 | 3.27E–02 | C4B (includes others), CDC7 (includes EG: 12545), KIF23, MCM10 (includes EG: 307126), PLXNB2, PPPIR3C, RAB5B, RAD54B | transcription regulator |
| RUNX2 | −0.09 | 7.90E–03 | ACTG2, Bglap (includes others), C4B (includes others), COL24A1, FN1, IBSP | transcription regulator |
| SMAD7 | −0.265 | 4.16E–02 | ACTG2, CITED2, FN1, MYLPF, TGFB3, TPM3 | transcription regulator |
| PGR (includes EG: 18667) | −0.275 | 5.84E–03 | CPT2, DDX21, IER3, IGFBP5, NEDD9, SRSF7, TGFB3, TK1, TSC22D3 | ligand-dependent nuclear receptor |
| TP53 (includes EG: 22059) | −0.709 | 1.68E–03 | ASNS, BMP1, CCDC80, CDC7 (includes EG: 12545), CSNKID, DBP, FABP3, FN1, GADD45G, GSTM1, HDC, HJURP, HK2, HSPA8, IER3, EGFBP5, IKBIP, IQCB1, KIF23, LPP, Ly6a (includes others), MYL4, Myl9, NDRG2, NRP1 (includes EG: 18186), PDGFRA, PEG3, PLNB2, POLD1, PPPIR15A, PQLC3, RAD54B, RAF1, RNASE4, SESN1, SGK1, TOP2A, TSC22D3 | transcription regulator |
| CEBPB (includes EG: 1051) | −1.133 | 2.42E–02 | ACTG2, ARPP19, ASNS, CIRBP, Gnas (mouse), HBB, HDC, IER3, MBP, MIA, NRP1 (includes EG: 18186), PDGFRA, PPPIR15A, SGK1 | transcription regulator |
| MITF | −1.373 | 3.65E–02 | CHKA, CMA1, EDNR8, GPNM8, MBP, MYL4, Tpsab 1 | transcription regulator |
| KDM5B | −1.459 | 1.71E–02 | EHD1, IARS2, KIF2C, NEDD9, PPOX, PSIP1, TOP2A | transcription regulator |
| GATA1 | −1.697 | 1.36E–02 | AHSP, ALAS2, CP1BB, HBA1/HBA2, HBB, MBP | transcription regulator |
| HIF1A | −1.714 | 3.60E–03 | ACTG2, ASNS, CHKA, CITED2, FN1, HIF3A, HIST1H1C, HK2, 1GFBPS, MEF, PFKL, SLC29A1, TGFBB, TMEM128 | transcription regulator |
| SMARCA4 | −1.791 | 9.94E–03 | ACTG2, ASNS, Bglap (includes others), BMP4CLK1, FN1, HBB, IGFBPS, LMNA, MYH3, MYL4, MYLPF, NRP1 (includes EG:18186) | transcription regulator |
| MYOD1 | −1.839 | 6.25E–03 | ACTC1, ACTG2, GADD45G, IGFBPS, MYH3, MYL4, MYLPF, SPTBN1, TNNC1, TNNT1 | transcription regulator |
| ATF4 | −1.848 | 7.63E–03 | ASNS, Bglap (includes others), IBSP, IGFBPS, PPP1R15A, SLC7A5, TNFRSF12A | transcription regulator |

The invention claimed is:

1. A method for the treatment of osteoarthritis in a subject in need thereof, comprising administering to a joint of the subject a helper-dependent adenoviral vector comprising a nucleic acid sequence encoding proteoglycan 4 (PRG4), a left inverted terminal repeat (LITR) and a right adenoviral inverted terminal repeat (RITR), adenoviral packaging signal sequences and non-viral, non-coding stuffer nucleic acid sequences, wherein PRG4 expression is controlled by an elongation factor 1 alpha (EF 1 alpha) promoter, wherein the helper-dependent adenoviral vector does not comprise a nucleic acid sequence encoding interleukin-1 receptor antagonist (Il-1Ra) and wherein the subject is not administered a second helper-dependent adenoviral vector comprising a nucleic acid sequence encoding Il-1Ra.

2. The method of claim 1, wherein the osteoarthritis is age-related osteoarthritis.

3. The method of claim 1, wherein the osteoarthritis is post-traumatic osteoarthritis.

4. The method of claim 1, wherein the nucleic acid sequence encoding PRG4 comprises a nucleic acid having at least 90% identity to the sequence set forth in SEQ ID NO: 3.

5. The method of claim 1, wherein the nucleic acid sequence encoding PRG4 comprises the nucleic acid sequence set forth in SEQ ID NO: 3.

6. The method of claim 1, wherein the helper-dependent adenoviral vector comprises a nucleic acid sequence which is at least 90% identical to the nucleic acid sequence set forth in SEQ ID NO: 1.

7. The method of claim 1, wherein the helper-dependent adenoviral vector comprises the nucleic acid sequence set forth in SEQ ID NO: 1.

8. The method of claim 1, wherein the amino acid sequence of PRG4 comprises an amino acid sequence that is at least 90% identical to the sequence set forth in SEQ ID NO: 5.

9. The method of claim 1, wherein the amino acid sequence of PRG4 comprises the sequence set forth in SEQ ID NO: 5.

10. The method of claim 1, where the administering to a joint of the subject comprises administration not more frequently than once in six weeks.

11. The method of claim 1, wherein the helper-dependent adenoviral vector comprises a nucleic acid sequence which is at least 90% identical to the nucleic acid sequence set forth in SEQ ID NO: 1 and the amino acid sequence of PRG4 encoded by the nucleic acid sequence encoding PRG4 comprises an amino acid sequence that is at least 90% identical to the sequence set forth in SEQ ID NO: 5.

12. The method of claim 11, wherein the amino acid sequence of PRG4 encoded by the nucleic acid sequence encoding PRG4 comprises an amino acid sequence that is at least identical to the sequence set forth in SEQ ID NO: 5.

13. A method for the prevention of post-traumatic osteoarthritis in a subject in need thereof, comprising administering to a joint of the subject a helper-dependent adenoviral vector comprising a nucleic acid sequence encoding PRG4, a LITR and a RITR, adenoviral packaging signal sequences and non-viral, non-coding stuffer nucleic acid sequences, wherein PRG4 expression is controlled by an elongation factor 1 alpha (EF 1 alpha) promoter, and wherein the helper-dependent adenoviral vector does not comprise a nucleic acid sequence encoding interleukin-1 receptor antagonist (Il-1Ra) and wherein the subject is not administered a second helper-dependent adenoviral vector comprising a nucleic acid sequence encoding Il-1Ra.

14. The method of claim 13, wherein the nucleic acid sequence encoding PRG4 comprises a nucleic acid having at least 90% identity to the sequence set forth in SEQ ID NO: 3.

15. The method of claim 13, wherein the nucleic acid sequence encoding PRG4 comprises the nucleic acid sequence set forth in SEQ ID NO: 3.

16. The method of claim 13, wherein the helper-dependent adenoviral vector comprises a nucleic acid sequence which is at least 90% identical to the nucleic acid sequence set forth in SEQ ID NO: 1.

17. The method of claim 13, wherein the helper-dependent adenoviral vector comprises the nucleic acid sequence set forth in SEQ ID NO: 1.

18. The method of claim 13, wherein the amino acid sequence of PRG4 comprises an amino acid sequence that is at least 90% identical to the sequence set forth in SEQ ID NO: 5.

19. The method of claim 13, wherein the amino acid sequence of PRG4 comprises the sequence set forth in SEQ ID NO: 5.

20. The method of claim 13, where the administering to a joint of the subject comprises administration not more frequently than once in four weeks.

21. The method of claim 13, wherein the helper-dependent adenoviral vector comprises a nucleic acid sequence which is at least 90% identical to the nucleic acid sequence set forth in SEQ ID NO: 1 and the amino acid sequence of PRG4 encoded by the nucleic acid sequence encoding PRG4 comprises an amino acid sequence that is at least 90% identical to the sequence set forth in SEQ ID NO: 5.

22. The method of claim 21, wherein the amino acid sequence of PRG4 encoded by the nucleic acid sequence encoding PRG4 comprises an amino acid sequence that is at least identical to the sequence set forth in SEQ ID NO: 5.

* * * * *

SEQUENCE LISTING

```
<160> NUMBER OF SEQ ID NOS: 41

<210> SEQ ID NO 1
<211> LENGTH: 33136
<212> TYPE: DNA
<213> ORGANISM: Artificial Sequence
<220> FEATURE:
<223> OTHER INFORMATION: HDV with human PRG4

<400> SEQUENCE: 1
aaacatcatc aataatatac cttattttgg attgaagcca atatgataat gagggggtgg      60
agtttgtgac gtggcgcggg gcgtgggaac ggggcgggtg acgtagtagt gtggcggaag     120
tgtgatgttg caagtgtggc ggaacacatg taagcgacgg atgtggcaaa agtgacgttt     180
ttggtgtgcg ccggtgtaca caggaagtga caattttcgc gcggttttag gcggatgttg     240
tagtaaattt gggcgtaacc gagtaagatt tggccatttt cgcgggaaaa ctgaataaga     300
ggaagtgaaa tctgaataat tttgtgttac tcatagcgcg taatatttgt ctagggccgc     360
ggggactttg accgtttacg tggagactcg cccaggtgtt tttctcaggt gttttccgcg     420
ttccgggtca aagttggcgt tttgatatca agcttatcga taccgtaaac aagtctttaa     480
ttcaagcaag actttaacaa gttaaaagga gcttatgggt aggaagtagt gttatgatgt     540
atgggcataa agggttttaa tgggatagtg aaaatgtcta taataatact aaaatggctg     600
cccaatcacc tacaggattg atgtaaacat ggaaaaggtc aaaaacttgg gtcactaaaa     660
tagatgatta atggagagga tgaggttgat agttaaatgt agataagtgg tcttattctc     720
aataaaaatg tgaacataag gcgagtttct acaaagatgg acaggactca ttcatgaaac     780
agcaaaaact ggacatttgt tctaatcttt gaagagtatg aaaaattcct attttaaagg     840
taaaacagta actcacagga ataccaacc caacataaaa tcagaaacaa tagtctaaag      900
taataaaaat caaacgtttg cacgatcaaa ttatgaatga aattcactac taaaattcac     960
actgattttg tttcatccac agtgtcaatg ttgtgatgca tttcaattgt gtgacacagg    1020
cagactgtgg atcaaaagtg gtttctggtg cgacttactc tcttgagtat acctgcagtc    1080
ccctttctta agtgtgttaa aaaaaaaggg ggatttcttc aattcgccaa tactctagct    1140
ctccatgtgc tttctaggaa acaagtgtta acccaccta tttgtcaaac ctagctccaa     1200 aggactttg actccccaca aaccgatgta gctcaagaga gggtatctgt caccagtatg     1260
tatagtgaaa aaagtatccc aagtcccaac agcaattcct aaaaggagtt tatttaaaaa    1320
accacacaca cctgtaaaat aagtatatat cctccaaggt gactagtttt aaaaaaacag    1380
tattggcttt gatgtaaagt actagtgaat atgttagaaa aatctcactg taaccaagtg    1440
aaatgaaagc aagtatggtt tgcagagatt caaagaaaat ataagaaaac ctactgttgc    1500
cactaaaaag aatcatatat taaatatact cacacaatag ctcttcagtc tgataaaatc    1560
tacagtcata ggaatggatc tatcactatt tctattcagt gctttgatgt aatccagcag    1620
gtcagcaaag aatttatagc ccccttgag cacacagagg ctacaatgt gatggcctcc      1680 catctccttc atcacatctc gagcaagacg ttcagtccta cagaaataaa atcaggaatt    1740
taatagaaag tttcatacat taaactttat aacaaacacc tcttagtcat taaacttcca    1800
caccaacctg ggcaatatag tgagacccca tgcctgcaaa aaaaaaaaa ttagccaggc     1860 atggtagcat gtacctgtag tcccagctac ttgagaggtg aggtgggaaa atcactttag    1920
tgcaggatgt tgaggctgga gtgaactgtg attgtgccac tgcactccag cctggacaat    1980
agagcaagac cttgtctcaa aaaaatgcat taaaaatttt ttttaaatct tccacgtatc    2040
```

```
acatcctttg ccctcatgtt tcataaggta aaaaatttga taccttcaaa aaaaccaagc    2100
ataccactat cataattttt tttaaatgca aataaaaaca agataccatt ttcacctatc    2160
agactggcag gttctgatta aatgaaattt tctggataat atacaatatt aagagagact    2220
gtagaaactg ggccagtggc tcatgcctgt aatcccagca ctttgggagg ctgggtaaca    2280
tggcgaaccc tgtttctaca aaataaaaat attagctggg agtggtggcg cacacctata    2340
gtcccagcta ctcaggaggc tgaggtggaa ggatcgcttg aacccaggag gttgagactg    2400
cagtgaactg tgatcattct gctgcactgc accccagcct gggcaacaga gaccttgtct    2460
caaaaaaaaa aaaaaaagag acaaattgtg aagagaaagg tactctcata taacatcagg    2520
agtataaaat gattcaactt cttagaggaa aatttggcaa taccaaaata ttcaataaac    2580
tctttcccct tgacccagaa attccacttg aataaagctg aacaagtacc aaacatgtaa    2640
aagaatgttt cttctagtac agtcggtaag aacaaaatag tgtctatcaa tagtggactg    2700
gttaaatcag ttatggtatc tccataagac agaatgctat gcaaccttta aaatatatta    2760
gatagctcta gacacactaa tattaaaagt gtccaataac atttaaaact atactcatac    2820
gttaaaatat aaatgtatat atgtactttt gcatatagta tacatgcata ggccagtgct    2880
tgagaagaaa tgtgtacaga aggctgaaag gagagaactt tagtcttctt gtttatggcc    2940
tccatagtta gaatatttta taacacaaat attttgatat tataatttta aaataaaaac    3000
acagaatagc cagacataca atgcaagcat tcaataccag gtaaggtttt tcactgtaat    3060
tgacttaaca gaaaattttc aagctagatg tgcataataa taaaaatctg accttgcctt    3120
catgtgattc agccccagtc cattaccctg tttaggactg agaaatgcaa gactctggct    3180
agagttcctt cttccatctc ccttcaatgt ttactttgtt ctggtcccta cagagtccca    3240
ctataccaca actgatacta agtaattagt aaggccctcc tcttttattt ttaataaaga    3300
agattttaga aagcatcagt tatttaataa gttggcctag tttatgttca aatagcaagt    3360
actcagaaca gctgctgatg tttgaaatta acacaagaaa aagtaaaaaa cctcatttta    3420
agatcttact tacctgtcca taattagtcc atgaggaata aacacccttt ccaaatcctc    3480
agcataatga ttaggtatgc aaaataaatc aaggtcataa cctggttcat catcactaat    3540
ctgaaaaaga aatatagctg tttcaatgag agcattacag gatacaaaca tttgattgga    3600
ttaagatgtt aaaaaataac cttagtctat cagagaaatt taggtgtaag atgatattag    3660
taactgttaa cttttgtaggt atgataatga attatgtaag aaaacaacag gccgggcggg    3720
ttggttcaca cgtgtaatcc cagcactttg ggaggctgag gcaggcagac tgcctgagct    3780
caggagttcg agaccagcct gggcaacacg gtgaaatccc gtctctacta aaaatacaaa    3840
aaaattagcc gggtgtggtg acacatgcct gtagtcccag ctacttggga ggctgaggca    3900
ggagaatcac ttgaacctgg gaggtgaagg ttgcagtgag ccaagatggc accacttcac    3960
tccagcctgg gaaacagagc aagactctgt ctctgagctg agatggcacc acttcactcc    4020
agcctgggaa acagagcaag actctgtctc aaaaaaaaca aaacacacaa acaaaaaaac    4080
aggctgggcg cggtggctca cgcctgtaat cccagcactt gggaggccg aggcgggtgg    4140 atcacctgag gtcaggagtt ccagaccagc cttgtcaaca tggtgaaacc tccccccgcc    4200
gtctctacta aaaatacaaa aattagccag gcgtggtggc aggagcctgt aatcccagct    4260
acttgggagg ctgaggcagg agaatcgctt gtacccagaa ggcagaggtt gcactgagct    4320
gagatggcac cattgcactc cagcctgggg gacaagagcg agatttcgtc tttaaaaaac    4380
```

-continued

```
aaaaacaaaa caaaaaacca tgtaactata tgtcttagtc atcttagtca agaatgtaga    4440
agtaaagtga taagatatgg aatttccttt aggtcacaaa gagaaaaaga aaaattttaa    4500
agagctaaga caaacgcagc aaaatcttta tatttaataa tattctaaac atgggtgatg    4560
aacatacggg tattcattat actattctct ccacttttga gtatgtttga aaatttagta    4620
aaacaagttt taacacactg tagtctaaca agataaaata tcacactgaa caggaaaaac    4680
tggcatggtg tggtggctca cacttgtaat cccagtgctt tgggaggctg agacaggaga    4740
gttgcttgag gccaggagtt caagaccgac atggggaatg tagcaagacc ccgtccctac    4800
aaaaaacttt gtaaaaattt gccaggtatg gtggtgcata cctgtagtcc cagctactcg    4860
ggaggcggag gcagaaggaa tcacttgagc ccaggagttt gaggctgcag tgagctacga    4920
tcataccaca gcactccagc gtggacaaca gagtaagacc ctatctcaaa aacaaaacaa    4980
aacaaaacaa acaaaaaaaa ccacaagaaa aactgctggc tgatgcagcg gctcatgcct    5040
gtaatcccag tattttggga ggcccaggtg ggcgtatcac ctgaggtcag gagttagaga    5100
ccagcctggc caacatggtg aaaccccatc tctactaaaa atacaaaatt agccaggcat    5160
gtggcacgcg cctgtagtcc cagttactgg gaggctgaag caggaggatc acctgagccc    5220
gggaggtgga ggttgcagtg agccgagatc acaccactgc actccagcct gggtgacaca    5280
gcaataccct acctcaaaat aaaaaagaaa aagaaaagaa aagttgctgt ccccgctacc    5340
ccaatcccaa atccaaacag cctctctcat ctcacagtaa gggggaaaaa tcacccaaaa    5400
aagctaagtg atcttttgaa aacccaaact cttagaagtc taagattatt atagtcaact    5460
catgaagtgt catcataaaa gatactctaa tattatttaa gtagaaccac atattggttg    5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaaatcata aaagcactta tctttgaaag aggagttaca gcaattttat    5700
ttagttcttt attgctttgc tatatattct aaatttttttt caatgaatat atatcacttt    5760
taaaaaaatt caatggtctt tcttataaat tatctttggc agcatgcgtt tttatatata    5820
catataaaat gtatgggaaa tttttaaagg atacattaaa ttaaagcaaa atatacaaac    5880
aaaaaatcag aatacaaaaa gataaaaaga ttgggaaggg agggaggggag taaggaggaa    5940 gggtgggtgg gtatagagaa atataccaaa taatggtaag aagtgggggtc ttgcacttt    6000 ctacactttt tttaaataaa aaaaatttttt ttctctctct tttttttttt tagagacgaa    6060
gtctcgctat gttgcccagg ctggtcttga actcctggga tcaagagatc ctcctgcctc    6120
agcctcccaa ggtgcttgga ttacaggtgt gagccaccac gcctggtcac tttctacact    6180
ttaatatata tattttttca ttttcaatgt cattttatt agttaattta taataccat    6240 tcaccattat attcaaagtc tatttgaaga aataaaccag aaagaatgaa atactctagc    6300
tcacatgcta ttcaatacta aattaccttt caaatcacat tcaagaagct gatgatttaa    6360
gctttggcgg tttccaataa atattggtca aaccataatt aaatctcaat atatcagtta    6420
gtacctattg agcatctcct tttacaacct aagcattgta ttaggtgctt aaatacaagc    6480
agcttgactt ttaatacatt taaaaataca tatttaagac ttaaaatctt atttatggaa    6540
ttcagttata ttttgaggtt tccagtgctg agaaatttga ggtttgtgct gtctttcagt    6600
ccccaaagct cagttctgag ttctcagact ttggtggaac ttcatgtatt gtcaggttgg    6660
cccgtaatac ctgtgggaca acttcagccc ctgtgcacat ggccaggagg ctggttgcaa    6720
acattttcag gtaggtggac caggacatgc ccctggtcat ggccaggtgg aggcatagtg    6780
```

```
ctatacagca ggcagaagtc aatattgatt tgtttttaaa gaaacatgta ctactttcat    6840
aagcagaaaa aatttctatt cttgggggaa aagattatgc cagatcctct aggattaaat    6900
gctgatgcat ctgctaaacc ttcacatatc agaacatatt tactatagaa agaatgaaaa    6960
tgggacattt gtgtgtcacc tatgtgaaca ttccaaaaat attttacaac aactaagtat    7020
tttataaatt ttatgaactg aaatttagtt caagttctag gaaaatacaa accttgctag    7080
atattataaa aatgatacaa tatatattca tttcaggctc atcagaatat atctgttatc    7140
acttgacaag aatgaaaatg caccattttg tagtgcttta aaatcaggaa gatccagagt    7200
actaaaaatg acttcttcct tgaagcttac tcaccaactt cctcccagtt actcactgct    7260
tctgccacaa gcataaacta ggacccagcc agaactccct tgaaatatac acttgcaacg    7320
attactgcat ctatcaaaat ggttcagtgc ctggctacag gttctgcaga tcgactaaga    7380
atttgaaaag tcttgtttat ttcaaaggaa gcccatgtga attctgccca gagttcatcc    7440
cagatatgca gtctaagaat acagacagat cagcagagat gtattctaaa acaggaattc    7500
tggcaatata acaaattgat ttccaatcaa aacagattta cataccatac ttatgtcaag    7560
aagttgtttt gttttattgc atcctagatt ttattttttt gatttatggt ttactttaag    7620
cataaaaaat ttgtcaatac aactcttccc aaaaggcata aacaaaaatt cataaaactt    7680
gcatcacttg agatacttca ggtatgaatt cacaactttg ttacaactta ctatatatat    7740
gcacacatat atatatattt gggtatattg ggggggttct aatttaagaa atgcataatt    7800
ggctatagac agacagttgt cagaacttgg caatgggtac gtgcaggttc attataccaa    7860
gtctacttgt agttgttcaa aatgtatcat aatacaaggc cgggcgaggt cgtcacgcct    7920
gtaatcccag cattttggga ggctaaggca ggaggattgc ttgaggtcag gagtttgtga    7980
ccagcctggg caacagagca agaccctgtc tccaaaaaga aaaaaaataa ttttttacaa    8040
aataaaaaca aaatgtatca tcagacgaaa ttaaataaga ggcaattcat ttaaatgaca    8100
acttttccca gcttgacatt taacaaaaag tctaagtcct cttaattcat atttaatgat    8160
caaatatcaa atactaattt tttttttttt ttttttttttg agacggagtc tcgctctgtc    8220
gcccaggctg gagtgcagtg gcgcgatcct ggctcactgc aagctccgcc tcccgggttc    8280
acgccattct cctgcctcag cctcccgagt agctgggatt acagacatgc gccaccacgc    8340
ccggctaatt ttgtattttt agtagagatg gggtttctcc atgttggtca ggctggtctt    8400
gaatttccca cctcaggtga tctgcctgcc tcagcctcac aaagcagtag ctgggactac    8460
aggcacccac caccacactt ggttaattct tttgtatttt ttttgtaaag acgggatttc    8520
accatgttag ccaggatggt ctcgatctcc tgatctcatg atccgcccgc ctcagcctcc    8580
caaagtgctg ggattacagg cgtgagccac cccgcccggc catcaaatac taattcttaa    8640
atggtaagga cccactattc agaacctgta tccttatcac taatatgcaa atatttattg    8700
aatacttact atgtcatgca tactagagag agttagataa atttgataca gctaccctca    8760
cagaacttac agtgtaatag atggcatgac atgtacatga gtaactgtga acagtgttaa    8820
attgctattt aaaaaaaaag acggctgggc gctgtggctc atgcctgtaa tcccagcact    8880
ttgggaggcc aaggcaagtt gatcgctcga ggtcaagagt tcgagaccag cctggccaac    8940
gtggtaaaac cccgtctcta ctaaaaatac aaaaaaaaaa ttagccaggc atggtggcac    9000
aggcctgtaa tcccagctac tagggaggct gagacatgga gaactgcttg aatccaggag    9060
gcagaggtta cagtgagccg agatcatacc actacactcc agcctgagtg acagagcgag    9120
```

-continued

```
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa atcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat   10020
ttaccaaaaa cagttatata tacacaaaaa gtaaacctag aacccaaagt tacccagcac   10080
caatgattct ctccctaagc agtatcaagt ttaaagcagt gattacattc tactgcctag   10140
attgtaaact gagtaaagga gaccagcacc tttctgctac tgaactagca cagccgtgta   10200
aaccaacaag gcaatggcag tgcccaactt tctgtatgaa tataagttac atctgtttta   10260
ttatttgtga cttggtgttg catgtggtta ttatcaacac cttctgaaag aacaactacc   10320
tgctcaggct gccataacaa aataccacag actgagtgac ttaacagaaa cttatttctc   10380
acagttttgg aggctgggaa gtccaaaatt aaggtacctg caaggtaggt ttcaatctca   10440
ggcctcttct ttggcttgaa ggtcttctaa ctgtgtgctc acatgacctc ttctaacaag   10500
ctctctggtg tctcttttt ttttttttc tttttttgaga cagagtctca ctctgtcacc   10560
caggctggag tacagtggca caatctgggc tcactgcaac ctccaactcc cgggttcaag   10620
tgattctcat gcctcaccct cccgagtagc ttggatgaca ggagcccgct accacaccca   10680
gctaattttt gtatttttag tagagatggt gtttcactac attggccagg ctggtctcaa   10740
actcctgacc tcgtgatcca cccaccttgg cctcccaaag tgctgggatt acaggtgtga   10800
gccactgcgc ccgtcctggt gtcttttcat ataagggcac taatccaatc agacctgggc   10860
ccaaccctcc cgacttcttc taactgtaat taccttccaa aggccctgtc tccaaatacc   10920
atcacactgg gggttaggac ttcaaaaaag gtatggggggg ggtgtgggag gacataaatg   10980
ctcagtccat aacaagcacc caacataaaa atggctagaa cagatcacaa aaaaaaggtc   11040
ctgtatggct ttggggaagg gctcaacccc aaaatatctg agagctctgg aggggcctag   11100
aagtggtaaa tgaatgaaaa cgtggttact ctccagatct gcctttccca aatatggcca   11160
ttcttggctg aatcagaaat caaaggacag gttattaatt actagctcta agttacttac   11220
catttgctga gacagttcag aaatctgact gcatctcctc agagatctag aacacagttc   11280
tcaaattcta acttacttgt gatatacttg tgaatgataa aaatcgctac aggtactttt   11340
attaatctga aagagtattg agaaattacc tttcattctg acttttgtct ggaatgaaaa   11400
tcaatacttt tgctataatc gattactgaa ataattttac tttccagtaa aactggcatt   11460
ataatttttt ttaatttta aaacttcata attttttgcc agactgaccc atgtaaacat   11520
```

```
acaaattact aataattatg cacgtcacat ctgtaataat ggccttcatg taaacatttt   11580
tgtggtttac acataaaatc tctaattaca aagctatatt atctaaaatt acagtaagca   11640
agaaaattaa tccaagctaa gacaatactt gcaacatcaa ttcatcatct gtgacaagga   11700
ctgcttaagt ctctttgtgg ttaaaaagga aaaaaaaaaa aaagacatgt tggccagatg   11760
cggtggctca cacctgtaat cccagcactt tgggaggctg aggtgggcgg atcacccctg   11820
gcctgcccaa catggtgaaa ccccgtctct actaaaaaca caaaaattag ctgggcgtgg   11880
tggcgggcgc ctgtaattcc agctactcgg gaggctgagg caggagaatt gctagaaccc   11940
aggaggcaga gattgcagtg agctgagatt gcaccattgc actacagtct gggcaacaaa   12000
agtgaaactc catcttaaaa aaaaaaagac aatgttcgtg ggtccaaaca agacttaatg   12060
gaagtgagtc taaaaatgag ctatgtgggc caggcgtagt ggctcccacc tgtaatccca   12120
gcactttggg aggccgaagc aggcagatca tgaggtcagg agatggagac catcctggcc   12180
aacacggtga aatcctgtct ctacaaaaat tagctgggcg tggtggtgcc tgcctgtaat   12240
cccagctact cagaaggctc aggcaggaga atcgcttgaa ccagggagtc ggtggctaga   12300
gtgagccgag atttgcatca ctgcactcct gcctggtgac agagcaagac tccatctcaa   12360
aaaaaacaaa caaaaataaa agataaaaat gagctatgtg aattaaaaga ggtataacaa   12420
tagataaacc atattttatt taattcctag taatgagtaa tatttccaaa cttctggaat   12480
gggcagaaat tgctagttgg catattttta ccttttatat tcagatacat taaaattctc   12540
aaaaaaaaac acctcaaagc agatgatccg ccatctcctt ggataaatttg tgttaactca   12600 ggataacaga aaaccaaaat tatgagttac tgatgcaata ttcctaaatg taaaaataat   12660
taaagctaat agtagattca tcttccaatt tcatatcagt cttacaaata aactacatat   12720
ataacttgct tgccttccct tctgagggat aaagctgtta gaagaattaa aatcagcatt   12780
cttgactatt caaccaaggg agggataaat tattactcat tctagggaca tgggctcata   12840
actactacat gtgtaaggac atgaatttac ccaatattac aatttttcct tttattagtg   12900
tgtacagtgg aagaatagac atgttcactc tggacaaaaa aaaaattata cttatcagtt   12960
atcagaagca caatgctgaa gacagtagtt ccataacaat ttgaagtatg tgatcgaact   13020
agtagattat cttagtagta gtgaattatt gtaaatgtta gtaatttggc agccactggg   13080
cagaaaaata agaattgagg ctcaatattg atattaatgg tggtgattga cacataaatt   13140
ttatcaagtc tacacaatat aaaattacag aaaggtagaa gagtatacca gtacaacttc   13200
aacatatctt cactacaagg gagtaaaatg acatggccta gttactatct aatgaactgc   13260
agaaaactaa aagaaaactc caaggcaact cttctctgct gatctggttg gtccttttcc   13320
taccttttgc aatacccaga tacaaacaat ggatagaaaa caaagtagac ttgtagtatg   13380
caggtcacag tgctaaattc acagaaagaa acccctgaac tgaactgctc tatttcctgg   13440
tggtcacaaa gagtaattct ggtttacacc tacagattga tgtcaatcta caccctgttg   13500
ataacagtgt ggccaaggac aaaaaaaagg tgctccgttt taccaattct gtaaaaaatt   13560
attggcaggg taagctcggc tagggcagga ttacatttct aggactacca tccccgaaat   13620
ttagaagata ttatatccac ataaagcata tctttcacat taatttgcaa aaatctaaaa   13680
gctttttctt agctcaagtg tgtccaagtt taccctggca gtttaaaacg atagttacaa   13740
gcagcatggt ttgtatcaga cacatttgag ggccaatttc atgtaagtga tattgggcaa   13800
gttacttcaa ctatctgtgc ctccaaggtc atactagtgt ttatttacct aaagggtacc   13860
```

-continued

```
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
cttgagctca ggagttcaag accagcctgg acaacatggc aaaacaccat ctctacaaaa  14460
aatacaaata ttaggccggg cgcagtggct cacgcctgta atcccagcac tttgggaggc  14520
caaggcgggt ggatcacctg agatcaggag ttcgagagta gcctggccaa catggtgaaa  14580
cctcgtctct attaaaaata caaaaaatta gccaggcatg gtggcaggcg cctgtaatcc  14640
cagctactca gggggatgag gtaggagaat cgcttgaacc cgggaggcag aggttgcact  14700
gagccgagat catgccactg tactccagcc cgggcaacaa gagcgaaact ccatctcaaa  14760
aaataaataa ataaataaat aaaataaagt acaaatatta gccagggatg gtggtgcgca  14820
cctgtagtcc cagctacttg ggaggctgaa gtggagaat cccctgagcc tggggagaat  14880
cacccgagcc cgggaagtcg aggctgcagt gagcagtgat gtgccactg cactccatcc  14940 taggtgacag agtgagaccc tgtctcaaaa aaagaaatt ggcagaatta agtaagttga  15000
tgtttagaga tgaaaaatca acatttttc ctcagcaact gaataaaaac aacagccact  15060 accattttt tgagtaccta tttgtagcct attttttaac tggtattact cgagagagag  15120
agagctaggt tcgagacaga gctccttctc ttaataactg tatgacctag ggtatgtctg  15180
ttagcctctc tgaggcttca aaggttcctc atctgtaaaa tggtaataat cataccattg  15240
ctacagggct gttttgaaga ctaattagga ctatgtaagt aaacatgatg atggctatta  15300
ttactgttcc ccgccagggg ccatgcaagg gttgctgatt cacatagact gtcttataat  15360
cctctcaata actccaagag gtagccagca cctcagatat acataaaatg acttaagccc  15420
agagaggtga agtaagttgc ccacagccac acaactagta aatagcccaa acaagctgga  15480
ttcccagtta gactccgtta atagcactgc tctttacctt aagtcattac aatgcctaat  15540
atgaaataga atcgcttctt tcttagggtt caagtggtta attatttaat gtattcattc  15600
aacaaaccat catcgaggac ctcttacaag ccaagtactg tgctaagtgc tagagttacg  15660
gcggtgattc ctgcccttaa aaagttttag tgggagaaac aacaggtaac caggtcattg  15720
ccaaaacaac aaaaataatc ataataaagc aggctaaagc atatttaact ggccggggtt  15780
ttgactattt tagcaagcat gatcagaacg gttgaggagg gaggccagca gcttggccgg  15840
ttcaacaaac aagaaaaaac cagtgagggt ggagctaaga taccagaggc tgattacggt  15900
taagaatgtt cttgaaggta aggaccagat tctcattttc tatatcctgg ggcatcggtc  15960
agcatggaat ctggattcta gcacatgtga atttcggctt gaaatgacct aatgcctttt  16020
ccctagttcc ttcgtgtgtc aaatacgcat ggttaccgct accagagctg tagtggggct  16080
tcaatgaggc catgagcatc tccataaaga tgaactacag tgtgtgcaaa actaaaggca  16140
aaacctggtc cccacacgcc ctcccaggtg gtcgctttcc gtgccgaggc ccctccagag  16200
gtgccccgag aacctcacca tcgcaccccca aacttccagg gaagggcctc tcccgagaaa  16260
```

```
gcccccacgc ccccaccccg cgccatcatt cccgaatctg ccctcggccc ctccccgcag    16320
cacgctcgca ggcggcacat gtcaaccaaa acgccatttc caccttctct tcccacacgc    16380
agtcctcttt tcccagggct cccccgagga gggacccacc ccaaaccccg ccattccgtc    16440
ctccctgccg ccctcgcgtg acgtaaagcc gaacccggga aactggccgc ccccgcctgc    16500
ggggttccct gggcccggcc gctctagaac tagtggatcc caattgaagg cctggtctaa    16560
atgactccaa aatcaccact taattcaaga gactgatttc cctgagtcag gccccttaaa    16620
gcagctattt caatgggaca gggaaacaac cctaggatct ggattagaat cacttggggg    16680
ctgccacacc cccagggctc tgatcctgcc cttctcccac acgcacattc acatactgct    16740
gcagtgacct tccatttcta atgggttcct gggccatctg tcaggtatag ggaatggaaa    16800
aggggttggg gaggctctgc ttcagaaagt ttgtgtcagg ggctcccaga gcctccacag    16860
atagatagca ggggtcccca ccctaccatg gcagctataa atgtgatcaa catttattgg    16920
cctaggatac agcagttagc aaaatgcctg atgtagttcc cactccgtgg aggttgcagg    16980
ctagccaaga agtcatgagt tcagcaaccc ttacgcacca gtgggatgag attggaccag    17040
gccgagggta gtcttgggaa cactcagcat ttgtctgagg gccagaagag gctgcttgcc    17100
ctcagacagg aggtcagcat ctttattgta gcccatgaca cctctacacc attgctcttc    17160
tggtcttatg gaagacatct ttgggcctga taacagcgga gtctgtgtcc cacttgtcca    17220
ggctggagtg ccacatcagg cacactccag ttgcagggac agcacagaca agtttcagga    17280
aggctggtgg cctccaggag gttaacctta taaggccaga ttgtaaccta gttgaaaaac    17340
atacacatgc catgataata aaagaaccta ggcaccatta caagagaaaa aatcattttt    17400
gtagatacga gcatggattc ttgggtgggt cagacacact gggcttgtgc tctgactgca    17460
ctgtctcccc tacctgacct tgggtaaacc ataagactgc tgcatgactc agtgtccacc    17520
ccaaaaaagt accggtagat attggccaca gtagatatca gctagagtgg actctcatga    17580
caatgagggg agatgtattc cccatcttag gcacctggga ctctaccttc catcttctgc    17640
tccgtgtctc tccatcccca ggctcttcag aactcaggga gtccagaatg tcagctccca    17700
gatttcagcc ttcagaaagg aaacccatta ccgttcagtt gaacaaatgt tgtctgagcc    17760
ccagatctgg gctcagaggc catctaggct atgagacaag aggggaacaa agcaccgtct    17820
gcactcactc accacactca cttgctgtcc caggtcacat ccatcgggta gagaatctaa    17880
gaggctgagc tagctcccgc caccagccca gcccacccca cctggcccct tccttccttc    17940
tacaaaatat gcaccacctg tcaaagggtg ggcagtgcca ggcctgcata cagagcactg    18000
agtgtaaaag cagacatgga ccctgacctc caggagcttc caattttctt gaagagacaa    18060
atcagctggc atttcagtcc agtgtgatct gctcttggtg agcacagacc tagggagttg    18120
gggcagcttc ccagaagaac tgcagtccag gctgagggca gagaaatgag gggaatggcg    18180
aggaattggg gagcaggggg gagctcagta gagagccaag ggcgggaggt gagaagtccg    18240
tgttgggcca ggagctaccc tccggtggcc acagccgaag tcgaggatgc ctttggaact    18300
catccccact tctctctttc tgtatgtagc cgtccaagaa caagtcacct ccaagtgtag    18360
ccggatcaag gcaagccccc catctagcaa gcacttgatg ccacccagaa ctgggcttct    18420
tcagaacaat ctgagtccag gaatgatccc actcaccagg caccagagct gcgagggcat    18480
gggagtgatc tcaccaactc tggggaagcg gcaaggaatt ttcacctcca gcccccagtg    18540
tcccatcctc tcacactcag gccagactcc cctgggcaga cttgactctg tctgccagca    18600
```

-continued

```
tatgcagagc cccaaggcca ccccaccaga agtgcccctg cctgggttct gtcccagctc   18660
cctgggcacc cagtccttga gtccccacca gctcagacgg cctagtgtgc caagaatgcc   18720
cactgcgttc aacaatgctg catgggtcac agcggcagca gctgtgacca cagcagtttc   18780
ggggaaaaca cccctcagcc aagtggataa tagcgttcag cagcactcac cttctggcca   18840
ggcctgcctt cagaggccat ctgattggga ggcacaagtg cccgctgcga tgggaacaca   18900
agtgcccctg gccaacaacc ccagcttcag cctgctgggc agccagagcc tcaggcagag   18960
cccggtacag ggcccggtgc ctgtagcaaa caccaccaag ttcctccagc agggtatggc   19020
cagctttagt cccctgagcc ccatacaggg catcgagcca ccaagctatg tggctgctgc   19080
tgccaccgct gctgctgctt ctgccgttgc tgccagccag ttcccaggtc cgttcgacag   19140
aacggatatt ccccctgagc tgccacctgc cgactttttg cgccagcccc aacccccact   19200
aaatgatctg atttcgtcac ctgactgcaa tgaggtagat ttcattgaag ctctcttgaa   19260
aggctcctgt gtgagcccag atgaagactg ggtgtgcaac ttgaggctga tcgacgacat   19320
tttggaacag catgctgctg ctcaaaatgc cacagcccag aattctgggc aagtcaccca   19380
ggatgctggg gcactttaaa tctgagcagg atgcccatag aaaccccat ggtgacatca   19440 ctctaggaag tggtgtcgat ccatacccgc agttgtctcc cgttacaatt tgagtggtgt   19500
tgtcagccca tgcttatccc tctctctacc tgtgacaaaa tggaaagctg gtgattttc   19560 aagctacgtg tacatatttg aaaatttgt aaatggtttt cctaaacatt aatgacagaa   19620
gtatttatac ttcattttgt gactttgtaa ataaagcgac ggcttttgtt tcagtagagt   19680
tgtgtttact atgcattgtt ttgtgtttat tatacaatgt tacaaatatg cagaccgtgt   19740
tgtttgctcc agtgatacct tgttaagcta ggtggctgag tcgcttatgg ttttaatgca   19800
atgagcaatg tggatatgac caagagttgt tgtgcaagtt gacaaatgcc aaatagaaaa   19860
ccacttggcc atttatttct atgttcacta aaaatcctat tgccttgtgt gattcttaat   19920
ctcttttgcg aacctttcag tctccgctag ctctttccta atgagcttta cagcagaagc   19980
tgttttatcg ttaagtgccc cacagagaca ctttaccagg aggctgggag agttctccag   20040
atttgggaga ggcgcagaga cagtgtgtga gccgagccct gtctcagcaa tccacctgga   20100
ggagctagag tatcctcctc cctttaccat tcagaccgag agaaaaagcc cagcttgtgt   20160
gcaccctcgt ggggttaagg cgagctgttc ctggtttaaa gcctttcagt atttgttttg   20220
atgtaaggct ctgtggtttg ggggggaaca tctgtaaaca ttattagttg atttggggtt   20280
tgtctttgat ggtttctatc tgcaattatc gtcatgtata tttaagtgtc tgttatagaa   20340
aacccacacc cactgtcctg taaacttttc tcagtgtcca gactttctgt aatcacattt   20400
taattgccac ctcgtatttc acctctacat ttgaaatctg gcgtctgttt caagccagtg   20460
tgttttttct tcgttctgta ataaacagcc aggagaaaag tgcctctatg tttttatttt   20520
tcaagggagt attcagtacc tacaaaccca agtcaggaag cctgctagtg gctttggttc   20580
tttcagaggc tgctcgatgc cttgtgtgtc agaaagaaag attcagcagt tttgcatcat   20640
ggcaaagaag cctgttattt tggggctcag cccctcattt tatagaggat gaaacagagg   20700
gggatgggag gtcacaaaga caactgcccc gggagcaggt gtgggggaga cttgccctga   20760
gggtctagac gctctgcacc accgtcctgt ctcccttgct gaagaccaca catgcccttc   20820
tttgaccaga ccctgccacc tgataggcca ggacctggta ggcgggtacc caggtttcat   20880
ggatggaacc acatctcccc aaaagtgggg aggtagctac tgggatgcac gcctcccgcc   20940
atgtgctata ggagagcagc tgaagcaaca gttgggatca gatgtagtca caattgaatg   21000
```

```
catcatcaca tttatccctc taagtggctg ggagagttga tatcctcatc cctaaggtac    21060
aaaatgttcc aatttgatca gtggctttca ggagctgaga aaggcatgtg ctctgaggca    21120
gagctgttat gtcccgcaga gcctaaaaat gctctaagaa catgctccct gccaaaattc    21180
tcaatggctg tgacaaggga caacgatcga ccaatggggg tggaagcaga cctccgcagt    21240
ccaggggcca gagctaggac agaggggtcg gagaaagagt cattttccca acactccagc    21300
tcttggccag tcctcacaca gtcccctcct gcttcctgct gagagagata tcctcatagg    21360
tctgggtaaa gtccttcagt cagctttcat tccctgtcac caactttgtc tctgttctcc    21420
ctgcccgtct caggcagcac tcctcaggaa acctctccaa gagccagcct cactgcagcg    21480
cccactattg tccctctgcc tcaagtgtcc catccatgcc aggccccagg caggctgcag    21540
ctttccctca gggccacacc aaagcacttg ggctcagctg tgctgtcccc ctccatcact    21600
gagctcaggg gcagcagggg tggggtgcca ggaggcccat tcacccttct ctggctctgt    21660
gttggaccca cctgcccagc cactgctgct tagaacctac ccgctgggaa aatgaagccc    21720
tcccggaggg gccacctcaa cctgagagcc tcacggatca cagttgtccc cactcagctc    21780
tgccagccct cagagaccca tagataaaag ctgagcttgg ctcgcagagc tggttccatc    21840
ttccattccc agagggttca acttcctacc ccaaccacac agggaacctc aaggctgagc    21900
cagtgtgggc tgcagtgcag accagcttcc tggacacgtc ctgccacctg accccaggct    21960
ggcctcactg cccctggcac tcctgaccct atcctcattc ctcctggcag tgcgtgttct    22020
gccattccgc tttcccttag ctgtcctctc actgtactgt cagcttctcc ttttccaggt    22080 gcccccagg ggctttccac atgaccctgt caccccacag cccatccagc accaattcca     22140
gctctctgcc acccttcaaa ggagtgacag tgccctgctt cacctcccac tcacccctca    22200
acccagagca atctggctcc agtcttgcct ccttcccct aagtactcta gtcacagttc     22260
caaattcctc ctggtcataa agccaaatga agcttcctgg tcctcagcgg acttgccact    22320
tcagcagtac tggactctct cctcccagaa acctgtttcc ccttggctcc tggagcccac    22380
actctgctgg aatccttctg cctctctggc ctgtagcctg gccctctctc ccaacctgag    22440
gtccattctc tcctgctcct ccacaagatg ttgctccttc cattacttcc tccctctcaa    22500
ccaaagctcc ttcattagct ctttatcttc tggtttcttc ccctgggcag acgaatggat    22560
tcaagagcct gtggcccagc agcccagcac tccaggatct cagcacttca gcatcccagt    22620
accctagcat ctcaataccc cagcacccca gcaccatagt attccagcac cccattgtcc    22680
aagcatctca gcactccagc atcccagcac cccaacactc cagcagccca gaatctcagc    22740
accctagcac tgcagcatct caggacccca gcacttcagc atcccagcac actagtactc    22800
cagcatctcg gcaccccagc acctaggcat cccaacaccc agcaccccag cacttaagca    22860
tcccaccact acagtatctc aacactccag cacccagca ccatagtgtt ccagcacccc     22920
agcatcccaa cacccagca cttaagcatc caacacctc ggcatcccaa cacccagca      22980 ctgcagcatc tcagcacctt agcatcccag tgccctagca tctcaatgct ccagcacacc    23040
agtactacag tattccagca ccccagcact ccagcatctc agcactgcag cactgcagca    23100
ctccagcatc ccaaaatccc agcatcccaa cacccagca gaccagcaga ccagcatctc     23160
agcaccgcag catccaagga ctatcccagc atcccagcaa cccagcacct cagcatccca    23220
acaccccagc atttcagcat ggcaacaccc cagtacccca gcacttcagc accccagtat    23280
cccagcatct cagcgaccca gtatcacaaa acctcagcat cctagcaccc cagcacccca    23340
```

-continued

```
gcaccttagc accttagcat cccagcatct cagcgcctca gcatcttgat attctggctg   23400
aggtcagcgt ggtgtatcta gtcagggtcc taactttcac ttcgcaggga aatgctgctg   23460
gactgggtct catgttgggc tgaagctctc tagacccctt gaagacagca taaaagagct   23520
tggagacgct gggtgtcccc catggaagag ttcactctca tcctgctttg acaacagcct   23580
tctctggggt ccctcacggg cccctctttc ttactgcaag tttgtctctg agaagactgt   23640
gatgcagaag tcactcagct gcctgtggct cctgaagagc tgaaggtgga ggcctgtagg   23700
cctccctatg agaggcgcag aaaaaaccat gattgctagt ggggaggtgc tccctctaca   23760
acccactcca taatctgccc ccgcccagct ctgaggccag ccccagggga aaatgccaga   23820
tccccaggga ggtgtgtgag acctcagggg ctccctcctc ccttacagca ggctcaggcc   23880
cctgggggcc tcagggccaa ggtctgtggg taagctacta tctctcactt gtcctctagc   23940
cacaaaagcc agggagatct ggcaatggac atgaggttct gaagaagcac atatgactgg   24000
cttcctaatg cgtggttgtt cagtgattca ataaacacgc atgggccagg catgggaaa   24060 tagacaaaca tgatccccaa cctctcccag agtgaactgg gagggaggag tgttcatccc   24120
tcaggattac accagagaaa caaaccagca ggagatatat atggttttgg ggggtcaaga   24180
aagaggaaaa acctggcaag gcaagtccaa aatcatagga caggctgtca ggaagggcag   24240
cctggaacct ctcaagcagg agctgatgct gcagtccaca ggcagaattt cttcttcctc   24300
ggggaaatct cagctttgtt cttaaggcct ttcaactgat tggctgaggt ctgccccttc   24360
ccccacattc tccaggataa tcttccttac ttaaagtcaa ctattaatca cagctacaaa   24420
atcccttcac agctacacat agatcagtgt ttgattgacg aacagcccct acagcctagc   24480
caagttgaca cataaaacta accatcacag ggggacaaat gatgtaaaca catcaacaaa   24540
taaaacagta acaagttaag gtctatggaa aaaacacaga aggggcagag agaaagaaag   24600
caagaaggag agtcccagtt tgctagggct tgtgggaagt ggggagcagt tctctttagc   24660
taggatattt gggaaaggca tatctgaagg agtgatattt gagcttagat taaaagatgg   24720
gaaggagcaa gccatgcaaa gagctaggat gttccaagca gagacggaac agcaagtgca   24780
aatgtcagga ggaatagaag gaggctggtg ggtggggtcc agtgagcaag aggagggcag   24840
gcaggagagg ggatggggag gtgggcaggc ccagaccacc cagggccctg gagactatcc   24900
tgatccaaca agggaagcct tgagtcactt cagtgtccat gtggagaatg gacctcagac   24960
tgaatgaggg aggcagtaag gagggcctct acctccaggg cttcgccctg tggactgcgc   25020
atagacatct ccaactcaga aagtctgaac caaactttcc atagttcccc caagtctggg   25080
catcctccta ctcagtgaaa ggcagccatc acacctccct gccctgctcc cggatgcccc   25140
aaatcctctt ggtctccaag tccagaacct gagacttgtc cttgatgttt gtctttccct   25200 cacccttct gtattctggg aagatgggtt tttttccccc agatgaatct gtaaaacttc    25260
tgtgatcaca ataaaaattc tggcagtatt attttctgga acatgacaaa gtgattcaaa   25320
attatttatc tggaagacta caaaacaaga atagccagga aatttctaaa aagaaagaag   25380
aaggaggagg agaaagaagg aggaggaaaa ggaggagaag aagaaagaa aaagaaccaa    25440 gaaagggttc tagctctacc aaatattaaa acatatcatg aagctattta aaacaatatg   25500
gttgtggata ctgaaaaaga tgtgaataaa gtggaaggaa aataaataga aatgcacatg   25560
gggattgaga ctgtgaaaaa ggcagcatct cacatcagtg agggatgttc aacacctggt   25620
gttgggaaaa ctggctagtc atttaaacca aacaactggg tcctctacct cactcctgac   25680
attaagatac atttagatga ttcaaagagt aagacagaaa aaataacacg tgaaaacact   25740
```

-continued

```
atcagaaaac aacgtgggcc aggtgtggtg ggtcacgcct gtaatcccag cactttggga   25800
ggccgaggca gacagatcac ctgaggtggg gagttcaaga ccagcctgac caacatggtg   25860
aaatcctgtc tctactaaaa atacaaaatt agctgagcgt ggtggcgcat gcctgtaatc   25920
ccagctactc aggaggccga ggcaggagaa tcacttgaac ctgggaggca gaggttgtgg   25980
tgagccgaga tcacgccatt gcactccagc ctgggcaaca agagtgaaaa tccatctaaa   26040
aaaaaaaaaa aaagccaagg tggatatttt tatagtatca gggtagatca agcttctcca   26100
atcatgacat gaaacccaga aaccataaaa gaaaagaatg ataaaattgc ccacgtaaag   26160
taaaaagctt gcacacagaa aaacaccata caggttacaa gatgagcagc aaaatcagag   26220
aaaaaacatt gcaattcagg acacacagag gctattgttc ctaatattta aaaataaaag   26280
tagtggattg tctacaaaaa gatgaagaca agaatttcag aaaaccaaat actgcatgtt   26340
ttcacttaca agtggaagct aaacactgag tacacgtgta cacaaagaat ggaaccatag   26400
gccaggcacc gtggctcacg cctgtaatcc cagtactttg cgaggccgaa gcgggcggat   26460
cacctgaggt gaggagttcg agaccatcct ggccaacatg gtgaaaccca gtctctacta   26520
aaaatacaaa aattagccgg gcgtggtggt gggtgcctgt aatcccagct actcgggagg   26580
ctgcggcagt agaatcgctt gaaccctgga ggtggacctt gcagtgagcc gagatcgcac   26640
cactgcactc cagcctgggc aacagagtga gactccatct caaaaaaaaa aaaaaggaat   26700
agaacaatag acactggggc ctacttgagg gaggagggtg aggatcaaaa acctgcctat   26760
caggtactat gcttattacc tgggtggtga aataatctgt acaccaaacc ccagtgacat   26820
gcaatttacc gatgtaacaa acctgcccat gtacccgctg aacctaaaat aaaagttgga   26880
aaaaaatata gaaattttct ttgtaatagc caaaaactgc aaacagccca ggtgtctatt   26940
agtagaatgc ataaacaaac tcgggcatgt tcatacaatg taaaactact catcaataaa   27000
aagtgatact tctcagcaat gaaaagaaac tagctactga taccagctac aacatggatg   27060
gatttcaagt gctttatgat gagagcaaga agccagacac aaaagtgtct atatatatat   27120
acagtatata tacgtatata tacacatata tacagtatat atatacatat acatgtatat   27180
atatactgta tatatactgt atatatatac acagtatata tatacatata tacagtgtat   27240
atatactgtg tatatataca tgtatatata ctgtgtatat atacatgtat atatactgtg   27300
tatatataca tgtatatata ctgtgtatat atacatgtat atatatgtat actgtatata   27360
tactgtatat atatacac atatatacag tatatatata cagtatatac tgtatatata   27420
cagtatatac gtgtatatat acatatatac agtatatatg taaatataca tatatacagt   27480
atatatgtaa atatacatat atacatgtat atatatacac tatatatata catatatagt   27540
gtatatatac atatatacat gtatatattt actatatgat tccatttata taaagtgcca   27600
aaacagtcaa aaataatcta tgtggaaaaa atcaacaaag ggatcccccg ggctgcagga   27660
attcgatggc gcgccgtcga cccaacgcgt tgggagctct ccggatccaa gcttcgaggg   27720
gctcgcatct ctccttcacg cgcccgccgc cctacctgag gccgccatcc acgccggttg   27780
agtcgcgttc tgccgcctcc cgcctgtggt gcctcctgaa ctgcgtccgc cgtctaggta   27840
agtttaaagc tcaggtcgag accgggcctt tgtccggcgc tcccttggag cctacctaga   27900
ctcagccggc tctccacgct ttgcctgacc ctgcttgctc aactctacgt ctttgtttcg   27960
ttttctgttc tgcgccgtta cagatccaag ctgtgaccgg cgcctacgta agtgatatct   28020
actagattta tcaaaaagag tgttgacttg tgagcgctca caattgatac ttagattcat   28080
```

```
cgagagggac acgtcgacta ctaaccttct tctctttcct acagctgaga tcaccggcga    28140
aggagggcca ccatgcatgg catggaaaac acttcccatt tacctgttgt tgctgctgtc    28200
tgttttcgtg attcagcaag tttcatctca agatttatca agctgtgcag ggagatgtgg    28260
ggaagggtat tctagagatg ccacctgcaa ctgtgattat aactgtcaac actacatgga    28320
gtgctgccct gatttcaaga gagtctgcac tgcggagctt tcctgtaaag gccgctgctt    28380
tgagtccttc gagagaggga gggagtgtga ctgcgacgcc caatgtaaga agtatgacaa    28440
gtgctgtccc gattatgaga gtttctgtgc agaagtgcat aatcccacat caccaccatc    28500
ttcaaagaaa gcacctccac cttcaggagc atctcaaacc atcaaatcaa caaccaaacg    28560
ttcacccaaa ccaccaaaca agaagaagac taagaaagtt atagaatcag aggaaataac    28620
agaagaacat tctgtttctg aaaatcaaga gtcctcctcc tcctcctcct cttcctcttc    28680
ttcttcaaca attcggaaaa tcaagtcttc caaaaattca gctgctaata gagaattaca    28740
gaagaaactc aaagtaaaag ataacaagaa gaacagaact aaaaagaaac ctacccccaa    28800
accaccagtt gtagatgaag ctggaagtgg attggacaat ggtgacttca aggtcacaac    28860
tcctgacacg tctaccaccc aacacaataa agtcagcaca tctcccaaga tcacaacagc    28920
aaaaccaata aatcccagac ccagtcttcc acctaattct gatacatcta aagagacgtc    28980
tttgacagtg aataaagaga caacagttga aactaaagaa actactacaa caaataaaca    29040
gacttcaact gatggaaaag agaagactac ttccgctaaa gagacacaaa gtatagaaa    29100 aacatctgct aaagatttag cacccacatc taaagtgctg gctaaaccta cacccaaagc    29160
tgaaactaca accaaaggcc ctgctctcac cactcccaag gagcccacgc ccaccactcc    29220
caaggagcct gcatctacca cacccaaaga gcccacacct accaccatca agtctgcacc    29280
caccaccccc aaggagcctg cacccaccac caccaagtct gcacccacca ctcccaagga    29340
gcctgcaccc accaccacca aggagcctgc acccaccact cccaaggagc ctgcacccac    29400
caccaccaag gagcctgcac ccaccaccac caagtctgca cccaccactc caaggagcc    29460 tgcacccacc accccaaga gcctgcccc aactacccc aaggagcctg cacccaccac    29520
tcccaaggag cctacaccca ccactccaa ggagcctgca cccaccacca aggagcctgc    29580
acccaccact cccaaagagc ctgcacccac tgcccccaag aagcctgccc caactacccc    29640
caaggagcct gcacccacca ctcccaagga gcctgcaccc accaccacca aggagccttc    29700
acccaccact cccaaggagc ctgcacccac caccaccaag tctgcaccca ccactaccaa    29760
ggagcctgca cccaccacta ccaagtctgc acccaccact cccaaggagc cttcacccac    29820
caccaccaag gagcctgcac ccaccactcc caaggagcct gcacccacca ccccaagaa    29880 gcctgcccca actaccccca aggagcctgc acccaccact cccaaggaac ctgcacccac    29940
caccaccaag aagcctgcac ccaccactcc caaagagcct gccccaacta ccccaagga    30000 gactgcaccc accaccccca agaagctcac gcccaccacc cccgagaagc tcgcacccac    30060 caccctgag aagcccgcac ccaccacccc tgaggagctc gcacccacca ccctgagga    30120 gcccacaccc accacccctg aggagcctgc tcccaccact cccaaggcag cggctcccaa    30180 caccctaag gagcctgctc caactacccc taaggagcct gctccaacta cccctaagga    30240
gcctgctcca actaccccta aggagactgc tccaactacc cctaaggga ctgctccaac    30300 taccctcaag gaacctgcac ccactactcc caagaagcct gccccaagg agcttgcacc    30360 caccaccacc aaggagccca catccaccac ctgtgacaag cccgctccaa ctaccccta    30420 ggggactgct ccaactaccc ctaaggagcc tgctccaact accccctaagg agcctgctcc    30480
```

```
aactacccct aaggggactg ctccaactac cctcaaggaa cctgcaccca ctactcccaa   30540
gaagcctgcc cccaaggagc ttgcacccac caccaccaag gggcccacat ccaccacctc   30600
tgacaagcct gctccaacta cacctaagga gactgctcca actacccca aggagcctgc    30660 acccactacc cccaagaagc ctgctccaac tactcctgag acacctcctc caaccacttc   30720
agaggtctct actccaacta ccaccaagga gcctaccact atccacaaaa gccctgatga   30780
atcaactcct gagctttctg cagaacccac accaaaagct cttgaaaaca gtcccaagga   30840
acctggtgta cctacaacta agactcctgc agcgactaaa cctgaaatga ctacaacagc   30900
taaagacaag acaacagaaa gagacttacg tactacacct gaaactacaa ctgctgcacc   30960
taagatgaca aaagagacag caactacaac agaaaaaact accgaatcca aaataacagc   31020
tacaaccaca caagtaacat ctaccacaac tcaagatacc acaccattca aaattactac   31080
tcttaaaaca actactcttg cacccaaagt aactacaaca aaaaagacaa ttactaccac   31140
tgagattatg aacaaacctg aagaaacagc taaaccaaaa gacagagcta ctaattctaa   31200
agcgacaact cctaaacctc aaaagccaac caaagcaccc aaaaaaccca cttctaccaa   31260
aaagccaaaa acaatgccta gagtgagaaa accaaagacg acaccaactc cccgcaagat   31320
gacatcaaca atgccagaat tgaaccctac ctcaagaata gcagaagcca tgctccaaac   31380
caccaccaga cctaaccaaa ctccaaactc caaactagtt gaagtaaatc caaagagtga   31440
agatgcaggt ggtgctgaag gagaaacacc tcatatgctt ctcaggcccc atgtgttcat   31500
gcctgaagtt actcccgaca tggattactt accgagagta cccaatcaag gcattatcat   31560
caatcccatg ctttccgatg agaccaatat atgcaatggt aagccagtag atggactgac   31620
tactttgcgc aatgggacat tagttgcatt ccgaggtcat tatttctgga tgctaagtcc   31680
attcagtcca ccatctccag ctcgcagaat tactgaagtt tggggtattc cttcccccat   31740
tgatactgtt tttactaggt gcaactgtga aggaaaaact ttcttcttta aggattctca   31800
gtactggcgt tttaccaatg atataaaaga tgcagggtac cccaaaccaa tttttcaaagg  31860 atttggagga ctaactggac aaatagtggc agcgctttca acagctaaat ataagaactg   31920
gcctgaatct gtgtattttt tcaagagagg tggcagcatt cagcagtata tttataaaca   31980
ggaacctgta cagaagtgcc ctggaagaag gcctgctcta aattatccag tgtatggaga   32040
aacgacacag gttaggagac gtcgctttga acgtgctata ggaccttctc aaacacacac   32100
catcagaatt caatattcac ctgccagact ggcttatcaa gacaaaggtg tccttcataa   32160
tgaagttaaa gtgagtatac tgtggagagg acttccaaat gtggttacct cagctatatc   32220
actgcccaac atcagaaaac ctgacggcta tgattactat gccttttcta aagatcaata   32280
ctataacatt gatgtgccta gtagaacagc aagagcaatt actactcgtt ctgggcagac   32340
cttatccaaa gtctggtaca actgtcctta gaaaaaaaaa aaaaaaaagg ccacatgtgc    32400
tcgagctgca ggtcgcggcc ctagctcgac atgataagat acattgatga gtttggacaa   32460
accacaacta gaatgcagtg aaaaaaatgc tttatttgtg aaatttgtga tgctattgct   32520
ttatttgtga aatttgtgat gctattgctt atttgtaac cattataagc tgcaataaac    32580
aagttaacaa caacaattgc attcatttta tgtttcaggt tcaggggggag gtgtgggagg   32640 ttttttaaag caagtaaaac ctctacaaat gtggtagatc atttgggta ccgaattcct     32700 cgagtctaga ggagcatgcg acgtcggcgc gcctaccagt aaaaaagaaa acctattaaa   32760
aaaacaccac tcgacacggc accagctcaa tcagtcacag tgtaaaaaag ggccaagtgc    32820
```

```
agagcgagta tatataggac taaaaaatga cgtaacggtt aaagtccaca aaaaacaccc      32880
agaaaaccgc acgcgaacct acgcccagaa acgaaagcca aaaaacccac aacttcctca      32940
aatcgtcact tccgttttcc cacgttacgt cacttcccat tttaagaaaa ctacaattcc      33000
caacacatac aagttactcc gccctaaaac ctacgtcacc cgccccgttc ccacgccccg      33060
cgccacgtca caaactccac cccctcatta tcatattggc ttcaatccaa aataaggtat      33120
attattgatg atgttt                                                     33136

<210> SEQ ID NO 2
<211> LENGTH: 31815
<212> TYPE: DNA
<213> ORGANISM: Artificial Sequence
<220> FEATURE:
<223> OTHER INFORMATION: HDAd with murine PRG4

<400> SEQUENCE: 2
aaacatcatc aataatatac cttattttgg attgaagcca atatgataat gagggggtgg        60
agtttgtgac gtggcgcggg gcgtgggaac ggggcgggtg acgtagtagt gtggcggaag       120
tgtgatgttg caagtgtggc ggaacacatg taagcgacgg atgtggcaaa agtgacgttt       180
ttggtgtgcg ccggtgtaca caggaagtga caattttcgc gcggttttag gcggatgttg       240
tagtaaattt gggcgtaacc gagtaagatt tggccatttt cgcgggaaaa ctgaataaga       300
ggaagtgaaa tctgaataat tttgtgttac tcatagcgcg taatatttgt ctagggccgc       360
ggggactttg accgtttacg tggagactcg cccaggtgtt tttctcaggt gttttccgcg       420
ttccgggtca aagttggcgt tttgatatca agcttatcga taccgtaaac aagtctttaa       480
ttcaagcaag actttaacaa gttaaaagga gcttatgggt aggaagtagt gttatgatgt       540
atgggcataa agggttttaa tgggatagtg aaaatgtcta taataatact aaaatggctg       600
cccaatcacc tacaggattg atgtaaacat ggaaaaggtc aaaaacttgg gtcactaaaa       660
tagatgatta atggagagga tgaggttgat agttaaatgt agataagtgg tcttattctc       720
aataaaaatg tgaacataag gcgagtttct acaaagatgg acaggactca ttcatgaaac       780
agcaaaaact ggacatttgt tctaatcttt gaagagtatg aaaaattcct attttaaagg       840
taaaacagta actcacagga aataccaacc aacataaaa tcagaaacaa tagtctaaag       900
taataaaaat caaacgtttg cacgatcaaa ttatgaatga aattcactac taaaattcac       960
actgattttg tttcatccac agtgtcaatg ttgtgatgca tttcaattgt gtgacacagg      1020
cagactgtgg atcaaaagtg gtttctggtg cgacttactc tcttgagtat acctgcagtc      1080 cccttctta agtgtgttaa aaaaaaggg ggatttcttc aattcgccaa tactctagct      1140
ctccatgtgc tttctaggaa acaagtgtta acccaccta tttgtcaaac ctagctccaa      1200 aggactttg actccccaca aaccgatgta gctcaagaga gggtatctgt caccagtatg      1260
tatagtgaaa aaagtatccc aagtcccaac agcaattcct aaaaggagtt tatttaaaaa      1320
accacacaca cctgtaaaat aagtatatat cctccaaggt gactagtttt aaaaaaacag      1380
tattggcttt gatgtaaagt actagtgaat atgttagaaa aatctcactg taaccaagtg      1440
aaatgaaagc aagtatggtt tgcagagatt caaagaaaat ataagaaaac ctactgttgc      1500
cactaaaaag aatcatatat taaatatact cacacaatag ctcttcagtc tgataaaatc      1560
tacagtcata ggaatggatc tatcactatt tctattcagt gctttgatgt aatccagcag      1620
gtcagcaaag aatttatagc cccccttgag cacacagagg ctacaatgt gatggcctcc      1680 catctccttc atcacatctc gagcaagacg ttcagtccta cagaaataaa atcaggaatt      1740
```

```
taatagaaag tttcatacat taaactttat aacaaacacc tcttagtcat taaacttcca    1800
caccaacctg ggcaatatag tgagacccca tgcctgcaaa aaaaaaaaaa ttagccaggc    1860
atggtagcat gtacctgtag tcccagctac ttgagaggtg aggtgggaaa atcactttag    1920
tgcaggatgt tgaggctgga gtgaactgtg attgtgccac tgcactccag cctggacaat    1980
agagcaagac cttgtctcaa aaaaatgcat taaaaatttt ttttaaatct tccacgtatc    2040
acatcctttg ccctcatgtt tcataaggta aaaaatttga taccttcaaa aaaaccaagc    2100
ataccactat cataattttt tttaaatgca aataaaaaca agataccatt ttcacctatc    2160
agactggcag gttctgatta aatgaaattt tctggataat atacaatatt aagagagact    2220
gtagaaactg ggccagtggc tcatgcctgt aatcccagca ctttgggagg ctgggtaaca    2280
tggcgaaccc tgtttctaca aaataaaaat attagctggg agtggtggcg cacacctata    2340
gtcccagcta ctcaggaggc tgaggtggaa ggatcgcttg aacccaggag gttgagactg    2400
cagtgaactg tgatcattct gctgcactgc accccagcct gggcaacaga gaccttgtct    2460
caaaaaaaaa aaaaaaagag acaaattgtg aagagaaagg tactctcata taacatcagg    2520
agtataaaat gattcaactt cttagaggaa aatttggcaa taccaaaata ttcaataaac    2580
tctttcccct tgacccagaa attccacttg aataaagctg aacaagtacc aaacatgtaa    2640
aagaatgttt cttctagtac agtcggtaag aacaaaatag tgtctatcaa tagtggactg    2700
gttaaatcag ttatggtatc tccataagac agaatgctat gcaaccttta aaatatatta    2760
gatagctcta gacacactaa tattaaaagt gtccaataac atttaaaact atactcatac    2820
gttaaaatat aaatgtatat atgtactttt gcatatagta tacatgcata ggccagtgct    2880
tgagaagaaa tgtgtacaga aggctgaaag gagagaactt tagtcttctt gtttatggcc    2940
tccatagtta gaatatttta taacacaaat attttgatat tataatttta aaataaaaac    3000
acagaatagc cagacataca atgcaagcat tcaataccag gtaaggtttt tcactgtaat    3060
tgacttaaca gaaaattttc aagctagatg tgcataataa taaaaatctg accttgcctt    3120
catgtgattc agccccagtc cattaccctg tttaggactg agaaatgcaa gactctggct    3180
agagttcctt cttccatctc ccttcaatgt ttactttgtt ctggtcccta cagagtccca    3240
ctataccaca actgatacta agtaattagt aaggccctcc tcttttattt ttaataaaga    3300
agattttaga aagcatcagt tatttaataa gttggcctag tttatgttca aatagcaagt    3360
actcagaaca gctgctgatg tttgaaatta acacaagaaa aagtaaaaaa cctcatttta    3420
agatcttact tacctgtcca taattagtcc atgaggaata aacacccttt ccaaatcctc    3480
agcataatga ttaggtatgc aaaataaatc aaggtcataa cctggttcat catcactaat    3540
ctgaaaaaga aatatagctg tttcaatgag agcattacag gatacaaaca tttgattgga    3600
ttaagatgtt aaaaaataac cttagtctat cagagaaatt taggtgtaag atgatattag    3660
taactgttaa ctttgtaggt atgataatga attatgtaag aaaacaacag gccgggcggg    3720
ttggttcaca cgtgtaatcc cagcactttg ggaggctgag gcaggcagac tgcctgagct    3780
caggagttcg agaccagcct gggcaacacg gtgaaatccc gtctctacta aaaatacaaa    3840
aaaattagcc gggtgtggtg acacatgcct gtagtcccag ctacttggga ggctgaggca    3900
ggagaatcac ttgaacctgg gaggtgaagg ttgcagtgag ccaagatggc accacttcac    3960
tccagcctgg gaaacagagc aagactctgt ctctgagctg agatggcacc acttcactcc    4020
agcctgggaa acagagcaag actctgtctc aaaaaaaaca aaacacacaa acaaaaaaac    4080
```

-continued

```
aggctgggcg cggtggctca cgcctgtaat cccagcactt tgggaggccg aggcgggtgg    4140
atcacctgag gtcaggagtt ccagaccagc cttgtcaaca tggtgaaacc tcccccgcc     4200 gtctctacta aaaatacaaa aattagccag gcgtggtggc aggagcctgt aatcccagct    4260
acttgggagg ctgaggcagg agaatcgctt gtacccagaa ggcagaggtt gcactgagct    4320
gagatggcac cattgcactc cagcctgggg acaagagcg agatttcgtc tttaaaaaac      4380
aaaaacaaaa caaaaaacca tgtaactata tgtcttagtc atcttagtca agaatgtaga     4440
agtaaagtga taagatatgg aatttccttt aggtcacaaa gagaaaaaga aaaattttaa    4500
agagctaaga caaacgcagc aaaatcttta tatttaataa tattctaaac atgggtgatg     4560
aacatacggg tattcattat actattctct ccacttttga gtatgtttga aaatttagta     4620
aaacaagttt taacacactg tagtctaaca agataaaata tcacactgaa caggaaaaac     4680
tggcatggtg tggtggctca cacttgtaat cccagtgctt tgggaggctg agacaggaga    4740
gttgcttgag gccaggagtt caagaccgac atggggaatg tagcaagacc ccgtccctac    4800
aaaaaacttt gtaaaaattt gccaggtatg gtggtgcata cctgtagtcc cagctactcg    4860
ggaggcggag gcagaaggaa tcacttgagc ccaggagttt gaggctgcag tgagctacga    4920
tcataccaca gcactccagc gtggacaaca gagtaagacc ctatctcaaa aacaaaacaa    4980
aacaaaacaa acaaaaaaaa cccacaagaaa aactgctggc tgatgcagcg gctcatgcct    5040
gtaatcccag tattttggga ggcccaggtg ggcgtatcac ctgaggtcag gagttagaga    5100
ccagcctggc caacatggtg aaaccccatc tctactaaaa atacaaaatt agccaggcat     5160
gtggcacgcg cctgtagtcc cagtactgg gaggctgaag caggaggatc acctgagccc     5220
gggaggtgga ggttgcagtg agccgagatc acaccactgc actccagcct gggtgacaca    5280
gcaataccct acctcaaaat aaaaaagaaa aagaaaagaa aagttgctgt ccccgctacc    5340
ccaatcccaa atccaaacag cctctctcat ctcacagtaa gggggaaaaa tcacccaaaa    5400
aagctaagtg atcttttgaa aacccaaact cttagaagtc taagattatt atagtcaact    5460
catgaagtgt catcataaaa gatactctaa tattatttaa gtagaaccac atattggttg     5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaaatcata aaagcactta tctttgaaag aggagttaca gcaattttat    5700
ttagttcttt attgctttgc tatatattct aaattttttt caatgaatat atatcacttt     5760
taaaaaaatt caatggtctt tcttataaat tatctttggc agcatgcgtt tttatatata     5820
catataaaat gtatgggaaa tttttaaagg atacattaaa ttaaagcaaa atatacaaac    5880
aaaaaatcag aatacaaaaa gataaaaaga ttgggaaggg agggagggag taaggaggaa    5940
gggtgggtgg gtatagagaa atataccaaa taatggtaag aagtggggtc ttgacacttt     6000
ctacactttt tttaaataaa aaaattttt ttctctctct ttttttttt tagagacgaa       6060 gtctcgctat gttgcccagg ctggtcttga actcctggga tcaagagatc ctcctgcctc    6120
agcctcccaa ggtgcttgga ttacaggtgt gagccaccac gcctggtcac tttctacact    6180
ttaatatata tattttttca ttttcaatgt cattttattt agttaattta taatacccat     6240
tcaccattat attcaaagtc tatttgaaga aataaaccag aaagaatgaa atactctagc     6300
tcacatgcta ttcaatacta aattacctt caaatcacat tcaagaagct gatgatttaa      6360
gctttggcgg tttccaataa atattggtca aaccataatt aaatctcaat atatcagtta    6420
gtacctattg agcatctcct tttacaacct aagcattgta ttaggtgctt aaatacaagc     6480
```

-continued

```
agcttgactt ttaatacatt taaaaataca tatttaagac ttaaaatctt atttatggaa    6540
ttcagttata ttttgaggtt tccagtgctg agaaatttga ggtttgtgct gtctttcagt    6600
ccccaaagct cagttctgag ttctcagact ttggtggaac ttcatgtatt gtcaggttgg    6660
cccgtaatac ctgtgggaca acttcagccc ctgtgcacat ggccaggagg ctggttgcaa    6720
acattttcag gtaggtggac caggacatgc ccctggtcat ggccaggtgg aggcatagtg    6780
ctatacagca ggcagaagtc aatattgatt tgttttaaa gaaacatgta ctactttcat     6840
aagcagaaaa aatttctatt cttgggggaa aagattatgc cagatcctct aggattaaat    6900
gctgatgcat ctgctaaacc ttcacatatc agaacatatt tactatagaa agaatgaaaa    6960
tgggacattt gtgtgtcacc tatgtgaaca ttccaaaaat attttacaac aactaagtat    7020
tttataaatt ttatgaactg aaatttagtt caagttctag gaaaatacaa accttgctag    7080
atattataaa aatgatacaa tatatattca tttcaggctc atcagaatat atctgttatc    7140
acttgacaag aatgaaaatg caccattttg tagtgcttta aaatcaggaa gatccagagt    7200
actaaaaatg acttcttcct tgaagcttac tcaccaactt cctcccagtt actcactgct    7260
tctgccacaa gcataaacta ggacccagcc agaactccct tgaaatatac acttgcaacg    7320
attactgcat ctatcaaaat ggttcagtgc ctggctacag gttctgcaga tcgactaaga    7380
atttgaaaag tcttgtttat ttcaaaggaa gcccatgtga attctgccca gagttcatcc    7440
cagatatgca gtctaagaat acagacagat cagcagagat gtattctaaa acaggaattc    7500
tggcaatata acaaattgat ttccaatcaa aacagattta cataccatac ttatgtcaag    7560
aagttgtttt gttttattgc atcctagatt ttattttttt gatttatggt ttactttaag    7620
cataaaaaat ttgtcaatac aactcttccc aaaaggcata aacaaaaatt cataaaactt    7680
gcatcacttg agatacttca ggtatgaatt cacaactttg ttacaactta ctatatatat    7740
gcacacatat atatatattt gggtatattg gggggggttct aatttaagaa atgcataatt    7800
ggctatagac agacagttgt cagaacttgg caatgggtac gtgcaggttc attataccaa    7860
gtctacttgt agttgttcaa aatgtatcat aatacaaggc cgggcgaggt cgtcacgcct    7920
gtaatcccag catttggga ggctaaggca ggaggattgc ttgaggtcag gagtttgtga    7980
ccagcctggg caacagagca agaccctgtc tccaaaaaga aaaaaataa ttttttacaa     8040 aataaaaaca aaatgtatca tcagacgaaa ttaaataaga ggcaattcat ttaaatgaca    8100
acttttccca gcttgacatt taacaaaaag tctaagtcct cttaattcat atttaatgat    8160
caaatatcaa atactaattt tttttttttt tttttttttg agacggagtc tcgctctgtc    8220
gcccaggctg gagtgcagtg gcgcgatcct ggctcactgc aagctccgcc tcccgggttc    8280
acgccattct cctgcctcag cctcccgagt agctgggatt acagacatgc gccaccacgc    8340
ccggctaatt ttgtattttt agtagagatg gggtttctcc atgttggtca ggctggtctt    8400
gaatttccca cctcaggtga tctgcctgcc tcagcctcac aaagcagtag ctgggactac    8460
aggcacccac caccacactt ggttaattct tttgtatttt ttttgtaaag acgggatttc    8520
accatgttag ccaggatggt ctcgatctcc tgatctcatg atccgcccgc ctcagcctcc    8580
caaagtgctg ggattacagg cgtgagccac cccgcccggc catcaaatac taattcttaa    8640
atggtaagga cccactattc agaacctgta tccttatcac taatatgcaa atatttattg    8700
aatacttact atgtcatgca tactagagag agttagataa atttgataca gctaccctca    8760
cagaacttac agtgtaatag atggcatgac atgtacatga gtaactgtga acagtgttaa    8820
```

-continued

```
attgctattt aaaaaaaaag acggctgggc gctgtggctc atgcctgtaa tcccagcact    8880
ttgggaggcc aaggcaagtt gatcgctcga ggtcaagagt tcgagaccag cctggccaac    8940
gtggtaaaac cccgtctcta ctaaaaatac aaaaaaaaaa ttagccaggc atggtggcac    9000
aggcctgtaa tcccagctac tagggaggct gagacatgga gaactgcttg aatccaggag    9060
gcagaggtta cagtgagccg agatcatacc actacactcc agcctgagtg acagagcgag    9120
actcctgtct aaaaaaaaaa aaaaaaaaaa agatacaggt taagtgttat ggtagttgaa    9180
gagagaactc aaactctgtc tcagaagcct cacttgcatg tggaccactg atatgaaata    9240
atataaatag gtataattca ataaatagga acttcagttt taatcatccc aaacaccaaa    9300
acttcctatc aaacaggtcc aataaactca atctctataa gagctagaca gaaatctact    9360
tggtggccta taatcttatt agcccttact tgtcccatct gatattaatt aaccccatct    9420
aatatggatt agttaacaat ccagtggctg ctttgacagg aacagttgga gagagttggg    9480
gattgcaaca tattcaatta tacaaaaatg cattcagcat ctaccttgat taaggcagtg    9540
tgcaacagaa tttgcaggag agtaaaagaa tgattataaa tttacaaccc ttaaagagct    9600
atagctgggc gtggtggctc atgcctgtaa atcccagcac tttgggaggc tgaggcgggt    9660
ggatcacctg aggccagaag ttcaagacca gcctagccaa catggcgaaa ccctgtctct    9720
acaaaaaata caaaaattag ccgggtgtgg tggcacgtgc ctgtagtccc agttacttgg    9780
gaggccgagg caggagaatc gcttgaacct aggaggtgga ggctgcagtg agccgagatt    9840
gtgccactgc actccacttc agcctgggcg acaagagcaa gactccgtca caaaaaaaaa    9900
aaaaaaaaaa aagcttaaaa tctagtggga aaggcatata tacatacaac taactgtata    9960
gcataataaa gctcataatc tgtaacaaaa tctaattcga caagcccaga aacttgtgat   10020
ttaccaaaaa cagttatata tacacaaaaa gtaaacctag aacccaaagt tacccagcac   10080
caatgattct ctccctaagc agtatcaagt ttaaagcagt gattacattc tactgcctag   10140
attgtaaact gagtaaagga gaccagcacc tttctgctac tgaactagca cagccgtgta   10200
aaccaacaag gcaatggcag tgcccaactt tctgtatgaa tataagttac atctgtttta   10260
ttatttgtga cttggtgttg catgtggtta ttatcaacac cttctgaaag aacaactacc   10320
tgctcaggct gccataacaa aataccacag actgagtgac ttaacagaaa cttatttctc   10380
acagttttgg aggctgggaa gtccaaaatt aaggtacctg caaggtaggt ttcaatctca   10440
ggcctcttct ttggcttgaa ggtcttctaa ctgtgtgctc acatgacctc ttctaacaag   10500
ctctctggtg tctctttttt tttttttttc tttttgaga cagagtctca ctctgtcacc   10560
caggctggag tacagtggca caatctgggc tcactgcaac ctccaactcc cgggttcaag   10620
tgattctcat gcctcaccct cccgagtagc ttggatgaca ggagcccgct accacaccca   10680 gctaatttt gtattttag tagagatggt gtttcactac attggccagg ctggtctcaa   10740
actcctgacc tcgtgatcca cccaccttgg cctcccaaag tgctgggatt acaggtgtga   10800
gccactgcgc ccgtcctggt gtcttttcat ataagggcac taatccaatc agacctgggc   10860
ccaaccctcc cgacttcttc taactgtaat taccttccaa aggccctgtc tccaaatacc   10920
atcacactgg gggttaggac ttcaaaaaag gtatgggggg ggtgtgggag gacataaatg   10980
ctcagtccat aacaagcacc caacataaaa atggctagaa cagatcacaa aaaaaaggtc   11040
ctgtatggct ttggggaagg gctcaacccc aaaatatctg agagctctgg aggggcctag   11100
aagtggtaaa tgaatgaaaa cgtggttact ctccagatct gcctttccca aatatggcca   11160
ttcttggctg aatcagaaat caaaggacag gttattaatt actagctcta agttacttac   11220
```

```
catttgctga gacagttcag aaatctgact gcatctcctc agagatctag aacacagttc   11280
tcaaattcta acttacttgt gatatacttg tgaatgataa aaatcgctac aggtactttt   11340
attaatctga aagagtattg agaaattacc tttcattctg acttttgtct ggaatgaaaa   11400
tcaatacttt tgctataatc gattactgaa ataattttac tttccagtaa aactggcatt   11460
ataatttttt ttaattttta aaacttcata attttttgcc agactgaccc atgtaaacat   11520
acaaattact aataattatg cacgtcacat ctgtaataat ggccttcatg taaacatttt   11580
tgtggtttac acataaaatc tctaattaca aagctatatt atctaaaatt acagtaagca   11640
agaaaattaa tccaagctaa gacaatactt gcaacatcaa ttcatcatct gtgacaagga   11700
ctgcttaagt ctctttgtgg ttaaaaagga aaaaaaaaa aaagacatgt tggccagatg   11760
cggtggctca cacctgtaat cccagcactt tgggaggctg aggtgggcgg atcacccctg   11820
gcctgcccaa catggtgaaa ccccgtctct actaaaaaca caaaaattag ctgggcgtgg   11880
tggcgggcgc ctgtaattcc agctactcgg gaggctgagg caggagaatt gctagaaccc   11940
aggaggcaga gattgcagtg agctgagatt gcaccattgc actacagtct gggcaacaaa   12000
agtgaaactc catcttaaaa aaaaaaagac aatgttcgtg ggtccaaaca agacttaatg   12060
gaagtgagtc taaaaatgag ctatgtgggc caggcgtagt ggctcccacc tgtaatccca   12120
gcactttggg aggccgaagc aggcagatca tgaggtcagg agatggagac catcctggcc   12180
aacacggtga aatcctgtct ctacaaaaat tagctgggcg tggtggtgcc tgcctgtaat   12240
cccagctact cagaaggctc aggcaggaga atcgcttgaa ccagggagtc ggtggctaga   12300
gtgagccgag atttgcatca ctgcactcct gcctggtgac agagcaagac tccatctcaa   12360
aaaaaacaaa caaaaataaa agataaaaat gagctatgtg aattaaaaga ggtataacaa   12420
tagataaacc atattttatt taattcctag taatgagtaa tatttccaaa cttctggaat   12480
gggcagaaat tgctagttgg catattttta cctttttatat tcagatacat taaaattctc   12540
aaaaaaaaac acctcaaagc agatgatccg ccatctcctt ggataatttg tgttaactca   12600
ggataacaga aaaccaaaat tatgagttac tgatgcaata ttcctaaatg taaaaataat   12660
taaagctaat agtagattca tcttccaatt tcatatcagt cttacaaata aactacatat   12720
ataacttgct tgccttccct tctgagggat aaagctgtta gaagaattaa aatcagcatt   12780
cttgactatt caaccaaggg agggataaat tattactcat tctagggaca tgggctcata   12840
actactacat gtgtaaggac atgaatttac ccaatattac aatttttcct tttattagtg   12900
tgtacagtgg aagaatagac atgttcactc tggacaaaaa aaaaattata cttatcagtt   12960
atcagaagca caatgctgaa gacagtagtt ccataacaat ttgaagtatg tgatcgaact   13020
agtagattat cttagtagta gtgaattatt gtaaatgtta gtaatttggc agccactggg   13080
cagaaaaata agaattgagg ctcaatattg atattaatgg tggtgattga cacataaatt   13140
ttatcaagtc tacacaatat aaaattacag aaaggtagaa gagtatacca gtacaacttc   13200
aacatatctt cactacaagg gagtaaaatg acatggccta gttactatct aatgaactgc   13260
agaaaactaa aagaaaactc caaggcaact cttctctgct gatctggttg gtccttttcc   13320
taccttttgc aatacccaga tacaaacaat ggatagaaaa caaagtagac ttgtagtatg   13380
caggtcacag tgctaaattc acagaaagaa acccctgaac tgaactgctc tatttcctgg   13440
tggtcacaaa gagtaattct ggtttacacc tacagattga tgtcaatcta caccctgttg   13500
ataacagtgt ggccaaggac aaaaaaaagg tgctccgttt taccaattct gtaaaaaatt   13560
```

-continued

```
attggcaggg taagctcggc tagggcagga ttacatttct aggactacca tccccgaaat   13620
ttagaagata ttatatccac ataaagcata tctttcacat taatttgcaa aaatctaaaa   13680
gctttttctt agctcaagtg tgtccaagtt taccctggca gtttaaaacg atagttacaa   13740
gcagcatggg ttgtatcaga cacatttgag ggccaatttc atgtaagtga tattgggcaa   13800
gttacttcaa ctatctgtgc ctccaaggtc atactagtgt ttatttacct aaagggtacc   13860
tgttatgtaa ctttagggtg tttacattag ataatgcctg caaaatattt acttcaacgc   13920
ctaaaacata gttaagtatt caataaatac ctactattgt cactactaac ttaaaagttt   13980
agagattaag agcagaatct ggggtgagac aaacttaggt tcaaatccta gtattgttgg   14040
gtaatcttgg gcaagttact taacctctct gatttgtgta atttaaaaaa ttagttaata   14100
tacataacag ggcttagaag agtatctagc acatagcacc atttaagcat ttgttattgc   14160
taacatgcaa acaatttaag ggaaagaaat tttttaaaaa ggaagaggga tttgcaaact   14220
aaaaacaatg agtatcttat gttcaaagaa aactaacaaa cagccagctc tagcaataat   14280
taaattcact atatactggg gcaggcatca caccccaaag ctaaaagcgt ctacctaggc   14340
caggcacggt ggctcatgcc tgtaatccca gcactttggg aagcagaggc gggcagatcg   14400
cttgagctca ggagttcaag accagcctgg acaacatggc aaaacaccat ctctacaaaa   14460
aatacaaata ttaggccggg cgcagtggct cacgcctgta atcccagcac tttgggaggc   14520
caaggcgggt ggatcacctg agatcaggag ttcgagagta gcctggccaa catggtgaaa   14580
cctcgtctct attaaaaata caaaaaatta gccaggcatg gtggcaggcg cctgtaatcc   14640
cagctactca gggggatgag gtaggagaat cgcttgaacc cgggaggcag aggttgcact   14700
gagccgagat catgccactg tactccagcc cgggcaacaa gagcgaaact ccatctcaaa   14760
aaataaataa ataaataaat aaaataaagt acaaatatta gccagggatg gtggtgcgca   14820
cctgtagtcc cagctacttg ggaggctgaa gtgggagaat cccctgagcc tggggagaat   14880
cacccgagcc cgggaagtcg aggctgcagt gagcagtgat tgtgccactg cactccatcc   14940
taggtgacag agtgagaccc tgtctcaaaa aaaagaaatt ggcagaatta agtaagttga   15000
tgtttagaga tgaaaaatca acatttttttc ctcagcaact gaataaaaac aacagccact   15060 accattttttt tgagtaccta tttgtagcct atttttttaac tggtattact cgagagagag   15120
agagctaggt tcgagacaga gctccttctc ttaataactg tatgacctag ggtatgtctg   15180
ttagcctctc tgaggcttca aaggttcctc atctgtaaaa tggtaataat cataccattg   15240
ctacagggct gttttgaaga ctaattagga ctatgtaagt aaacatgatg atggctatta   15300
ttactgttcc ccgccagggg ccatgcaagg gttgctgatt cacatagact gtcttataat   15360
cctctcaata actccaagag gtagccagca cctcagatat acataaaatg acttaagccc   15420
agagaggtga agtaagttgc ccacagccac acaactagta aatagcccaa acaagctgga   15480
ttcccagtta gactccgtta atagcactgc tctttacctt aagtcattac aatgcctaat   15540
atgaaataga atcgcttctt tcttagggtt caagtggtta attatttaat gtattcattc   15600
aacaaaccat catcgaggac ctcttacaag ccaagtactg tgctaagtgc tagagttacg   15660
gcggtgattc ctgcccttaa aaagttttag tgggagaaac aacaggtaac caggtcattg   15720
ccaaaacaac aaaaataatc ataataaagc aggctaaagc atatttaact ggccggggtt   15780
ttgactattt tagcaagcat gatcagaacg gttgaggagg gaggccagca gcttggccgg   15840
ttcaacaaac aagaaaaaac cagtgagggt ggagctaaga taccagaggc tgattacggt   15900
taagaatgtt cttgaaggta aggaccagat tctcattttc tatatcctgg ggcatcggtc   15960
```

-continued

```
agcatggaat ctggattcta gcacatgtga atttcggctt gaaatgacct aatgcctttt   16020
ccctagttcc ttcgtgtgtc aaatacgcat ggttaccgct accagagctg tagtgggggct  16080 tcaatgaggc catgagcatc tccataaaga tgaactacag tgtgtgcaaa actaaaggca   16140
aaacctggtc cccacacgcc ctcccaggtg gtcgctttcc gtgccgaggc ccctccagag   16200
gtgccccgag aacctcacca tcgcacccca aacttccagg gaagggcctc tcccgagaaa   16260
gcccccacgc ccccaccccg cgccatcatt cccgaatctg ccctcggccc ctccccgcag   16320
cacgctcgca ggcggcacat gtcaaccaaa acgccatttc caccttctct tcccacacgc   16380
agtcctcttt tcccagggct ccccccgagga gggacccacc ccaaaccccg ccattccgtc   16440
ctccctgccg ccctcgcgtg acgtaaagcc gaacccggga aactggccgc ccccgcctgc   16500
ggggttccct gggcccggcc gctctagaac tagtggatcc caattgaagg cctggtctaa   16560
atgactccaa aatcaccact taattcaaga gactgatttc cctgagtcag gcccttaaa    16620 gcagctattt caatgggaca gggaaacaac cctaggatct ggattagaat cacttggggg   16680
ctgccacacc cccagggctc tgatcctgcc cttctcccac acgcacattc acatactgct   16740
gcagtgacct tccatttcta atgggttcct gggccatctg tcaggtatag ggaatggaaa   16800
aggggttggg gaggctctgc ttcagaaagt ttgtgtcagg ggctcccaga gcctccacag   16860
atagatagca ggggtcccca ccctaccatg gcagctataa atgtgatcaa catttattgg   16920
cctaggatac agcagttagc aaaatgcctg atgtagttcc cactccgtgg aggttgcagg   16980
ctagccaaga agtcatgagt tcagcaaccc ttacgcacca gtgggatgag attggaccag   17040
gccgagggta gtcttgggaa cactcagcat ttgtctgagg gccagaagag gctgcttgcc   17100
ctcagacagg aggtcagcat ctttattgta gcccatgaca cctctacacc attgctcttc   17160
tggtcttatg gaagacatct ttgggcctga taacagcgga gtctgtgtcc cacttgtcca   17220
ggctggagtg ccacatcagg cacactccag ttgcagggac agcacagaca agtttcagga   17280
aggctggtgg cctccaggag gttaacctta taaggccaga ttgtaaccta gttgaaaaac   17340
atacacatgc catgataata aaagaaccta ggcaccatta caagagaaaa aatcatttt    17400 gtagatacga gcatggattc ttgggtgggt cagacacact gggcttgtgc tctgactgca   17460
ctgtctcccc tacctgacct tgggtaaacc ataagactgc tgcatgactc agtgtccacc   17520
ccaaaaaagt accggtagat attggccaca gtagatatca gctagagtgg actctcatga   17580
caatgagggg agatgtattc cccatcttag gcacctggga ctctaccttc catcttctgc   17640
tccgtgtctc tccatcccca ggctcttcag aactcaggga gtccagaatg tcagctccca   17700
gatttcagcc ttcagaaagg aaacccatta ccgttcagtt gaacaaatgt tgtctgagcc   17760
ccagatctgg gctcagaggc catctaggct atgagacaag aggggaacaa agcaccgtct   17820
gcactcactc accacactca cttgctgtcc caggtcacat ccatcgggta gagaatctaa   17880
gaggctgagc tagctcccgc caccagccca gcccacccca cctggcccct tcttccttc    17940 tacaaaatat gcaccacctg tcaaagggtg ggcagtgcca ggcctgcata cagagcactg   18000
agtgtaaaag cagacatgga ccctgacctc caggagcttc caattttctt gaagagacaa   18060
atcagctggc atttcagtcc agtgtgatct gctcttggtg agcacagacc tagggagttg   18120
gggcagcttc ccagaagaac tgcagtccag gctgagggca gagaaatgag gggaatggcg   18180
aggaattggg gagcagggg gagctcagta gagagccaag ggcgggaggt gagaagtccg   18240
tgttgggcca ggagctaccc tccggtggcc acagccgaag tcgaggatgc ctttggaact   18300
```

-continued

```
catccccact tctctctttc tgtatgtagc cgtccaagaa caagtcacct ccaagtgtag    18360
ccggatcaag gcaagccccc catctagcaa gcacttgatg ccacccagaa ctgggcttct    18420
tcagaacaat ctgagtccag gaatgatccc actcaccagg caccagagct gcgagggcat    18480
gggagtgatc tcaccaactc tggggaagcg gcaaggaatt ttcacctcca gcccccagtg    18540
tcccatcctc tcacactcag gccagactcc cctgggcaga cttgactctg tctgccagca    18600
tatgcagagc cccaaggcca ccccaccaga agtgccctg cctgggttct gtcccagctc    18660
cctgggcacc cagtccttga gtccccacca gctcagacgg cctagtgtgc caagaatgcc    18720
cactgcgttc aacaatgctg catgggtcac agcggcagca gctgtgacca cagcagtttc    18780
ggggaaaaca cccctcagcc aagtggataa tagcgttcag cagcactcac cttctggcca    18840
ggcctgcctt cagaggccat ctgattggga ggcacaagtg cccgctgcga tgggaacaca    18900
agtgcccctg gccaacaacc ccagcttcag cctgctgggc agccagagcc tcaggcagag    18960
cccggtacag ggcccggtgc ctgtagcaaa caccaccaag ttcctccagc agggtatggc    19020
cagctttagt cccctgagcc ccatacaggg catcgagcca ccaagctatg tggctgctgc    19080
tgccaccgct gctgctgctt ctgccgttgc tgccagccag ttcccaggtc cgttcgacag    19140
aacggatatt cccctgagc tgccacctgc cgacttttg cgccagcccc aacccccact    19200
aaatgatctg atttcgtcac ctgactgcaa tgaggtagat ttcattgaag ctctcttgaa    19260
aggctcctgt gtgagcccag atgaagactg ggtgtgcaac ttgaggctga tcgacgacat    19320
tttggaacag catgctgctg ctcaaaatgc cacagcccag aattctgggc aagtcaccca    19380
ggatgctggg gcactttaaa tctgagcagg atgcccatag aaaccccat ggtgacatca    19440 ctctaggaag tggtgtcgat ccatacccgc agttgtctcc cgttacaatt tgagtggtgt    19500
tgtcagccca tgcttatccc tctctctacc tgtgacaaaa tggaaagctg gtgatttttc    19560
aagctacgtg tacatatttg aaaattttgt aaatggtttt cctaaacatt aatgacagaa    19620
gtatttatac ttcattttgt gactttgtaa ataaagcgac ggcttttgtt tcagtagagt    19680
tgtgtttact atgcattgtt ttgtgtttat tatacaatgt tacaaatatg cagaccgtgt    19740
tgtttgctcc agtgatacct tgttaagcta ggtggctgag tcgcttatgg ttttaatgca    19800
atgagcaatg tggatatgac caagagttgt tgtgcaagtt gacaaatgcc aaatagaaaa    19860
ccacttggcc atttatttct atgttcacta aaaatcctat tgccttgtgt gattcttaat    19920
ctcttttgcg aacctttcag tctccgctag ctctttccta atgagcttta cagcagaagc    19980
tgttttatcg ttaagtgccc cacagagaca ctttaccagg aggctgggag agttctccag    20040
atttgggaga ggcgcagaga cagtgtgtga gccgagccct gtctcagcaa tccacctgga    20100
ggagctagag tatcctcctc cctttaccat tcagaccgag agaaaaagcc cagcttgtgt    20160
gcaccctcgt ggggttaagg cgagctgttc ctggtttaaa gcctttcagt atttgttttg    20220
atgtaaggct ctgtggtttg gggggaaaca tctgtaaaca ttattagttg atttgggggtt    20280 tgtctttgat ggtttctatc tgcaattatc gtcatgtata tttaagtgtc tgttatagaa    20340
aacccacacc cactgtcctg taaacttttc tcagtgtcca gactttctgt aatcacattt    20400
taattgccac ctcgtatttc acctctacat ttgaaatctg cgtctgtttc caagccagtg    20460 tgtttttttct tcgttctgta ataaacagcc aggagaaaag tgcctctatg ttttttatttt    20520 tcaagggagt attcagtacc tacaaaccca agtcaggaag cctgctagtg gctttggttc    20580
tttcagaggc tgctcgatgc cttgtgtgtc agaaagaaag attcagcagt tttgcatcat    20640
ggcaaagaag cctgttattt tggggctcag cccctcattt tatagaggat gaaacagagg    20700
```

-continued

```
gggatgggag gtcacaaaga caactgcccc gggagcaggt gtgggggaga cttgccctga   20760
gggtctagac gctctgcacc accgtcctgt ctcccttgct gaagaccaca catgcccttc   20820
tttgaccaga ccctgccacc tgataggcca ggacctggta ggcgggtacc caggtttcat   20880
ggatggaacc acatctcccc aaaagtgggg aggtagctac tgggatgcac gcctcccgcc   20940
atgtgctata ggagagcagc tgaagcaaca gttgggatca gatgtagtca caattgaatg   21000
catcatcaca tttatccctc taagtggctg ggagagttga tatcctcatc cctaaggtac   21060
aaaatgttcc aatttgatca gtggctttca ggagctgaga aaggcatgtg ctctgaggca   21120
gagctgttat gtcccgcaga gcctaaaaat gctctaagaa catgctccct gccaaaattc   21180
tcaatggctg tgacaaggga caacgatcga ccaatggggg tggaagcaga cctccgcagt   21240
ccaggggcca gagctaggac agaggggtcg gagaaagagt cattttccca acactccagc   21300
tcttggccag tcctcacaca gtcccctcct gcttcctgct gagagagata tcctcatagg   21360
tctgggtaaa gtccttcagt cagctttcat tccctgtcac caactttgtc tctgttctcc   21420
ctgcccgtct caggcagcac tcctcaggaa acctctccaa gagccagcct cactgcagcg   21480
cccactattg tccctctgcc tcaagtgtcc catccatgcc aggccccagg caggctgcag   21540
ctttccctca gggccacacc aaagcacttg ggctcagctg tgctgtcccc ctccatcact   21600
gagctcaggg gcagcagggg tggggtgcca ggaggcccat tcaccttct ctggctctgt   21660 gttggaccca cctgcccagc cactgctgct tagaacctac ccgctgggaa aatgaagccc   21720
tcccggaggg gccacctcaa cctgagagcc tcacggatca cagttgtccc cactcagctc   21780
tgccagccct cagagaccca tagataaaag ctgagcttgg ctcgcagagc tggttccatc   21840
ttccattccc agagggttca acttcctacc ccaaccacac agggaacctc aaggctgagc   21900
cagtgtgggc tgcagtgcag accagcttcc tggacacgtc ctgccacctg accccaggct   21960
ggcctcactg cccctggcac tcctgaccct atcctcattc ctcctggcag tgcgtgttct   22020
gccattccgc tttcccttag ctgtcctctc actgtactgt cagcttctcc tttttccaggt   22080 gcccccagg ggctttccac atgaccctgt caccccacag cccatccagc accaattcca   22140
gctctctgcc acccttcaaa ggagtgacag tgccctgctt cacctcccac tcacccctca   22200
acccagagca atctggctcc agtcttgcct ccttccccct aagtactcta gtcacagttc   22260
caaattcctc ctggtcataa agccaaatga agcttcctgg tcctcagcgg acttgccact   22320
tcagcagtac tggactctct cctcccagaa acctgtttcc ccttggctcc tggagcccac   22380
actctgctgg aatccttctg cctctctggc ctgtagcctg gccctctctc ccaacctgag   22440
gtccattctc tcctgctcct ccacaagatg ttgctccttc cattacttcc tccctctcaa   22500
ccaaagctcc ttcattagct ctttatcttc tggtttcttc ccctgggcag acgaatggat   22560
tcaagagcct gtggcccagc agcccagcac tccaggatct cagcacttca gcatcccagt   22620
accctagcat ctcaataccc cagcacccca gcaccatagt attccagcac cccattgtcc   22680
aagcatctca gcactccagc atcccagcac cccaacactc cagcagccca gaatctcagc   22740
accctagcac tgcagcatct caggacccca gcacttcagc atcccagcac actagtactc   22800
cagcatctcg gcaccccagc acctaggcat cccaacaccc agcaccccag cacttaagca   22860
tcccaccact acagtatctc aacactccag caccccagca ccatagtgtt ccagcacccc   22920
agcatcccaa caccccagca cttaagcatc ccaacacctc ggcatcccaa caccccagca   22980
ctgcagcatc tcagcacctt agcatcccag tgccctagca tctcaatgct ccagcacacc   23040
```

-continued

```
agtactacag tattccagca ccccagcact ccagcatctc agcactgcag cactgcagca   23100
ctccagcatc ccaaaatccc agcatcccaa caccccagca gaccagcaga ccagcatctc   23160
agcaccgcag catccaagga ctatcccagc atcccagcaa cccagcacct cagcatccca   23220
acaccccagc atttcagcat ggcaacaccc cagtacccca gcacttcagc accccagtat   23280
cccagcatct cagcgaccca gtatcacaaa acctcagcat cctagcaccc cagcacccca   23340
gcaccttagc accttagcat cccagcatct cagcgcctca gcatcttgat attctggctg   23400
aggtcagcgt ggtgtatcta gtcagggtcc taactttcac ttcgcaggga aatgctgctg   23460
gactgggtct catgttgggc tgaagctctc tagacccctt gaagacagca taaaagagct   23520
tggagacgct gggtgtcccc catggaagag ttcactctca tcctgctttg acaacagcct   23580 tctctgggt cccctcacggg cccctctttc ttactgcaag tttgtctctg agaagactgt   23640
gatgcagaag tcactcagct gcctgtggct cctgaagagc tgaaggtgga ggcctgtagg   23700
cctccctatg agaggcgcag aaaaaaccat gattgctagt ggggaggtgc tccctctaca   23760
acccactcca taatctgccc ccgcccagct ctgaggccag ccccagggga aaatgccaga   23820
tccccaggga ggtgtgtgag acctcagggg ctccctcctc ccttacagca ggctcaggcc   23880
cctgggggcc tcagggccaa ggtctgtggg taagctacta tctctcactt gtcctctagc   23940
cacaaaagcc agggagatct ggcaatggac atgaggttct gaagaagcac atatgactgg   24000
cttcctaatg cgtggttgtt cagtgattca ataaacacgc atgggccagg catgggaaa   24060 tagacaaaca tgatccccaa cctctcccag agtgaactgg gagggaggag tgttcatccc   24120
tcaggattac accagagaaa caaaccagca ggagatatat atggtttggg ggggtcaaga   24180
aagaggaaaa acctggcaag gcaagtccaa aatcatagga caggctgtca ggaagggcag   24240
cctggaacct ctcaagcagg agctgatgct gcagtccaca ggcagaattt cttcttcctc   24300
ggggaaatct cagctttgtt cttaaggcct ttcaactgat tggctgaggt ctgcccttc   24360 ccccacattc tccaggataa tcttccttac ttaaagtcaa ctattaatca cagctacaaa   24420
atcccttcac agctacacat agatcagtgt ttgattgacg aacagcccct acagcctagc   24480
caagttgaca cataaaacta accatcacag ggggacaaat gatgtaaaca catcaacaaa   24540
taaaacagta acaagttaag gtctatggaa aaaacacaga aggggcagag agaaagaaag   24600
caagaaggag agtcccagtt tgctagggct tgtgggaagt ggggagcagt tctctttagc   24660
taggatattt gggaaaggca tatctgaagg agtgatattt gagcttagat taaaagatgg   24720
gaaggagcaa gccatgcaaa gagctaggat gttccaagca gagacggaac agcaagtgca   24780
aatgtcagga ggaatagaag gaggctggtg ggtggggtcc agtgagcaag aggagggcag   24840
gcaggagagg ggatgggggag gtgggcaggc ccagaccacc cagggccctg gagactatcc   24900
tgatccaaca agggaagcct tgagtcactt cagtgtccat gtggagaatg gacctcagac   24960
tgaatgaggg aggcagtaag gagggcctct acctccaggg cttcgccctg tggactgcgc   25020
atagacatct ccaactcaga aagtctgaac caaacttcc atagttcccc caagtctggg   25080
catcctccta ctcagtgaaa ggcagccatc acacctccct gccctgctcc cggatgcccc   25140
aaatcctctt ggtctccaag tccagaacct gagacttgtc cttgatgttt gtctttccct   25200
caccctttct gtattctggg aagatgggtt tttttccccc agatgaatct gtaaaacttc   25260
tgtgatcaca ataaaaattc tggcagtatt attttctgga acatgacaaa gtgattcaaa   25320
attatttatc tggaagacta caaaacaaga atagccagga aatttctaaa aagaaagaag   25380
aaggaggagg agaaagaagg aggaggaaaa ggaggagaag aagaaaagaa aaagaaccaa   25440
```

-continued

```
gaaagggttc tagctctacc aaatattaaa acatatcatg aagctattta aaacaatatg   25500
gttgtggata ctgaaaaaga tgtgaataaa gtggaaggaa aataaataga aatgcacatg   25560
gggattgaga ctgtgaaaaa ggcagcatct cacatcagtg agggatgttc aacacctggt   25620
gttgggaaaa ctggctagtc atttaaacca aacaactggg tcctctacct cactcctgac   25680
attaagatac atttagatga ttcaaagagt aagacagaaa aaataacacg tgaaaacact   25740
atcagaaaac aacgtgggcc aggtgtggtg ggtcacgcct gtaatcccag cactttggga   25800
ggccgaggca gacagatcac ctgaggtggg gagttcaaga ccagcctgac caacatggtg   25860
aaatcctgtc tctactaaaa atacaaaatt agctgagcgt ggtggcgcat gcctgtaatc   25920
ccagctactc aggaggccga ggcaggagaa tcacttgaac ctgggaggca gaggttgtgg   25980
tgagccgaga tcacgccatt gcactccagc ctgggcaaca agagtgaaaa tccatctaaa   26040
aaaaaaaaaa aaagccaagg tggatatttt tatagtatca gggtagatca agcttctcca   26100
atcatgacat gaaacccaga aaccataaaa gaaaagaatg ataaaattgc ccacgtaaag   26160
taaaaagctt gcacacagaa aaacaccata caggttacaa gatgagcagc aaaatcagag   26220
aaaaaacatt gcaattcagg acacacagag gctattgttc ctaatattta aaaataaaag   26280
tagtggattg tctacaaaaa gatgaagaca agaatttcag aaaaccaaat actgcatgtt   26340
ttcacttaca agtggaagct aaacactgag tacacgtgta cacaaagaat ggaaccatag   26400
gccaggcacc gtggctcacg cctgtaatcc cagtactttg cgaggccgaa gcgggcggat   26460
cacctgaggt gaggagttcg agaccatcct ggccaacatg gtgaaaccca gtctctacta   26520
aaaatacaaa aattagccgg gcgtggtggt gggtgcctgt aatcccagct actcgggagg   26580
ctgcggcagt agaatcgctt gaaccctgga ggtggacctt gcagtgagcc gagatcgcac   26640
cactgcactc cagcctgggc aacagagtga gactccatct caaaaaaaaa aaaaggaat   26700 agaacaatag acactggggc ctacttgagg gaggagggtg aggatcaaaa acctgcctat   26760
caggtactat gcttattacc tgggtggtga aataatctgt acaccaaacc ccagtgacat   26820
gcaatttacc gatgtaacaa acctgcccat gtacccgctg aacctaaaat aaaagttgga   26880
aaaaaatata gaaattttct ttgtaatagc caaaaactgc aaacagccca ggtgtctatt   26940
agtagaatgc ataaacaaac tcgggcatgt tcatacaatg taaaactact catcaataaa   27000
aagtgatact tctcagcaat gaaaagaaac tagctactga taccagctac aacatggatg   27060
gatttcaagt gctttatgat gagagcaaga agccagacac aaaagtgtct atatatatat   27120
acagtatata tacgtatata tacacatata tacagtatat atatacatat acatgtatat   27180
atatactgta tatatactgt atatatatac acagtatata tatacatata tacagtgtat   27240
atatactgtg tatatataca tgtatatata ctgtgtatat atacatgtat atatactgtg   27300
tatatataca tgtatatata ctgtgtatat atacatgtat atatgtat actgtatata   27360 tactgtatat atatacac atatatacag tatatatata cagtatatac tgtatatata   27420
cagtatatac gtgtatatat acatatatac agtatatatg taaatataca tatatacagt   27480
atatatgtaa atatacatat atacatgtat atatatacac tatatatata catatatagt   27540
gtatatatac atatatacat gtatatattt actatatgat tccatttata taaagtgcca   27600
aaacagtcaa aaataatcta tgtggaaaaa atcaacaaag ggatcccccg ggctgcagga   27660
attcgatggc gcgccgtcga cccaacgcgt tgggagctct ccggatccaa gcttcgaggg   27720
gctcgcatct ctccttcacg cgcccgccgc cctacctgag gccgccatcc acgccggttg   27780
```

-continued

```
agtcgcgttc tgccgcctcc cgcctgtggt gcctcctgaa ctgcgtccgc cgtctaggta   27840
agtttaaagc tcaggtcgag accgggcctt tgtccggcgc tcccttggag cctacctaga   27900
ctcagccggc tctccacgct ttgcctgacc ctgcttgctc aactctacgt ctttgtttcg   27960
ttttctgttc tgcgccgtta cagatccaag ctgtgaccgg cgcctacgta agtgatatct   28020
actagattta tcaaaaagag tgttgacttg tgagcgctca caattgatac ttagattcat   28080
cgagagggac acgtcgacta ctaaccttct tctctttcct acagctgaga tcaccggcga   28140
aggagggcca ccatgcatgg ggtggaaaat acttcccgtc tgcttgtcgc tgctgcttcc   28200
tgttgtcttg attcaacagg tttcatctca agagctctcc tgcaaaggac gctgcttcga   28260
gtccttcgct cgagggaggg agtgtgactg tgactcccag tgtaaacagt atggcaagtg   28320
ctgtgcagat tatgacagct tctgtgaaga agtaaaagat aacaagaaaa acacccctaa   28380
aaagaaaccc aatccagaac cgccggctgt ggatgaagct ggaagcgggc tggataatgg   28440
tgagttcaag ctcaccccac ctcctcctga ccctcctact actccacaca gcaaagtcgc   28500
cacatctccc aagactacag cagcaaaacc agtaactcct aaacccagtc ttgcacctaa   28560
ttctgagaca tccaaagagg catctttagc atccaataaa gagacaacag ttgaaacgaa   28620
agagactact gcaacaaata aacaatcttc tgccagtaaa aaaaagacga cttcagttaa   28680
agagacacgg agtgcagaga aaacatctga taaagatgtt gagcccacat ctacaactcc   28740
caagaactca gctcccacta ctaccaagaa gcctgttact acaaccaagg aatccaagtt   28800
cctaccactc ccacaggagc ctgaacccac aactgccaag gaaccacctc caaccaccaa   28860
gaagcctgaa cccaccaccc gcaaggagcc tgaacccaca actcccaagg agcctgaacc   28920
caccaccccc aaggagcctg aacccaccac tcccaaggag cctgaaccca caactcccaa   28980
ggaaccacct ccaaccacca agaagcctga acccaccacc cccaaggagc ctggacccac   29040
aactcccaag gagcctgaac ccaccaccac caaggagcct gaacccacca ccaccaagga   29100
gcctgaatcc accactcgca aggagcctga acccaccact cccaaggagc ctgaacccac   29160
aactcccaag gagcctgaac ctacaaccct caaggagcct gaacccacaa ctcccaagga   29220
gcctgaaccc accactccca aggagcctga acccacaact cccaaggagc ctgaacccac   29280
aactcccaag gagcctgaac ccaccacgcc caaggagcct gaacccacaa ctcccaagga   29340
gcctgaaccc accacgccca aggagcctga acccacaacc cccaaggagc ctgaacccac   29400
aactcccaag aaacctgaac ccacaactcc caaggagcct gtacctacaa cccccaagga   29460
gcctgaaccc accacccca aggagcctga acccaccacg cccaaggagc ctgaacccac   29520
aactcgcaag gagcctgaac ctacaactcc caaggagcct gaacctacaa cccccaagga   29580
gcctgaaccc acaactccca agaagcctga acccaccacc acatcaccca aaaccactac   29640
tctgaaagca acaactcttg cacccaaagt aactgctcca gcagaagaga ttcagaacaa   29700
acctgaagaa acaactcctg catcagaaga ttctgatgat tctaaaacaa ctctaaaacc   29760
acagaagcca accaaagcac ccaagcctac caaaaagcca accaaagcac ccaagaagcc   29820
cacctctacc aaaaagccaa agacaccaaa aacaagaaaa ccaaaaacta caccagctcc   29880
tctaaagacg acttcagcaa cacctgaact gaataccacc cctctagaag tcatgctgcc   29940
aaccaccacc atccctaaac aaaactccaa ccctgaaaca gctgaagtaa atccagatca   30000
tgaagatgca gatggaggtg aaggagaaaa acctctgatt cccgggcccc ctgtgctatt   30060
ccccacagct attccaggca ctgatctttt ggccgggaga ctcaatcgag gcattaacat   30120
caatcccatg ccttcagatg agaccaattt atgcaatggt aagccagtgg atggactgac   30180
```

```
tacgctgcgc aatgggacat tagttgcatt tcgaggtcat tatttctgga tgctgaatcc   30240
attcagacca ccatctccac cacgcagaat taccgaagtt tggggtattc cctctcctat   30300
tgacacagtt tttactagat gtaactgtga aggaaaaact ttcttcttta aggattctca   30360
gtactggcgc ttcaccaatg atgtggtaga tcctgggtat cctaaacaaa ttgtcaaagg   30420
ctttggagga ctaacaggga agatagtggc tgctctttca atagccaagt acaaggacag   30480
gcctgaatct gtgtacttct tcaagagagg tggcaacatt cagcagtaca cttataaaca   30540
ggagccaatg aagaagtgca cagggaggcg gcctgccatc aactactcgg tgtacgggga   30600
ggcagcacag gtcaggaggc gccgctttga gcgtgctgtt ggacctttcc agacacacac   30660
cttcaggatc cattactcgg tgcccatgag agtttcttat caagacaaag gtttcctcca   30720
caatgaagtc aaagtgagta caatgtggag agggtttcca aatgttgtta cttcagcgat   30780
aacactgcct aacattagga aacctgatgg ctatgattac tacgcctttt ccaaagatca   30840
atactataac attgatgtgc ctacaagaac agcaagagca attaccacac gttcagggca   30900
gaccctctcc aaaatctggt acaactgtcc ttgaactgat tgacaaagaa gagtcatcaa   30960
aatgaaatga agaaacagt gatacttttt gacattgaaa tacattttat taataaagaa   31020
tgttgaaatg agcataccta tttaaataca aaaaaaaaaa aaaaaaaggc cacatgtgct   31080
cgagctgcag gtcgcggccc tagctcgaca tgataagata cattgatgag tttgacaaa   31140 ccacaactag aatgcagtga aaaaaatgct ttatttgtga aatttgtgat gctattgctt   31200
tatttgtgaa atttgtgatg ctattgcttt atttgtaacc attataagct gcaataaaca   31260
agttaacaac aacaattgca ttcattttat gtttcaggtt caggggagg tgtgggaggt   31320 tttttaaagc aagtaaaacc tctacaaatg tggtagatca tttggggtac cgaattcctc   31380
gagtctagag gagcatgcga cgtcggcgcg cctaccagta aaaagaaaa cctattaaaa   31440 aaacaccact cgacacggca ccagctcaat cagtcacagt gtaaaaaagg gccaagtgca   31500
gagcgagtat atataggact aaaaaatgac gtaacggtta aagtccacaa aaaacaccca   31560
gaaaaccgca cgcgaaccta cgcccagaaa cgaaagccaa aaaacccaca acttcctcaa   31620
atcgtcactt ccgttttccc acgttacgtc acttcccatt ttaagaaaac tacaattccc   31680
aacacataca agttactccg ccctaaaacc tacgtcaccc gccccgttcc cacgccccgc   31740
gccacgtcac aaactccacc ccctcattat catattggct tcaatccaaa ataaggtata   31800
ttattgatga tgttt                                                   31815
```

```
<210> SEQ ID NO 3
<211> LENGTH: 4215
<212> TYPE: DNA
<213> ORGANISM: Homo sapiens

<400> SEQUENCE: 3
```

```
atggcatgga aaacacttcc catttacctg ttgttgctgc tgtctgtttt cgtgattcag    60
caagtttcat ctcaagattt atcaagctgt gcagggagat gtggggaagg gtattctaga   120
gatgccacct gcaactgtga ttataactgt caacactaca tggagtgctg ccctgatttc   180
aagagagtct gcactgcgga gctttcctgt aaaggccgct gctttgagtc cttcgagaga   240
gggagggagt gtgactgcga cgcccaatgt aagaagtatg acaagtgctg tcccgattat   300
gagagtttct gtgcagaagt gcataatccc acatcaccac catcttcaaa gaaagcacct   360
ccaccttcag gagcatctca aaccatcaaa tcaacaacca aacgttcacc caaaccacca   420
```

-continued

```
aacaagaaga agactaagaa agttatagaa tcagaggaaa taacagaaga acattctgtt      480
tctgaaaatc aagagtcctc ctcctcctcc tcctcttcct cttcttcttc aacaattcgg      540
aaaatcaagt cttccaaaaa ttcagctgct aatagagaat tacagaagaa actcaaagta      600
aaagataaca agaagaacag aactaaaaag aaacctaccc ccaaaccacc agttgtagat      660
gaagctggaa gtggattgga caatggtgac ttcaaggtca caactcctga cacgtctacc      720
acccaacaca ataaagtcag cacatctccc aagatcacaa cagcaaaacc aataaatccc      780
agacccagtc ttccacctaa ttctgataca tctaaagaga cgtctttgac agtgaataaa      840
gagacaacag ttgaaactaa agaaactact acaacaaata aacagacttc aactgatgga      900
aaagagaaga ctacttccgc taaagagaca caaagtatag agaaacatc tgctaaagat        960 ttagcaccca catctaaagt gctggctaaa cctacaccca aagctgaaac tacaaccaaa      1020
ggccctgctc tcaccactcc caaggagccc acgcccacca ctcccaagga gcctgcatct      1080
accacaccca aagagcccac acctaccacc atcaagtctg cacccaccac ccccaaggag      1140
cctgcaccca ccaccaccaa gtctgcaccc accactccca aggagcctgc acccaccacc      1200
accaaggagc ctgcacccac cactcccaag gagcctgcac ccaccaccac caaggagcct      1260
gcacccacca ccaccaagtc tgcacccacc actcccaagg agcctgcacc caccaccccc      1320
aagaagcctg ccccaactac ccccaaggag cctgcaccca ccactcccaa ggagcctaca      1380
cccaccactc ccaaggagcc tgcacccacc accaaggagc ctgcacccac cactcccaaa      1440
gagcctgcac ccactgcccc caagaagcct gccccaacta ccccccaagga gcctgcaccc      1500 accactccca aggagcctgc acccaccacc accaaggagc cttcacccac cactcccaag      1560
gagcctgcac ccaccaccac caagtctgca cccaccacta ccaaggagcc tgcacccacc      1620
actaccaagt ctgcacccac cactcccaag gagccttcac ccaccaccac caaggagcct      1680
gcacccacca ctcccaagga gcctgcaccc accacccccca agaagcctgc cccaactacc      1740
cccaaggagc ctgcacccac cactcccaag gaacctgcac ccaccaccac caagaagcct      1800
gcacccacca ctcccaaaga gcctgcccca actaccccca aggagactgc acccaccacc      1860
cccaagaagc tcacgcccac cacccccgag aagctcgcac ccaccacccc tgagaagccc      1920
gcacccacca cccctgagga gctcgcaccc accacccctg aggagcccac acccaccacc      1980
cctgaggagc ctgctccac cactcccaag gcagcggctc ccaacacccc taaggagcct        2040
gctccaacta cccctaagga gcctgctcca actaccccta aggagcctgc tccaactacc      2100
cctaaggaga ctgctccaac tacccctaaa gggactgctc caactaccct caaggaacct      2160
gcacccacta ctcccaagaa gcctgccccc aaggagcttg cacccaccac caccaaggag      2220
cccacatcca ccacctgtga caagcccgct ccaactaccc ctaaggggac tgctccaact      2280 accccctaagg agcctgctcc aactacccct aaggagcctg ctccaactac ccctaagggg      2340
actgctccaa ctaccctcaa ggaacctgca cccactactc caagaagcc tgcccccaag       2400 gagcttgcac ccaccaccac caaggggccc acatccacca cctctgacaa gcctgctcca      2460
actacaccta aggagactgc tccaactacc cccaaggagc ctgcacccac tacccccaag      2520
aagcctgctc caactactcc tgagacacct cctccaacca cttcagaggt ctctactcca      2580
actaccacca aggagcctac cactatccac aaaaagccctg atgaatcaac tcctgagctt      2640
tctgcagaac ccacaccaaa agctcttgaa aacagtccca aggaacctgg tgtacctaca      2700
actaagactc ctgcagcgac taaacctgaa atgactacaa cagctaaaga caagacaaca      2760
gaaagagact acgtactac acctgaaact acaactgctg cacctaagat gacaaaagag      2820
```

-continued

```
acagcaacta caacagaaaa aactaccgaa tccaaaataa cagctacaac cacacaagta   2880
acatctacca caactcaaga taccacacca ttcaaaatta ctactcttaa aacaactact   2940
cttgcaccca aagtaactac aacaaaaaag acaattacta ccactgagat tatgaacaaa   3000
cctgaagaaa cagctaaacc aaaagacaga gctactaatt ctaaagcgac aactcctaaa   3060
cctcaaaagc caaccaaagc acccaaaaaa cccacttcta ccaaaaagcc aaaaacaatg   3120
cctagagtga gaaaaccaaa gacgacacca actccccgca agatgacatc aacaatgcca   3180
gaattgaacc ctacctcag aatagcagaa gccatgctcc aaaccaccac cagacctaac    3240
caaactccaa actccaaact agttgaagta aatccaaaga gtgaagatgc aggtggtgct   3300
gaaggagaaa cacctcatat gcttctcagg ccccatgtgt tcatgcctga agttactccc   3360
gacatggatt acttaccgag agtacccaat caaggcatta tcatcaatcc catgctttcc   3420
gatgagacca atatatgcaa tggtaagcca gtagatggac tgactacttt gcgcaatggg   3480
acattagttg cattccgagg tcattatttc tggatgctaa gtccattcag tccaccatct   3540
ccagctcgca gaattactga agtttggggt attccttccc ccattgatac tgtttttact   3600
aggtgcaact gtgaaggaaa aactttcttc tttaaggatt ctcagtactg gcgtttttacc  3660 aatgatataa aagatgcagg gtaccccaaa ccaattttca aaggatttgg aggactaact   3720
ggacaaatag tggcagcgct ttcaacagct aaatataaga actggcctga atctgtgtat   3780
tttttcaaga gaggtggcag cattcagcag tatatttata aacaggaacc tgtacagaag   3840
tgccctggaa gaaggcctgc tctaaattat ccagtgtatg gagaaacgac acaggttagg   3900
agacgtcgct ttgaacgtgc tataggacct tctcaaacac acaccatcag aattcaatat   3960
tcacctgcca gactggctta tcaagacaaa ggtgtccttc ataatgaagt taaagtgagt   4020
atactgtgga gaggacttcc aaatgtggtt acctcagcta tatcactgcc caacatcaga   4080
aaacctgacg gctatgatta ctatgccttt tctaaagatc aatactataa cattgatgtg   4140
cctagtagaa cagcaagagc aattactact cgttctgggc agaccttatc caaagtctgg   4200
tacaactgtc cttag                                                    4215
```

```
<210> SEQ ID NO 4
<211> LENGTH: 2894
<212> TYPE: DNA
<213> ORGANISM: Mus musculus

<400> SEQUENCE: 4
```

```
atggggtgga aaatacttcc cgtctgcttg tcgctgctgc ttcctgttgt cttgattcaa    60
caggtttcat ctcaagagct ctcctgcaaa ggacgctgct tcgagtcctt cgctcgaggg   120
agggagtgtg actgtgactc ccagtgtaaa cagtatggca agtgctgtgc agattatgac   180
agcttctgtg aagaagtaaa agataacaag aaaaacaccc taaaaagaa acccaatcca    240 gaaccgccgg ctgtggatga agctggaagc gggctggata tggtgagtt caagctcacc    300 ccacctcctc ctgaccctcc tactactcca cacagcaaag tcgccacatc tcccaagact   360
acagcagcaa aaccagtaac tcctaaaccc agtcttgcac ctaattctga gacatccaaa   420
gaggcatctt tagcatccaa taaagagaca acagttgaaa cgaaagagac tactgcaaca   480
aataaacaat cttctgccag taaaaaaaag acgacttcag ttaaagagac acggagtgca   540
gagaaaacat ctgataaaga tgttgagccc acatctacaa ctcccaagaa ctcagctccc    600
actactacca agaagcctgt tactacaacc aaggaatcca agttcctacc actcccacag   660
```

-continued

```
gagcctgaac ccacaactgc caaggaacca cctccaacca ccaagaagcc tgaacccacc      720
acccgcaagg agcctgaacc cacaactccc aaggagcctg aacccaccac ccccaaggag      780 cctgaacccca ccactcccaa ggagcctgaa cccacaactc caaggaacc acctccaacc      840 accaagaagc ctgaacccac cacccccaag gagcctggac ccacaactcc caaggagcct      900
gaacccacca ccaccaagga gcctgaaccc accaccacca aggagcctga atccaccact      960
cgcaaggagc ctgaacccac cactcccaag gagcctgaac ccacaactcc caaggagcct     1020
gaacctacaa ccctcaagga gcctgaaccc acaactccca aggagcctga acccaccact     1080
cccaaggagc ctgaacccac aactcccaag gagcctgaac ccacaactcc caaggagcct     1140
gaacccacca cgcccaagga gcctgaaccc acaactccca aggagcctga acccaccacg     1200
cccaaggagc ctgaacccac aacccccaag gagcctgaac ccacaactcc caagaaacct     1260
gaacccacaa ctcccaagga gcctgtacct acaaccccca aggagcctga acccaccacc     1320
cccaaggagc ctgaacccac cacgcccaag gagcctgaac ccacaactcg caaggagcct     1380
gaacctacaa ctcccaagga gcctgaacct acaaccccca aggagcctga acccacaact     1440
cccaagaagc ctgaacccac caccacatca cccaaaacca ctactctgaa agcaacaact     1500
cttgcaccca aagtaactgc tccagcagaa gagattcaga acaaacctga agaaacaact     1560
cctgcatcag aagattctga tgattctaaa acaactctaa aaccacagaa gccaaccaaa     1620
gcacccaagc ctaccaaaaa gccaaccaaa gcacccaaga agcccaccctc taccaaaaag     1680 ccaaagacac caaaaacaag aaaaccaaaa actacaccag ctcctctaaa gacgacttca     1740
gcaacacctg aactgaatac cacccctcta gaagtcatgc tgccaaccac caccatccct     1800
aaacaaactc caaaccctga aacagctgaa gtaaatccag atcatgaaga tgcagatgga     1860
ggtgaaggag aaaaaacctct gattcccggg cccctgtgc tattccccac agctattcca     1920
ggcactgatc ttttggccgg gagactcaat cgaggcatta acatcaatcc catgccttca     1980
gatgagacca atttatgcaa tggtaagcca gtggatggac tgactacgct gcgcaatggg     2040
acattagttg catttcgagg tcattatttc tggatgctga atccattcag accaccatct     2100
ccaccacgca gaattaccga gtttgggggt attccctctc ctattgacac agttttttact     2160 agatgtaact gtgaaggaaa aactttcttc tttaaggatt ctcagtactg gcgcttcacc     2220
aatgatgtgg tagatcctgg gtatcctaaa caaattgtca aaggctttgg aggactaaca     2280
gggaagatag tggctgctct ttcaatagcc aagtacaagg acaggcctga atctgtgtac     2340
ttcttcaaga gaggtggcaa cattcagcag tacacttata aacaggagcc aatgaagaag     2400
tgcacaggga ggcggcctgc catcaactac tcggtgtacg gggaggcagc acaggtcagg     2460
aggcgccgct ttgagcgtgc tgttggacct ttccagacac acaccttcag gatccattac     2520
tcggtgccca tgagagtttc ttatcaagac aaaggtttcc tccacaatga gtcaaagtg     2580 agtacaatgt ggagagggtt tccaaatgtt gttacttcag cgataacact gcctaacatt     2640
aggaaacctg atggctatga ttactacgcc ttttccaaag atcaatacta taacattgat     2700
gtgcctacaa gaacagcaag agcaattacc acacgttcag ggcagaccct ctccaaaatc     2760
tggtacaact gtcctgaac tgattgacaa agaagagtca tcaaaatgaa atgaagaaaa     2820
cagtgatact ttttgacatt gaaatacatt ttattaataa agaatgttga aatgagcata     2880
cctatttaaa taca                                                       2894
```

<210> SEQ ID NO 5
<211> LENGTH: 1404

-continued

<212> TYPE: PRT
<213> ORGANISM: Homo sapiens

<400> SEQUENCE: 5

```
Met Ala Trp Lys Thr Leu Pro Ile Tyr Leu Leu Leu Leu Ser Val
1               5                   10                  15

Phe Val Ile Gln Gln Val Ser Ser Gln Asp Leu Ser Ser Cys Ala Gly
            20                  25                  30

Arg Cys Gly Glu Gly Tyr Ser Arg Asp Ala Thr Cys Asn Cys Asp Tyr
        35                  40                  45

Asn Cys Gln His Tyr Met Glu Cys Cys Pro Asp Phe Lys Arg Val Cys
    50                  55                  60

Thr Ala Glu Leu Ser Cys Lys Gly Arg Cys Phe Glu Ser Phe Glu Arg
65                  70                  75                  80

Gly Arg Glu Cys Asp Cys Asp Ala Gln Cys Lys Lys Tyr Asp Lys Cys
                85                  90                  95

Cys Pro Asp Tyr Glu Ser Phe Cys Ala Glu Val His Asn Pro Thr Ser
                100                 105                 110

Pro Pro Ser Ser Lys Lys Ala Pro Pro Pro Ser Gly Ala Ser Gln Thr
            115                 120                 125

Ile Lys Ser Thr Thr Lys Arg Ser Pro Lys Pro Pro Asn Lys Lys Lys
            130                 135                 140

Thr Lys Lys Val Ile Glu Ser Glu Glu Ile Thr Glu Glu His Ser Val
145                 150                 155                 160

Ser Glu Asn Gln Glu Ser Ser Ser Ser Ser Ser Ser Ser Ser Ser Ser
                165                 170                 175

Ser Thr Ile Arg Lys Ile Lys Ser Ser Lys Asn Ser Ala Ala Asn Arg
                180                 185                 190

Glu Leu Gln Lys Lys Leu Lys Val Lys Asp Asn Lys Lys Asn Arg Thr
            195                 200                 205

Lys Lys Lys Pro Thr Pro Lys Pro Pro Val Val Asp Glu Ala Gly Ser
        210                 215                 220

Gly Leu Asp Asn Gly Asp Phe Lys Val Thr Thr Pro Asp Thr Ser Thr
225                 230                 235                 240

Thr Gln His Asn Lys Val Ser Thr Ser Pro Lys Ile Thr Thr Ala Lys
                245                 250                 255

Pro Ile Asn Pro Arg Pro Ser Leu Pro Pro Asn Ser Asp Thr Ser Lys
                260                 265                 270

Glu Thr Ser Leu Thr Val Asn Lys Glu Thr Thr Val Glu Thr Lys Glu
            275                 280                 285

Thr Thr Thr Thr Asn Lys Gln Thr Ser Thr Asp Gly Lys Glu Lys Thr
        290                 295                 300

Thr Ser Ala Lys Glu Thr Gln Ser Ile Glu Lys Thr Ser Ala Lys Asp
305                 310                 315                 320

Leu Ala Pro Thr Ser Lys Val Leu Ala Lys Pro Thr Pro Lys Ala Glu
                325                 330                 335

Thr Thr Thr Lys Gly Pro Ala Leu Thr Thr Pro Lys Glu Pro Thr Pro
            340                 345                 350

Thr Thr Pro Lys Glu Pro Ala Ser Thr Thr Pro Lys Glu Pro Thr Pro
            355                 360                 365

Thr Thr Ile Lys Ser Ala Pro Thr Thr Pro Lys Glu Pro Ala Pro Thr
        370                 375                 380

Thr Thr Lys Ser Ala Pro Thr Thr Pro Lys Glu Pro Ala Pro Thr Thr
385                 390                 395                 400
```

-continued

```
Thr Lys Glu Pro Ala Pro Thr Thr Pro Lys Glu Pro Ala Pro Thr Thr
                405             410             415

Thr Lys Glu Pro Ala Pro Thr Thr Thr Lys Ser Ala Pro Thr Thr Pro
                420             425             430

Lys Glu Pro Ala Pro Thr Thr Pro Lys Lys Pro Ala Pro Thr Thr Pro
        435             440             445

Lys Glu Pro Ala Pro Thr Thr Pro Lys Glu Pro Thr Pro Thr Thr Pro
    450             455             460

Lys Glu Pro Ala Pro Thr Thr Lys Glu Pro Ala Pro Thr Thr Pro Lys
465             470             475             480

Glu Pro Ala Pro Thr Ala Pro Lys Lys Pro Ala Pro Thr Thr Pro Lys
            485             490             495

Glu Pro Ala Pro Thr Thr Pro Lys Glu Pro Ala Pro Thr Thr Thr Lys
        500             505             510

Glu Pro Ser Pro Thr Thr Pro Lys Glu Pro Ala Pro Thr Thr Thr Lys
        515             520             525

Ser Ala Pro Thr Thr Thr Lys Glu Pro Ala Pro Thr Thr Thr Lys Ser
    530             535             540

Ala Pro Thr Thr Pro Lys Glu Pro Ser Pro Thr Thr Thr Lys Glu Pro
545             550             555             560

Ala Pro Thr Thr Pro Lys Glu Pro Ala Pro Thr Thr Pro Lys Lys Pro
            565             570             575

Ala Pro Thr Thr Pro Lys Glu Pro Ala Pro Thr Thr Pro Lys Glu Pro
        580             585             590

Ala Pro Thr Thr Thr Lys Lys Pro Ala Pro Thr Thr Pro Lys Glu Pro
        595             600             605

Ala Pro Thr Thr Pro Lys Glu Thr Ala Pro Thr Thr Pro Lys Lys Leu
    610             615             620

Thr Pro Thr Thr Pro Glu Lys Leu Ala Pro Thr Thr Pro Glu Lys Pro
625             630             635             640

Ala Pro Thr Thr Pro Glu Glu Leu Ala Pro Thr Thr Pro Glu Glu Pro
            645             650             655

Thr Pro Thr Thr Pro Glu Glu Pro Ala Pro Thr Thr Pro Lys Ala Ala
        660             665             670

Ala Pro Asn Thr Pro Lys Glu Pro Ala Pro Thr Thr Pro Lys Glu Pro
        675             680             685

Ala Pro Thr Thr Pro Lys Glu Pro Ala Pro Thr Thr Pro Lys Glu Thr
    690             695             700

Ala Pro Thr Thr Pro Lys Gly Thr Ala Pro Thr Thr Leu Lys Glu Pro
705             710             715             720

Ala Pro Thr Thr Pro Lys Lys Pro Ala Pro Lys Glu Leu Ala Pro Thr
            725             730             735

Thr Thr Lys Glu Pro Thr Ser Thr Thr Cys Asp Lys Pro Ala Pro Thr
            740             745             750

Thr Pro Lys Gly Thr Ala Pro Thr Thr Pro Lys Glu Pro Ala Pro Thr
        755             760             765

Thr Pro Lys Glu Pro Ala Pro Thr Thr Pro Lys Gly Thr Ala Pro Thr
        770             775             780

Thr Leu Lys Glu Pro Ala Pro Thr Thr Pro Lys Lys Pro Ala Pro Lys
785             790             795             800

Glu Leu Ala Pro Thr Thr Thr Lys Gly Pro Thr Ser Thr Thr Ser Asp
            805             810             815
```

Lys Pro Ala Pro Thr Thr Pro Lys Glu Thr Ala Pro Thr Thr Pro Lys
        820                 825                 830

Glu Pro Ala Pro Thr Thr Pro Lys Lys Pro Ala Pro Thr Thr Pro Glu
        835                 840                 845

Thr Pro Pro Pro Thr Thr Ser Glu Val Ser Thr Pro Thr Thr Thr Lys
        850                 855                 860

Glu Pro Thr Thr Ile His Lys Ser Pro Asp Glu Ser Thr Pro Glu Leu
865                 870                 875                 880

Ser Ala Glu Pro Thr Pro Lys Ala Leu Glu Asn Ser Pro Lys Glu Pro
                885                 890                 895

Gly Val Pro Thr Thr Lys Thr Pro Ala Ala Thr Lys Pro Glu Met Thr
                900                 905                 910

Thr Thr Ala Lys Asp Lys Thr Thr Glu Arg Asp Leu Arg Thr Thr Pro
                915                 920                 925

Glu Thr Thr Thr Ala Ala Pro Lys Met Thr Lys Glu Thr Ala Thr Thr
        930                 935                 940

Thr Glu Lys Thr Thr Glu Ser Lys Ile Thr Ala Thr Thr Thr Gln Val
945                 950                 955                 960

Thr Ser Thr Thr Thr Gln Asp Thr Thr Pro Phe Lys Ile Thr Thr Leu
                965                 970                 975

Lys Thr Thr Thr Leu Ala Pro Lys Val Thr Thr Thr Lys Lys Thr Ile
                980                 985                 990

Thr Thr Thr Glu Ile Met Asn Lys Pro Glu Glu Thr Ala Lys Pro Lys
                995                 1000                1005

Asp Arg Ala Thr Asn Ser Lys Ala Thr Thr Pro Lys Pro Gln Lys
        1010                1015                1020

Pro Thr Lys Ala Pro Lys Lys Pro Thr Ser Thr Lys Lys Pro Lys
        1025                1030                1035

Thr Met Pro Arg Val Arg Lys Pro Lys Thr Thr Pro Thr Pro Arg
        1040                1045                1050

Lys Met Thr Ser Thr Met Pro Glu Leu Asn Pro Thr Ser Arg Ile
        1055                1060                1065

Ala Glu Ala Met Leu Gln Thr Thr Thr Arg Pro Asn Gln Thr Pro
        1070                1075                1080

Asn Ser Lys Leu Val Glu Val Asn Pro Lys Ser Glu Asp Ala Gly
        1085                1090                1095

Gly Ala Glu Gly Glu Thr Pro His Met Leu Leu Arg Pro His Val
        1100                1105                1110

Phe Met Pro Glu Val Thr Pro Asp Met Asp Tyr Leu Pro Arg Val
        1115                1120                1125

Pro Asn Gln Gly Ile Ile Ile Asn Pro Met Leu Ser Asp Glu Thr
        1130                1135                1140

Asn Ile Cys Asn Gly Lys Pro Val Asp Gly Leu Thr Thr Leu Arg
        1145                1150                1155

Asn Gly Thr Leu Val Ala Phe Arg Gly His Tyr Phe Trp Met Leu
        1160                1165                1170

Ser Pro Phe Ser Pro Pro Ser Pro Ala Arg Arg Ile Thr Glu Val
        1175                1180                1185

Trp Gly Ile Pro Ser Pro Ile Asp Thr Val Phe Thr Arg Cys Asn
        1190                1195                1200

Cys Glu Gly Lys Thr Phe Phe Phe Lys Asp Ser Gln Tyr Trp Arg
        1205                1210                1215

Phe Thr Asn Asp Ile Lys Asp Ala Gly Tyr Pro Lys Pro Ile Phe

-continued

```
        1220                    1225                    1230

Lys Gly  Phe Gly Gly Leu Thr  Gly Gln Ile Val Ala  Ala Leu Ser
    1235                    1240                    1245

Thr Ala  Lys Tyr Lys Asn Trp  Pro Glu Ser Val Tyr  Phe Phe Lys
    1250                    1255                    1260

Arg Gly  Gly Ser Ile Gln Gln  Tyr Ile Tyr Lys Gln  Glu Pro Val
    1265                    1270                    1275

Gln Lys  Cys Pro Gly Arg Arg  Pro Ala Leu Asn Tyr  Pro Val Tyr
    1280                    1285                    1290

Gly Glu  Thr Thr Gln Val Arg  Arg Arg Arg Phe Glu  Arg Ala Ile
    1295                    1300                    1305

Gly Pro  Ser Gln Thr His Thr  Ile Arg Ile Gln Tyr  Ser Pro Ala
    1310                    1315                    1320

Arg Leu  Ala Tyr Gln Asp Lys  Gly Val Leu His Asn  Glu Val Lys
    1325                    1330                    1335

Val Ser  Ile Leu Trp Arg Gly  Leu Pro Asn Val Val  Thr Ser Ala
    1340                    1345                    1350

Ile Ser  Leu Pro Asn Ile Arg  Lys Pro Asp Gly Tyr  Asp Tyr Tyr
    1355                    1360                    1365

Ala Phe  Ser Lys Asp Gln Tyr  Tyr Asn Ile Asp Val  Pro Ser Arg
    1370                    1375                    1380

Thr Ala  Arg Ala Ile Thr Thr  Arg Ser Gly Gln Thr  Leu Ser Lys
    1385                    1390                    1395

Val Trp  Tyr Asn Cys Pro
    1400

<210> SEQ ID NO 6
<211> LENGTH: 925
<212> TYPE: PRT
<213> ORGANISM: Mus musculus

<400> SEQUENCE: 6

Met Gly Trp Lys Ile Leu Pro Val Cys Leu Ser Leu Leu Leu Pro Val
1               5                   10                  15

Val Leu Ile Gln Gln Val Ser Ser Gln Glu Leu Ser Cys Lys Gly Arg
            20                  25                  30

Cys Phe Glu Ser Phe Ala Arg Gly Arg Glu Cys Asp Cys Asp Ser Gln
        35                  40                  45

Cys Lys Gln Tyr Gly Lys Cys Cys Ala Asp Tyr Asp Ser Phe Cys Glu
    50                  55                  60

Glu Val Lys Asp Asn Lys Lys Asn Thr Pro Lys Lys Pro Asn Pro
65                  70                  75                  80

Glu Pro Pro Ala Val Asp Glu Ala Gly Ser Gly Leu Asp Asn Gly Glu
                85                  90                  95

Phe Lys Leu Thr Pro Pro Pro Asp Pro Pro Thr Thr Pro His Ser
            100                 105                 110

Lys Val Ala Thr Ser Pro Lys Thr Thr Ala Ala Lys Pro Val Thr Pro
        115                 120                 125

Lys Pro Ser Leu Ala Pro Asn Ser Glu Thr Ser Lys Glu Ala Ser Leu
    130                 135                 140

Ala Ser Asn Lys Glu Thr Thr Val Glu Thr Lys Glu Thr Thr Ala Thr
145                 150                 155                 160

Asn Lys Gln Ser Ser Ala Ser Lys Lys Lys Thr Thr Ser Val Lys Glu
                165                 170                 175
```

-continued

```
Thr Arg Ser Ala Glu Lys Thr Ser Asp Lys Asp Val Glu Pro Thr Ser
            180                 185                 190

Thr Thr Pro Lys Asn Ser Ala Pro Thr Thr Thr Lys Lys Pro Val Thr
            195                 200                 205

Thr Thr Lys Glu Ser Lys Phe Leu Pro Leu Pro Gln Glu Pro Glu Pro
            210                 215                 220

Thr Thr Ala Lys Glu Pro Pro Pro Thr Thr Lys Lys Pro Glu Pro Thr
225                 230                 235                 240

Thr Arg Lys Glu Pro Glu Pro Thr Thr Pro Lys Glu Pro Glu Pro Thr
                245                 250                 255

Thr Pro Lys Glu Pro Glu Pro Thr Thr Pro Lys Glu Pro Glu Pro Thr
                260                 265                 270

Thr Pro Lys Glu Pro Pro Pro Thr Thr Lys Lys Pro Glu Pro Thr Thr
                275                 280                 285

Pro Lys Glu Pro Gly Pro Thr Thr Pro Lys Glu Pro Glu Pro Thr Thr
    290                 295                 300

Thr Lys Glu Pro Glu Pro Thr Thr Thr Lys Glu Pro Glu Ser Thr Thr
305                 310                 315                 320

Arg Lys Glu Pro Glu Pro Thr Thr Pro Lys Glu Pro Glu Pro Thr Thr
                325                 330                 335

Pro Lys Glu Pro Glu Pro Thr Thr Leu Lys Glu Pro Glu Pro Thr Thr
                340                 345                 350

Pro Lys Glu Pro Glu Pro Thr Thr Pro Lys Glu Pro Glu Pro Thr Thr
                355                 360                 365

Pro Lys Glu Pro Glu Pro Thr Thr Pro Lys Glu Pro Glu Pro Thr Thr
    370                 375                 380

Pro Lys Glu Pro Glu Pro Thr Thr Pro Lys Glu Pro Glu Pro Thr Thr
385                 390                 395                 400

Pro Lys Glu Pro Glu Pro Thr Thr Pro Lys Glu Pro Glu Pro Thr Thr
                405                 410                 415

Pro Lys Lys Pro Glu Pro Thr Thr Pro Lys Glu Pro Val Pro Thr Thr
                420                 425                 430

Pro Lys Glu Pro Glu Pro Thr Thr Pro Lys Glu Pro Glu Pro Thr Thr
                435                 440                 445

Pro Lys Glu Pro Glu Pro Thr Thr Arg Lys Glu Pro Glu Pro Thr Thr
    450                 455                 460

Pro Lys Glu Pro Glu Pro Thr Thr Pro Lys Glu Pro Glu Pro Thr Thr
465                 470                 475                 480

Pro Lys Lys Pro Glu Pro Thr Thr Thr Ser Pro Lys Thr Thr Thr Leu
                485                 490                 495

Lys Ala Thr Thr Leu Ala Pro Lys Val Thr Ala Pro Ala Glu Glu Ile
            500                 505                 510

Gln Asn Lys Pro Glu Glu Thr Thr Pro Ala Ser Glu Asp Ser Asp Asp
            515                 520                 525

Ser Lys Thr Thr Leu Lys Pro Gln Lys Pro Thr Lys Ala Pro Lys Pro
    530                 535                 540

Thr Lys Lys Pro Thr Lys Ala Pro Lys Lys Pro Thr Ser Thr Lys Lys
545                 550                 555                 560

Pro Lys Thr Pro Lys Thr Arg Lys Pro Lys Thr Thr Pro Ala Pro Leu
                565                 570                 575

Lys Thr Thr Ser Ala Thr Pro Glu Leu Asn Thr Thr Pro Leu Glu Val
            580                 585                 590

Met Leu Pro Thr Thr Thr Ile Pro Lys Gln Thr Pro Asn Pro Glu Thr
```

-continued

```
                595                    600                    605

Ala Glu Val Asn Pro Asp His Glu Asp Ala Asp Gly Gly Glu Gly Glu
        610                    615                    620

Lys Pro Leu Ile Pro Gly Pro Pro Val Leu Phe Pro Thr Ala Ile Pro
625                    630                    635                    640

Gly Thr Asp Leu Leu Ala Gly Arg Leu Asn Arg Gly Ile Asn Ile Asn
                645                    650                    655

Pro Met Pro Ser Asp Glu Thr Asn Leu Cys Asn Gly Lys Pro Val Asp
                660                    665                    670

Gly Leu Thr Thr Leu Arg Asn Gly Thr Leu Val Ala Phe Arg Gly His
                675                    680                    685

Tyr Phe Trp Met Leu Asn Pro Phe Arg Pro Pro Ser Pro Pro Arg Arg
        690                    695                    700

Ile Thr Glu Val Trp Gly Ile Pro Ser Pro Ile Asp Thr Val Phe Thr
705                    710                    715                    720

Arg Cys Asn Cys Glu Gly Lys Thr Phe Phe Phe Lys Asp Ser Gln Tyr
                725                    730                    735

Trp Arg Phe Thr Asn Asp Val Val Asp Pro Gly Tyr Pro Lys Gln Ile
                740                    745                    750

Val Lys Gly Phe Gly Gly Leu Thr Gly Lys Ile Val Ala Ala Leu Ser
                755                    760                    765

Ile Ala Lys Tyr Lys Asp Arg Pro Glu Ser Val Tyr Phe Phe Lys Arg
        770                    775                    780

Gly Gly Asn Ile Gln Gln Tyr Thr Tyr Lys Gln Glu Pro Met Lys Lys
785                    790                    795                    800

Cys Thr Gly Arg Arg Pro Ala Ile Asn Tyr Ser Val Tyr Gly Glu Ala
                805                    810                    815

Ala Gln Val Arg Arg Arg Arg Phe Glu Arg Ala Val Gly Pro Phe Gln
                820                    825                    830

Thr His Thr Phe Arg Ile His Tyr Ser Val Pro Met Arg Val Ser Tyr
                835                    840                    845

Gln Asp Lys Gly Phe Leu His Asn Glu Val Lys Val Ser Thr Met Trp
        850                    855                    860

Arg Gly Phe Pro Asn Val Val Thr Ser Ala Ile Thr Leu Pro Asn Ile
865                    870                    875                    880

Arg Lys Pro Asp Gly Tyr Asp Tyr Tyr Ala Phe Ser Lys Asp Gln Tyr
                885                    890                    895

Tyr Asn Ile Asp Val Pro Thr Arg Thr Ala Arg Ala Ile Thr Thr Arg
                900                    905                    910

Ser Gly Gln Thr Leu Ser Lys Ile Trp Tyr Asn Cys Pro
        915                    920                    925
```

<210> SEQ ID NO 7
<211> LENGTH: 29265
<212> TYPE: DNA
<213> ORGANISM: Artificial Sequence
<220> FEATURE:
<223> OTHER INFORMATION: helper-dependent adenoviral vector containing
      human II-1Ra

<400> SEQUENCE: 7

```
aaacatcatc aataatatac cttattttgg attgaagcca atatgataat gagggggtgg        60
agtttgtgac gtggcgcggg gcgtgggaac ggggcgggtg acgtagtagt gtggcggaag       120
tgtgatgttg caagtgtggc ggaacacatg taagcgacgg atgtggcaaa agtgacgttt       180
```

-continued

```
ttggtgtgcg ccggtgtaca caggaagtga caattttcgc gcggtttag gcggatgttg      240 tagtaaattt gggcgtaacc gagtaagatt tggccatttt cgcgggaaaa ctgaataaga      300
ggaagtgaaa tctgaataat tttgtgttac tcatagcgcg taatatttgt ctagggccgc      360
ggggactttg accgtttacg tggagactcg cccaggtgtt tttctcaggt gttttccgcg      420
ttccgggtca aagttggcgt tttgatatca agcttatcga taccgtaaac aagtctttaa      480
ttcaagcaag actttaacaa gttaaaagga gcttatgggt aggaagtagt gttatgatgt      540
atgggcataa agggtttaa tgggatagtg aaaatgtcta taataatact aaaatggctg      600
cccaatcacc tacaggattg atgtaaacat ggaaaaggtc aaaaacttgg gtcactaaaa      660
tagatgatta atggagagga tgaggttgat agttaaatgt agataagtgg tcttattctc      720
aataaaaatg tgaacataag gcgagtttct acaaagatgg acaggactca ttcatgaaac      780
agcaaaaact ggacatttgt tctaatcttt gaagagtatg aaaaattcct attttaaagg      840
taaaacagta actcacagga aataccaacc caacataaaa tcagaaacaa tagtctaaag      900
taataaaaat caaacgtttg cacgatcaaa ttatgaatga aattcactac taaaattcac      960
actgattttg tttcatccac agtgtcaatg ttgtgatgca tttcaattgt gtgacacagg     1020
cagactgtgg atcaaaagtg gtttctggtg cgacttactc tcttgagtat acctgcagtc     1080 cccttttctta agtgtgttaa aaaaaaaggg ggatttcttc aattcgccaa tactctagct     1140
ctccatgtgc tttctaggaa acaagtgtta acccacctta tttgtcaaac ctagctccaa     1200 aggactttg actccccaca aaccgatgta gctcaagaga gggtatctgt caccagtatg     1260
tatagtgaaa aaagtatccc aagtcccaac agcaattcct aaaaggagtt tatttaaaaa     1320
accacacaca cctgtaaaat aagtatatat cctccaaggt gactagtttt aaaaaaacag     1380
tattggcttt gatgtaaagt actagtgaat atgttagaaa aatctcactg taaccaagtg     1440
aaatgaaagc aagtatggtt tgcagagatt caaagaaaat ataagaaaac ctactgttgc     1500
cactaaaaag aatcatatat taaatatact cacacaatag ctcttcagtc tgataaaatc     1560
tacagtcata ggaatggatc tatcactatt tctattcagt gctttgatgt aatccagcag     1620
gtcagcaaag aatttatagc ccccttgag cacacagagg ctacaatgt gatggcctcc     1680 catctccttc atcacatctc gagcaagacg ttcagtccta cagaaataaa atcaggaatt     1740
taatagaaag tttcatacat taaactttat aacaaacacc tcttagtcat taaacttcca     1800
caccaacctg ggcaatatag tgagacccca tgcctgcaaa aaaaaaaaaa ttagccaggc     1860
atggtagcat gtacctgtag tcccagctac ttgagaggtg aggtgggaaa atcactttag     1920
tgcaggatgt tgaggctgga gtgaactgtg attgtgccac tgcactccag cctggacaat     1980
agagcaagac cttgtctcaa aaaaatgcat taaaaatttt ttttaaatct tccacgtatc     2040
acatcctttg ccctcatgtt tcataaggta aaaaatttga taccttcaaa aaaaccaagc     2100
ataccactat cataattttt tttaaatgca aataaaaaca agataccatt ttcacctatc     2160
agactggcag gttctgatta aatgaaattt tctggataat atacaatatt aagagagact     2220
gtagaaactg ggccagtggc tcatgcctgt aatcccagca ctttgggagg ctgggtaaca     2280
tggcgaaccc tgtttctaca aaataaaaat attagctggg agtggtggcg cacacctata     2340
gtcccagcta ctcaggaggc tgaggtggaa ggatcgcttg aacccaggag gttgagactg     2400
cagtgaactg tgatcattct gctgcactgc accccagcct gggcaacaga gaccttgtct     2460
caaaaaaaaa aaaaaagag acaaattgtg aagagaaagg tactctcata taacatcagg     2520
agtataaaat gattcaactt cttagaggaa aatttggcaa taccaaaata ttcaataaac     2580
```

-continued

```
tctttcccct tgacccagaa attccacttg aataaagctg aacaagtacc aaacatgtaa    2640
aagaatgttt cttctagtac agtcggtaag aacaaaatag tgtctatcaa tagtggactg    2700
gttaaatcag ttatggtatc tccataagac agaatgctat gcaaccttta aaatatatta    2760
gatagctcta gacacactaa tattaaaagt gtccaataac atttaaaact atactcatac    2820
gttaaaatat aaatgtatat atgtactttt gcatatagta tacatgcata ggccagtgct    2880
tgagaagaaa tgtgtacaga aggctgaaag gagagaactt tagtcttctt gtttatggcc    2940
tccatagtta gaatatttta taacacaaat attttgatat tataatttta aaataaaaac    3000
acagaatagc cagacataca atgcaagcat tcaataccag gtaaggtttt tcactgtaat    3060
tgacttaaca gaaaattttc aagctagatg tgcataataa taaaaatctg accttgcctt    3120
catgtgattc agccccagtc cattaccctg tttaggactg agaaatgcaa gactctggct    3180
agagttcctt cttccatctc ccttcaatgt ttactttgtt ctggtcccta cagagtccca    3240
ctataccaca actgatacta agtaattagt aaggccctcc tcttttattt ttaataaaga    3300
agattttaga aagcatcagt tatttaataa gttggcctag tttatgttca aatagcaagt    3360
actcagaaca gctgctgatg tttgaaatta acacaagaaa aagtaaaaaa cctcatttta    3420
agatcttact tacctgtcca taattagtcc atgaggaata aacacccttt ccaaatcctc    3480
agcataatga ttaggtatgc aaaataaatc aaggtcataa cctggttcat catcactaat    3540
ctgaaaaaga aatatagctg tttcaatgag agcattacag gatacaaaca tttgattgga    3600
ttaagatgtt aaaaaataac cttagtctat cagagaaatt taggtgtaag atgatattag    3660
taactgttaa ctttgtaggt atgataatga attatgtaag aaaacaacag gccgggcggg    3720
ttggttcaca cgtgtaatcc cagcactttg ggaggctgag gcaggcagac tgcctgagct    3780
caggagttcg agaccagcct gggcaacacg gtgaaatccc gtctctacta aaaatacaaa    3840
aaaattagcc gggtgtggtg acacatgcct gtagtcccag ctacttggga ggctgaggca    3900
ggagaatcac ttgaacctgg gaggtgaagg ttgcagtgag ccaagatggc accacttcac    3960
tccagcctgg gaaacagagc aagactctgt ctctgagctg agatggcacc acttcactcc    4020
agcctgggaa acagagcaag actctgtctc aaaaaaaaca aaacacacaa acaaaaaaac    4080
aggctgggcg cggtggctca cgcctgtaat cccagcactt tgggaggccg aggcgggtgg    4140
atcacctgag gtcaggagtt ccagaccagc cttgtcaaca tggtgaaacc tcccccgcc     4200 gtctctacta aaaatacaaa aattagccag gcgtggtggc aggagcctgt aatcccagct    4260
acttgggagg ctgaggcagg agaatcgctt gtacccagaa ggcagaggtt gcactgagct    4320
gagatggcac cattgcactc cagcctgggg acaagagcg agatttcgtc tttaaaaaac     4380
aaaaacaaaa caaaaaacca tgtaactata tgtcttagtc atcttagtca agaatgtaga    4440
agtaaagtga taagatatgg aatttccttt aggtcacaaa gagaaaaaga aaaattttaa    4500
agagctaaga caaacgcagc aaaatcttta tatttaataa tattctaaac atgggtgatg    4560
aacatacggg tattcattat actattctct ccacttttga gtatgtttga aaatttagta    4620
aaacaagttt taacacactg tagtctaaca agataaaata tcacactgaa caggaaaaac    4680
tggcatggtg tggtggctca cacttgtaat cccagtgctt gggaggctg agacaggaga     4740 gttgcttgag gccaggagtt caagaccgac atggggaatg tagcaagacc ccgtccctac    4800
aaaaaacttt gtaaaaattt gccaggtatg gtggtgcata cctgtagtcc cagctactcg    4860
ggaggcggag gcagaaggaa tcacttgagc ccaggagttt gaggctgcag tgagctacga    4920
```

-continued

```
tcataccaca gcactccagc gtggacaaca gagtaagacc ctatctcaaa aacaaaacaa    4980
aacaaaacaa acaaaaaaaa ccacaagaaa aactgctggc tgatgcagcg gctcatgcct    5040
gtaatcccag tattttggga ggcccaggtg ggcgtatcac ctgaggtcag gagttagaga    5100
ccagcctggc caacatggtg aaacccatc tctactaaaa atacaaaatt agccaggcat     5160
gtggcacgcg cctgtagtcc cagttactgg gaggctgaag caggaggatc acctgagccc    5220
gggaggtgga ggttgcagtg agccgagatc acaccactgc actccagcct gggtgacaca    5280
gcaataccct acctcaaaat aaaaaagaaa aagaaaagaa aagttgctgt ccccgctacc    5340
ccaatcccaa atccaaacag cctctctcat ctcacagtaa gggggaaaaa tcacccaaaa    5400
aagctaagtg atcttttgaa aacccaaact cttagaagtc taagattatt atagtcaact    5460
catgaagtgt catcataaaa gatactctaa tattatttaa gtagaaccac atattggttg    5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaaatcata aaagcactta tctttgaaag aggagttaca gcaattttat    5700
ttagttcttt attgctttgc tatatattct aaatttttt caatgaatat atatcacttt     5760
taaaaaaatt caatggtctt tcttataaat tatctttggc agcatgcgtt tttatatata    5820
catataaaat gtatgggaaa tttttaaagg atacattaaa ttaaagcaaa atatacaaac    5880
aaaaaatcag aatacaaaaa gataaaaaga ttgggaaggg agggagggag taaggaggaa    5940
gggtgggtgg gtatagagaa atataccaaa taatggtaag aagtggggtc ttgacacttt    6000 ctacacttt tttaaataaa aaaaatttt ttctctctct tttttttttt tagagacgaa       6060
gtctcgctat gttgcccagg ctggtcttga actcctggga tcaagagatc ctcctgcctc    6120
agcctcccaa ggtgcttgga ttacaggtgt gagccaccac gcctggtcac tttctacact    6180
ttaatatata tattttttca ttttcaatgt cattttatt agttaattta taatacccat      6240
tcaccattat attcaaagtc tatttgaaga aataaaccag aaagaatgaa atactctagc    6300
tcacatgcta ttcaatacta aattaccttt caaatcacat tcaagaagct gatgatttaa    6360
gctttggcgg tttccaataa atattggtca aaccataatt aaatctcaat atatcagtta    6420
gtacctattg agcatctcct tttacaacct aagcattgta ttaggtgctt aaatacaagc    6480
agcttgactt ttaatacatt taaaaataca tatttaagac ttaaaatctt atttatggaa    6540
ttcagttata ttttgaggtt tccagtgctg agaaatttga ggtttgtgct gtctttcagt    6600
ccccaaagct cagttctgag ttctcagact ttggtggaac ttcatgtatt gtcaggttgg    6660
cccgtaatac ctgtgggaca acttcagccc ctgtgcacat ggccaggagg ctggttgcaa    6720
acattttcag gtaggtggac caggacatgc ccctggtcat ggccaggtgg aggcatagtg    6780
ctatacagca ggcagaagtc aatattgatt tgttttaaa gaaacatgta ctactttcat     6840
aagcagaaaa aatttctatt cttgggggaa aagattatgc cagatcctct aggattaaat    6900
gctgatgcat ctgctaaacc ttcacatatc agaacatatt tactatagaa agaatgaaaa    6960
tgggacattt gtgtgtcacc tatgtgaaca ttccaaaaat attttacaac aactaagtat    7020
tttataaatt ttatgaactg aaatttagtt caagttctag gaaaatacaa accttgctag    7080
atattataaa aatgatacaa tatatattca tttcaggctc atcagaatat atctgttatc    7140
acttgacaag aatgaaaatg caccattttg tagtgcttta aaatcaggaa gatccagagt    7200
actaaaaatg acttcttcct tgaagcttac tcaccaactt cctcccagtt actcactgct    7260
tctgccacaa gcataaacta ggacccagcc agaactccct tgaaatatac acttgcaacg    7320
```

```
attactgcat ctatcaaaat ggttcagtgc ctggctacag gttctgcaga tcgactaaga    7380
atttgaaaag tcttgtttat ttcaaaggaa gcccatgtga attctgccca gagttcatcc    7440
cagatatgca gtctaagaat acagacagat cagcagagat gtattctaaa acaggaattc    7500
tggcaatata acaaattgat ttccaatcaa aacagattta cataccatac ttatgtcaag    7560
aagttgtttt gttttattgc atcctagatt ttattttttt gatttatggt ttactttaag    7620
cataaaaaat ttgtcaatac aactcttccc aaaaggcata aacaaaaatt cataaaactt    7680
gcatcacttg agatacttca ggtatgaatt cacaactttg ttacaactta ctatatatat    7740
gcacacatat atatatattt gggtatattg gggggggttct aatttaagaa atgcataatt    7800
ggctatagac agacagttgt cagaacttgg caatgggtac gtgcaggttc attataccaa    7860
gtctacttgt agttgttcaa aatgtatcat aatacaaggc cgggcgaggt cgtcacgcct    7920
gtaatcccag catttttggga ggctaaggca ggaggattgc ttgaggtcag gagtttgtga    7980
ccagcctggg caacagagca agaccctgtc tccaaaaaga aaaaaaataa ttttttacaa    8040
aataaaaaca aaatgtatca tcagacgaaa ttaaataaga ggcaattcat ttaaatgaca    8100
acttttccca gcttgacatt taacaaaaag tctaagtcct cttaattcat atttaatgat    8160
caaatatcaa atactaattt ttttttttttt tttttttttg agacggagtc tcgctctgtc    8220
gcccaggctg gagtgcagtg gcgcgatcct ggctcactgc aagctccgcc tcccgggttc    8280
acgccattct cctgcctcag cctcccgagt agctgggatt acagacatgc gccaccacgc    8340
ccggctaatt ttgtattttt agtagagatg gggtttctcc atgttggtca ggctggtctt    8400
gaatttccca cctcaggtga tctgcctgcc tcagcctcac aaagcagtag ctgggactac    8460
aggcacccac caccacactt ggttaattct tttgtatttt ttttgtaaag acgggatttc    8520
accatgttag ccaggatggt ctcgatctcc tgatctcatg atccgcccgc ctcagcctcc    8580
caaagtgctg ggattacagg cgtgagccac cccgcccggc catcaaatac taattcttaa    8640
atggtaagga cccactattc agaacctgta tccttatcac taatatgcaa atatttattg    8700
aatacttact atgtcatgca tactagagag agttagataa atttgataca gctaccctca    8760
cagaacttac agtgtaatag atggcatgac atgtacatga gtaactgtga acagtgttaa    8820
attgctattt aaaaaaaaag acggctgggc gctgtggctc atgcctgtaa tcccagcact    8880
ttgggaggcc aaggcaagtt gatcgctcga ggtcaagagt tcgagaccag cctgccaac    8940 gtggtaaaac cccgtctcta ctaaaaatac aaaaaaaaaa ttagccaggc atggtggcac    9000
aggcctgtaa tcccagctac tagggaggct gagacatgga gaactgcttg aatccaggag    9060
gcagaggtta cagtgagccg agatcatacc actacactcc agcctgagtg acagagcgag    9120
actcctgtct aaaaaaaaaa aaaaaaaaaa agatacaggt taagtgttat ggtagttgaa    9180
gagagaactc aaactctgtc tcagaagcct cacttgcatg tggaccactg atatgaaata    9240
atataaatag gtataattca ataaataggga acttcagttt taatcatccc aaacaccaaa    9300
acttcctatc aaacaggtcc aataaactca atctctataa gagctagaca gaaatctact    9360
tggtggccta taatcttatt agcccttact tgtcccatct gatattaatt aaccccatct    9420
aatatggatt agttaacaat ccagtggctg ctttgacagg aacagttgga gagagttggg    9480
gattgcaaca tattcaatta tacaaaaatg cattcagcat ctaccttgat taaggcagtg    9540
tgcaacagaa tttgcaggag agtaaaagaa tgattataaa tttacaaccc ttaaagagct    9600
atagctgggc gtggtggctc atgcctgtaa tcccagcac tttgggaggc tgaggcgggt    9660
```

-continued

```
ggatcacctg aggccagaag ttcaagacca gcctagccaa catggcgaaa ccctgtctct    9720
acaaaaaata caaaaattag ccgggtgtgg tggcacgtgc ctgtagtccc agttacttgg    9780
gaggccgagg caggagaatc gcttgaacct aggaggtgga ggctgcagtg agccgagatt    9840
gtgccactgc actccacttc agcctgggcg acaagagcaa gactccgtca caaaaaaaaa    9900
aaaaaaaaaa aagcttaaaa tctagtggga aaggcatata tacatacaac taactgtata    9960
gcataataaa gctcataatc tgtaacaaaa tctaattcga caagcccaga aacttgtgat    10020
ttaccaaaaa cagttatata tacacaaaaa gtaaacctag aacccaaagt tacccagcac    10080
caatgattct ctccctaagc agtatcaagt ttaaagcagt gattacattc tactgcctag    10140
attgtaaact gagtaaagga gaccagcacc tttctgctac tgaactagca cagccgtgta    10200
aaccaacaag gcaatggcag tgcccaactt tctgtatgaa tataagttac atctgtttta    10260
ttatttgtga cttggtgttg catgtggtta ttatcaacac cttctgaaag aacaactacc    10320
tgctcaggct gccataacaa aataccacag actgagtgac ttaacagaaa cttatttctc    10380
acagttttgg aggctgggaa gtccaaaatt aaggtacctg caaggtaggt ttcaatctca    10440
ggcctcttct ttggcttgaa ggtcttctaa ctgtgtgctc acatgacctc ttctaacaag    10500
ctctctggtg tctctttttt tttttttttc tttttgaga cagagtctca ctctgtcacc    10560
caggctggag tacagtggca caatctgggc tcactgcaac ctccaactcc cgggttcaag    10620
tgattctcat gcctcaccct cccgagtagc ttggatgaca ggagcccgct accacaccca    10680
gctaattttt gtatttttag tagagatggt gtttcactac attggccagg ctggtctcaa    10740
actcctgacc tcgtgatcca cccaccttgg cctcccaaag tgctgggatt acaggtgtga    10800
gccactgcgc ccgtcctggt gtcttttcat ataagggcac taatccaatc agacctgggc    10860 ccaacccctcc cgacttcttc taactgtaat taccttccaa aggccctgtc tccaaatacc    10920
atcacactgg gggttaggac ttcaaaaaag gtatgggggg ggtgtgggag gacataaatg    10980
ctcagtccat aacaagcacc caacataaaa atggctagaa cagatcacaa aaaaaaggtc    11040
ctgtatggct ttggggaagg gctcaacccc aaaatatctg agagctctgg aggggcctag    11100
aagtggtaaa tgaatgaaaa cgtggttact ctccagatct gcctttccca aatatggcca    11160
ttcttggctg aatcagaaat caaaggacag gttattaatt actagctcta agttacttac    11220
catttgctga gacagttcag aaatctgact gcatctcctc agagatctag aacacagttc    11280
tcaaattcta acttacttgt gatatacttg tgaatgataa aaatcgctac aggtactttt    11340
attaatctga aagagtattg agaaattacc tttcattctg acttttgtct ggaatgaaaa    11400
tcaatacttt tgctataatc gattactgaa ataattttac tttccagtaa aactggcatt    11460
ataatttttt ttaattttta aaacttcata attttttgcc agactgaccc atgtaaacat    11520
acaaattact aataattatg cacgtcacat ctgtaataat ggccttcatg taaacatttt    11580
tgtggtttac acataaaatc tctaattaca aagctatatt atctaaaatt acagtaagca    11640
agaaaattaa tccaagctaa gacaatactt gcaacatcaa ttcatcatct gtgacaagga    11700
ctgcttaagt ctctttgtgg ttaaaaagga aaaaaaaaa aaagacatgt tggccagatg    11760
cggtggctca cacctgtaat cccagcactt tgggaggctg aggtgggcgg atcacccctg    11820
gcctgcccaa catggtgaaa ccccgtctct actaaaaaca caaaaattag ctgggcgtgg    11880
tggcgggcgc ctgtaattcc agctactcgg gaggctgagg caggagaatt gctagaaccc    11940
aggaggcaga gattgcagtg agctgagatt gcaccattgc actacagtct gggcaacaaa    12000
agtgaaactc catcttaaaa aaaaaaagac aatgttcgtg ggtccaaaca agacttaatg    12060
```

-continued

```
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta ccttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aattttttcct tttattagtg  12900 tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
agaaaactaa aagaaaactc caaggcaact cttctctgct gatctggttg gtcctttttcc  13320 taccttttgc aatacccaga tacaaacaat ggatagaaaa caaagtagac ttgtagtatg  13380
caggtcacag tgctaaattc acagaaagaa acccctgaac tgaactgctc tatttcctgg  13440
tggtcacaaa gagtaattct ggtttacacc tacagattga tgtcaatcta caccctgttg  13500
ataacagtgt ggccaaggac aaaaaaaagg tgctccgttt taccaattct gtaaaaaatt  13560
attggcaggg taagctcggc tagggcagga ttacatttct aggactacca tccccgaaat  13620
ttagaagata ttatatccac ataaagcata tctttcacat taatttgcaa aaatctaaaa  13680
gctttttctt agctcaagtg tgtccaagtt taccctggca gtttaaaacg atagttacaa  13740
gcagcatggg ttgtatcaga cacatttgag ggccaatttc atgtaagtga tattgggcaa  13800
gttacttcaa ctatctgtgc ctccaaggtc atactagtgt ttatttacct aaagggtacc  13860
tgttatgtaa ctttagggtg tttacattag ataatgcctg caaaatattt acttcaacgc  13920
ctaaaacata gttaagtatt caataaatac ctactattgt cactactaac ttaaaagttt  13980
agagattaag agcagaatct ggggtgagac aaacttaggt tcaaatccta gtattgttgg  14040
gtaatcttgg gcaagttact taacctctct gatttgtgta atttaaaaaa ttagttaata  14100
tacataacag ggcttagaag agtatctagc acatagcacc atttaagcat ttgttattgc  14160
taacatgcaa acaatttaag ggaaagaaat tttttaaaaa ggaagaggga tttgcaaact  14220
aaaaacaatg agtatcttat gttcaaagaa aactaacaaa cagccagctc tagcaataat  14280
taaattcact atatactggg gcaggcatca caccccaaag ctaaaagcgt ctacctaggc  14340
caggcacggt ggctcatgcc tgtaatccca gcactttggg aagcagaggc gggcagatcg  14400
```

-continued

```
cttgagctca ggagttcaag accagcctgg acaacatggc aaaacaccat ctctacaaaa    14460
aatacaaata ttaggccggg cgcagtggct cacgcctgta atcccagcac tttgggaggc    14520
caaggcgggt ggatcacctg agatcaggag ttcgagagta gcctggccaa catggtgaaa    14580
cctcgtctct attaaaaata caaaaaatta gccaggcatg gtggcaggcg cctgtaatcc    14640
cagctactca gggggatgag gtaggagaat cgcttgaacc cgggaggcag aggttgcact    14700
gagccgagat catgccactg tactccagcc cgggcaacaa gagcgaaact ccatctcaaa    14760
aaataaataa ataaataaat aaaataaagt acaaatatta gccagggatg gtggtgcgca    14820
cctgtagtcc cagctacttg ggaggctgaa gtgggagaat cccctgagcc tggggagaat    14880
cacccgagcc cgggaagtcg aggctgcagt gagcagtgat tgtgccactg cactccatcc    14940
taggtgacag agtgagaccc tgtctcaaaa aaagaaatt ggcagaatta agtaagttga    15000
tgtttagaga tgaaaaatca acattttttc ctcagcaact gaataaaaac aacagccact    15060
accatttttt tgagtaccta tttgtagcct atttttttaac tggtattact cgagagagag    15120
agagctaggt tcgagacaga gctccttctc ttaataactg tatgacctag ggtatgtctg    15180
ttagcctctc tgaggcttca aaggttcctc atctgtaaaa tggtaataat cataccattg    15240
ctacagggct gttttgaaga ctaattagga ctatgtaagt aaacatgatg atggctatta    15300
ttactgttcc ccgccagggg ccatgcaagg gttgctgatt cacatagact gtcttataat    15360
cctctcaata actccaagag gtagccagca cctcagatat acataaaatg acttaagccc    15420
agagaggtga agtaagttgc ccacagccac acaactagta aatagcccaa acaagctgga    15480
ttcccagtta gactccgtta atagcactgc tctttacctt aagtcattac aatgcctaat    15540
atgaaataga atcgcttctt tcttagggtt caagtggtta attatttaat gtattcattc    15600
aacaaaccat catcgaggac ctcttacaag ccaagtactg tgctaagtgc tagagttacg    15660
gcggtgattc ctgcccttaa aaagttttag tgggagaaac aacaggtaac caggtcattg    15720
ccaaaacaac aaaaataatc ataataaagc aggctaaagc atatttaact ggccggggtt    15780
ttgactattt tagcaagcat gatcagaacg gttgaggagg gaggccagca gcttggccgg    15840
ttcaacaaac aagaaaaaac cagtgagggt ggagctaaga taccagaggc tgattacggt    15900
taagaatgtt cttgaaggta aggaccagat tctcattttc tatatcctgg ggcatcggtc    15960
agcatggaat ctggattcta gcacatgtga atttcggctt gaaatgacct aatgcctttt    16020
ccctagttcc ttcgtgtgtc aaatacgcat ggttaccgct accagagctg tagtggggct    16080
tcaatgaggc catgagcatc tccataaaga tgaactacag tgtgtgcaaa actaaaggca    16140
aaacctggtc cccacacgcc ctcccaggtg gtcgctttcc gtgccgaggc ccctccagag    16200
gtgccccgag aacctcacca tcgcacccca aacttccagg gaagggcctc tcccgagaaa    16260 gccccacgc ccccaccccg cgccatcatt cccgaatctg ccctcggccc ctccccgcag    16320
cacgctcgca ggcggcacat gtcaaccaaa acgccatttc caccttctct tcccacacgc    16380
agtcctcttt tcccagggct cccccgagga gggacccacc ccaaaccccg ccattccgtc    16440
ctccctgccg ccctcgcgtg acgtaaagcc gaacccggga aactggccgc ccccgcctgc    16500
ggggttccct gggcccggcc gctctagaac tagtggatcc caattgaagg cctggtctaa    16560
atgactccaa aatcaccact taattcaaga gactgatttc cctgagtcag gccccttaaa    16620
gcagctattt caatgggaca gggaaacaac cctaggatct ggattagaat cacttggggg    16680
ctgccacacc cccagggctc tgatcctgcc cttctcccac acgcacattc acatactgct    16740
gcagtgacct tccatttcta atgggttcct gggccatctg tcaggtatag ggaatggaaa    16800
```

-continued

```
aggggttggg gaggctctgc ttcagaaagt ttgtgtcagg ggctcccaga gcctccacag   16860
atagatagca ggggtcccca ccctaccatg gcagctataa atgtgatcaa catttattgg   16920
cctaggatac agcagttagc aaaatgcctg atgtagttcc cactccgtgg aggttgcagg   16980
ctagccaaga agtcatgagt tcagcaaccc ttacgcacca gtgggatgag attggaccag   17040
gccgagggta gtcttgggaa cactcagcat ttgtctgagg gccagaagag gctgcttgcc   17100
ctcagacagg aggtcagcat ctttattgta gcccatgaca cctctacacc attgctcttc   17160
tggtcttatg gaagacatct ttgggcctga taacagcgga gtctgtgtcc cacttgtcca   17220
ggctggagtg ccacatcagg cacactccag ttgcagggac agcacagaca agtttcagga   17280
aggctggtgg cctccaggag gttaacctta taaggccaga ttgtaaccta gttgaaaaac   17340
atacacatgc catgataata aaagaaccta ggcaccatta caagagaaaa aatcattttt   17400
gtagatacga gcatggattc ttgggtgggt cagacacact gggcttgtgc tctgactgca   17460
ctgtctcccc tacctgacct tgggtaaacc ataagactgc tgcatgactc agtgtccacc   17520
ccaaaaaagt accggtagat attggccaca gtagatatca gctagagtgg actctcatga   17580
caatgagggg agatgtattc cccatcttag gcacctggga ctctaccttc catcttctgc   17640
tccgtgtctc tccatcccca ggctcttcag aactcaggga gtccagaatg tcagctccca   17700
gatttcagcc ttcagaaagg aaacccatta ccgttcagtt gaacaaatgt tgtctgagcc   17760
ccagatctgg gctcagaggc catctaggct atgagacaag aggggaacaa agcaccgtct   17820
gcactcactc accacactca cttgctgtcc caggtcacat ccatcgggta gagaatctaa   17880
gaggctgagc tagctcccgc caccagccca gcccacccca cctggcccct tccttccttc   17940
tacaaaatat gcaccacctg tcaaagggtg ggcagtgcca ggcctgcata cagagcactg   18000
agtgtaaaag cagacatgga ccctgacctc caggagcttc caattttctt gaagagacaa   18060
atcagctggc atttcagtcc agtgtgatct gctcttggtg agcacagacc tagggagttg   18120
gggcagcttc ccagaagaac tgcagtccag gctgagggca gagaaatgag gggaatggcg   18180
aggaattggg gagcaggggg gagctcagta gagagccaag ggcggaggt gagaagtccg    18240 tgttgggcca ggagctaccc tccggtggcc acagccgaag tcgaggatgc ctttggaact   18300
catccccact tctctctttc tgtatgtagc cgtccaagaa caagtcacct ccaagtgtag   18360
ccggatcaag gcaagcccc catctagcaa gcacttgatg ccacccagaa ctgggcttct    18420
tcagaacaat ctgagtccag gaatgatccc actcaccagg caccagagct gcgagggcat   18480
gggagtgatc tcaccaactc tggggaagcg gcaaggaatt ttcacctcca gcccccagtg   18540
tcccatcctc tcacactcag gccagactcc cctgggcaga cttgactctg tctgccagca   18600
tatgcagagc cccaaggcca ccccaccaga agtgccctg cctgggttct gtcccagctc    18660
cctgggcacc cagtccttga gtccccacca gctcagacgg cctagtgtgc caagaatgcc   18720
cactgcgttc aacaatgctg catgggtcac agcggcagca gctgtgacca cagcagtttc   18780
ggggaaaaca cccctcagcc aagtggataa tagcgttcag cagcactcac cttctggcca   18840
ggcctgcctt cagaggccat ctgattggga ggcacaagtg cccgctgcga tgggaacaca   18900
agtgcccctg gccaacaacc ccagcttcag cctgctgggc agccagagcc tcaggcagag   18960
cccggtacag ggcccggtgc ctgtagcaaa caccaccaag ttcctccagc agggtatggc   19020
cagctttagt cccctgagcc ccatacaggg catcgagcca ccaagctatg tggctgctgc   19080
tgccaccgct gctgctgctt ctgccgttgc tgccagccag ttcccaggtc cgttcgacag   19140
```

-continued

```
aacggatatt ccccctgagc tgccacctgc cgactttttg cgccagcccc aaccccact  19200 aaatgatctg atttcgtcac ctgactgcaa tgaggtagat ttcattgaag ctctcttgaa  19260
aggctcctgt gtgagcccag atgaagactg ggtgtgcaac ttgaggctga tcgacgacat  19320
tttggaacag catgctgctg ctcaaaatgc cacagcccag aattctgggc aagtcaccca  19380
ggatgctggg gcactttaaa tctgagcagg atgcccatag aaaccccat ggtgacatca  19440 ctctaggaag tggtgtcgat ccatacccgc agttgtctcc cgttacaatt tgagtggtgt  19500
tgtcagccca tgcttatccc tctctctacc tgtgacaaaa tggaaagctg gtgattttc  19560 aagctacgtg tacatatttg aaaattttgt aaatggtttt cctaaacatt aatgacagaa  19620
gtatttatac ttcattttgt gactttgtaa ataaagcgac ggcttttgtt tcagtagagt  19680
tgtgtttact atgcattgtt ttgtgtttat tatacaatgt tacaaatatg cagaccgtgt  19740
tgtttgctcc agtgatacct tgttaagcta ggtggctgag tcgcttatgg ttttaatgca  19800
atgagcaatg tggatatgac caagagttgt tgtgcaagtt gacaaatgcc aaatagaaaa  19860
ccacttggcc atttatttct atgttcacta aaaatcctat tgccttgtgt gattcttaat  19920
ctcttttgcg aacctttcag tctccgctag ctctttccta atgagcttta cagcagaagc  19980
tgttttatcg ttaagtgccc cacagagaca ctttaccagg aggctgggag agttctccag  20040
atttgggaga ggcgcagaga cagtgtgtga gccgagccct gtctcagcaa tccacctgga  20100
ggagctagag tatcctcctc cctttaccat tcagaccgag agaaaaagcc cagcttgtgt  20160
gcaccctcgt ggggttaagg cgagctgttc ctggtttaaa gcctttcagt atttgttttg  20220
atgtaaggct ctgtggtttg gggggggaaca tctgtaaaca ttattagttg atttgggggtt  20280 tgtctttgat ggtttctatc tgcaattatc gtcatgtata tttaagtgtc tgttatagaa  20340
aacccacacc cactgtcctg taaacttttc tcagtgtcca gactttctgt aatcacattt  20400
taattgccac ctcgtatttc acctctacat ttgaaatctg gcgtctgttt caagccagtg  20460
tgttttttct tcgttctgta ataaacagcc aggagaaaag tgcctctatg tttttatttt  20520
tcaagggagt attcagtacc tacaaaccca agtcaggaag cctgctagtg gctttggttc  20580
tttcagaggc tgctcgatgc cttgtgtgtc agaaagaaag attcagcagt tttgcatcat  20640
ggcaaagaag cctgttattt tggggctcag cccctcattt tatagaggat gaaacagagg  20700
gggatgggag gtcacaaaga caactgcccc gggagcaggt gtggggggaga cttgccctga  20760 gggtctagac gctctgcacc accgtcctgt ctcccttgct gaagaccaca catgcccttc  20820
tttgaccaga ccctgccacc tgataggcca ggacctggta ggcgggtacc caggtttcat  20880
ggatggaacc acatctcccc aaaagtgggg aggtagctac tgggatgcac gcctcccgcc  20940
atgtgctata ggagagcagc tgaagcaaca gttgggatca gatgtagtca caattgaatg  21000
catcatcaca tttatccctc taagtggctg ggagagttga tatcctcatc cctaaggtac  21060
aaaatgttcc aatttgatca gtggctttca ggagctgaga aaggcatgtg ctctgaggca  21120
gagctgttat gtcccgcaga gcctaaaaat gctctaagaa catgctccct gccaaaattc  21180
tcaatggctg tgacaaggga caacgatcga ccaatggggg tggaagcaga cctccgcagt  21240
ccaggggcca gagctaggac agaggggtcg gagaaagagt cattttccca acactccagc  21300
tcttggccag tcctcacaca gtcccctcct gcttcctgct gagagagata tcctcatagg  21360
tctgggtaaa gtccttcagt cagctttcat tccctgtcac caactttgtc tctgttctcc  21420
ctgcccgtct caggcagcac tcctcaggaa acctctccaa gagccagcct cactgcagcg  21480
cccactattg tccctctgcc tcaagtgtcc catccatgcc aggccccagg caggctgcag  21540
```

```
ctttccctca gggccacacc aaagcacttg ggctcagctg tgctgtcccc ctccatcact   21600
gagctcaggg gcagcagggg tggggtgcca ggaggcccat tcacccttct ctggctctgt   21660
gttggaccca cctgcccagc cactgctgct tagaacctac ccgctgggaa aatgaagccc   21720
tcccggaggg gccacctcaa cctgagagcc tcacggatca cagttgtccc cactcagctc   21780
tgccagccct cagagaccca tagataaaag ctgagcttgg ctcgcagagc tggttccatc   21840
ttccattccc agagggttca acttcctacc ccaaccacac agggaacctc aaggctgagc   21900
cagtgtgggc tgcagtgcag accagcttcc tggacacgtc ctgccacctg accccaggct   21960
ggcctcactg cccctggcac tcctgaccct atcctcattc ctcctggcag tgcgtgttct   22020
gccattccgc tttcccttag ctgtcctctc actgtactgt cagcttctcc ttttccaggt   22080 gcccccagg ggctttccac atgaccctgt caccccacag cccatccagc accaattcca   22140
gctctctgcc acccttcaaa ggagtgacag tgccctgctt cacctcccac tcacccctca   22200
acccagagca atctggctcc agtcttgcct ccttccccct aagtactcta gtcacagttc   22260
caaattcctc ctggtcataa agccaaatga agcttcctgg tcctcagcgg acttgccact   22320
tcagcagtac tggactctct cctcccagaa acctgtttcc ccttggctcc tggagcccac   22380
actctgctgg aatccttctg cctctctggc ctgtagcctg gccctctctc ccaacctgag   22440
gtccattctc tcctgctcct ccacaagatg ttgctccttc cattacttcc tccctctcaa   22500
ccaaagctcc ttcattagct ctttatcttc tggtttcttc ccctgggcag acgaatggat   22560
tcaagagcct gtggcccagc agcccagcac tccaggatct cagcacttca gcatcccagt   22620
accctagcat ctcaataccc cagcacccca gcaccatagt attccagcac cccattgtcc   22680
aagcatctca gcactccagc atcccagcac cccaacactc cagcagccca gaatctcagc   22740
accctagcac tgcagcatct caggacccca gcacttcagc atcccagcac actagtactc   22800
cagcatctcg gcaccccagc acctaggcat cccaacaccc agcaccccag cacttaagca   22860
tcccaccact acagtatctc aacactccag caccccagca ccatagtgtt ccagcacccc   22920
agcatcccaa caccccagca cttaagcatc ccaacacctc ggcatcccaa caccccagca   22980
ctgcagcatc tcagcacctt agcatcccag tgccctagca tctcaatgct ccagcacacc   23040
agtactacag tattccagca ccccagcact ccagcatctc agcactgcag cactgcagca   23100
ctccagcatc ccaaaatccc agcatcccaa caccccagca gaccagcaga ccagcatctc   23160
agcaccgcag catccaagga ctatcccagc atcccagcaa cccagcacct cagcatccca   23220
acaccccagc atttcagcat ggcaacaccc cagtacccca gcacttcagc accccagtat   23280
cccagcatct cagcgaccca gtatcacaaa acctcagcat cctagcaccc cagcacccca   23340
gcaccttagc accttagcat cccagcatct cagcgcctca gcatcttgat attctggctg   23400
aggtcagcgt ggtgtatcta gtcagggtcc taactttcac ttcgcaggga aatgctgctg   23460
gactgggtct catgttgggc tgaagctctc tagacccctt gaagacagca taaaagagct   23520
tggagacgct gggtgtcccc catggaagag ttcactctca tcctgctttg acaacagcct   23580
tctctggggt ccctcacggg cccctctttc ttactgcaag tttgtctctg agaagactgt   23640
gatgcagaag tcactcagct gcctgtggct cctgaagagc tgaaggtgga ggcctgtagg   23700
cctccctatg agaggcgcag aaaaaaccat gattgctagt ggggaggtgc tccctctaca   23760
acccactcca taatctgccc ccgcccagct ctgaggccag ccccaggga aaatgccaga   23820 tccccaggga ggtgtgtgag acctcagggg ctccctcctc ccttacagca ggctcaggcc   23880
```

-continued

```
cctgggggcc tcagggccaa ggtctgtggg taagctacta tctctcactt gtcctctagc     23940
cacaaaagcc agggagatct ggcaatggac atgaggttct gaagaagcac atatgactgg     24000
cttcctaatg cgtggttgtt cagtgattca ataaacacgc atgggccagg catggggaaa     24060
tagacaaaca tgatccccaa cctctcccag agtgaactgg gagggaggag tgttcatccc     24120
tcaggattac accagagaaa caaaccagca ggagatatat atggttttgg ggggtcaaga     24180
aagaggaaaa acctggcaag gcaagtccaa aatcatagga caggctgtca ggaagggcag     24240
cctggaacct ctcaagcagg agctgatgct gcagtccaca ggcagaattt cttcttcctc     24300
ggggaaatct cagctttgtt cttaaggcct ttcaactgat tggctgaggt ctgccccttc     24360
ccccacattc tccaggataa tcttccttac ttaaagtcaa ctattaatca cagctacaaa     24420
atcccttcac agctacacat agatcagtgt ttgattgacg aacagcccct acagcctagc     24480
caagttgaca cataaaacta accatcacag ggggacaaat gatgtaaaca catcaacaaa     24540
taaaacagta acaagttaag gtctatggaa aaaacacaga aggggcagag agaaagaaag     24600
caagaaggag agtcccagtt tgctagggct tgtgggaagt ggggagcagt tctctttagc     24660
taggatattt gggaaaggca tatctgaagg agtgatattt gagcttagat taaaagatgg     24720
gaaggagcaa gccatgcaaa gagctaggat gttccaagca gagacggaac agcaagtgca     24780
aatgtcagga ggaatagaag gaggctggtg ggtggggtcc agtgagcaag aggagggcag     24840
gcaggagagg ggatggggag gtgggcaggc ccagaccacc cagggccctg gagactatcc     24900
tgatccaaca agggaagcct tgagtcactt cagtgtccat gtggagaatg gacctcagac     24960
tgaatgaggg aggcagtaag gagggcctct acctccaggg cttcgccctg tggactgcgc     25020
atagacatct ccaactcaga aagtctgaac caaactttcc atagttcccc caagtctggg     25080
catcctccta ctcagtgaaa ggcagccatc acacctccct gccctgctcc cggatgcccc     25140
aaatcctctt ggtctccaag tccagaacct gagacttgtc cttgatgttt gtctttccct     25200 cacccttct gtattctggg aagatgggtt tttttccccc agatgaatct gtaaaacttc      25260
tgtgatcaca ataaaaattc tggcagtatt attttctgga acatgacaaa gtgattcaaa     25320
attatttatc tggaagacta caaaacaaga atagccagga aatttctaaa aagaaagaag     25380
aaggaggagg agaaagaagg aggaggaaaa ggaggagaag aagaaagaa aaagaaccaa      25440 gaaagggttc tagctctacc aaatattaaa acatatcatg aagctattta aaacaatatg     25500
gttgtggata ctgaaaaaga tgtgaataaa gtggaaggaa aataaataga aatgcacatg     25560
gggattgaga ctgtgaaaaa ggcagcatct cacatcagtg agggatgttc aacacctggt     25620
gttgggaaaa ctggctagtc atttaaacca aacaactggg tcctctacct cactcctgac     25680
attaagatac atttagatga ttcaaagagt aagacagaaa aaataacacg tgaaaacact     25740
atcagaaaac aacgtgggcc aggtgtggtg ggtcacgcct gtaatcccag cactttggga     25800
ggccgaggca gacagatcac ctgaggtggg gagttcaaga ccagcctgac caacatggtg     25860
aaatcctgtc tctactaaaa atacaaaatt agctgagcgt ggtggcgcat gcctgtaatc     25920
ccagctactc aggaggccga ggcaggagaa tcacttgaac ctgggaggca gaggttgtgg     25980
tgagccgaga tcacgccatt gcactccagc ctgggcaaca agagtgaaaa tccatctaaa     26040
aaaaaaaaaa aaagccaagg tggatatttt tatagtatca gggtagatca agcttctcca     26100
atcatgacat gaaacccaga aaccataaaa gaaaagaatg ataaaattgc ccacgtaaag     26160
taaaaagctt gcacacagaa aaacaccata caggttacaa gatgagcagc aaaatcagag     26220
aaaaaacatt gcaattcagg acacacagag gctattgttc ctaatattta aaaataaaag     26280
```

-continued

```
tagtggattg tctacaaaaa gatgaagaca agaatttcag aaaaccaaat actgcatgtt   26340
ttcacttaca agtggaagct aaacactgag tacacgtgta cacaaagaat ggaaccatag   26400
gccaggcacc gtggctcacg cctgtaatcc cagtactttg cgaggccgaa gcgggcggat   26460
cacctgaggt gaggagttcg agaccatcct ggccaacatg gtgaaaccca gtctctacta   26520
aaaatacaaa aattagccgg gcgtggtggt gggtgcctgt aatcccagct actcgggagg   26580
ctgcggcagt agaatcgctt gaaccctgga ggtggacctt gcagtgagcc gagatcgcac   26640
cactgcactc cagcctgggc aacagagtga gactccatct caaaaaaaaa aaaaggaat   26700 agaacaatag acactggggc ctacttgagg gaggagggtg aggatcaaaa acctgcctat   26760
caggtactat gcttattacc tgggtggtga aataatctgt acaccaaacc ccagtgacat   26820
gcaatttacc gatgtaacaa acctgcccat gtacccgctg aacctaaaat aaaagttgga   26880
aaaaaatata gaaattttct ttgtaatagc caaaaactgc aaacagccca ggtgtctatt   26940
agtagaatgc ataaacaaac tcgggcatgt tcatacaatg taaaactact catcaataaa   27000
aagtgatact tctcagcaat gaaaagaaac tagctactga taccagctac aacatggatg   27060
gatttcaagt gctttatgat gagagcaaga agccagacac aaaagtgtct atatatatat   27120
acagtatata tacgtatata tacacatata tacagtatat atatacatat acatgtatat   27180
atatactgta tatatactgt atatatatac acagtatata tatacatata tacagtgtat   27240
atatactgtg tatatataca tgtatatata ctgtgtatat atacatgtat atatactgtg   27300
tatatataca tgtatatata ctgtgtatat atacatgtat atatgtat actgtatata   27360 tactgtatat atatatacac atatatacag tatatatata cagtatatac tgtatatata   27420
cagtatatac gtgtatatat acatatatac agtatatatg taaatataca tatatacagt   27480
atatatgtaa atatacatat atacatgtat atatatacac tatatatata catatatagt   27540
gtatatatac atatatacat gtatatattt actatatgat tccatttata taaagtgcca   27600
aaacagtcaa aaataatcta tgtggaaaaa atcaacaaag ggatcccccg ggctgcagga   27660
attcgatggc gcgccgtcga cccaacgcgt tgggagctct ccggatccaa gcttgttggg   27720
tcgaagctcg acatgataag atacattgat gagtttggac aaaccacaac tagaatgcag   27780
tgaaaaaaat gctttatttg tgaaatttgt gatgctattg ctttatttgt gaaatttgtg   27840
atgctattgc tttatttgta accattataa gctgcaataa acaagttaac aacaacaatt   27900
gcattcattt tatgtttcag gttcagggggg aggtgtggga ggttttttaa agcaagtaaa   27960
acctctacaa atgtggtaga tccatttaaa tgttaaggat cccgcggccg cctactcgtc   28020
ctcctggaag tagaatttgg tgaccatgac gccttcgtca ggcatattgg tgaggctgac   28080
gggctggtca gcttccatcg ctgtgcagag gaaccaaccg gggcaggcgg cagactcaaa   28140
actggtggtg gggccactgt ctgagcggat gaaggcgaag cgcttgtcct gctttctgtt   28200
ctcgctcagg tcagtgatgt taactgcctc cagctggagt ctggtctcat caccagactt   28260
gacacaggac aggcacatct tccctccatg gattcccaag aacagagcat gaggctcaat   28320
gggtaccaca tctatctttt cttctaaatt gacatttggt ccttgcaagt atccagcaac   28380
tagttggttg ttcctcagat agaaggtctt ctggttaaca tcccagattc tgaaggcttg   28440
catcttgctg gattttctcc cagagggtcg gcagatcgtc tctgaatgga acaggaagag   28500
gaggagagtg attaggtgac tgcggaggcc tctgcagatt tccataccgg tggatccatg   28560
gctctgtctc aggtcagtat aggagctttg atgtgaagtc agccaagaac agctgaacac   28620
```

-continued

```
tacttcctct gaggcccttt tataggaggg attgcttcct gtgaataata ggaggatatt   28680
gtccacatcc agtaaagagg aaatccccaa ctgcatccaa aaagtttcct gggaatatcc   28740
actgctgcag gagtggaaag tccccagtgg aaagtcccca gtggaaagtc cccagtggaa   28800
agtccccagt ggaaagtccc cagaatttcg acgtctagag gagcatgcga cgtcggcgcg   28860
cctaccagta aaaagaaaa cctattaaaa aaacaccact cgacacggca ccagctcaat   28920
cagtcacagt gtaaaaaagg gccaagtgca gagcgagtat atataggact aaaaaatgac   28980
gtaacggtta aagtccacaa aaaacaccca gaaaaccgca cgcgaaccta cgcccagaaa   29040
cgaaagccaa aaaacccaca acttcctcaa atcgtcactt ccgttttccc acgttacgtc   29100
acttcccatt ttaagaaaac tacaattccc aacacataca agttactccg ccctaaaacc   29160
tacgtcaccc gccccgttcc cacgccccgc gccacgtcac aaactccacc ccctcattat   29220
catattggct tcaatccaaa ataaggtata ttattgatga tgttt          29265
```

```
<210> SEQ ID NO 8
<211> LENGTH: 29612
<212> TYPE: DNA
<213> ORGANISM: Artificial Sequence
<220> FEATURE:
<223> OTHER INFORMATION: helper-dependent adenoviral vector containing
      murine Il-1Ra

<400> SEQUENCE: 8
```

```
aaacatcatc aataatatac cttattttgg attgaagcca atatgataat gaggggggtgg     60 agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatatttgt ctagggccgc    360
ggggactttg accgtttacg tggagactcg cccaggtgtt tttctcaggt gttttccgcg    420
ttccgggtca aagttggcgt tttgatatca agcttatcga taccgtaaac aagtctttaa    480
ttcaagcaag actttaacaa gttaaaagga gcttatgggg aggaagtagt gttatgatgt    540
atgggcataa agggttttaa tgggatagtg aaaatgtcta taataatact taaatggctg    600
cccaatcacc tacaggattg atgtaaacat ggaaaaggtc aaaaacttgg gtcactaaaa    660
tagatgatta atggagagga tgaggttgat agttaaatgt agataagtgg tcttattctc    720
aataaaaatg tgaacataag gcgagtttct acaaagatgg acaggactca ttcatgaaac    780
agcaaaaact ggacatttgt tctaatcttt gaagagtatg aaaaattcct atttttaaagg    840 taaaacagta actcacagga aataccaacc caacatataa tcagaaacaa tagtctaaag    900
taataaaaat caaacgtttg cacgatcaaa ttatgaatga aattcactac taaaattcac    960
actgattttg tttcatccac agtgtcaatg ttgtgatgca tttcaattgt gtgacacagg   1020
cagactgtgg atcaaaagtg gtttctggtg cgacttactc tcttgagtat acctgcagtc   1080 cccttcta agtgtgttaa aaaaaaaggg ggatttcttc aattcgccaa tactctagct   1140
ctccatgtgc tttctaggaa acaagtgtta acccaccta tttgtcaaac ctagctccaa   1200
aggacttttg actccccaca aaccgatgta gctcaagaga gggtatctgt caccagtatg   1260
tatagtgaaa aaagtatccc aagtcccaac agcaattcct aaaaggagtt tatttaaaaa   1320
accacacaca cctgtaaaat aagtatatat cctccaaggt gactagtttt aaaaaaacag   1380
```

-continued

```
tattggcttt gatgtaaagt actagtgaat atgttagaaa aatctcactg taaccaagtg      1440
aaatgaaagc aagtatggtt tgcagagatt caaagaaaat ataagaaaac ctactgttgc      1500
cactaaaaag aatcatatat taaatatact cacacaatag ctcttcagtc tgataaaatc      1560
tacagtcata ggaatggatc tatcactatt tctattcagt gctttgatgt aatccagcag      1620
gtcagcaaag aatttatagc cccccttgag cacacagagg ctacaatgt gatggcctcc       1680 catctccttc atcacatctc gagcaagacg ttcagtccta cagaaataaa atcaggaatt      1740
taatagaaag tttcatacat taaactttat aacaaacacc tcttagtcat taaacttcca      1800
caccaacctg ggcaatatag tgagacccca tgcctgcaaa aaaaaaaaaa ttagccaggc      1860
atggtagcat gtacctgtag tcccagctac ttgagaggtg aggtgggaaa atcactttag      1920
tgcaggatgt tgaggctgga gtgaactgtg attgtgccac tgcactccag cctggacaat      1980
agagcaagac cttgtctcaa aaaaatgcat taaaaatttt ttttaaatct tccacgtatc      2040
acatcctttg ccctcatgtt tcataaggta aaaaatttga taccttcaaa aaaaccaagc      2100
ataccactat cataattttt tttaaatgca aataaaaaca agataccatt ttcacctatc      2160
agactggcag gttctgatta aatgaaattt tctggataat atacaatatt aagagagact      2220
gtagaaactg ggccagtggc tcatgcctgt aatcccagca ctttgggagg ctgggtaaca      2280
tggcgaaccc tgtttctaca aaataaaaat attagctggg agtggtggcg cacacctata      2340
gtcccagcta ctcaggaggc tgaggtggaa ggatcgcttg aacccaggag gttgagactg      2400
cagtgaactg tgatcattct gctgcactgc accccagcct gggcaacaga gaccttgtct      2460
caaaaaaaaa aaaaaaagag acaaattgtg aagagaaagg tactctcata taacatcagg      2520
agtataaaat gattcaactt cttagaggaa aatttggcaa taccaaaata ttcaataaac      2580
tctttcccct tgacccagaa attccacttg aataaagctg aacaagtacc aaacatgtaa      2640
aagaatgttt cttctagtac agtcggtaag aacaaaatag tgtctatcaa tagtggactg      2700
gttaaatcag ttatggtatc tccataagac agaatgctat gcaaccttta aaatatatta      2760
gatagctcta gacacactaa tattaaaagt gtccaataac atttaaaact atactcatac      2820
gttaaaatat aaatgtatat atgtactttt gcatatagta tacatgcata ggccagtgct      2880
tgagaagaaa tgtgtacaga aggctgaaag gagagaactt tagtcttctt gtttatggcc      2940
tccatagtta gaatatttta taacacaaat attttgatat tataatttta aaataaaaac      3000
acagaatagc cagacataca atgcaagcat tcaataccag gtaaggtttt tcactgtaat      3060
tgacttaaca gaaaattttc aagctagatg tgcataataa taaaaatctg accttgcctt      3120
catgtgattc agccccagtc cattaccctg tttaggactg agaaatgcaa gactctggct      3180
agagttcctt cttccatctc ccttcaatgt ttactttgtt ctggtcccta cagagtccca      3240
ctataccaca actgatacta agtaattagt aaggccctcc tcttttattt ttaataaaga      3300
agattttaga aagcatcagt tatttaataa gttggcctag tttatgttca aatagcaagt      3360
actcagaaca gctgctgatg tttgaaatta acacaagaaa aagtaaaaaa cctcatttta      3420
agatcttact tacctgtcca taattagtcc atgaggaata aacacccttt ccaaatcctc      3480
agcataatga ttaggtatgc aaaataaatc aaggtcataa cctggttcat catcactaat      3540
ctgaaaaaga aatatagctg tttcaatgag agcattacag gatacaaaca tttgattgga      3600
ttaagatgtt aaaaaataac cttagtctat cagagaaatt taggtgtaag atgatattag      3660
taactgttaa ctttgtaggt atgataatga attatgtaag aaaacaacag gccgggcggg      3720
ttggttcaca cgtgtaatcc cagcactttg ggaggctgag gcaggcagac tgcctgagct      3780
```

-continued

```
caggagttcg agaccagcct gggcaacacg gtgaaatccc gtctctacta aaaatacaaa    3840
aaaattagcc gggtgtggtg acacatgcct gtagtcccag ctacttggga ggctgaggca    3900
ggagaatcac ttgaacctgg gaggtgaagg ttgcagtgag ccaagatggc accacttcac    3960
tccagcctgg gaaacagagc aagactctgt ctctgagctg agatggcacc acttcactcc    4020
agcctgggaa acagagcaag actctgtctc aaaaaaaaca aaacacacaa acaaaaaaac    4080
aggctgggcg cggtggctca cgcctgtaat cccagcactt tgggaggccg aggcgggtgg    4140
atcacctgag gtcaggagtt ccagaccagc cttgtcaaca tggtgaaacc tcccccgcc    4200 gtctctacta aaaatacaaa aattagccag gcgtggtggc aggagcctgt aatcccagct    4260
acttgggagg ctgaggcagg agaatcgctt gtacccagaa ggcagaggtt gcactgagct    4320
gagatggcac cattgcactc cagcctgggg acaagagcg agatttcgtc tttaaaaaac    4380
aaaaacaaaa caaaaaacca tgtaactata tgtcttagtc atcttagtca agaatgtaga    4440
agtaaagtga taagatatgg aatttccttt aggtcacaaa gagaaaaaga aaaattttaa    4500
agagctaaga caaacgcagc aaaatcttta tatttaataa tattctaaac atgggtgatg    4560
aacatacggg tattcattat actattctct ccacttttga gtatgtttga aaatttagta    4620
aaacaagttt taacacactg tagtctaaca agataaaata tcacactgaa caggaaaaac    4680
tggcatggtg tggtggctca cacttgtaat cccagtgctt tgggaggctg agacaggaga    4740
gttgcttgag gccaggagtt caagaccgac atggggaatg tagcaagacc ccgtccctac    4800
aaaaaacttt gtaaaaattt gccaggtatg gtggtgcata cctgtagtcc cagctactcg    4860
ggaggcggag gcagaaggaa tcacttgagc ccaggagttt gaggctgcag tgagctacga    4920
tcataccaca gcactccagc gtggacaaca gagtaagacc ctatctcaaa aacaaaacaa    4980
aacaaaacaa acaaaaaaaa ccacaagaaa aactgctggc tgatgcagcg gctcatgcct    5040
gtaatcccag tattttggga ggcccaggtg ggcgtatcac ctgaggtcag gagttagaga    5100
ccagcctggc aacatggtg aaaccccatc tctactaaaa atacaaaatt agccaggcat    5160
gtggcacgcg cctgtagtcc cagttactgg gaggctgaag caggaggatc acctgagccc    5220
gggaggtgga ggttgcagtg agccgagatc acaccactgc actccagcct gggtgacaca    5280
gcaataccct acctcaaaat aaaaaagaaa aagaaaagaa aagttgctgt ccccgctacc    5340
ccaatcccaa atccaaacag cctctctcat ctcacagtaa gggggaaaaa tcacccaaaa    5400
aagctaagtg atcttttgaa aacccaaact cttagaagtc taagattatt atagtcaact    5460
catgaagtgt catcataaaa gatactctaa tattatttaa gtagaaccac atattggttg    5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaaatcata aaagcactta tctttgaaag aggagttaca gcaattttat    5700
ttagttcttt attgctttgc tatatattct aaatttttt caatgaatat atatcacttt    5760
taaaaaaatt caatggtctt tcttataaat tatctttggc agcatgcgtt tttatatata    5820
catataaaat gtatgggaaa tttttaaagg atacattaaa ttaaagcaaa atatacaaac    5880
aaaaaatcag aatacaaaaa gataaaaaga ttgggaaggg agggagggag taaggaggaa    5940
gggtgggtgg gtatagagaa atataccaaa taatggtaag aagtggggtc ttgacacttt    6000
ctacactttt tttaaataaa aaaatttttt ttctctctct ttttttttt tagagacgaa    6060 gtctcgctat gttgcccagg ctggtcttga actcctggga tcaagagatc ctcctgcctc    6120
```

-continued

```
agcctcccaa ggtgcttgga ttacaggtgt gagccaccac gcctggtcac tttctacact      6180
ttaatatata tattttttca ttttcaatgt cattttttatt agttaattta taatacccat     6240
tcaccattat attcaaagtc tatttgaaga aataaaccag aaagaatgaa atactctagc      6300
tcacatgcta ttcaatacta aattaccttt caaatcacat tcaagaagct gatgatttaa      6360
gctttggcgg tttccaataa atattggtca aaccataatt aaatctcaat atatcagtta     6420
gtacctattg agcatctcct tttacaacct aagcattgta ttaggtgctt aaatacaagc      6480
agcttgactt ttaatacatt taaaaataca tatttaagac ttaaaatctt atttatggaa      6540
ttcagttata ttttgaggtt tccagtgctg agaaatttga ggtttgtgct gtctttcagt      6600
ccccaaagct cagttctgag ttctcagact ttggtggaac ttcatgtatt gtcaggttgg      6660
cccgtaatac ctgtgggaca acttcagccc ctgtgcacat ggccaggagg ctggttgcaa      6720
acattttcag gtaggtggac caggacatgc ccctggtcat ggccaggtgg aggcatagtg      6780
ctatacagca ggcagaagtc aatattgatt tgttttttaaa gaaacatgta ctactttcat     6840
aagcagaaaa aatttctatt cttgggggaa aagattatgc cagatcctct aggattaaat      6900
gctgatgcat ctgctaaacc ttcacatatc agaacatatt tactatagaa agaatgaaaa      6960
tgggacattt gtgtgtcacc tatgtgaaca ttccaaaaat attttacaac aactaagtat      7020
tttataaatt ttatgaactg aaatttagtt caagttctag gaaaatacaa accttgctag      7080
atattataaa aatgatacaa tatatattca tttcaggctc atcagaatat atctgttatc      7140
acttgacaag aatgaaaatg caccattttg tagtgcttta aaatcaggaa gatccagagt      7200
actaaaaatg acttcttcct tgaagcttac tcaccaactt cctcccagtt actcactgct      7260
tctgccacaa gcataaacta ggacccagcc agaactccct tgaaatatac acttgcaacg      7320
attactgcat ctatcaaaat ggttcagtgc ctggctacag gttctgcaga tcgactaaga      7380
atttgaaaag tcttgtttat ttcaaaggaa gcccatgtga attctgccca gagttcatcc      7440
cagatatgca gtctaagaat acagacagat cagcagagat gtattctaaa acaggaattc      7500
tggcaatata acaaattgat ttccaatcaa aacagattta cataccatac ttatgtcaag      7560
aagttgtttt gttttattgc atcctagatt ttatttttttt gatttatggt ttactttaag     7620
cataaaaaat ttgtcaatac aactcttccc aaaaggcata aacaaaaatt cataaaactt      7680
gcatcacttg agatacttca ggtatgaatt cacaactttg ttacaactta ctatatatat      7740
gcacacatat atatatattt gggtatattg ggggggttct aatttaagaa atgcataatt      7800
ggctatagac agacagttgt cagaacttgg caatgggtac gtgcaggttc attataccaa      7860
gtctacttgt agttgttcaa aatgtatcat aatacaaggc cgggcgaggt cgtcacgcct      7920
gtaatcccag cattttggga ggctaaggca ggaggattgc ttgaggtcag gagtttgtga      7980
ccagcctggg caacagagca agaccctgtc tccaaaaaga aaaaaaataa ttttttacaa      8040
aataaaaaca aaatgtatca tcagacgaaa ttaaataaga ggcaattcat ttaaatgaca      8100
acttttccca gcttgacatt taacaaaaag tctaagtcct cttaattcat atttaatgat      8160
caaatatcaa atactaattt ttttttttttt ttttttttttg agacggagtc tcgctctgtc     8220
gcccaggctg gagtgcagtg gcgcgatcct ggctcactgc aagctccgcc tcccgggttc      8280
acgccattct cctgcctcag cctcccgagt agctgggatt acagacatgc gccaccacgc      8340
ccggctaatt ttgtattttt agtagagatg gggtttctcc atgttggtca ggctggtctt      8400
gaatttccca cctcaggtga tctgcctgcc tcagcctcac aaagcagtag ctgggactac      8460
aggcacccac caccacactt ggttaattct tttgtatttt ttttgtaaag acgggatttc      8520
```

-continued

```
accatgttag ccaggatggt ctcgatctcc tgatctcatg atccgcccgc ctcagcctcc   8580
caaagtgctg ggattacagg cgtgagccac cccgcccggc catcaaatac taattcttaa   8640
atggtaagga cccactattc agaacctgta tccttatcac taatatgcaa atatttattg   8700
aatacttact atgtcatgca tactagagag agttagataa atttgataca gctaccctca   8760
cagaacttac agtgtaatag atggcatgac atgtacatga gtaactgtga acagtgttaa   8820
attgctattt aaaaaaaaag acggctgggc gctgtggctc atgcctgtaa tcccagcact   8880
ttgggaggcc aaggcaagtt gatcgctcga ggtcaagagt tcgagaccag cctggccaac   8940
gtggtaaaac cccgtctcta ctaaaaatac aaaaaaaaaa ttagccaggc atggtggcac   9000
aggcctgtaa tcccagctac tagggaggct gagacatgga gaactgcttg aatccaggag   9060
gcagaggtta cagtgagccg agatcatacc actacactcc agcctgagtg acagagcgag   9120
actcctgtct aaaaaaaaaa aaaaaaaaaa agatacaggt taagtgttat ggtagttgaa   9180
gagagaactc aaactctgtc tcagaagcct cacttgcatg tggaccactg atatgaaata   9240
atataaatag gtataattca ataaatagga acttcagttt taatcatccc aaacaccaaa   9300
acttcctatc aaacaggtcc aataaactca atctctataa gagctagaca gaaatctact   9360
tggtggccta taatcttatt agcccttact tgtcccatct gatattaatt aaccccatct   9420
aatatggatt agttaacaat ccagtggctg ctttgacagg aacagttgga gagagttggg   9480
gattgcaaca tattcaatta tacaaaaatg cattcagcat ctaccttgat taaggcagtg   9540
tgcaacagaa tttgcaggag agtaaaagaa tgattataaa tttacaaccc ttaaagagct   9600
atagctgggc gtggtggctc atgcctgtaa tcccagcac tttgggaggc tgaggcgggt   9660
ggatcacctg aggccagaag ttcaagacca gcctagccaa catggcgaaa ccctgtctct   9720
acaaaaaata caaaaattag ccgggtgtgg tggcacgtgc ctgtagtccc agttacttgg   9780
gaggccgagg caggagaatc gcttgaacct aggaggtgga ggctgcagtg agccgagatt   9840
gtgccactgc actccacttc agcctgggcg acaagagcaa gactccgtca caaaaaaaaa   9900
aaaaaaaaaa aagcttaaaa tctagtggga aaggcatata tacatacaac taactgtata   9960
gcataataaa gctcataatc tgtaacaaaa tctaattcga caagcccaga aacttgtgat  10020
ttaccaaaaa cagttatata tacacaaaaa gtaaacctag aacccaaagt tacccagcac  10080
caatgattct ctccctaagc agtatcaagt ttaaagcagt gattacattc tactgcctag  10140
attgtaaact gagtaaagga gaccagcacc tttctgctac tgaactagca cagccgtgta  10200
aaccaacaag gcaatggcag tgcccaactt tctgtatgaa tataagttac atctgtttta  10260
ttatttgtga cttggtgttg catgtggtta ttatcaacac cttctgaaag aacaactacc  10320
tgctcaggct gccataacaa aataccacag actgagtgac ttaacagaaa cttatttctc  10380
acagttttgg aggctgggaa gtccaaaatt aaggtacctg caaggtaggt ttcaatctca  10440
ggcctcttct ttggcttgaa ggtcttctaa ctgtgtgctc acatgacctc ttctaacaag  10500
ctctctggtg tctctttttt tttttttttc tttttgaga cagagtctca ctctgtcacc  10560
caggctggag tacagtggca caatctgggc tcactgcaac ctccaactcc cgggttcaag  10620
tgattctcat gcctcaccct cccgagtagc ttggatgaca ggagcccgct accacaccca  10680
gctaattttt gtatttttag tagagatggt gtttcactac attggccagg ctggtctcaa  10740
actcctgacc tcgtgatcca cccaccttgg cctcccaaag tgctgggatt acaggtgtga  10800
gccactgcgc ccgtcctggt gtcttttcat ataagggcac taatccaatc agacctgggc  10860
```

-continued

```
ccaaccctcc cgacttcttc taactgtaat taccttccaa aggccctgtc tccaaatacc  10920
atcacactgg gggttaggac ttcaaaaaag gtatggggg ggtgtgggag gacataaatg  10980
ctcagtccat aacaagcacc caacataaaa atggctagaa cagatcacaa aaaaaaggtc  11040
ctgtatggct ttggggaagg gctcaacccc aaaatatctg agagctctgg aggggcctag  11100
aagtggtaaa tgaatgaaaa cgtggttact ctccagatct gcctttccca aatatggcca  11160
ttcttggctg aatcagaaat caaaggacag gttattaatt actagctcta agttacttac  11220
catttgctga gacagttcag aaatctgact gcatctcctc agagatctag aacacagttc  11280
tcaaattcta acttacttgt gatatacttg tgaatgataa aaatcgctac aggtactttt  11340
attaatctga aagagtattg agaaattacc tttcattctg acttttgtct ggaatgaaaa  11400
tcaatacttt tgctataatc gattactgaa ataattttac tttccagtaa aactggcatt  11460
ataatttttt ttaattttta aaacttcata attttttgcc agactgaccc atgtaaacat  11520
acaaattact aataattatg cacgtcacat ctgtaataat ggccttcatg taaacatttt  11580
tgtggtttac acataaaatc tctaattaca aagctatatt atctaaaatt acagtaagca  11640
agaaaattaa tccaagctaa gacaatactt gcaacatcaa ttcatcatct gtgacaagga  11700
ctgcttaagt ctctttgtgg ttaaaaagga aaaaaaaaa aaagacatgt tggccagatg  11760
cggtggctca cacctgtaat cccagcactt tgggaggctg aggtgggcgg atcacccctg  11820
gcctgcccaa catggtgaaa ccccgtctct actaaaaaca caaaaattag ctgggcgtgg  11880
tggcgggcgc ctgtaattcc agctactcgg gaggctgagg caggagaatt gctagaaccc  11940
aggaggcaga gattgcagtg agctgagatt gcaccattgc actacagtct gggcaacaaa  12000
agtgaaactc catcttaaaa aaaaaaagac aatgttcgtg ggtccaaaca agacttaatg  12060
gaagtgagtc taaaaatgag ctatgtgggc caggcgtagt ggctcccacc tgtaatccca  12120
gcactttggg aggccgaagc aggcagatca tgaggtcagg agatggagac catcctggcc  12180
aacacggtga aatcctgtct ctacaaaaat tagctgggcg tggtggtgcc tgcctgtaat  12240
cccagctact cagaaggctc aggcaggaga atcgcttgaa ccagggagtc ggtggctaga  12300
gtgagccgag atttgcatca ctgcactcct gcctggtgac agagcaagac tccatctcaa  12360
aaaaaacaaa caaaaataaa agataaaaat gagctatgtg aattaaaaga ggtataacaa  12420
tagataaacc atattttatt taattcctag taatgagtaa tatttccaaa cttctggaat  12480
gggcagaaat tgctagttgg catattttta cctttttatat tcagatacat taaaattctc  12540
aaaaaaaaac acctcaaagc agatgatccg ccatctcctt ggataatttg tgttaactca  12600
ggataacaga aaaccaaaat tatgagttac tgatgcaata ttcctaaatg taaaaataat  12660
taaagctaat agtagattca tcttccaatt tcatatcagt cttacaaata aactacatat  12720
ataacttgct tgccttccct tctgagggat aaagctgtta gaagaattaa aatcagcatt  12780
cttgactatt caaccaaggg agggataaat tattactcat tctagggaca tgggctcata  12840
actactacat gtgtaaggac atgaatttac ccaatattac aatttttcct tttattagtg  12900
tgtacagtgg aagaatagac atgttcactc tggacaaaaa aaaaattata cttatcagtt  12960
atcagaagca caatgctgaa gacagtagtt ccataacaat ttgaagtatg tgatcgaact  13020
agtagattat cttagtagta gtgaattatt gtaaatgtta gtaatttggc agccactggg  13080
cagaaaaata agaattgagg ctcaatattg atattaatgg tggtgattga cacataaatt  13140
ttatcaagtc tacacaatat aaaattacag aaaggtagaa gagtatacca gtacaacttc  13200
aacatatctt cactacaagg gagtaaaatg acatggccta gttactatct aatgaactgc  13260
```

-continued

```
agaaaactaa aagaaaactc caaggcaact cttctctgct gatctggttg gtccttttcc   13320 tacctttgc aatacccaga tacaaacaat ggatagaaaa caaagtagac ttgtagtatg   13380
caggtcacag tgctaaattc acagaaagaa acccctgaac tgaactgctc tatttcctgg   13440
tggtcacaaa gagtaattct ggtttacacc tacagattga tgtcaatcta caccctgttg   13500
ataacagtgt ggccaaggac aaaaaaaagg tgctccgttt taccaattct gtaaaaaatt   13560
attggcaggg taagctcggc tagggcagga ttacatttct aggactacca tccccgaaat   13620
ttagaagata ttatatccac ataaagcata tctttcacat taatttgcaa aaatctaaaa   13680 gcttttttctt agctcaagtg tgtccaagtt taccctggca gtttaaaacg atagttacaa   13740
gcagcatggg ttgtatcaga cacatttgag ggccaatttc atgtaagtga tattgggcaa   13800
gttacttcaa ctatctgtgc ctccaaggtc atactagtgt ttatttacct aaagggtacc   13860
tgttatgtaa ctttagggtg tttacattag ataatgcctg caaaatattt acttcaacgc   13920
ctaaaacata gttaagtatt caataaatac ctactattgt cactactaac ttaaaagttt   13980
agagattaag agcagaatct ggggtgagac aaacttaggt tcaaatccta gtattgttgg   14040
gtaatcttgg gcaagttact taacctctct gatttgtgta atttaaaaaa ttagttaata   14100
tacataacag ggcttagaag agtatctagc acatagcacc atttaagcat ttgttattgc   14160
taacatgcaa acaatttaag ggaaagaaat tttttaaaaa ggaagaggga tttgcaaact   14220
aaaaacaatg agtatcttat gttcaaagaa aactaacaaa cagccagctc tagcaataat   14280
taaattcact atatactggg gcaggcatca caccccaaag ctaaaagcgt ctacctaggc   14340
caggcacggt ggctcatgcc tgtaatccca gcactttggg aagcagaggc gggcagatcg   14400
cttgagctca ggagttcaag accagcctgg acaacatggc aaaacaccat ctctacaaaa   14460
aatacaaata ttaggccggg cgcagtggct cacgcctgta atcccagcac tttgggaggc   14520
caaggcgggt ggatcacctg agatcaggag ttcgagagta gcctggccaa catggtgaaa   14580
cctcgtctct attaaaaata caaaaaatta gccaggcatg gtggcaggcg cctgtaatcc   14640
cagctactca gggggatgag gtaggagaat cgcttgaacc cgggaggcag aggttgcact   14700
gagccgagat catgccactg tactccagcc cgggcaacaa gagcgaaact ccatctcaaa   14760
aaataaataa ataaataaat aaaataaagt acaaatatta gccagggatg gtggtgcgca   14820
cctgtagtcc cagctacttg ggaggctgaa gtgggagaat cccctgagcc tggggagaat   14880
cacccgagcc cgggaagtcg aggctgcagt gagcagtgat tgtgccactg cactccatcc   14940
taggtgacag agtgagaccc tgtctcaaaa aaagaaatt ggcagaatta agtaagttga   15000
tgtttagaga tgaaaaatca acattttttc ctcagcaact gaataaaaac aacagccact   15060
accatttttt tgagtaccta tttgtagcct attttttaac tggtattact cgagagagag   15120
agagctaggt tcgagacaga gctccttctc ttaataactg tatgacctag ggtatgtctg   15180
ttagcctctc tgaggcttca aaggttcctc atctgtaaaa tggtaataat cataccattg   15240
ctacagggct gttttgaaga ctaattagga ctatgtaagt aaacatgatg atggctatta   15300
ttactgttcc ccgccagggg ccatgcaagg gttgctgatt cacatagact gtcttataat   15360
cctctcaata actccaagag gtagccagca cctcagatat acataaaatg acttaagccc   15420
agagaggtga agtaagttgc ccacagccac acaactagta aatagcccaa acaagctgga   15480
ttcccagtta gactccgtta atagcactgc tctttacctt aagtcattac aatgcctaat   15540
atgaaataga atcgcttctt tcttagggtt caagtggtta attatttaat gtattcattc   15600
```

-continued

```
aacaaaccat catcgaggac ctcttacaag ccaagtactg tgctaagtgc tagagttacg    15660
gcggtgattc ctgcccttaa aaagttttag tgggagaaac aacaggtaac caggtcattg    15720
ccaaaacaac aaaaataatc ataataaagc aggctaaagc atatttaact ggccggggtt    15780
ttgactattt tagcaagcat gatcagaacg gttgaggagg gaggccagca gcttggccgg    15840
ttcaacaaac aagaaaaaac cagtgagggt ggagctaaga taccagaggc tgattacggt    15900
taagaatgtt cttgaaggta aggaccagat tctcattttc tatatcctgg ggcatcggtc    15960
agcatggaat ctggattcta gcacatgtga atttcggctt gaaatgacct aatgcctttt    16020
ccctagttcc ttcgtgtgtc aaatacgcat ggttaccgct accagagctg tagtggggct    16080
tcaatgaggc catgagcatc tccataaaga tgaactacag tgtgtgcaaa actaaaggca    16140
aaacctggtc cccacacgcc ctcccaggtg gtcgctttcc gtgccgaggc ccctccagag    16200
gtgccccgag aacctcacca tcgcacccca aacttccagg gaagggcctc tcccgagaaa    16260 gccccacgc ccccacccg cgccatcatt cccgaatctg ccctcggccc ctccccgcag    16320
cacgctcgca ggcggcacat gtcaaccaaa acgccatttc caccttctct tcccacacgc    16380
agtcctcttt tcccagggct cccccgagga gggacccacc ccaaaccccg ccattccgtc    16440
ctccctgccg ccctcgcgtg acgtaaagcc gaacccggga aactggccgc ccccgcctgc    16500
ggggttccct gggcccggcc gctctagaac tagtggatcc caattgaagg cctggtctaa    16560
atgactccaa aatcaccact taattcaaga gactgatttc cctgagtcag gcccttaaa    16620 gcagctattt caatgggaca gggaaacaac cctaggatct ggattagaat cacttggggg    16680
ctgccacacc cccagggctc tgatcctgcc cttctcccac acgcacattc acatactgct    16740
gcagtgacct tccatttcta atgggttcct gggccatctg tcaggtatag ggaatggaaa    16800
aggggttggg gaggctctgc ttcagaaagt ttgtgtcagg ggctcccaga gcctccacag    16860
atagatagca ggggtcccca ccctaccatg gcagctataa atgtgatcaa catttattgg    16920
cctaggatac agcagttagc aaaatgcctg atgtagttcc cactccgtgg aggttgcagg    16980
ctagccaaga agtcatgagt tcagcaaccc ttacgcacca gtgggatgag attggaccag    17040
gccgagggta gtcttgggaa cactcagcat ttgtctgagg gccagaagag gctgcttgcc    17100
ctcagacagg aggtcagcat ctttattgta gcccatgaca cctctacacc attgctcttc    17160
tggtcttatg gaagacatct ttgggcctga taacagcgga gtctgtgtcc cacttgtcca    17220
ggctggagtg ccacatcagg cacactccag ttgcagggac agcacagaca agtttcagga    17280
aggctggtgg cctccaggag gttaacctta taaggccaga ttgtaaccta gttgaaaaac    17340
atacacatgc catgataata aaagaaccta ggcaccatta caagagaaaa aatcattttt    17400
gtagatacga gcatggattc ttgggtgggt cagacacact gggcttgtgc tctgactgca    17460
ctgtctcccc tacctgacct tgggtaaacc ataagactgc tgcatgactc agtgtccacc    17520
ccaaaaaagt accggtagat attggccaca gtagatatca gctagagtgg actctcatga    17580
caatgagggg agatgtattc cccatcttag gcacctggga ctctaccttc catcttctgc    17640
tccgtgtctc tccatcccca ggctcttcag aactcaggga gtccagaatg tcagctccca    17700
gatttcagcc ttcagaaagg aaacccatta ccgttcagtt gaacaaatgt tgtctgagcc    17760
ccagatctgg gctcagaggc catctaggct atgagacaag aggggaacaa agcaccgtct    17820
gcactcactc accacactca cttgctgtcc caggtcacat ccatcgggta gagaatctaa    17880
gaggctgagc tagctcccgc caccagccca gcccacccca cctggcccct tccttccttc    17940
tacaaaatat gcaccacctg tcaaagggtg ggcagtgcca ggcctgcata cagagcactg    18000
```

-continued

```
agtgtaaaag cagacatgga ccctgacctc caggagcttc caattttctt gaagagacaa   18060
atcagctggc atttcagtcc agtgtgatct gctcttggtg agcacagacc tagggagttg   18120
gggcagcttc ccagaagaac tgcagtccag gctgagggca gagaaatgag gggaatggcg   18180
aggaattggg gagcaggggg gagctcagta gagagccaag ggcgggaggt gagaagtccg   18240
tgttgggcca ggagctaccc tccggtggcc acagccgaag tcgaggatgc ctttggaact   18300
catccccact tctctctttc tgtatgtagc cgtccaagaa caagtcacct ccaagtgtag   18360
ccggatcaag gcaagccccc catctagcaa gcacttgatg ccacccagaa ctgggcttct   18420
tcagaacaat ctgagtccag gaatgatccc actcaccagg caccagagct gcgagggcat   18480
gggagtgatc tcaccaactc tggggaagcg gcaaggaatt ttcacctcca gcccccagtg   18540
tcccatcctc tcacactcag gccagactcc cctgggcaga cttgactctg tctgccagca   18600
tatgcagagc cccaaggcca ccccaccaga agtgcccctg cctgggttct gtcccagctc   18660
cctgggcacc cagtccttga gtccccacca gctcagacgg cctagtgtgc caagaatgcc   18720
cactgcgttc aacaatgctg catgggtcac agcggcagca gctgtgacca cagcagtttc   18780
ggggaaaaca cccctcagcc aagtggataa tagcgttcag cagcactcac cttctggcca   18840
ggcctgcctt cagaggccat ctgattggga ggcacaagtg cccgctgcga tgggaacaca   18900
agtgcccctg gccaacaacc ccagcttcag cctgctgggc agccagagcc tcaggcagag   18960
cccggtacag ggcccggtgc ctgtagcaaa caccaccaag ttcctccagc agggtatggc   19020
cagctttagt cccctgagcc ccatacaggg catcgagcca ccaagctatg tggctgctgc   19080
tgccaccgct gctgctgctt ctgccgttgc tgccagccag ttcccaggtc cgttcgacag   19140
aacggatatt ccccctgagc tgccacctgc cgactttttg cgccagcccc aacccccact   19200
aaatgatctg atttcgtcac ctgactgcaa tgaggtagat ttcattgaag ctctcttgaa   19260
aggctcctgt gtgagcccag atgaagactg ggtgtgcaac ttgaggctga tcgacgacat   19320
tttggaacag catgctgctg ctcaaaatgc cacagcccag aattctgggc aagtcaccca   19380
ggatgctggg gcactttaaa tctgagcagg atgcccatag aaaccccat ggtgacatca   19440 ctctaggaag tggtgtcgat ccatacccgc agttgtctcc cgttacaatt tgagtggtgt   19500
tgtcagccca tgcttatccc tctctctacc tgtgacaaaa tggaaagctg gtgatttttc   19560
aagctacgtg tacatatttg aaaattttgt aaatggtttt cctaaacatt aatgacagaa   19620
gtatttatac ttcattttgt gactttgtaa ataaagcgac ggcttttgtt tcagtagagt   19680
tgtgtttact atgcattgtt ttgtgtttat tatacaatgt tacaaatatg cagaccgtgt   19740
tgtttgctcc agtgatacct tgttaagcta ggtggctgag tcgcttatgg ttttaatgca   19800
atgagcaatg tggatatgac caagagttgt tgtgcaagtt gacaaatgcc aaatagaaaa   19860
ccacttggcc atttatttct atgttcacta aaaatcctat tgccttgtgt gattcttaat   19920
ctcttttgcg aacctttcag tctccgctag ctctttccta atgagcttta cagcagaagc   19980
tgttttatcg ttaagtgccc cacagagaca ctttaccagg aggctgggag agttctccag   20040
atttgggaga ggcgcagaga cagtgtgtga gccgagccct gtctcagcaa tccacctgga   20100
ggagctagag tatcctcctc cctttaccat tcagaccgag agaaaaagcc cagcttgtgt   20160
gcaccctcgt ggggttaagg cgagctgttc ctggtttaaa gcctttcagt atttgttttg   20220
atgtaaggct ctgtggtttg gggggaaca tctgtaaaca ttattagttg atttgggggtt   20280 tgtctttgat ggtttctatc tgcaattatc gtcatgtata tttaagtgtc tgttatagaa   20340
```

-continued

```
aacccacacc cactgtcctg taaacttttc tcagtgtcca gactttctgt aatcacattt   20400
taattgccac ctcgtatttc acctctacat ttgaaatctg gcgtctgttt caagccagtg   20460 tgtttttct tcgttctgta ataaacagcc aggagaaaag tgcctctatg tttttatttt   20520
tcaagggagt attcagtacc tacaaaccca agtcaggaag cctgctagtg gctttggttc   20580
tttcagaggc tgctcgatgc cttgtgtgtc agaaagaaag attcagcagt tttgcatcat   20640
ggcaaagaag cctgttattt tggggctcag cccctcattt tatagaggat gaaacagagg   20700
gggatgggag gtcacaaaga caactgcccc gggagcaggt gtgggggaga cttgccctga   20760
gggtctagac gctctgcacc accgtcctgt ctcccttgct gaagaccaca catgcccttc   20820
tttgaccaga ccctgccacc tgataggcca ggacctggta ggcgggtacc caggtttcat   20880
ggatggaacc acatctcccc aaaagtgggg aggtagctac tgggatgcac gcctcccgcc   20940
atgtgctata ggagagcagc tgaagcaaca gttgggatca gatgtagtca caattgaatg   21000
catcatcaca tttatccctc taagtggctg ggagagttga tatcctcatc cctaaggtac   21060
aaaatgttcc aatttgatca gtggctttca ggagctgaga aaggcatgtg ctctgaggca   21120
gagctgttat gtcccgcaga gcctaaaaat gctctaagaa catgctccct gccaaaattc   21180
tcaatggctg tgacaaggga caacgatcga ccaatggggg tggaagcaga cctccgcagt   21240
ccaggggcca gagctaggac agaggggtcg gagaaagagt cattttccca acactccagc   21300
tcttggccag tcctcacaca gtcccctcct gcttcctgct gagagagata tcctcatagg   21360
tctgggtaaa gtccttcagt cagctttcat tccctgtcac caactttgtc tctgttctcc   21420
ctgcccgtct caggcagcac tcctcaggaa acctctccaa gagccagcct cactgcagcg   21480
cccactattg tccctctgcc tcaagtgtcc catccatgcc aggccccagg caggctgcag   21540
ctttccctca gggccacacc aaagcacttg ggctcagctg tgctgtcccc ctccatcact   21600
gagctcaggg gcagcagggg tggggtgcca ggaggcccat tcacccttct ctggctctgt   21660 gttgaccca cctgcccagc cactgctgct tagaacctac ccgctgggaa aatgaagccc   21720
tcccggaggg gccacctcaa cctgagagcc tcacggatca cagttgtccc cactcagctc   21780
tgccagccct cagagaccca tagataaaag ctgagcttgg ctcgcagagc tggttccatc   21840
ttccattccc agagggttca acttcctacc ccaaccacac agggaacctc aaggctgagc   21900
cagtgtgggc tgcagtgcag accagcttcc tggacacgtc ctgccacctg accccaggct   21960
ggcctcactg cccctggcac tcctgaccct atcctcattc ctcctggcag tgcgtgttct   22020
gccattccgc tttcccttag ctgtcctctc actgtactgt cagcttctcc tttttccaggt   22080 gcccccagg ggctttccac atgaccctgt caccccacag cccatccagc accaattcca   22140
gctctctgcc accccttcaaa ggagtgacag tgccctgctt cacctcccac tcacccctca   22200
acccagagca atctggctcc agtcttgcct ccttccccct aagtactcta gtcacagttc   22260
caaattcctc ctggtcataa agccaaatga agcttcctgg tcctcagcgg acttgccact   22320
tcagcagtac tggactctct cctcccagaa acctgtttcc ccttggctcc tggagcccac   22380
actctgctgg aatccttctg cctctctggc ctgtagcctg gccctctctc ccaacctgag   22440
gtccattctc tcctgctcct ccacaagatg ttgctccttc cattacttcc tccctctcaa   22500
ccaaagctcc ttcattagct ctttatcttc tggtttcttc ccctgggcag acgaatggat   22560
tcaagagcct gtggcccagc agcccagcac tccaggatct cagcacttca gcatcccagt   22620
accctagcat ctcaataccc cagcacccca gcaccatagt attccagcac cccattgtcc   22680
aagcatctca gcactccagc atcccagcac cccaacactc cagcagccca gaatctcagc   22740
```

-continued

```
accctagcac tgcagcatct caggacccca gcacttcagc atcccagcac actagtactc   22800
cagcatctcg gcaccccagc acctaggcat cccaacaccc agcaccccag cacttaagca   22860
tcccaccact acagtatctc aacactccag caccccagca ccatagtgtt ccagcacccc   22920
agcatcccaa caccccagca cttaagcatc ccaacacctc ggcatcccaa caccccagca   22980
ctgcagcatc tcagcacctt agcatcccag tgccctagca tctcaatgct ccagcacacc   23040
agtactacag tattccagca ccccagcact ccagcatctc agcactgcag cactgcagca   23100
ctccagcatc ccaaaatccc agcatcccaa caccccagca gaccagcaga ccagcatctc   23160
agcaccgcag catccaagga ctatcccagc atcccagcaa cccagcacct cagcatccca   23220 acacccagc atttcagcat ggcaacaccc cagtacccca gcacttcagc accccagtat   23280
cccagcatct cagcgaccca gtatcacaaa acctcagcat cctagcaccc cagcacccca   23340
gcaccttagc accttagcat cccagcatct cagcgcctca gcatcttgat attctggctg   23400
aggtcagcgt ggtgtatcta gtcagggtcc taactttcac ttcgcaggga aatgctgctg   23460
gactgggtct catgttgggc tgaagctctc tagacccctt gaagacagca taaaagagct   23520
tggagacgct gggtgtcccc catggaagag ttcactctca tcctgctttg acaacagcct   23580
tctctggggt ccctcacggg cccctctttc ttactgcaag tttgtctctg agaagactgt   23640
gatgcagaag tcactcagct gcctgtggct cctgaagagc tgaaggtgga ggcctgtagg   23700
cctccctatg agaggcgcag aaaaaaccat gattgctagt ggggaggtgc tccctctaca   23760
acccactcca taatctgccc ccgcccagct ctgaggccag ccccaggga aaatgccaga   23820 tccccaggga ggtgtgtgag acctcagggg ctccctcctc ccttacagca ggctcaggcc   23880
cctgggggcc tcagggccaa ggtctgtggg taagctacta tctctcactt gtcctctagc   23940
cacaaaagcc agggagatct ggcaatggac atgaggttct gaagaagcac atatgactgg   24000
cttcctaatg cgtggttgtt cagtgattca ataaacacgc atgggccagg catgggaaa   24060 tagacaaaca tgatccccaa cctctcccag agtgaactgg gagggaggag tgttcatccc   24120
tcaggattac accagagaaa caaaccagca ggagatatat atggttttgg ggggtcaaga   24180
aagaggaaaa acctggcaag gcaagtccaa aatcatagga caggctgtca ggaagggcag   24240
cctggaacct ctcaagcagg agctgatgct gcagtccaca ggcagaattt cttcttcctc   24300
ggggaaatct cagctttgtt cttaaggcct ttcaactgat tggctgaggt ctgccccttc   24360
ccccacattc tccaggataa tcttccttac ttaaagtcaa ctattaatca cagctacaaa   24420
atcccttcac agctacacat agatcagtgt ttgattgacg aacagcccct acagcctagc   24480
caagttgaca cataaaacta accatcacag ggggacaaat gatgtaaaca catcaacaaa   24540
taaaacagta acaagttaag gtctatggaa aaaacacaga aggggcagag agaaagaaag   24600
caagaaggag agtcccagtt tgctagggct tgtgggaagt ggggagcagt tctctttagc   24660
taggatattt gggaaaggca tatctgaagg agtgatattt gagcttagat taaaagatgg   24720
gaaggagcaa gccatgcaaa gagctaggat gttccaagca gagacggaac agcaagtgca   24780
aatgtcagga ggaatagaag gaggctggtg ggtggggtcc agtgagcaag aggagggcag   24840
gcaggagagg ggatggggag gtgggcaggc ccagaccacc cagggccctg gagactatcc   24900
tgatccaaca agggaagcct tgagtcactt cagtgtccat gtggagaatg gacctcagac   24960
tgaatgaggg aggcagtaag gagggcctct acctccaggg cttcgccctg tggactgcgc   25020
atagacatct ccaactcaga aagtctgaac caaacttttcc atagttcccc caagtctggg   25080
```

-continued

```
catcctccta ctcagtgaaa ggcagccatc acacctccct gccctgctcc cggatgcccc  25140
aaatcctctt ggtctccaag tccagaacct gagacttgtc cttgatgttt gtctttccct  25200
caccctttct gtattctggg aagatgggtt tttttccccc agatgaatct gtaaaacttc  25260
tgtgatcaca ataaaaattc tggcagtatt attttctgga acatgacaaa gtgattcaaa  25320
attatttatc tggaagacta caaaacaaga atagccagga aatttctaaa aagaaagaag  25380
aaggaggagg agaaagaagg aggaggaaaa ggaggagaag aagaaaagaa aaagaaccaa  25440
gaaagggttc tagctctacc aaatattaaa acatatcatg aagctattta aaacaatatg  25500
gttgtggata ctgaaaaaga tgtgaataaa gtggaaggaa aataaataga aatgcacatg  25560
gggattgaga ctgtgaaaaa ggcagcatct cacatcagtg agggatgttc aacacctggt  25620
gttgggaaaa ctggctagtc atttaaacca aacaactggg tcctctacct cactcctgac  25680
attaagatac atttagatga ttcaaagagt aagacagaaa aaataacacg tgaaaacact  25740
atcagaaaac aacgtgggcc aggtgtggtg ggtcacgcct gtaatcccag cactttggga  25800
ggccgaggca gacagatcac ctgaggtggg gagttcaaga ccagcctgac caacatggtg  25860
aaatcctgtc tctactaaaa atacaaaatt agctgagcgt ggtggcgcat gcctgtaatc  25920
ccagctactc aggaggccga ggcaggagaa tcacttgaac ctgggaggca gaggttgtgg  25980
tgagccgaga tcacgccatt gcactccagc ctgggcaaca agagtgaaaa tccatctaaa  26040
aaaaaaaaaa aaagccaagg tggatatttt tatagtatca gggtagatca agcttctcca  26100
atcatgacat gaaacccaga aaccataaaa gaaaagaatg ataaaattgc ccacgtaaag  26160
taaaaagctt gcacacagaa aaacaccata caggttacaa gatgagcagc aaaatcagag  26220
aaaaaacatt gcaattcagg acacacagag gctattgttc ctaatattta aaaataaaag  26280
tagtggattg tctacaaaaa gatgaagaca agaatttcag aaaaccaaat actgcatgtt  26340
ttcacttaca agtggaagct aaacactgag tacacgtgta cacaaagaat ggaaccatag  26400
gccaggcacc gtggctcacg cctgtaatcc cagtactttg cgaggccgaa gcgggcggat  26460
cacctgaggt gaggagttcg agaccatcct ggccaacatg gtgaaaccca gtctctacta  26520
aaaatacaaa aattagccgg gcgtggtggt gggtgcctgt aatcccagct actcgggagg  26580
ctgcggcagt agaatcgctt gaaccctgga ggtggacctt gcagtgagcc gagatcgcac  26640
cactgcactc cagcctgggc aacagagtga gactccatct caaaaaaaaa aaaaaggaat  26700
agaacaatag acactggggc ctacttgagg gaggagggtg aggatcaaaa acctgcctat  26760
caggtactat gcttattacc tgggtggtga aataatctgt acaccaaacc ccagtgacat  26820
gcaatttacc gatgtaacaa acctgcccat gtacccgctg aacctaaaat aaaagttgga  26880
aaaaaatata gaaattttct ttgtaatagc caaaaactgc aaacagccca ggtgtctatt  26940
agtagaatgc ataaacaaac tcgggcatgt tcatacaatg taaaactact catcaataaa  27000
aagtgatact tctcagcaat gaaaagaaac tagctactga taccagctac aacatggatg  27060
gatttcaagt gctttatgat gagagcaaga agccagacac aaaagtgtct atatatatat  27120
acagtatata tacgtatata tacacatata tacagtatat atatacatat acatgtatat  27180
atatactgta tatatactgt atatatatac acagtatata tatacatata tacagtgtat  27240
atatactgtg tatatataca tgtatatata ctgtgtatat atacatgtat atatactgtg  27300
tatatataca tgtatatata ctgtgtatat atacatgtat atatgtat actgtatata  27360 tactgtatat atatatacac atatatacag tatatatata cagtatatac tgtatatata  27420
cagtatatac gtgtatatat acatatatac agtatatatg taaatataca tatatacagt  27480
```

-continued

```
atatatgtaa atatacatat atacatgtat atatatacac tatatatata catatatagt   27540
gtatatatac atatatacat gtatatattt actatatgat tccatttata taaagtgcca   27600
aaacagtcaa aaataatcta tgtggaaaaa atcaacaaag ggatcccccg ggctgcagga   27660
attcgatggc gcgccgacgt cgcatgctcc tctagactcg aggaattcgg taccccgggt   27720
tcgaaatcga taagcttgga tcggccgcaa taaaatatct ttattttcat tacatctgtg   27780
tgttggtttt ttgtgtgaat cgtaactaac atacgctctc catcaaaaca aaacgaaaca   27840
aaacaaacta gcaaaatagg ctgtccccag tgcaagtgca ggtgccagaa catttctcta   27900
tcgaggatct gcgatcgctg aattctgggg actttccact ggggactttc cactggggac   27960
tttccactgg ggactttcca ctggggactt tccactcctg cagcagtgga tattcccaga   28020
aaactttttg gatgcagttg gggatttcct ctttactgga tgtggacaat atcctcctat   28080
tattcacagg aagcaatccc tcctataaaa gggcctcaga ggaagtagtg ttcagctgtt   28140
cttggctgac ttcacatcaa agctcctata ctgacctgag acagagccat gaattccgtt   28200
tttttttttt tttttggaaa tatgagggtt tttccgcttc tgacagtgga acggaatgac   28260
agcagcacag gctggtgaat gactactttc tttataagca accaccttga gcctgaaatg   28320
gcagtcgcta gtctctattg ccttgctgtg gcctcgggat ggaaatctgc tggggaccct   28380
acagtcacct aatctctctc cttctcatcc ttctgtttca ttcagaggca gcctgccgcc   28440
cttctgggaa aagaccctgc aagatgcaag ccttcagaat ctgggatact aaccagaaga   28500
ccttttacct gagaaacaac cagctcattg ctgggtactt acaaggacca aatatcaaac   28560
tagaagaaaa gatagacatg gtgcctattg accttcatag tgtgttcttg ggcatccacg   28620
ggggcaagct gtgcctgtct tgtgccaagt ctggagatga tatcaagctc cagctggagg   28680
aagttaacat cactgatctg agcaagaaca aagaagaaga caagcgcttt accttcatcc   28740
gctctgagaa aggcccccacc accagctttg agtcagctgc ctgtccagga tggttcctct   28800
gcacaacact agaggctgac cgtcctgtga gcctcaccaa cacaccggaa gagcccctta   28860
tagtcacgaa gttctacttc caggaagacc aatagtctag ctcgacatga taagatacat   28920
tgatgagttt ggacaaacca caactagaat gcagtgaaaa aaatgcttta tttgtgaaat   28980
ttgtgatgct attgctttat ttgtgaaatt tgtgatgcta ttgctttatt tgtaaccatt   29040
ataagctgca ataaacaagt taacaacaac aattgcattc attttatgtt tcaggttcag   29100
ggggaggtgt gggaggtttt ttaaagcaag taaaacctct acaaatgtgg tagatccatt   29160
taaatgttag atccggagag ctcccaacgc gttgggtcga cggcgcgcct accagtaaaa   29220
aagaaaacct attaaaaaaa caccactcga cacggcacca gctcaatcag tcacagtgta   29280
aaaaagggcc aagtgcagag cgagtatata taggactaaa aaatgacgta acggttaaag   29340
tccacaaaaa acacccagaa aaccgcacgc gaacctacgc ccagaaacga agccaaaaa    29400 acccacaact tcctcaaatc gtcacttccg ttttcccacg ttacgtcact tcccatttta   29460
agaaaactac aattcccaac acatacaagt tactccgccc taaaacctac gtcacccgcc   29520
ccgttcccac gccccgcgcc acgtcacaaa ctccaccccc tcattatcat attggcttca   29580
atccaaaata aggtatatta ttgatgatgt tt                                29612
```

<210> SEQ ID NO 9
<211> LENGTH: 29273
<212> TYPE: DNA
<213> ORGANISM: Artificial Sequence
<220> FEATURE:

-continued

```
<223> OTHER INFORMATION: helper-dependent adenoviral vector containing
      equine Il-1Ra

<400> SEQUENCE: 9
aaacatcatc aataatatac cttattttgg attgaagcca atatgataat gagggggtgg    60
agtttgtgac gtggcgcggg gcgtgggaac ggggcgggtg acgtagtagt gtggcggaag   120
tgtgatgttg caagtgtggc ggaacacatg taagcgacgg atgtggcaaa agtgacgttt   180
ttggtgtgcg ccggtgtaca caggaagtga caattttcgc gcggttttag gcggatgttg   240
tagtaaattt gggcgtaacc gagtaagatt tggccatttt cgcgggaaaa ctgaataaga   300
ggaagtgaaa tctgaataat tttgtgttac tcatagcgcg taatatttgt ctagggccgc   360
ggggactttg accgtttacg tggagactcg cccaggtgtt tttctcaggt gttttccgcg   420
ttccgggtca aagttggcgt tttgatatca agcttatcga taccgtaaac aagtctttaa   480
ttcaagcaag actttaacaa gttaaaagga gcttatgggt aggaagtagt gttatgatgt   540
atgggcataa agggttttaa tgggatagtg aaaatgtcta taataatact aaaatggctg   600
cccaatcacc tacaggattg atgtaaacat ggaaaaggtc aaaaacttgg gtcactaaaa   660
tagatgatta atggagagga tgaggttgat agttaaatgt agataagtgg tcttattctc   720
aataaaaatg tgaacataag gcgagtttct acaaagatgg acaggactca ttcatgaaac   780
agcaaaaact ggacatttgt tctaatcttt gaagagtatg aaaaattcct attttaaagg   840
taaaacagta actcacagga aataccaacc caacataaaa tcagaaacaa tagtctaaag   900
taataaaaat caaacgtttg cacgatcaaa ttatgaatga aattcactac taaaattcac   960
actgattttg tttcatccac agtgtcaatg ttgtgatgca tttcaattgt gtgacacagg  1020
cagactgtgg atcaaaagtg gtttctggtg cgacttactc tcttgagtat acctgcagtc  1080 cccttttctta agtgtgttaa aaaaaaaggg ggatttcttc aattcgccaa tactctagct  1140
ctccatgtgc tttctaggaa acaagtgtta acccaccta tttgtcaaac ctagctccaa  1200
aggacttttg actccccaca aaccgatgta gctcaagaga gggtatctgt caccagtatg  1260
tatagtgaaa aaagtatccc aagtcccaac agcaattcct aaaaggagtt tatttaaaaa  1320
accacacaca cctgtaaaat aagtatatat cctccaaggt gactagtttt aaaaaaacag  1380
tattggcttt gatgtaaagt actagtgaat atgttagaaa aatctcactg taaccaagtg  1440
aaatgaaagc aagtatggtt tgcagagatt caaagaaaat ataagaaaac ctactgttgc  1500
cactaaaaag aatcatatat taaatatact cacacaatag ctcttcagtc tgataaaatc  1560
tacagtcata ggaatggatc tatcactatt tctattcagt gctttgatgt aatccagcag  1620
gtcagcaaag aatttatagc cccccttgag cacacagagg ctacaatgt gatggcctcc  1680 catctccttc atcacatctc gagcaagacg ttcagtccta cagaaataaa atcaggaatt  1740
taatagaaag tttcatacat taaacttttat aacaaacacc tcttagtcat taaacttcca  1800
caccaacctg ggcaatatag tgagacccca tgcctgcaaa aaaaaaaaaa ttagccaggc  1860
atggtagcat gtacctgtag tcccagctac ttgagaggtg aggtgggaaa atcactttag  1920
tgcaggatgt tgaggctgga gtgaactgtg attgtgccac tgcactccag cctggacaat  1980
agagcaagac cttgtctcaa aaaatgcat taaaaatttt ttttaaatct tccacgtatc  2040
acatcctttg ccctcatgtt tcataaggta aaaaatttga taccttcaaa aaaaccaagc  2100
ataccactat cataattttt tttaaatgca aataaaaaca agataccatt ttcacctatc  2160
agactggcag gttctgatta aatgaaattt tctggataat atacaatatt aagagagact  2220
```

-continued

```
gtagaaactg ggccagtggc tcatgcctgt aatcccagca ctttgggagg ctgggtaaca   2280
tggcgaaccc tgtttctaca aaataaaaat attagctggg agtggtggcg cacacctata   2340
gtcccagcta ctcaggaggc tgaggtggaa ggatcgcttg aacccaggag gttgagactg   2400
cagtgaactg tgatcattct gctgcactgc accccagcct gggcaacaga gaccttgtct   2460
caaaaaaaaa aaaaaaagag acaaattgtg aagagaaagg tactctcata taacatcagg   2520
agtataaaat gattcaactt cttagaggaa aatttggcaa taccaaaata ttcaataaac   2580
tctttcccct tgacccagaa attccacttg aataaagctg aacaagtacc aaacatgtaa   2640
aagaatgttt cttctagtac agtcggtaag aacaaaatag tgtctatcaa tagtggactg   2700
gttaaatcag ttatggtatc tccataagac agaatgctat gcaaccttta aaatatatta   2760
gatagctcta gacacactaa tattaaaagt gtccaataac atttaaaact atactcatac   2820
gttaaaatat aaatgtatat atgtactttt gcatatagta tacatgcata ggccagtgct   2880
tgagaagaaa tgtgtacaga aggctgaaag gagagaactt tagtcttctt gtttatggcc   2940
tccatagtta gaatatttta taacacaaat attttgatat tataatttta aaataaaaac   3000
acagaatagc cagacataca atgcaagcat tcaataccag gtaaggtttt tcactgtaat   3060
tgacttaaca gaaaattttc aagctagatg tgcataataa taaaaatctg accttgcctt   3120
catgtgattc agccccagtc cattaccctg tttaggactg agaaatgcaa gactctggct   3180
agagttcctt cttccatctc ccttcaatgt ttactttgtt ctggtcccta cagagtccca   3240
ctataccaca actgatacta agtaattagt aaggccctcc tcttttattt ttaataaaga   3300
agattttaga aagcatcagt tatttaataa gttggcctag tttatgttca aatagcaagt   3360
actcagaaca gctgctgatg tttgaaatta acacaagaaa aagtaaaaaa cctcatttta   3420
agatcttact tacctgtcca taattagtcc atgaggaata aacacccttt ccaaatcctc   3480
agcataatga ttaggtatgc aaaataaatc aaggtcataa cctggttcat catcactaat   3540
ctgaaaaaga aatatagctg tttcaatgag agcattacag gatacaaaca tttgattgga   3600
ttaagatgtt aaaaaataac cttagtctat cagagaaatt taggtgtaag atgatattag   3660
taactgttaa ctttgtaggt atgataatga attatgtaag aaaacaacag gccgggcggg   3720
ttggttcaca cgtgtaatcc cagcactttg ggaggctgag gcaggcagac tgcctgagct   3780
caggagttcg agaccagcct gggcaacacg gtgaaatccc gtctctacta aaaatacaaa   3840
aaaattagcc gggtgtggtg acacatgcct gtagtcccag ctacttggga ggctgaggca   3900
ggagaatcac ttgaacctgg gaggtgaagg ttgcagtgag ccaagatggc accacttcac   3960
tccagcctgg gaaacagagc aagactctgt ctctgagctg agatggcacc acttcactcc   4020
agcctgggaa acagagcaag actctgtctc aaaaaaaaca aaacacacaa acaaaaaaac   4080
aggctgggcg cggtggctca cgcctgtaat cccagcactt gggaggccg aggcgggtgg   4140 atcacctgag gtcaggagtt ccagaccagc cttgtcaaca tggtgaaacc tcccccgcc   4200 gtctctacta aaaatacaaa aattagccag gcgtggtggc aggagcctgt aatcccagct   4260
acttgggagg ctgaggcagg agaatcgctt gtacccagaa ggcagaggtt gcactgagct   4320
gagatggcac cattgcactc cagcctgggg acaagagcg agatttcgtc tttaaaaaac   4380
aaaaacaaaa caaaaaacca tgtaactata tgtcttagtc atcttagtca agaatgtaga   4440
agtaaagtga taagatatgg aatttccttt aggtcacaaa gagaaaaaga aaaattttaa   4500
agagctaaga caaacgcagc aaaatcttta tatttaataa tattctaaac atgggtgatg   4560
aacatacggg tattcattat actattctct ccacttttga gtatgtttga aaatttagta   4620
```

-continued

```
aaacaagttt taacacactg tagtctaaca agataaaata tcacactgaa caggaaaaac    4680
tggcatggtg tggtggctca cacttgtaat cccagtgctt tgggaggctg agacaggaga    4740
gttgcttgag gccaggagtt caagaccgac atggggaatg tagcaagacc ccgtccctac    4800
aaaaaacttt gtaaaaattt gccaggtatg gtggtgcata cctgtagtcc cagctactcg    4860
ggaggcggag gcagaaggaa tcacttgagc ccaggagttt gaggctgcag tgagctacga    4920
tcataccaca gcactccagc gtggacaaca gagtaagacc ctatctcaaa aacaaaacaa    4980
aacaaaacaa acaaaaaaaa ccacaagaaa aactgctggc tgatgcagcg gctcatgcct    5040
gtaatcccag tattttggga ggcccaggtg ggcgtatcac ctgaggtcag gagttagaga    5100
ccagcctggc caacatggtg aaaccccatc tctactaaaa atacaaaatt agccaggcat    5160
gtggcacgcg cctgtagtcc cagttactgg gaggctgaag caggaggatc acctgagccc    5220
gggaggtgga ggttgcagtg agccgagatc acaccactgc actccagcct gggtgacaca    5280
gcaataccct acctcaaaat aaaaaagaaa aagaaaagaa aagttgctgt ccccgctacc    5340
ccaatcccaa atccaaacag cctctctcat ctcacagtaa gggggaaaaa tcacccaaaa    5400
aagctaagtg atcttttgaa aacccaaact cttagaagtc taagattatt atagtcaact    5460
catgaagtgt catcataaaa gatactctaa tattatttaa gtagaaccac atattggttg    5520
tcttggtatg tctagcccct ggcatacaaa atatttaata acactgatat ggtacctgtg    5580
atgtgaaaat gtactatgag tacagcttta taaatactat atatgtacct atatacagaa    5640
aaaaatacaa caaaatcata aaagcactta tctttgaaag aggagttaca gcaattttat    5700
ttagttcttt attgctttgc tatatattct aaattttttt caatgaatat atatcacttt    5760
taaaaaaatt caatggtctt tcttataaat tatctttggc agcatgcgtt tttatatata    5820
catataaaat gtatgggaaa tttttaaagg atacattaaa ttaaagcaaa atatacaaac    5880
aaaaaatcag aatacaaaaa gataaaaaga ttgggaaggg agggagggag taaggaggaa    5940
gggtgggtgg gtatagagaa atataccaaa taatggtaag aagtggggtc ttgacacttt    6000
ctacactttt tttaaataaa aaaaattttt ttctctctct ttttttttt tagagacgaa    6060 gtctcgctat gttgcccagg ctggtcttga actcctggga tcaagagatc ctcctgcctc    6120
agcctcccaa ggtgcttgga ttacaggtgt gagccaccac gcctggtcac tttctacact    6180
ttaatatata tattttttca ttttcaatgt catttttatt agttaattta taatacccat    6240
tcaccattat attcaaagtc tatttgaaga aataaaccag aaagaatgaa atactctagc    6300
tcacatgcta ttcaatacta aattacctttt caaatcacat tcaagaagct gatgatttaa    6360
gctttggcgg tttccaataa atattggtca aaccataatt aaatctcaat atatcagtta    6420
gtacctattg agcatctcct tttacaacct aagcattgta ttaggtgctt aaatacaagc    6480
agcttgactt ttaatacatt taaaaataca tatttaagac ttaaaatctt atttatggaa    6540
ttcagttata ttttgaggtt tccagtgctg agaaatttga ggtttgtgct gtctttcagt    6600
ccccaaagct cagttctgag ttctcagact ttggtggaac ttcatgtatt gtcaggttgg    6660
cccgtaatac ctgtgggaca acttcagccc ctgtgcacat ggccaggagg ctggttgcaa    6720
acattttcag gtaggtggac caggacatgc ccctggtcat ggccaggtgg aggcatagtg    6780
ctatacagca ggcagaagtc aatattgatt tgtttttaaa gaaacatgta ctactttcat    6840
aagcagaaaa aatttctatt cttgggggaa aagattatgc cagatcctct aggattaaat    6900
gctgatgcat ctgctaaacc ttcacatatc agaacatatt tactatagaa agaatgaaaa    6960
```

-continued

```
tgggacattt gtgtgtcacc tatgtgaaca ttccaaaaat attttacaac aactaagtat    7020
tttataaatt ttatgaactg aaatttagtt caagttctag gaaaatacaa accttgctag    7080
atattataaa aatgatacaa tatatattca tttcaggctc atcagaatat atctgttatc    7140
acttgacaag aatgaaaatg caccattttg tagtgcttta aaatcaggaa gatccagagt    7200
actaaaaatg acttcttcct tgaagcttac tcaccaactt cctcccagtt actcactgct    7260
tctgccacaa gcataaacta ggacccagcc agaactccct tgaaatatac acttgcaacg    7320
attactgcat ctatcaaaat ggttcagtgc ctggctacag gttctgcaga tcgactaaga    7380
atttgaaaag tcttgtttat ttcaaaggaa gcccatgtga attctgccca gagttcatcc    7440
cagatatgca gtctaagaat acagacagat cagcagagat gtattctaaa acaggaattc    7500
tggcaatata acaaattgat ttccaatcaa aacagattta cataccatac ttatgtcaag    7560
aagttgtttt gttttattgc atcctagatt ttattttttt gatttatggt ttactttaag    7620
cataaaaaat ttgtcaatac aactcttccc aaaaggcata aacaaaaatt cataaaactt    7680
gcatcacttg agatacttca ggtatgaatt cacaactttg ttacaactta ctatatatat    7740
gcacacatat atatatattt gggtatattg ggggggttct aatttaagaa atgcataatt    7800
ggctatagac agacagttgt cagaacttgg caatgggtac gtgcaggttc attataccaa    7860
gtctacttgt agttgttcaa aatgtatcat aatacaaggc cgggcgaggt cgtcacgcct    7920
gtaatcccag cattttggga ggctaaggca ggaggattgc ttgaggtcag gagtttgtga    7980
ccagcctggg caacagagca agaccctgtc tccaaaaaga aaaaaaataa ttttttacaa    8040
aataaaaaca aaatgtatca tcagacgaaa ttaaataaga ggcaattcat ttaaatgaca    8100
acttttccca gcttgacatt taacaaaaag tctaagtcct cttaattcat atttaatgat    8160
caaatatcaa atactaattt tttttttttt tttttttttg agacggagtc tcgctctgtc    8220
gcccaggctg gagtgcagtg gcgcgatcct ggctcactgc aagctccgcc tcccgggttc    8280
acgccattct cctgcctcag cctcccgagt agctgggatt acagacatgc gccaccacgc    8340
ccggctaatt ttgtattttt agtagagatg gggtttctcc atgttggtca ggctggtctt    8400
gaatttccca cctcaggtga tctgcctgcc tcagcctcac aaagcagtag ctgggactac    8460
aggcacccac caccacactt ggttaattct tttgtatttt ttttgtaaag acgggatttc    8520
accatgttag ccaggatggt ctcgatctcc tgatctcatg atccgcccgc ctcagcctcc    8580
caaagtgctg ggattacagg cgtgagccac cccgcccggc catcaaatac taattcttaa    8640
atggtaagga cccactattc agaacctgta tccttatcac taatatgcaa atatttattg    8700
aatacttact atgtcatgca tactagagag agttagataa atttgataca gctaccctca    8760
cagaacttac agtgtaatag atggcatgac atgtacatga gtaactgtga acagtgttaa    8820
attgctattt aaaaaaaaag acggctgggc gctgtggctc atgcctgtaa tcccagcact    8880
ttgggaggcc aaggcaagtt gatcgctcga ggtcaagagt tcgagaccag cctggccaac    8940
gtggtaaaac cccgtctcta ctaaaaatac aaaaaaaaaa ttagccaggc atggtggcac    9000
aggcctgtaa tcccagctac tagggaggct gagacatgga gaactgcttg aatccaggag    9060
gcagaggtta cagtgagccg agatcatacc actacactcc agcctgagtg acagagcgag    9120
actcctgtct aaaaaaaaaa aaaaaaaaaa agatacaggt taagtgttat ggtagttgaa    9180
gagagaactc aaactctgtc tcagaagcct cacttgcatg tggaccactg atatgaaata    9240 atataaaatag gtataattca ataaatagga acttcagttt taatcatccc aaacaccaaa    9300
acttcctatc aaacaggtcc aataaactca atctctataa gagctagaca gaaatctact    9360
```

```
tggtggccta taatcttatt agcccttact tgtcccatct gatattaatt aaccccatct    9420
aatatggatt agttaacaat ccagtggctg ctttgacagg aacagttgga gagagttggg    9480
gattgcaaca tattcaatta tacaaaaatg cattcagcat ctaccttgat taaggcagtg    9540
tgcaacagaa tttgcaggag agtaaaagaa tgattataaa tttacaaccc ttaaagagct    9600
atagctgggc gtggtggctc atgcctgtaa atcccagcac tttgggaggc tgaggcgggt    9660
ggatcacctg aggccagaag ttcaagacca gcctagccaa catggcgaaa ccctgtctct    9720
acaaaaaata caaaaattag ccgggtgtgg tggcacgtgc ctgtagtccc agttacttgg    9780
gaggccgagg caggagaatc gcttgaacct aggaggtgga ggctgcagtg agccgagatt    9840
gtgccactgc actccacttc agcctgggcg acaagagcaa gactccgtca caaaaaaaaa    9900
aaaaaaaaaa aagcttaaaa tctagtggga aaggcatata tacatacaac taactgtata    9960
gcataataaa gctcataatc tgtaacaaaa tctaattcga caagcccaga aacttgtgat   10020
ttaccaaaaa cagttatata tacacaaaaa gtaaacctag aacccaaagt tacccagcac   10080
caatgattct ctccctaagc agtatcaagt ttaaagcagt gattacattc tactgcctag   10140
attgtaaact gagtaaagga gaccagcacc tttctgctac tgaactagca cagccgtgta   10200
aaccaacaag gcaatggcag tgcccaactt tctgtatgaa tataagttac atctgtttta   10260
ttatttgtga cttggtgttg catgtggtta ttatcaacac cttctgaaag aacaactacc   10320
tgctcaggct gccataacaa aataccacag actgagtgac ttaacagaaa cttatttctc   10380
acagttttgg aggctgggaa gtccaaaatt aaggtacctg caaggtaggt ttcaatctca   10440
ggcctcttct ttggcttgaa ggtcttctaa ctgtgtgctc acatgacctc ttctaacaag   10500
ctctctggtg tctctttttt tttttttttc tttttgaga cagagtctca ctctgtcacc   10560
caggctggag tacagtggca caatctgggc tcactgcaac ctccaactcc cgggttcaag   10620
tgattctcat gcctcaccct cccgagtagc ttggatgaca ggagcccgct accacaccca   10680
gctaattttt gtattttag tagagatggt gtttcactac attggccagg ctggtctcaa    10740
actcctgacc tcgtgatcca cccaccttgg cctcccaaag tgctgggatt acaggtgtga   10800
gccactgcgc ccgtcctggt gtctttcat ataagggcac taatccaatc agacctgggc    10860
ccaaccctcc cgacttcttc taactgtaat taccttccaa aggccctgtc tccaaatacc   10920
atcacactgg gggttaggac ttcaaaaaag gtatgggggg ggtgtgggag gacataaatg   10980
ctcagtccat aacaagcacc caacataaaa atggctagaa cagatcacaa aaaaaaggtc   11040
ctgtatggct ttggggaagg gctcaacccc aaaatatctg agagctctgg aggggcctag   11100
aagtggtaaa tgaatgaaaa cgtggttact ctccagatct gcctttccca aatatggcca   11160
ttcttggctg aatcagaaat caaaggacag gttattaatt actagctcta agttacttac   11220
catttgctga gacagttcag aaatctgact gcatctcctc agagatctag aacacagttc   11280
tcaaattcta acttacttgt gatatacttg tgaatgataa aaatcgctac aggtactttt   11340
attaatctga aagagtattg agaaattacc tttcattctg acttttgtct ggaatgaaaa   11400
tcaatacttt tgctataatc gattactgaa ataattttac tttccagtaa aactggcatt   11460
ataatttttt ttaattttta aaacttcata attttttgcc agactgaccc atgtaaacat   11520
acaaattact aataattatg cacgtcacat ctgtaataat ggccttcatg taaacatttt   11580
tgtggtttac acataaaatc tctaattaca aagctatatt atctaaaatt acagtaagca   11640
agaaaattaa tccaagctaa gacaatactt gcaacatcaa ttcatcatct gtgacaagga   11700
```

-continued

```
ctgcttaagt ctctttgtgg ttaaaaagga aaaaaaaaa aaagacatgt tggccagatg   11760
cggtggctca cacctgtaat cccagcactt tgggaggctg aggtgggcgg atcaccctg    11820 gcctgcccaa catggtgaaa ccccgtctct actaaaaaca caaaaattag ctgggcgtgg   11880
tggcgggcgc ctgtaattcc agctactcgg gaggctgagg caggagaatt gctagaaccc   11940
aggaggcaga gattgcagtg agctgagatt gcaccattgc actacagtct gggcaacaaa   12000
agtgaaactc catcttaaaa aaaaaaagac aatgttcgtg ggtccaaaca agacttaatg   12060
gaagtgagtc taaaaatgag ctatgtgggc caggcgtagt ggctcccacc tgtaatccca   12120
gcactttggg aggccgaagc aggcagatca tgaggtcagg agatggagac catcctggcc   12180
aacacggtga atcctgtct ctacaaaaat tagctgggcg tggtggtgcc tgcctgtaat   12240
cccagctact cagaaggctc aggcaggaga atcgcttgaa ccagggagtc ggtggctaga   12300
gtgagccgag atttgcatca ctgcactcct gcctggtgac agagcaagac tccatctcaa   12360
aaaaaacaaa caaaaataaa agataaaaat gagctatgtg aattaaaaga ggtataacaa   12420
tagataaacc atattttatt taattcctag taatgagtaa tatttccaaa cttctggaat   12480
gggcagaaat tgctagttgg catatttta cctttatat tcagatacat taaaattctc     12540
aaaaaaaaac acctcaaagc agatgatccg ccatctcctt ggataatttg tgttaactca   12600
ggataacaga aaaccaaaat tatgagttac tgatgcaata ttcctaaatg taaaaataat   12660
taaagctaat agtagattca tcttccaatt tcatatcagt cttacaaata aactacatat   12720
ataacttgct tgccttccct tctgagggat aaagctgtta gaagaattaa aatcagcatt   12780
cttgactatt caaccaaggg agggataaat tattactcat tctagggaca tgggctcata   12840
actactacat gtgtaaggac atgaatttac ccaatattac aattttttcct tttattagtg   12900 tgtacagtgg aagaatagac atgttcactc tggacaaaaa aaaaattata cttatcagtt   12960
atcagaagca caatgctgaa gacagtagtt ccataacaat ttgaagtatg tgatcgaact   13020
agtagattat cttagtagta gtgaattatt gtaaatgtta gtaatttggc agccactggg   13080
cagaaaaata agaattgagg ctcaatattg atattaatgg tggtgattga cacataaatt   13140
ttatcaagtc tacacaatat aaaattacag aaaggtagaa gagtatacca gtacaacttc   13200
aacatatctt cactacaagg gagtaaaatg acatggccta gttactatct aatgaactgc   13260
agaaaactaa aagaaaactc caaggcaact cttctctgct gatctggttg gtccttttcc   13320 tacctttgc aatacccaga tacaaacaat ggatagaaaa caaagtagac ttgtagtatg    13380
caggtcacag tgctaaattc acagaaagaa acccctgaac tgaactgctc tatttcctgg   13440
tggtcacaaa gagtaattct ggtttacacc tacagattga tgtcaatcta cacctgttg    13500 ataacagtgt ggccaaggac aaaaaaaagg tgctccgttt taccaattct gtaaaaaatt   13560
attggcaggg taagctcggc tagggcagga ttacatttct aggactacca tccccgaaat   13620
ttagaagata ttatatccac ataaagcata tctttcacat taatttgcaa aaatctaaaa   13680 gcttttttctt agctcaagtg tgtccaagtt taccctggca gtttaaaacg atagttacaa   13740
gcagcatggg ttgtatcaga cacatttgag ggccaatttc atgtaagtga tattgggcaa   13800
gttacttcaa ctatctgtgc ctccaaggtc atactagtgt ttatttacct aaagggtacc   13860
tgttatgtaa ctttagggtg tttacattag ataatgcctg caaaatattt acttcaacgc   13920
ctaaaacata gttaagtatt caataaatac ctactattgt cactactaac ttaaaagttt   13980
agagattaag agcagaatct ggggtgagac aaacttaggt tcaaatccta gtattgttgg   14040
gtaatcttgg gcaagttact taacctctct gatttgtgta atttaaaaaa ttagttaata   14100
```

```
tacataacag ggcttagaag agtatctagc acatagcacc atttaagcat ttgttattgc   14160
taacatgcaa acaatttaag ggaaagaaat tttttaaaaa ggaagaggga tttgcaaact   14220
aaaaacaatg agtatcttat gttcaaagaa aactaacaaa cagccagctc tagcaataat   14280
taaattcact atatactggg gcaggcatca caccccaaag ctaaaagcgt ctacctaggc   14340
caggcacggt ggctcatgcc tgtaatccca gcactttggg aagcagaggc gggcagatcg   14400
cttgagctca ggagttcaag accagcctgg acaacatggc aaaacaccat ctctacaaaa   14460
aatacaaata ttaggccggg cgcagtggct cacgcctgta atcccagcac tttgggaggc   14520
caaggcgggt ggatcacctg agatcaggag ttcgagagta gcctggccaa catggtgaaa   14580
cctcgtctct attaaaaata caaaaaatta gccaggcatg gtggcaggcg cctgtaatcc   14640
cagctactca gggggatgag gtaggagaat cgcttgaacc cgggaggcag aggttgcact   14700
gagccgagat catgccactg tactccagcc cgggcaacaa gagcgaaact ccatctcaaa   14760
aaataaataa ataaataaat aaaataaagt acaaatatta gccagggatg gtggtgcgca   14820
cctgtagtcc cagctacttg ggaggctgaa gtgggagaat cccctgagcc tggggagaat   14880
cacccgagcc cgggaagtcg aggctgcagt gagcagtgat tgtgccactg cactccatcc   14940
taggtgacag agtgagaccc tgtctcaaaa aaagaaatt ggcagaatta agtaagttga   15000
tgtttagaga tgaaaaatca acatttttc ctcagcaact gaataaaaac aacagccact   15060 accattttt tgagtaccta tttgtagcct atttttaac tggtattact cgagagagag   15120
agagctaggt tcgagacaga gctccttctc ttaataactg tatgacctag ggtatgtctg   15180
ttagcctctc tgaggcttca aaggttcctc atctgtaaaa tggtaataat cataccattg   15240
ctacagggct gttttgaaga ctaattagga ctatgtaagt aaacatgatg atggctatta   15300
ttactgttcc ccgccagggg ccatgcaagg gttgctgatt cacatagact gtcttataat   15360
cctctcaata actccaagag gtagccagca cctcagatat acataaaatg acttaagccc   15420
agagaggtga agtaagttgc ccacagccac acaactagta aatagcccaa acaagctgga   15480
ttcccagtta gactccgtta atagcactgc tctttacctt aagtcattac aatgcctaat   15540
atgaaataga atcgcttctt tcttagggtt caagtggtta attatttaat gtattcattc   15600
aacaaaccat catcgaggac ctcttacaag ccaagtactg tgctaagtgc tagagttacg   15660
gcggtgattc ctgcccttaa aaagttttag tgggagaaac aacaggtaac caggtcattg   15720
ccaaaacaac aaaaataatc ataataaagc aggctaaagc atatttaact ggccggggtt   15780
ttgactattt tagcaagcat gatcagaacg gttgaggagg gaggccagca gcttggccgg   15840
ttcaacaaac aagaaaaaac cagtgagggt ggagctaaga taccagaggc tgattacggt   15900
taagaatgtt cttgaaggta aggaccagat tctcattttc tatatcctgg ggcatcggtc   15960
agcatggaat ctggattcta gcacatgtga atttcggctt gaaatgacct aatgcctttt   16020
ccctagttcc ttcgtgtgtc aaatacgcat ggttaccgct accagagctg tagtgggct   16080 tcaatgaggc catgagcatc tccataaaga tgaactacag tgtgtgcaaa actaaaggca   16140
aaacctggtc cccacacgcc ctcccaggtg gtcgctttcc gtgccgaggc ccctccagag   16200
gtgccccgag aacctcacca tcgcacccca aacttccagg gaagggcctc tcccgagaaa   16260
gcccccacgc ccccaccccg cgccatcatt cccgaatctg ccctcggccc ctccccgcag   16320
cacgctcgca ggcggcacat gtcaaccaaa acgccatttc caccttctct tcccacacgc   16380
agtcctcttt tcccagggct cccccgagga gggacccacc ccaaacccg ccattccgtc   16440
```

-continued

```
ctccctgccg ccctcgcgtg acgtaaagcc gaacccggga aactggccgc ccccgcctgc   16500
ggggttccct gggcccggcc gctctagaac tagtggatcc caattgaagg cctggtctaa   16560
atgactccaa aatcaccact taattcaaga gactgatttc cctgagtcag gccccttaaa   16620
gcagctattt caatgggaca gggaaacaac cctaggatct ggattagaat cacttggggg   16680
ctgccacacc cccagggctc tgatcctgcc cttctcccac acgcacattc acatactgct   16740
gcagtgacct tccatttcta atgggttcct gggccatctg tcaggtatag ggaatggaaa   16800
aggggttggg gaggctctgc ttcagaaagt ttgtgtcagg ggctcccaga gcctccacag   16860
atagatagca ggggtcccca ccctaccatg gcagctataa atgtgatcaa catttattgg   16920
cctaggatac agcagttagc aaaatgcctg atgtagttcc cactccgtgg aggttgcagg   16980
ctagccaaga agtcatgagt tcagcaaccc ttacgcacca gtgggatgag attggaccag   17040
gccgagggta gtcttgggaa cactcagcat ttgtctgagg gccagaagag gctgcttgcc   17100
ctcagacagg aggtcagcat ctttattgta gcccatgaca cctctacacc attgctcttc   17160
tggtcttatg gaagacatct ttgggcctga taacagcgga gtctgtgtcc cacttgtcca   17220
ggctggagtg ccacatcagg cacactccag ttgcagggac agcacagaca agtttcagga   17280
aggctggtgg cctccaggag gttaacctta taaggccaga ttgtaaccta gttgaaaaac   17340
atacacatgc catgataata aaagaaccta ggcaccatta caagagaaaa aatcattttt   17400
gtagatacga gcatggattc ttgggtgggt cagacacact gggcttgtgc tctgactgca   17460
ctgtctcccc tacctgacct tgggtaaacc ataagactgc tgcatgactc agtgtccacc   17520
ccaaaaaagt accggtagat attggccaca gtagatatca gctagagtgg actctcatga   17580
caatgagggg agatgtattc cccatcttag gcacctggga ctctaccttc catcttctgc   17640
tccgtgtctc tccatcccca ggctcttcag aactcaggga gtccagaatg tcagctccca   17700
gatttcagcc ttcagaaagg aaacccatta ccgttcagtt gaacaaatgt tgtctgagcc   17760
ccagatctgg gctcagaggc catctaggct atgagacaag aggggaacaa agcaccgtct   17820
gcactcactc accacactca cttgctgtcc caggtcacat ccatcgggta gagaatctaa   17880
gaggctgagc tagctcccgc caccagccca gcccacccca cctggcccct tccttccttc   17940
tacaaaatat gcaccacctg tcaaagggtg ggcagtgcca ggcctgcata cagagcactg   18000
agtgtaaaag cagacatgga ccctgacctc caggagcttc caattttctt gaagagacaa   18060
atcagctggc atttcagtcc agtgtgatct gctcttggtg agcacagacc tagggagttg   18120
gggcagcttc ccagaagaac tgcagtccag gctgagggca gagaaatgag gggaatggcg   18180
aggaattggg gagcagggggg gagctcagta gagagccaag ggcgggaggt gagaagtccg   18240
tgttgggcca ggagctaccc tccggtggcc acagccgaag tcgaggatgc ctttggaact   18300
catccccact tctctctttc tgtatgtagc cgtccaagaa caagtcacct ccaagtgtag   18360
ccggatcaag gcaagccccc catctagcaa gcacttgatg ccacccagaa ctgggcttct   18420
tcagaacaat ctgagtccag gaatgatccc actcaccagg caccagagct gcgagggcat   18480
gggagtgatc tcaccaactc tggggaagcg gcaaggaatt ttcacctcca gcccccagtg   18540
tcccatcctc tcacactcag gccagactcc cctgggcaga cttgactctg tctgccagca   18600
tatgcagagc cccaaggcca ccccaccaga agtgccctg cctgggttct gtcccagctc   18660
cctgggcacc cagtccttga gtccccacca gctcagacgg cctagtgtgc caagaatgcc   18720
cactgcgttc aacaatgctg catgggtcac agcggcagca gctgtgacca cagcagtttc   18780
ggggaaaaca cccctcagcc aagtggataa tagcgttcag cagcactcac cttctggcca   18840
```

```
ggcctgcctt cagaggccat ctgattggga ggcacaagtg cccgctgcga tgggaacaca   18900
agtgcccctg gccaacaacc ccagcttcag cctgctgggc agccagagcc tcaggcagag   18960
cccggtacag ggcccggtgc ctgtagcaaa caccaccaag ttcctccagc agggtatggc   19020
cagctttagt cccctgagcc ccatacaggg catcgagcca ccaagctatg tggctgctgc   19080
tgccaccgct gctgctgctt ctgccgttgc tgccagccag ttcccaggtc cgttcgacag   19140
aacggatatt ccccctgagc tgccacctgc cgactttttg cgccagcccc aacccccact   19200
aaatgatctg atttcgtcac ctgactgcaa tgaggtagat ttcattgaag ctctcttgaa   19260
aggctcctgt gtgagcccag atgaagactg ggtgtgcaac ttgaggctga tcgacgacat   19320
tttggaacag catgctgctg ctcaaaatgc cacagcccag aattctgggc aagtcaccca   19380
ggatgctggg gcactttaaa tctgagcagg atgcccatag aaacccccat ggtgacatca   19440
ctctaggaag tggtgtcgat ccatacccgc agttgtctcc cgttacaatt tgagtggtgt   19500
tgtcagccca tgcttatccc tctctctacc tgtgacaaaa tggaaagctg gtgatttttc   19560
aagctacgtg tacatatttg aaaattttgt aaatggtttt cctaaacatt aatgacagaa   19620
gtatttatac ttcattttgt gactttgtaa ataaagcgac ggcttttgtt tcagtagagt   19680
tgtgtttact atgcattgtt ttgtgtttat tatacaatgt tacaaatatg cagaccgtgt   19740
tgtttgctcc agtgatacct tgttaagcta ggtggctgag tcgcttatgg ttttaatgca   19800
atgagcaatg tggatatgac caagagttgt tgtgcaagtt gacaaatgcc aaatagaaaa   19860
ccacttggcc atttatttct atgttcacta aaaatcctat tgccttgtgt gattcttaat   19920
ctcttttgcg aacctttcag tctccgctag ctctttccta atgagcttta cagcagaagc   19980
tgttttatcg ttaagtgccc cacagagaca ctttaccagg aggctgggag agttctccag   20040
atttgggaga ggcgcagaga cagtgtgtga gccgagccct gtctcagcaa tccacctgga   20100
ggagctagag tatcctcctc cctttaccat tcagaccgag agaaaaagcc cagcttgtgt   20160
gcaccctcgt ggggttaagg cgagctgttc ctggtttaaa gcctttcagt atttgttttg   20220
atgtaaggct ctgtggtttg ggggggaaca tctgtaaaca ttattagttg atttggggtt   20280
tgtctttgat ggtttctatc tgcaattatc gtcatgtata tttaagtgtc tgttatagaa   20340
aacccacacc cactgtcctg taaacttttc tcagtgtcca gactttctgt aatcacattt   20400
taattgccac ctcgtatttc acctctacat ttgaaatctg gcgtctgttt caagccagtg   20460
tgttttttct tcgttctgta ataaacagcc aggagaaaag tgcctctatg tttttatttt   20520
tcaagggagt attcagtacc tacaaaccca agtcaggaag cctgctagtg gctttggttc   20580
tttcagaggc tgctcgatgc cttgtgtgtc agaaagaaag attcagcagt tttgcatcat   20640
ggcaaagaag cctgttattt tggggctcag cccctcattt tatagaggat gaaacagagg   20700
gggatgggag gtcacaaaga caactgcccc gggagcaggt gtgggggaga cttgccctga   20760
gggtctagac gctctgcacc accgtcctgt ctcccttgct gaagaccaca catgcccttc   20820
tttgaccaga ccctgccacc tgataggcca ggacctggta ggcgggtacc caggtttcat   20880
ggatggaacc acatctcccc aaaagtgggg aggtagctac tgggatgcac gcctcccgcc   20940
atgtgctata ggagagcagc tgaagcaaca gttgggatca gatgtagtca caattgaatg   21000
catcatcaca tttatccctc taagtggctg ggagagttga tatcctcatc cctaaggtac   21060
aaaatgttcc aatttgatca gtggctttca ggagctgaga aaggcatgtg ctctgaggca   21120
gagctgttat gtcccgcaga gcctaaaaat gctctaagaa catgctccct gccaaaattc   21180
```

-continued

```
tcaatggctg tgacaaggga caacgatcga ccaatggggg tggaagcaga cctccgcagt   21240
ccagggccca gagctaggac agaggggtcg gagaaagagt cattttccca acactccagc   21300
tcttggccag tcctcacaca gtcccctcct gcttcctgct gagagagata tcctcatagg   21360
tctgggtaaa gtccttcagt cagctttcat tccctgtcac caactttgtc tctgttctcc   21420
ctgcccgtct caggcagcac tcctcaggaa acctctccaa gagccagcct cactgcagcg   21480
cccactattg tccctctgcc tcaagtgtcc catccatgcc aggccccagg caggctgcag   21540
ctttccctca gggccacacc aaagcacttg ggctcagctg tgctgtcccc ctccatcact   21600
gagctcaggg gcagcagggg tggggtgcca ggaggcccat tcacccttct ctggctctgt   21660
gttggaccca cctgcccagc cactgctgct tagaacctac ccgctgggaa aatgaagccc   21720
tcccggaggg gccacctcaa cctgagagcc tcacggatca cagttgtccc cactcagctc   21780
tgccagccct cagagaccca tagataaaag ctgagcttgg ctcgcagagc tggttccatc   21840
ttccattccc agagggttca acttcctacc ccaaccacac agggaacctc aaggctgagc   21900
cagtgtgggc tgcagtgcag accagcttcc tggacacgtc ctgccacctg accccaggct   21960
ggcctcactg cccctggcac tcctgaccct atcctcattc ctcctggcag tgcgtgttct   22020
gccattccgc tttcccttag ctgtcctctc actgtactgt cagcttctcc ttttccaggt   22080 gcccccagg ggctttccac atgaccctgt caccccacag cccatccagc accaattcca   22140
gctctctgcc acccttcaaa ggagtgacag tgccctgctt cacctcccac tcacccctca   22200
acccagagca atctggctcc agtcttgcct ccttcccct aagtactcta gtcacagttc   22260
caaattcctc ctggtcataa agccaaatga agcttcctgg tcctcagcgg acttgccact   22320
tcagcagtac tggactctct cctcccagaa acctgtttcc ccttggctcc tggagcccac   22380
actctgctgg aatccttctg cctctctggc ctgtagcctg gccctctctc ccaacctgag   22440
gtccattctc tcctgctcct ccacaagatg ttgctccttc cattacttcc tccctctcaa   22500
ccaaagctcc ttcattagct ctttatcttc tggtttcttc ccctgggcag acgaatggat   22560
tcaagagcct gtggcccagc agcccagcac tccaggatct cagcacttca gcatcccagt   22620
accctagcat ctcaataccc cagcacccca gcaccatagt attccagcac cccattgtcc   22680
aagcatctca gcactccagc atcccagcac cccaacactc cagcagccca gaatctcagc   22740
accctagcac tgcagcatct caggacccca gcacttcagc atcccagcac actagtactc   22800
cagcatctcg gcaccccagc acctaggcat cccaacaccc agcaccccag cacttaagca   22860
tcccaccact acagtatctc aacactccag caccccagca ccatagtgtt ccagcacccc   22920
agcatcccaa caccccagca cttaagcatc ccaacacctc ggcatcccaa cacccccagca   22980 ctgcagcatc tcagcacctt agcatcccag tgccctagca tctcaatgct ccagcacacc   23040
agtactacag tattccagca ccccagcact ccagcatctc agcactgcag cactgcagca   23100
ctccagcatc ccaaaatccc agcatcccaa caccccagca gaccagcaga ccagcatctc   23160
agcaccgcag catccaagga ctatcccagc atcccagcaa cccagcacct cagcatccca   23220
acaccccagc atttcagcat ggcaacaccc cagtacccca gcacttcagc accccagtat   23280
cccagcatct cagcgaccca gtatcacaaa acctcagcat cctagcaccc cagcacccca   23340
gcaccttagc accttagcat cccagcatct cagcgcctca gcatcttgat attctggctg   23400
aggtcagcgt ggtgtatcta gtcagggtcc taactttcac ttcgcaggga aatgctgctg   23460
gactgggtct catgttgggc tgaagctctc tagacccctt gaagacagca taaaagagct   23520
tggagacgct gggtgtcccc catggaagag ttcactctca tcctgctttg acaacagcct   23580
```

-continued

```
tctctggggt ccctcacggg cccctctttc ttactgcaag tttgtctctg agaagactgt   23640
gatgcagaag tcactcagct gcctgtggct cctgaagagc tgaaggtgga ggcctgtagg   23700
cctccctatg agaggcgcag aaaaaaccat gattgctagt ggggaggtgc tccctctaca   23760
acccactcca taatctgccc ccgcccagct ctgaggccag ccccagggga aaatgccaga   23820
tccccaggga ggtgtgtgag acctcagggg ctccctcctc ccttacagca ggctcaggcc   23880
cctgggggcc tcagggccaa ggtctgtggg taagctacta tctctcactt gtcctctagc   23940
cacaaaagcc agggagatct ggcaatggac atgaggttct gaagaagcac atatgactgg   24000
cttcctaatg cgtggttgtt cagtgattca ataaacacgc atgggccagg catgggggaaa   24060 tagacaaaca tgatccccaa cctctcccag agtgaactgg gagggaggag tgttcatccc   24120
tcaggattac accagagaaa caaaccagca ggagatatat atggttttgg ggggtcaaga   24180
aagaggaaaa acctggcaag gcaagtccaa aatcatagga caggctgtca ggaagggcag   24240
cctggaacct ctcaagcagg agctgatgct gcagtccaca ggcagaattt cttcttcctc   24300
ggggaaatct cagctttgtt cttaaggcct ttcaactgat tggctgaggt ctgccccttc   24360
ccccacattc tccaggataa tcttccttac ttaaagtcaa ctattaatca cagctacaaa   24420
atcccttcac agctacacat agatcagtgt ttgattgacg aacagcccct acagcctagc   24480
caagttgaca cataaaacta accatcacag ggggacaaat gatgtaaaca catcaacaaa   24540
taaaacagta acaagttaag gtctatggaa aaaacacaga aggggcagag agaaagaaag   24600
caagaaggag agtcccagtt tgctagggct tgtgggaagt ggggagcagt tctctttagc   24660
taggatattt gggaaaggca tatctgaagg agtgatattt gagcttagat taaaagatgg   24720
gaaggagcaa gccatgcaaa gagctaggat gttccaagca gagacggaac agcaagtgca   24780
aatgtcagga ggaatagaag gaggctggtg ggtgggggtcc agtgagcaag aggagggcag   24840
gcaggagagg ggatggggag gtgggcaggc ccagaccacc cagggccctg gagactatcc   24900
tgatccaaca agggaagcct tgagtcactt cagtgtccat gtggagaatg gacctcagac   24960
tgaatgaggg aggcagtaag gagggcctct acctccaggg cttcgccctg tggactgcgc   25020
atagacatct ccaactcaga aagtctgaac caaacttttcc atagttcccc caagtctggg   25080
catcctccta ctcagtgaaa ggcagccatc acacctccct gccctgctcc cggatgcccc   25140
aaatcctctt ggtctccaag tccagaacct gagacttgtc cttgatgttt gtctttccct   25200 cacccttttct gtattctggg aagatgggtt ttttttcccccc agatgaatct gtaaaacttc   25260
tgtgatcaca ataaaaattc tggcagtatt attttctgga acatgacaaa gtgattcaaa   25320
attatttatc tggaagacta caaaacaaga atagccagga aatttctaaa aagaaagaag   25380
aaggaggagg agaaagaagg aggaggaaaa ggaggagaag aagaaaagaa aaagaaccaa   25440
gaaagggttc tagctctacc aaatattaaa acatatcatg aagctattta aaacaatatg   25500
gttgtggata ctgaaaaaga tgtgaataaa gtggaaggaa aataaataga aatgcacatg   25560
gggattgaga ctgtgaaaaa ggcagcatct cacatcagtg agggatgttc aacacctggt   25620
gttgggaaaa ctggctagtc atttaaacca aacaactggg tcctctacct cactcctgac   25680
attaagatac atttagatga ttcaaagagt aagacagaaa aaataacacg tgaaaacact   25740
atcagaaaac aacgtgggcc aggtgtggtg ggtcacgcct gtaatcccag cactttggga   25800
ggccgaggca gacagatcac ctgaggtggg gagttcaaga ccagcctgac caacatggtg   25860
aaatcctgtc tctactaaaa atacaaaatt agctgagcgt ggtggcgcat gcctgtaatc   25920
```

-continued

```
ccagctactc aggaggccga ggcaggagaa tcacttgaac ctgggaggca gaggttgtgg   25980
tgagccgaga tcacgccatt gcactccagc ctgggcaaca agagtgaaaa tccatctaaa   26040
aaaaaaaaaa aaagccaagg tggatatttt tatagtatca gggtagatca agcttctcca   26100
atcatgacat gaaacccaga aaccataaaa gaaaagaatg ataaaattgc ccacgtaaag   26160
taaaaagctt gcacacagaa aaacaccata caggttacaa gatgagcagc aaaatcagag   26220
aaaaaacatt gcaattcagg acacacagag gctattgttc ctaatattta aaaataaaag   26280
tagtggattg tctacaaaaa gatgaagaca agaatttcag aaaaccaaat actgcatgtt   26340
ttcacttaca agtggaagct aaacactgag tacacgtgta cacaaagaat ggaaccatag   26400
gccaggcacc gtggctcacg cctgtaatcc cagtactttg cgaggccgaa gcgggcggat   26460
cacctgaggt gaggagttcg agaccatcct ggccaacatg gtgaaaccca gtctctacta   26520
aaaatacaaa aattagccgg gcgtggtggt gggtgcctgt aatcccagct actcgggagg   26580
ctgcggcagt agaatcgctt gaaccctgga ggtggacctt gcagtgagcc gagatcgcac   26640
cactgcactc cagcctgggc aacagagtga gactccatct caaaaaaaaa aaaaaggaat   26700
agaacaatag acactggggc ctacttgagg gaggagggtg aggatcaaaa acctgcctat   26760
caggtactat gcttattacc tgggtggtga aataatctgt acaccaaacc ccagtgacat   26820
gcaatttacc gatgtaacaa acctgcccat gtacccgctg aacctaaaat aaaagttgga   26880
aaaaaatata gaaattttct ttgtaatagc caaaaactgc aaacagccca ggtgtctatt   26940
agtagaatgc ataaacaaac tcgggcatgt tcatacaatg taaaactact catcaataaa   27000
aagtgatact tctcagcaat gaaaagaaac tagctactga taccagctac aacatggatg   27060
gatttcaagt gctttatgat gagagcaaga agccagacac aaaagtgtct atatatatat   27120
acagtatata tacgtatata tacacatata tacagtatat atatacatat acatgtatat   27180
atatactgta tatatactgt atatatatac acagtatata tatacatata tacagtgtat   27240
atatactgtg tatatataca tgtatatata ctgtgtatat atacatgtat atatactgtg   27300
tatatataca tgtatatata ctgtgtatat atacatgtat atatgtat actgtatata    27360 tactgtatat atatatacac atatatacag tatatatata cagtatatac tgtatatata   27420
cagtatatac gtgtatatat acatatatac agtatatatg taaatataca tatatacagt   27480
atatatgtaa atatacatat atacatgtat atatatacac tatatatata catatatagt   27540
gtatatatac atatatacat gtatatattt actatatgat tccatttata taaagtgcca   27600
aaacagtcaa aaataatcta tgtggaaaaa atcaacaaag ggatcccccg ggctgcagga   27660
attcgatggc gcgccgacgt cgcatgctcc tctagactcg aggaattcgg taccccgggt   27720
tcgaaatcga taagcttgga tccggagagc tcgataacat ttaaatggat ctaccacatt   27780
tgtagaggtt ttacttgctt taaaaaacct cccacacctc cccctgaacc tgaaacataa   27840
aatgaatgca attgttgttg ttaacttgtt tattgcagct tataatggtt acaaataaag   27900
caatagcatc acaaatttca caaataaagc aatagcatca caaatttcac aaataaagca   27960 ttttttttcac tgcattctag ttgtggtttg tccaaactca tcaatgtatc ttatcatgtc   28020
gagctaggat cccgcggccg cctactggtc ctcctggagg tagaacttgg tgaccatgaa   28080
ggactctttg ggcttgttgg tgaggctgac gggccggtct gcctcctgcg ccgtgcagag   28140
gaaccagcca gggcaggcgg cagactcgaa gctggtggtg gggccactgt ttgagcggat   28200
gaaggtgaag cgcttgttct cctccttgtt cttgctcagg tcagtgatgt taactgcctc   28260
caattggaac ctaatctcat caccagactt gacacaggcc aggcacagct tcctcccatg   28320
```

-continued

```
gagtcccagg aatagagcat caggctcaat gggcaccaca tctatcttct cttgtaattt      28380
agtatttgat tcttgcaagt atccagcaac tagttggtta ttcctcatgt agaaggtctt      28440
ctggttaaca tcccagattc tgaaggcttg catcttgcag ggtctcttcc ccaaagggtg      28500
gcaggctgtc tctgagtaga gcaagaaaag gaggagagag attaggtgtc tgacagaacg      28560
cctgcggatt tccataccgg tggatccatg gctctgtctc aggtcagtat aggagctttg      28620
atgtgaagtc agccaagaac agctgaacac tacttcctct gaggcccttt tataggaggg      28680
attgcttcct gtgaataata ggaggatatt gtccacatcc agtaaagagg aaatccccaa      28740
ctgcatccaa aaagttttct gggaatatcc actgctgcag gagtggaaag tccccagtgg      28800
aaagtcccca gtggaaagtc cccagtggaa agtccccagt ggaaagtccc cagaatttcg      28860
acggcgcgcc taccagtaaa aaagaaaacc tattaaaaaa acaccactcg acacggcacc      28920
agctcaatca gtcacagtgt aaaaaagggc caagtgcaga gcgagtatat ataggactaa      28980
aaaatgacgt aacggttaaa gtccacaaaa aacacccaga aaaccgcacg cgaacctacg      29040
cccagaaacg aaagccaaaa aacccacaac ttcctcaaat cgtcacttcc gttttcccac      29100
gttacgtcac ttcccatttt aagaaaacta caattcccaa cacatacaag ttactccgcc      29160
ctaaaaccta cgtcacccgc cccgttccca cgccccgcgc cacgtcacaa actccacccc      29220
ctcattatca tattggcttc aatccaaaat aaggtatatt attgatgatg ttt            29273
```

<210> SEQ ID NO 10
<211> LENGTH: 534
<212> TYPE: DNA
<213> ORGANISM: Homo sapiens

<400> SEQUENCE: 10

```
atggaaatct gcagaggcct ccgcagtcac ctaatcactc tcctcctctt cctgttccat        60
tcagagacga tctgccgacc ctctgggaga aaatccagca agatgcaagc cttcagaatc       120
tgggatgtta accagaagac cttctatctg aggaacaacc aactagttgc tggatacttg       180
caaggaccaa atgtcaattt agaagaaaag atagatgtgg tacccattga gcctcatgct       240
ctgttcttgg gaatccatgg agggaagatg tgcctgtcct gtgtcaagtc tggtgatgag       300
accagactcc agctggaggc agttaacatc actgacctga gcgagaacag aaagcaggac       360
aagcgcttcg ccttcatccg ctcagacagt ggccccacca ccagttttga gtctgccgcc       420
tgccccggtt ggttcctctg cacagcgatg gaagctgacc agcccgtcag cctcaccaat       480
atgcctgacg aaggcgtcat ggtcaccaaa ttctacttcc aggaggacga gtag             534
```

<210> SEQ ID NO 11
<211> LENGTH: 535
<212> TYPE: DNA
<213> ORGANISM: Mus musculus

<400> SEQUENCE: 11

```
atggaaatct gctggggacc ctacagtcac ctaatctctc tccttctcat ccttctgttt        60
cattcagagg cagcctgccg cccttctggg aaaagaccct gcaagatgca agccttcaga       120
atctgggata ctaaccagaa gacctttttac ctgagaaaca accagctcat tgctgggtac       180
ttacaaggac caaatatcaa actagaagaa aagatagaca tggtgcctat tgaccttcat       240
agtgtgttct tgggcatcca cgggggcaag ctgtgcctgt cttgtgccaa gtctggagat       300
gatatcaagc tccagctgga ggaagttaac atcactgatc tgagcaagaa caaagaagaa       360
```

```
gacaagcgct ttaccttcat ccgctctgag aaaggcccca ccaccagctt tgagtcagct    420
gcctgtccag gatggttcct ctgcacaaca ctagaggctg accgtcctgt gagcctcacc    480
aacacaccgg aagagcccct tatagtcacg aagttctact tccaggaaga ccaat        535
```

<210> SEQ ID NO 12
<211> LENGTH: 534
<212> TYPE: DNA
<213> ORGANISM: Unknown
<220> FEATURE:
<223> OTHER INFORMATION: Equus sp.

<400> SEQUENCE: 12

```
atggaaatcc gcaggcgttc tgtcagacac ctaatctctc tcctcctttt cttgctctac     60
tcagagacag cctgccaccc tttggggaag agaccctgca agatgcaagc cttcagaatc    120
tgggatgtta accagaagac cttctacatg aggaataacc aactagttgc tggatacttg    180
caagaatcaa atactaaatt acaagagaag atagatgtgg tgcccattga gcctgatgct    240
ctattcctgg gactccatgg gaggaagctg tgcctggcct gtgtcaagtc tggtgatgag    300
attaggttcc aattggaggc agttaacatc actgacctga gcaagaacaa ggaggagaac    360
aagcgcttca ccttcatccg ctcaaacagt ggccccacca ccagcttcga gtctgccgcc    420
tgccctggct ggttcctctg cacggcgcag gaggcagacc ggcccgtcag cctcaccaac    480
aagcccaaag agtccttcat ggtcaccaag ttctacctcc aggaggacca gtag         534
```

<210> SEQ ID NO 13
<211> LENGTH: 177
<212> TYPE: PRT
<213> ORGANISM: Homo sapiens

<400> SEQUENCE: 13

```
Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu
```

<210> SEQ ID NO 14

```
<211> LENGTH: 178
<212> TYPE: PRT
<213> ORGANISM: Mus musculus

<400> SEQUENCE: 14

Met Glu Ile Cys Trp Gly Pro Tyr Ser His Leu Ile Ser Leu Leu Leu
1               5                   10                  15

Ile Leu Leu Phe His Ser Glu Ala Ala Cys Arg Pro Ser Gly Lys Arg
                20                  25                  30

Pro Cys Lys Met Gln Ala Phe Arg Ile Trp Asp Thr Asn Gln Lys Thr
            35                  40                  45

Phe Tyr Leu Arg Asn Asn Gln Leu Ile Ala Gly Tyr Leu Gln Gly Pro
        50                  55                  60

Asn Ile Lys Leu Glu Glu Lys Ile Asp Met Val Pro Ile Asp Leu His
65                  70                  75                  80

Ser Val Phe Leu Gly Ile His Gly Gly Lys Leu Cys Leu Ser Cys Ala
                85                  90                  95

Lys Ser Gly Asp Asp Ile Lys Leu Gln Leu Glu Glu Val Asn Ile Thr
            100                 105                 110

Asp Leu Ser Lys Asn Lys Glu Glu Asp Lys Arg Phe Thr Phe Ile Arg
        115                 120                 125

Ser Glu Lys Gly Pro Thr Thr Ser Phe Glu Ser Ala Ala Cys Pro Gly
        130                 135                 140

Trp Phe Leu Cys Thr Thr Leu Glu Ala Asp Arg Pro Val Ser Leu Thr
145                 150                 155                 160

Asn Thr Pro Glu Glu Pro Leu Ile Val Thr Lys Phe Tyr Phe Gln Glu
                165                 170                 175

Asp Gln

<210> SEQ ID NO 15
<211> LENGTH: 177
<212> TYPE: PRT
<213> ORGANISM: Unknown
<220> FEATURE:
<223> OTHER INFORMATION: Equus sp.

<400> SEQUENCE: 15

Met Glu Ile Arg Arg Arg Ser Val Arg His Leu Ile Ser Leu Leu Leu
1               5                   10                  15

Phe Leu Leu Tyr Ser Glu Thr Ala Cys His Pro Leu Gly Lys Arg Pro
                20                  25                  30

Cys Lys Met Gln Ala Phe Arg Ile Trp Asp Val Asn Gln Lys Thr Phe
            35                  40                  45

Tyr Met Arg Asn Asn Gln Leu Val Ala Gly Tyr Leu Gln Glu Ser Asn
        50                  55                  60

Thr Lys Leu Gln Glu Lys Ile Asp Val Val Pro Ile Glu Pro Asp Ala
65                  70                  75                  80

Leu Phe Leu Gly Leu His Gly Arg Lys Leu Cys Leu Ala Cys Val Lys
                85                  90                  95

Ser Gly Asp Glu Ile Arg Phe Gln Leu Glu Ala Val Asn Ile Thr Asp
            100                 105                 110

Leu Ser Lys Asn Lys Glu Glu Asn Lys Arg Phe Thr Phe Ile Arg Ser
        115                 120                 125

Asn Ser Gly Pro Thr Thr Ser Phe Glu Ser Ala Ala Cys Pro Gly Trp
        130                 135                 140

Phe Leu Cys Thr Ala Gln Glu Ala Asp Arg Pro Val Ser Leu Thr Asn
```

-continued

```
145              150              155              160

Lys Pro Lys Glu Ser Phe Met Val Thr Lys Phe Tyr Leu Gln Glu Asp
                 165                 170                 175

Gln

<210> SEQ ID NO 16
<211> LENGTH: 24
<212> TYPE: DNA
<213> ORGANISM: Artificial Sequence
<220> FEATURE:
<223> OTHER INFORMATION: PRG4-F Primer

<400> SEQUENCE: 16
acttcagcta aagagacacg gagt                                             24

<210> SEQ ID NO 17
<211> LENGTH: 27
<212> TYPE: DNA
<213> ORGANISM: Artificial Sequence
<220> FEATURE:
<223> OTHER INFORMATION: PRG4-R Primer

<400> SEQUENCE: 17
gttcaggtgg ttccttggtt gtagtaa                                          27

<210> SEQ ID NO 18
<211> LENGTH: 20
<212> TYPE: DNA
<213> ORGANISM: Artificial Sequence
<220> FEATURE:
<223> OTHER INFORMATION: Sox9-F Primer

<400> SEQUENCE: 18
aagccacacg tcaagcgacc                                                  20

<210> SEQ ID NO 19
<211> LENGTH: 20
<212> TYPE: DNA
<213> ORGANISM: Artificial Sequence
<220> FEATURE:
<223> OTHER INFORMATION: Sox9-R Primer

<400> SEQUENCE: 19
gtgctgctga tgccgtaact                                                  20

<210> SEQ ID NO 20
<211> LENGTH: 26
<212> TYPE: DNA
<213> ORGANISM: Artificial Sequence
<220> FEATURE:
<223> OTHER INFORMATION: Col2a1-F Primer

<400> SEQUENCE: 20
gctcatccag ggctccaatg atgtag                                           26

<210> SEQ ID NO 21
<211> LENGTH: 23
<212> TYPE: DNA
<213> ORGANISM: Artificial Sequence
<220> FEATURE:
<223> OTHER INFORMATION: Col2a1-R Primer

<400> SEQUENCE: 21
cgggaggtct tctgtgatcg gta                                              23
```

-continued

```
<210> SEQ ID NO 22
<211> LENGTH: 21
<212> TYPE: DNA
<213> ORGANISM: Artificial Sequence
<220> FEATURE:
<223> OTHER INFORMATION: Gapdh-F Primer

<400> SEQUENCE: 22
gcaagagagg ccctatccca a                                          21

<210> SEQ ID NO 23
<211> LENGTH: 23
<212> TYPE: DNA
<213> ORGANISM: Artificial Sequence
<220> FEATURE:
<223> OTHER INFORMATION: Gapdh-R Primer

<400> SEQUENCE: 23
ctccctaggc ccctcctgtt att                                        23

<210> SEQ ID NO 24
<211> LENGTH: 24
<212> TYPE: DNA
<213> ORGANISM: Artificial Sequence
<220> FEATURE:
<223> OTHER INFORMATION: Vegf-F Primer

<400> SEQUENCE: 24
tggacttgtg ttgggaggag gatg                                       24

<210> SEQ ID NO 25
<211> LENGTH: 23
<212> TYPE: DNA
<213> ORGANISM: Artificial Sequence
<220> FEATURE:
<223> OTHER INFORMATION: Vegf-R Primer

<400> SEQUENCE: 25
gcctcttctt ccaccaccgt gtc                                        23

<210> SEQ ID NO 26
<211> LENGTH: 24
<212> TYPE: DNA
<213> ORGANISM: Artificial Sequence
<220> FEATURE:
<223> OTHER INFORMATION: Mmp13-F Primer

<400> SEQUENCE: 26
gcaatctttc tttggcttag aggt                                       24

<210> SEQ ID NO 27
<211> LENGTH: 22
<212> TYPE: DNA
<213> ORGANISM: Artificial Sequence
<220> FEATURE:
<223> OTHER INFORMATION: Mmp13-R Primer

<400> SEQUENCE: 27
ggtgttttgg gatgcttagg gt                                         22

<210> SEQ ID NO 28
<211> LENGTH: 20
<212> TYPE: DNA
<213> ORGANISM: Artificial Sequence
<220> FEATURE:
<223> OTHER INFORMATION: Col10a1-F Primer
```

<400> SEQUENCE: 28
aaagcttacc cagcagtagg                                                          20

<210> SEQ ID NO 29
<211> LENGTH: 20
<212> TYPE: DNA
<213> ORGANISM: Artificial Sequence
<220> FEATURE:
<223> OTHER INFORMATION: Col10a1-R Primer

<400> SEQUENCE: 29
acgtactcag aggagtagag                                                          20

<210> SEQ ID NO 30
<211> LENGTH: 24
<212> TYPE: DNA
<213> ORGANISM: Artificial Sequence
<220> FEATURE:
<223> OTHER INFORMATION: GAPDH_F Primer

<400> SEQUENCE: 30
ataccaggaa atgagcttga caaa                                                     24

<210> SEQ ID NO 31
<211> LENGTH: 20
<212> TYPE: DNA
<213> ORGANISM: Artificial Sequence
<220> FEATURE:
<223> OTHER INFORMATION: GAPDH_R Primer

<400> SEQUENCE: 31
tgaaggtcgg agtcaacgga                                                          20

<210> SEQ ID NO 32
<211> LENGTH: 26
<212> TYPE: DNA
<213> ORGANISM: Artificial Sequence
<220> FEATURE:
<223> OTHER INFORMATION: VEGF_F Primer

<400> SEQUENCE: 32
gatcggtgac agtcactagc ttatct                                                   26

<210> SEQ ID NO 33
<211> LENGTH: 22
<212> TYPE: DNA
<213> ORGANISM: Artificial Sequence
<220> FEATURE:
<223> OTHER INFORMATION: VEGF_R Primer

<400> SEQUENCE: 33
tacacacaaa tacaagttgc ca                                                       22

<210> SEQ ID NO 34
<211> LENGTH: 29
<212> TYPE: DNA
<213> ORGANISM: Artificial Sequence
<220> FEATURE:
<223> OTHER INFORMATION: MMP13_F Primer

<400> SEQUENCE: 34
tgcccttctt cacacagaca ctaacgaaa                                                29

<210> SEQ ID NO 35

-continued

```
<211> LENGTH: 29
<212> TYPE: DNA
<213> ORGANISM: Artificial Sequence
<220> FEATURE:
<223> OTHER INFORMATION: MMP13_R Primer

<400> SEQUENCE: 35
ggccacatct actattctta ccactgctc                                             29

<210> SEQ ID NO 36
<211> LENGTH: 22
<212> TYPE: DNA
<213> ORGANISM: Artificial Sequence
<220> FEATURE:
<223> OTHER INFORMATION: COL10A1_F Primer

<400> SEQUENCE: 36
gcccactacc caagaccaag ac                                                    22

<210> SEQ ID NO 37
<211> LENGTH: 21
<212> TYPE: DNA
<213> ORGANISM: Artificial Sequence
<220> FEATURE:
<223> OTHER INFORMATION: COL10A1_R Primer

<400> SEQUENCE: 37
gacccctctc acctggacga c                                                     21

<210> SEQ ID NO 38
<211> LENGTH: 20
<212> TYPE: DNA
<213> ORGANISM: Artificial Sequence
<220> FEATURE:
<223> OTHER INFORMATION: HIF3A_F Primer

<400> SEQUENCE: 38
ggctgttccg cctacgagta                                                       20

<210> SEQ ID NO 39
<211> LENGTH: 19
<212> TYPE: DNA
<213> ORGANISM: Artificial Sequence
<220> FEATURE:
<223> OTHER INFORMATION: HIF3A_R Primer

<400> SEQUENCE: 39
agcaaggtgg atgctcttg                                                        19

<210> SEQ ID NO 40
<211> LENGTH: 24
<212> TYPE: DNA
<213> ORGANISM: Artificial Sequence
<220> FEATURE:
<223> OTHER INFORMATION: WPRE Forward Primer

<400> SEQUENCE: 40
tctctttatg aggagttgtg gccc                                                  24

<210> SEQ ID NO 41
<211> LENGTH: 24
```

-continued

```
<212> TYPE: DNA
<213> ORGANISM: Artificial Sequence
<220> FEATURE:
<223> OTHER INFORMATION: WPRE Reverse Primer

<400> SEQUENCE: 41
cgacaacacc acggaattgt cagt                                                    24
```